US012150945B2

(12) United States Patent
Patel et al.

(10) Patent No.: US 12,150,945 B2
(45) Date of Patent: *Nov. 26, 2024

(54) LIVER DISEASE

(71) Applicant: Lipocine Inc., Salt Lake City, UT (US)

(72) Inventors: Mahesh V. Patel, Salt Lake City, UT (US); Nachiappan Chidambaram, Sandy, UT (US); Satish K. Nachaegari, Holladay, UT (US); Burke Byrne, Salt Lake City, UT (US); Kilyoung Kim, West Jordan, UT (US); Jonathan A. Baker, Salt Lake City, UT (US)

( * ) Notice: Subject to any disclaimer, the term of this patent is extended or adjusted under 35 U.S.C. 154(b) by 117 days.

This patent is subject to a terminal disclaimer.

(21) Appl. No.: 16/517,533

(22) Filed: Jul. 19, 2019

(65) Prior Publication Data

US 2020/0155570 A1 May 21, 2020

Related U.S. Application Data

(60) Provisional application No. 62/701,309, filed on Jul. 20, 2018, provisional application No. 62/714,968, filed on Aug. 6, 2018, provisional application No. 62/728,580, filed on Sep. 7, 2018, provisional application No. 62/783,190, filed on Dec. 20, 2018, provisional application No. 62/793,724, filed on Jan. 17, 2019.

(51) Int. Cl.
| | | |
|---|---|---|
| *A61K 31/568* | (2006.01) | |
| *A61K 31/201* | (2006.01) | |
| *A61K 31/355* | (2006.01) | |
| *A61K 45/06* | (2006.01) | |
| *A61P 1/16* | (2006.01) | |
| *G01N 33/92* | (2006.01) | |

(52) U.S. Cl.
CPC .......... *A61K 31/568* (2013.01); *A61K 31/201* (2013.01); *A61K 31/355* (2013.01); *A61P 1/16* (2018.01); *G01N 33/92* (2013.01); *A61K 45/06* (2013.01); *G01N 2800/085* (2013.01); *G01N 2800/52* (2013.01)

(58) Field of Classification Search
CPC .. A61K 31/568; A61K 31/201; A61K 31/355; A61K 45/06; A61P 1/16
See application file for complete search history.

(56) References Cited

U.S. PATENT DOCUMENTS

| | | |
|---|---|---|
| 2,680,749 A | 6/1954 | Cawley et al. |
| 2,742,487 A | 4/1956 | Robledano |
| 3,097,139 A | 7/1963 | Thorp |
| 3,097,144 A | 7/1963 | Banker |
| 3,164,520 A | 1/1965 | Huber |
| 3,266,991 A | 8/1966 | Wettstein et al. |
| 3,510,561 A | 5/1970 | Koh |
| 4,098,802 A | 7/1978 | Van der Vies |
| 4,147,782 A | 4/1979 | Klein et al. |
| 4,147,783 A | 4/1979 | Van der Vies |
| 4,156,719 A | 5/1979 | Sezaki et al. |
| 4,177,188 A | 12/1979 | Hansen et al. |
| 4,196,188 A | 4/1980 | Besins |
| 4,220,599 A | 9/1980 | Van der Vies |
| 4,239,754 A | 12/1980 | Sache et al. |
| 4,388,307 A | 6/1983 | Cavanak |
| 4,439,432 A | 3/1984 | Peat |
| 4,572,915 A | 2/1986 | Crooks |
| 4,579,730 A | 4/1986 | Kidron et al. |
| 4,628,052 A | 12/1986 | Peat |
| 4,628,098 A | 12/1986 | Nohara et al. |
| 4,654,327 A | 3/1987 | Teng |
| 4,656,161 A | 4/1987 | Herr |
| 4,689,333 A | 8/1987 | Nohara et al. |
| 4,695,450 A | 9/1987 | Bauer |
| 4,703,042 A | 10/1987 | Bodor |
| 4,713,246 A | 12/1987 | Begum et al. |
| 4,717,569 A | 1/1988 | Harrison et al. |
| 4,717,596 A | 1/1988 | Barbee et al. |
| 4,719,239 A | 1/1988 | Muller et al. |
| 4,727,109 A | 2/1988 | Schmidt et al. |
| 4,731,384 A | 3/1988 | Dell |
| 4,795,327 A | 1/1989 | Gaylord et al. |
| 4,832,952 A | 5/1989 | Hersh et al. |
| 4,834,965 A | 5/1989 | Martani et al. |
| 4,849,227 A | 7/1989 | Cho |
| 4,867,984 A | 9/1989 | Patel |

(Continued)

FOREIGN PATENT DOCUMENTS

| | | |
|---|---|---|
| CA | 2295028 A1 | 1/1999 |
| CA | 2302735 A1 | 1/2000 |

(Continued)

OTHER PUBLICATIONS

Kim et al., A low level of serum total testosterone is independently associated with nonalcoholic fatty liver disease. BioMed Central Gastroenterology, vol. 12(69) (Year: 2012).*
Caldwell et al. "Hepatocellular Ballooning in NASH", J. Hepatol., vol. 53(4), pp. 719-723 (Year: 2010).*
Ratziu et al., Sampling variability of liver biopsy in nonalcoholic fatty liver disease. Gastroenterology, vol. 128, pp. 1898-1906 (Year: 2005).*
Addo et al.; "Non Polar Extracts of Serum From Males Contain Covert Radioimmunoassayable Testosterone;" Steroids; (Sep. 1989); pp. 25-269; vol. 54(3).
Aguilar et al.; "Androgen Profiles Among Egyptian Adults Considering Liver Status;" Journal of Gastroenterology and Hepatology, Author Manuscript; (Jul. 2008); 6 pages; vol. 23, No. 702, e137-e145; <doi: 10.1111/j.1440-1746.2007.04949.x >.

(Continued)

*Primary Examiner* — Barbara P Badio
(74) *Attorney, Agent, or Firm* — Michael R. Schramm

(57) ABSTRACT

Methods of treating a liver disease or condition, or a symptom thereof, in a subject in need of treatment, are disclosed and described. One method comprises orally administering to a subject, a pharmaceutical composition having an amount of a testosterone, or an ester thereof, sufficient to treat the liver disease or condition, or symptom thereof.

30 Claims, 21 Drawing Sheets

(56) References Cited

U.S. PATENT DOCUMENTS

| | | |
|---|---|---|
| 4,874,795 A | 10/1989 | Yesair |
| 4,880,634 A | 11/1989 | Speiser |
| 4,895,726 A | 1/1990 | Curtet et al. |
| 4,897,269 A | 1/1990 | Mezei |
| 4,900,734 A | 2/1990 | Maxson et al. |
| 4,925,672 A | 5/1990 | Gremm |
| 4,944,949 A | 7/1990 | Story |
| 4,961,890 A | 10/1990 | Boyer |
| 4,963,540 A | 10/1990 | Maxson et al. |
| 4,994,439 A | 2/1991 | Longenecker et al. |
| 5,023,108 A | 6/1991 | Bageria et al. |
| 5,026,560 A | 6/1991 | Makino et al. |
| 5,035,891 A | 7/1991 | Runkel et al. |
| 5,045,321 A | 9/1991 | Makino et al. |
| 5,057,319 A | 10/1991 | Gottwald |
| 5,071,643 A | 12/1991 | Yu et al. |
| 5,091,187 A | 2/1992 | Haynes |
| 5,091,188 A | 2/1992 | Haynes |
| 5,093,132 A | 3/1992 | Makino et al. |
| 5,104,656 A | 4/1992 | Seth et al. |
| 5,120,710 A | 6/1992 | Liedtke |
| 5,140,021 A | 8/1992 | Maxon et al. |
| 5,145,684 A | 9/1992 | Liversidge |
| 5,152,997 A | 10/1992 | Ebert et al. |
| 5,206,219 A | 4/1993 | Desai |
| 5,244,925 A | 9/1993 | Wretlind |
| 5,252,339 A | 10/1993 | Cristofori et al. |
| 5,270,005 A | 12/1993 | Raible |
| 5,270,055 A | 12/1993 | Moest |
| 5,300,529 A | 4/1994 | Narayanan |
| 5,340,589 A | 8/1994 | Stetsko et al. |
| 5,342,625 A | 8/1994 | Hauer et al. |
| 5,350,741 A | 9/1994 | Takada |
| 5,364,632 A | 11/1994 | Benita et al. |
| 5,374,446 A | 12/1994 | Ferenz et al. |
| 5,376,688 A | 12/1994 | Morton et al. |
| 5,380,535 A | 1/1995 | Geyer et al. |
| 5,384,133 A | 1/1995 | Boyes et al. |
| 5,389,382 A | 2/1995 | List et al. |
| 5,403,593 A | 4/1995 | Royce |
| 5,433,959 A | 7/1995 | Makino et al. |
| 5,444,041 A | 8/1995 | Owen |
| 5,500,224 A | 3/1996 | Vranckx et al. |
| 5,532,002 A | 7/1996 | Story |
| 5,539,000 A | 7/1996 | Leonard |
| 5,543,393 A | 8/1996 | Kim et al. |
| 5,545,628 A | 8/1996 | DeBoeck et al. |
| 5,560,931 A | 10/1996 | Eickhoff et al. |
| 5,571,533 A | 11/1996 | Santus et al. |
| 5,571,536 A | 11/1996 | Eickhoff et al. |
| 5,573,783 A | 11/1996 | Desieno et al. |
| 5,589,455 A | 12/1996 | Woo |
| 5,589,513 A | 12/1996 | Magyar et al. |
| 5,593,971 A | 1/1997 | Tschollar et al. |
| 5,614,491 A | 3/1997 | Walch et al. |
| 5,616,330 A | 4/1997 | Kaufman et al. |
| 5,622,721 A | 4/1997 | Dansereau et al. |
| 5,624,687 A | 4/1997 | Yano et al. |
| 5,626,869 A | 5/1997 | Nyqvist et al. |
| 5,629,021 A | 5/1997 | Wright |
| 5,633,015 A | 5/1997 | Gillis et al. |
| 5,633,226 A | 5/1997 | Owen |
| 5,635,520 A | 6/1997 | Uda |
| 5,639,474 A | 6/1997 | Woo |
| 5,639,478 A | 6/1997 | Makino et al. |
| 5,639,724 A | 6/1997 | Cavanak |
| 5,645,856 A | 7/1997 | Lacy et al. |
| 5,646,109 A | 7/1997 | Owen et al. |
| 5,653,987 A | 8/1997 | Modi et al. |
| 5,656,277 A | 8/1997 | Berlati et al. |
| 5,656,289 A | 8/1997 | Cho et al. |
| 5,665,379 A | 9/1997 | Herslof et al. |
| 5,681,584 A | 10/1997 | Savatano et al. |
| 5,686,105 A | 11/1997 | Kelm et al. |
| 5,688,761 A | 11/1997 | Owen et al. |
| 5,698,155 A | 12/1997 | Grosswald et al. |
| 5,707,648 A | 1/1998 | Yiv |
| 5,714,477 A | 2/1998 | Einarsson |
| 5,726,181 A | 3/1998 | Hausheer et al. |
| 5,731,355 A | 3/1998 | Jones et al. |
| 5,736,161 A | 4/1998 | Garces et al. |
| 5,741,512 A | 4/1998 | Hauer et al. |
| 5,741,822 A | 4/1998 | Yesair |
| 5,747,066 A | 5/1998 | Pittrof et al. |
| 5,756,450 A | 5/1998 | Hahn et al. |
| 5,759,997 A | 6/1998 | Cavanak |
| 5,766,629 A | 6/1998 | Cho et al. |
| 5,767,069 A | 6/1998 | Ko et al. |
| 5,776,495 A | 7/1998 | Duclos et al. |
| 5,795,883 A | 8/1998 | Hesch et al. |
| 5,798,333 A | 8/1998 | Sherman |
| 5,811,120 A | 9/1998 | Gibson et al. |
| 5,817,320 A | 10/1998 | Stone |
| 5,827,536 A | 10/1998 | Laruelle |
| 5,846,971 A | 12/1998 | Sangekar et al. |
| 5,853,748 A | 12/1998 | New |
| 5,855,905 A | 1/1999 | Oettel et al. |
| 5,858,398 A | 1/1999 | Cho |
| 5,858,401 A | 1/1999 | Bhalani et al. |
| 5,866,159 A | 2/1999 | Hauer et al. |
| 5,874,418 A | 2/1999 | Stella et al. |
| 5,880,148 A | 3/1999 | Edgar et al. |
| 5,883,109 A | 3/1999 | Gregg et al. |
| 5,891,469 A | 4/1999 | Amselem |
| 5,891,845 A | 4/1999 | Myers |
| 5,916,589 A | 6/1999 | Hauer et al. |
| 5,922,355 A | 7/1999 | Parikh et al. |
| 5,948,773 A | 9/1999 | Akiyama et al. |
| 5,948,825 A | 9/1999 | Takahashi et al. |
| 5,962,014 A | 10/1999 | Hauer et al. |
| 5,962,017 A | 10/1999 | Hauer et al. |
| 5,965,161 A | 10/1999 | Oshlack |
| 5,976,574 A | 11/1999 | Gordon |
| 5,981,479 A | 11/1999 | Ko et al. |
| 5,981,586 A | 11/1999 | Pershadsingh |
| 5,989,583 A | 11/1999 | Amselem |
| 5,993,880 A | 11/1999 | Frost et al. |
| 6,007,840 A | 12/1999 | Hauer et al. |
| 6,008,192 A | 12/1999 | Al-Razzak et al. |
| 6,013,665 A | 1/2000 | DeMichele et al. |
| 6,017,560 A | 1/2000 | Makino et al. |
| 6,022,852 A | 2/2000 | Klokkers et al. |
| 6,024,978 A | 2/2000 | Hauer et al. |
| 6,027,747 A | 2/2000 | Terracol et al. |
| 6,042,847 A | 3/2000 | Kerc et al. |
| 6,046,177 A | 4/2000 | Stella et al. |
| 6,057,339 A | 5/2000 | Gregg |
| 6,066,653 A | 5/2000 | Gregg et al. |
| 6,074,670 A | 6/2000 | Stamm et al. |
| 6,086,376 A | 7/2000 | Moussa et al. |
| 6,096,338 A | 8/2000 | Lacy et al. |
| 6,123,962 A | 9/2000 | Makino et al. |
| 6,160,007 A | 12/2000 | DeMichele et al. |
| 6,174,547 B1 | 1/2001 | Dong et al. |
| 6,180,138 B1 | 1/2001 | Engh et al. |
| 6,189,486 B1 | 2/2001 | Lindholm |
| 6,193,985 B1 | 2/2001 | Sonne |
| 6,221,395 B1 | 4/2001 | Maggi et al. |
| 6,224,840 B1 | 5/2001 | Kim et al. |
| 6,228,399 B1 | 5/2001 | Parikh et al. |
| 6,228,400 B1 | 5/2001 | Lee et al. |
| 6,248,363 B1 | 6/2001 | Patel et al. |
| 6,255,100 B1 | 7/2001 | Ko et al. |
| 6,267,985 B1 | 7/2001 | Chen et al. |
| 6,287,594 B1 | 9/2001 | Wilson |
| 6,294,192 B1 | 9/2001 | Patel et al. |
| 6,296,876 B1 | 10/2001 | Odidi et al. |
| 6,299,904 B1 | 10/2001 | Shimizu et al. |
| 6,303,662 B1 | 10/2001 | Nagahama et al. |
| 6,306,825 B1 | 10/2001 | Cavanak |
| 6,309,663 B1 | 10/2001 | Patel et al. |
| 6,328,993 B1 | 12/2001 | Linder et al. |
| 6,328,994 B1 | 12/2001 | Shimizu et al. |
| 6,340,471 B1 | 1/2002 | Kershman et al. |

(56) References Cited

U.S. PATENT DOCUMENTS

| | | | |
|---|---|---|---|
| 6,342,246 B2 | 1/2002 | Johnson et al. |
| 6,361,796 B1 | 3/2002 | Rudnic et al. |
| 6,368,634 B1 | 4/2002 | Remon |
| 6,379,705 B1 | 4/2002 | Mendes et al. |
| 6,383,471 B1 | 5/2002 | Chen et al. |
| 6,383,510 B1 | 5/2002 | Linder et al. |
| 6,383,517 B1 | 5/2002 | Qiu et al. |
| 6,391,342 B1 | 5/2002 | Henriksen et al. |
| 6,432,445 B1 | 8/2002 | Ambuhl et al. |
| 6,444,225 B1 | 9/2002 | Sherman |
| 6,447,806 B1 | 9/2002 | Gassmann et al. |
| 6,451,339 B2 | 9/2002 | Patel et al. |
| 6,455,518 B2 | 9/2002 | Zenke et al. |
| 6,458,373 B1 | 10/2002 | Lambert et al. |
| 6,458,383 B2 | 10/2002 | Chen et al. |
| 6,465,016 B2 | 10/2002 | Parikh et al. |
| 6,468,559 B1 | 10/2002 | Chen et al. |
| 6,475,519 B1 | 11/2002 | Minzer et al. |
| 6,503,894 B1 | 1/2003 | Dudley et al. |
| 6,531,139 B1 | 3/2003 | Gao et al. |
| 6,569,463 B2 | 5/2003 | Patel et al. |
| 6,589,552 B2 | 7/2003 | Stamm et al. |
| 6,589,562 B1 | 7/2003 | Shefer et al. |
| 6,623,755 B2 | 9/2003 | Chen et al. |
| 6,630,134 B1 | 10/2003 | Klein |
| 6,652,880 B1 | 11/2003 | Aylwin et al. |
| 6,660,286 B1 | 12/2003 | Lambert et al. |
| 6,665,880 B2 | 12/2003 | Pope |
| 6,667,048 B1 | 12/2003 | Lambert et al. |
| 6,692,766 B1 | 2/2004 | Rubinstein et al. |
| 6,696,482 B2 | 2/2004 | Schenoy et al. |
| 6,720,001 B2 | 4/2004 | Chen et al. |
| 6,737,082 B1 | 5/2004 | Picornell Darder |
| 6,761,903 B2 | 7/2004 | Chen et al. |
| 6,881,745 B2 | 4/2005 | Hayes et al. |
| 6,887,493 B2 | 5/2005 | Shefer et al. |
| 6,913,244 B1 | 7/2005 | Atkinson et al. |
| 6,923,988 B2 | 8/2005 | Patel et al. |
| 6,977,083 B1 | 12/2005 | Huebler et al. |
| 6,982,281 B1 | 1/2006 | Chen et al. |
| 7,025,979 B2 | 4/2006 | Neischlag et al. |
| 7,138,389 B2 | 11/2006 | Amory et al. |
| 7,374,779 B2 | 5/2008 | Chen et al. |
| 7,658,944 B2 | 2/2010 | Holm et al. |
| 7,718,640 B2 | 5/2010 | Hubler et al. |
| 8,241,664 B2 | 8/2012 | Dudley et al. |
| 8,338,395 B2 | 12/2012 | Hubler et al. |
| 8,492,369 B2 | 7/2013 | Dudley et al. |
| 8,778,922 B2 | 7/2014 | Giliyar et al. |
| 8,828,428 B1 | 9/2014 | Dudley et al. |
| 8,865,695 B2 | 10/2014 | Giliyar et al. |
| 9,034,858 B2 | 5/2015 | Giliyar et al. |
| 9,205,057 B2 | 10/2015 | Giliyar et al. |
| 9,358,241 B2 | 6/2016 | Giliyar et al. |
| 9,498,485 B2 | 6/2016 | Patel et al. |
| 9,480,690 B2 | 11/2016 | Giliyar et al. |
| 9,757,389 B2 | 9/2017 | Patel et al. |
| 9,757,390 B2 | 9/2017 | Gilivar et al. |
| 9,943,527 B2 | 4/2018 | Giliyar et al. |
| 9,949,985 B2 | 4/2018 | Giliyar et al. |
| 10,226,473 B2 | 3/2019 | Giliyar et al. |
| 2001/0018069 A1 | 8/2001 | Johnson et al. |
| 2002/0006443 A1 | 1/2002 | Curatolo et al. |
| 2002/0013304 A1 | 1/2002 | Wilson et al. |
| 2002/0058066 A1 | 5/2002 | Tomohira et al. |
| 2002/0068693 A1 | 6/2002 | Jeng et al. |
| 2002/0102301 A1 | 8/2002 | Schwarz |
| 2002/0103139 A1 | 8/2002 | Weisspapir et al. |
| 2002/0183296 A1 | 12/2002 | Dudley et al. |
| 2003/0022875 A1 | 1/2003 | Wilson et al. |
| 2003/0072798 A1 | 4/2003 | Schwarz et al. |
| 2003/0077297 A1 | 4/2003 | Chen et al. |
| 2003/0082215 A1 | 5/2003 | Lemut et al. |
| 2003/0104048 A1 | 6/2003 | Patel et al. |
| 2003/0109508 A1 | 6/2003 | Yanni et al. |
| 2003/0209508 A1 | 6/2003 | Yanni et al. |
| 2003/0180352 A1 | 9/2003 | Patel et al. |
| 2003/0181431 A1 | 9/2003 | Hodgen |
| 2003/0186892 A1 | 10/2003 | Taneja |
| 2003/0216260 A1 | 11/2003 | Ruther |
| 2003/0216360 A1 | 11/2003 | Grawe et al. |
| 2003/0228358 A1 | 12/2003 | Perlman et al. |
| 2003/0235595 A1 | 12/2003 | Chen et al. |
| 2003/0236236 A1 | 12/2003 | Chen et al. |
| 2004/0002445 A1 | 1/2004 | Taneja |
| 2004/0002482 A1 | 1/2004 | Dudley et al. |
| 2004/0048896 A1 | 3/2004 | Phillips |
| 2004/0127476 A1 | 7/2004 | Kershaman et al. |
| 2005/0031693 A1 | 2/2005 | Babcock et al. |
| 2005/0032762 A1 | 2/2005 | Hubler et al. |
| 2005/0070516 A1 | 3/2005 | Wilson |
| 2005/0080075 A1 | 4/2005 | Nichols et al. |
| 2005/0096296 A1 | 5/2005 | Fikstad et al. |
| 2005/0096365 A1 | 5/2005 | Fikstad et al. |
| 2005/0100608 A1 | 5/2005 | Ebert |
| 2005/0101517 A1 | 5/2005 | De Nijs et al. |
| 2005/0171193 A1 | 8/2005 | Chen et al. |
| 2005/0176692 A1 | 8/2005 | Amory et al. |
| 2005/0209345 A1 | 9/2005 | Charman |
| 2005/0220825 A1 | 10/2005 | Funke et al. |
| 2005/0269251 A1 | 12/2005 | Cork |
| 2005/0287203 A1 | 12/2005 | De Nijs et al. |
| 2005/0287212 A1 | 12/2005 | Dong et al. |
| 2006/0003002 A1 | 1/2006 | Fikstad et al. |
| 2006/0034937 A1 | 2/2006 | Patel |
| 2006/0051406 A1 | 3/2006 | Parmar |
| 2006/0106004 A1 | 5/2006 | Brody et al. |
| 2006/0142257 A1 | 6/2006 | Nieschlag |
| 2007/0110777 A1 | 5/2007 | Joabsson et al. |
| 2007/0134336 A1 | 6/2007 | Worle et al. |
| 2007/0154533 A1 | 7/2007 | Dudley |
| 2007/0232548 A1 | 10/2007 | Taneja |
| 2008/0020053 A1 | 1/2008 | Persson et al. |
| 2008/0217692 A1 | 9/2008 | Anderson et al. |
| 2008/0317844 A1 | 12/2008 | Dudley et al. |
| 2008/0317850 A1 | 12/2008 | Hewitt et al. |
| 2008/0317859 A1 | 12/2008 | Sournac et al. |
| 2009/0074859 A1 | 3/2009 | Patel |
| 2010/0136105 A1 | 6/2010 | Chen et al. |
| 2010/0137271 A1 | 6/2010 | Chen et al. |
| 2010/0148675 A1 | 6/2010 | Meijer et al. |
| 2010/0173882 A1* | 7/2010 | Giliyar ............ A61K 9/4875 514/178 |
| 2010/0266645 A1 | 10/2010 | Liang et al. |
| 2011/0039814 A1 | 2/2011 | Huatan et al. |
| 2011/0142945 A1 | 6/2011 | Chen et al. |
| 2011/0160168 A1 | 6/2011 | Dhingra |
| 2011/0251167 A1 | 10/2011 | Dudley et al. |
| 2011/0263552 A1 | 10/2011 | Dhingra et al. |
| 2012/0135074 A1 | 5/2012 | Giliyar et al. |
| 2012/0148675 A1 | 6/2012 | Chickmath et al. |
| 2012/0244215 A1 | 9/2012 | Giliyar |
| 2012/0309731 A1 | 12/2012 | Dudley et al. |
| 2012/0322780 A1 | 12/2012 | Giliyar et al. |
| 2013/0022674 A1 | 1/2013 | Dudley et al. |
| 2013/0023505 A1 | 1/2013 | Garfield et al. |
| 2013/0052263 A1 | 2/2013 | Fikstad et al. |
| 2013/0178454 A1 | 7/2013 | Bhasin et al. |
| 2013/0225544 A1 | 8/2013 | Nachaegari et al. |
| 2013/0226644 A1 | 8/2013 | Alonzo et al. |
| 2014/0011780 A1 | 1/2014 | Dhingra |
| 2014/0178466 A1 | 6/2014 | Giliyar et al. |
| 2014/0179652 A1 | 6/2014 | Giliyar et al. |
| 2014/0288039 A1 | 9/2014 | Nachaegari et al. |
| 2014/0303130 A1 | 10/2014 | Giliyar et al. |
| 2014/0303132 A1 | 10/2014 | Nachaegari et al. |
| 2014/0309202 A1 | 10/2014 | Giliyar |
| 2014/0323452 A1 | 10/2014 | Nachaegari et al. |
| 2014/0323453 A1 | 10/2014 | Nachaegari et al. |
| 2015/0038475 A1 | 2/2015 | Chickmath et al. |
| 2015/0064243 A1 | 3/2015 | Chen et al. |
| 2015/0224059 A1 | 8/2015 | Giliyar |
| 2015/0273067 A1 | 10/2015 | Patel |
| 2015/0320765 A1 | 11/2015 | Giliyar |

(56) References Cited

U.S. PATENT DOCUMENTS

| | | |
|---|---|---|
| 2015/0328233 A1 | 11/2015 | Hojgaard |
| 2016/0074416 A1 | 3/2016 | Giliyar et al. |
| 2016/0184320 A1 | 6/2016 | Patel |
| 2016/0184324 A1 | 6/2016 | Patel et al. |
| 2016/0193225 A1 | 7/2016 | Patel |
| 2016/0317553 A1 | 11/2016 | Salameh et al. |
| 2016/0361322 A1 | 12/2016 | Patel |
| 2016/0367569 A1 | 12/2016 | Giliyar et al. |
| 2017/0007622 A1 | 1/2017 | Giliyar et al. |
| 2017/0020893 A1* | 1/2017 | Nachaegari ............ A61K 45/06 |
| 2017/0056415 A1 | 3/2017 | Patel et al. |
| 2017/0065614 A1 | 3/2017 | Betageri et al. |
| 2017/0106002 A1 | 4/2017 | Dudley et al. |
| 2017/0136033 A1 | 5/2017 | Schoonus-Gerritsma |
| 2017/0246187 A1 | 8/2017 | Patel et al. |
| 2017/0354663 A1 | 12/2017 | Giliyar et al. |
| 2018/0021349 A1 | 1/2018 | Dhingra et al. |
| 2018/0028542 A1 | 2/2018 | Dudley et al. |
| 2018/0110786 A1 | 4/2018 | Dudley et al. |
| 2018/0125787 A1 | 5/2018 | Chickmath et al. |
| 2018/0125857 A1 | 5/2018 | Giliyar et al. |
| 2018/0147215 A1 | 5/2018 | Chidambaram et al. |
| 2018/0153905 A1 | 6/2018 | Chidambaram et al. |
| 2018/0228816 A1 | 8/2018 | Giliyar et al. |
| 2018/0228817 A1 | 8/2018 | Giliyar et al. |
| 2018/0243320 A1 | 8/2018 | Giliyar et al. |
| 2019/0125760 A1 | 5/2019 | Giliyar et al. |

FOREIGN PATENT DOCUMENTS

| | | |
|---|---|---|
| CN | 101217963 A | 7/2008 |
| DE | 10108614 A1 | 9/2002 |
| EP | 0036145 B1 | 5/1985 |
| EP | 0184942 A2 | 6/1986 |
| EP | 0537070 A1 | 4/1993 |
| EP | 0724877 A1 | 8/1996 |
| EP | 0981328 A1 | 3/2000 |
| EP | 0988858 A1 | 3/2000 |
| EP | 1103252 A1 | 5/2001 |
| EP | 1624855 A2 | 2/2006 |
| EP | 1879456 A1 | 1/2008 |
| EP | 2000130 A1 | 12/2008 |
| FR | 2647346 B1 | 9/1991 |
| FR | 2758459 A1 | 7/1998 |
| GB | 1264677 A | 2/1973 |
| GB | 2098865 A | 12/1982 |
| GB | 2228198 A | 8/1990 |
| JP | S52-148060 A | 12/1977 |
| JP | H01139526 A | 6/1989 |
| JP | 5194209 A | 8/1993 |
| JP | 07041422 A | 2/1995 |
| JP | H07-508724 A | 9/1995 |
| JP | 09241152 A | 9/1997 |
| JP | 11049664 A | 2/1999 |
| JP | 11152227 A | 6/1999 |
| JP | 2001/500368 A | 1/2001 |
| JP | 2001/508445 A | 6/2001 |
| JP | 2001/514626 A | 9/2001 |
| JP | 2002/510311 A | 4/2002 |
| JP | 2002/520377 A | 7/2002 |
| JP | 2003/500368 A | 1/2003 |
| JP | 2005500347 A | 1/2005 |
| JP | 2008537960 A | 10/2008 |
| JP | 2008/540451 A | 11/2008 |
| RU | 2246296 C2 | 2/2005 |
| RU | 2482847 C2 | 5/2013 |
| WO | WO 82/01649 A1 | 5/1982 |
| WO | WO 84/02076 A1 | 6/1984 |
| WO | WO 88/00059 A1 | 1/1988 |
| WO | WO 92/18147 A1 | 10/1992 |
| WO | WO 93/02664 A1 | 2/1993 |
| WO | WO 93/06921 A1 | 4/1993 |
| WO | WO 93/25192 A1 | 12/1993 |
| WO | WO 94/08610 A1 | 4/1994 |
| WO | WO 94/25068 A1 | 11/1994 |
| WO | WO 95/01785 A1 | 1/1995 |
| WO | WO 95/01786 A1 | 1/1995 |
| WO | WO 95/24893 A1 | 9/1995 |
| WO | WO 95/34287 A1 | 12/1995 |
| WO | WO 96/17597 A1 | 6/1996 |
| WO | WO 97/04749 A1 | 2/1997 |
| WO | WO 97/40823 A1 | 11/1997 |
| WO | WO 97/48382 A2 | 12/1997 |
| WO | WO 98/00116 A1 | 1/1998 |
| WO | WO 98/30205 A1 | 7/1998 |
| WO | WO 98/33512 A1 | 8/1998 |
| WO | WO 98/38984 A2 | 9/1998 |
| WO | WO 98/50077 A1 | 11/1998 |
| WO | WO 98/56357 A1 | 12/1998 |
| WO | WO 99/00111 A1 | 1/1999 |
| WO | WO 99/29300 A1 | 6/1999 |
| WO | WO 99/40904 A2 | 8/1999 |
| WO | WO 99/44584 A1 | 9/1999 |
| WO | WO 99/48498 A1 | 9/1999 |
| WO | WO 00/003753 A2 | 1/2000 |
| WO | WO 00/016749 A1 | 3/2000 |
| WO | WO 00/025772 A1 | 5/2000 |
| WO | WO 00/037057 A2 | 6/2000 |
| WO | WO 00/050007 A1 | 8/2000 |
| WO | WO 00/057859 A1 | 10/2000 |
| WO | WO 00/057918 A2 | 10/2000 |
| WO | WO 00/059482 A1 | 10/2000 |
| WO | WO 00/059512 A1 | 10/2000 |
| WO | WO0059512 * | 10/2000 |
| WO | WO 00/071163 A1 | 11/2000 |
| WO | WO 00/072825 A1 | 12/2000 |
| WO | WO 00/076482 A1 | 12/2000 |
| WO | WO 01/001960 A1 | 1/2001 |
| WO | WO 01/012155 A1 | 2/2001 |
| WO | WO 01/021154 A2 | 3/2001 |
| WO | WO 01/028555 A1 | 4/2001 |
| WO | WO 01/037808 A1 | 5/2001 |
| WO | WO 01/049262 A1 | 7/2001 |
| WO | WO 02/039983 A2 | 5/2002 |
| WO | WO 03/068186 A1 | 8/2003 |
| WO | WO 2004/087052 A2 | 10/2004 |
| WO | WO 2004/105694 A2 | 12/2004 |
| WO | WO 2005/041929 A2 | 5/2005 |
| WO | WO 2006/013369 A2 | 2/2006 |
| WO | WO 2006/113505 A2 | 10/2006 |
| WO | WO 2006/119498 A2 | 11/2006 |
| WO | WO 2007/018943 A2 | 2/2007 |
| WO | WO 2007/100614 A2 | 9/2007 |
| WO | WO 2010/081032 A2 | 7/2010 |
| WO | WO 2010/102737 A1 | 9/2010 |
| WO | WO 2011/082384 A2 | 7/2011 |
| WO | WO 2011/129812 A1 | 10/2011 |
| WO | WO 2012/075081 A2 | 7/2012 |
| WO | WO 2012/101016 A1 | 8/2012 |
| WO | WO 2014/049131 A1 | 4/2014 |
| WO | WO 2014/145518 A2 | 9/2014 |
| WO | 2015192854 A2 | 12/2015 |
| WO | WO2015192854 * | 12/2015 |

OTHER PUBLICATIONS

Ajmera et al.; "Refining Sample-Size Estimations Based Upon Placebo Response in Trials of Agents for Nonalcoholic Fatty Liver Disease;" Clinical Gastroenterology and Hepatology; (2018); 3 pages; Editorial; <doi: 10.1016/j.cgh.2018.08.055 >.

Albhaisi et al.; AASLD Abstracts #2121 "LPCN 1144 Resolves Non-Alcoholic Fatty Liver Disease;" Hepatology; (Oct. 2019); p. 1256 A; (can also be found at <URL: https://aasldpubs.onlinelibrary.wiley.com/doi/full/10.1002/hep.30941 7af=R >.

Alkhouri et al.; "Looking Into the Crystal Ball: Predicting the Future Challenges of Fibrotic NASH Treatment;" Hepatology Communications; (2019); pp. 605-613; vol. 3, No. 5; <doi: 10.1002/hep4.1342 >.

Alvarez et al.; "The Role of Calcium Ions and Bile Salts on the Pancreatic Lipase-Catalyzed Hydrolysis of Triglyceride Emulsions Stabilized with Lecithin;" Pharmaceutical Research; (1989); pp. 449-457; vol. 6(6).

(56) References Cited

OTHER PUBLICATIONS

ANDRIOL® TESTOCAPS®; "Testosterone Undecanoate;" Consumer Medicine Information; [insert]; (Jul. 2011); 3 pages.
ANDRIOL® TESTOCAPS®; Consumer Medicine Information; (Sep. 2003).
ANDRODERM® Product Label and Medication Guide; 1995; Labeler—Watson Pharma, Inc.; Revised Nov. 2013; 23 pages.
ANDROGEL® Product Label and Medication Guide; (May 2013): Labeler—AbbVie Inc.; Revised Oct. 2013; 28 pages.
Arab et al.; "Bile Acids and Nonalcoholic Fatty Liver Disease: Molecular Insights and Therapeutic Perspectives;" Hepatology; (2017); pp. 350-362; vol. 65, No. 1; <doi: 10.1002/hep.28709 >.
Aschenbrenner; "Drug Watch: Information on Drugs, Including New Approvals and Indications, Warnings, and Other Regulatory Updates, First Oral Testosterone Product Now Available;" American Journal of Nursing; (Aug. 2019); pp. 22-23; vol. 119, No. 8.
Atkinson et al.; "Long Term Experience with Testosterone Replacement Through Scrotal Skin; Testosterone: Action, Deficiency and Substitution;" Nieschlag et al. Eds.; (1998); pp. 365-388.
Aungst; "Intestinal Permeation Enhancers;" Journal of Pharmaceutical Sciences; (2000); pp. 429-442; vol. 89(4).
Baert et al.; "Analytical, biopharmaceutical and regulatory evaluation of topical testosterone preparations;" European Journal of Pharmaceutics and Biopharmaceutics; (2009); pp. 275-281; vol. 72; <doi: 10.1016/j.ejpb.2008.10.014 >.
Bagchus et al.; "Important Effect of Food on the bioavailability of Oral Testosterone Undecanoate;" Pharmacotherapy; (2003); pp. 319-325; vol. 23(3).
Baker et al.; "LPCN 1144, an Androgen Receptor Agonist Targeted for NASH, Reduces Liver Fat and Key Serum Biomarkers" [Poster Presentations LBP-03]; Journal of Hepatology; (2019); p. e142; vol. 70; (can also be found at https://www.journal-of-hepatology.en/article/S0618-8278(19)30249-X/pdf ) EASL 2019.
Baker et al.; "SAT-LB004 Therapeutic Potential of LPCN 1144 in NAFLD and Nash" Journal of Endocrine Society; (Apr.-May 2009); 2 pages; vol. 3, Issue Supplement_1; (can also be found at https://academic.oup.com/jes/article/3/Supplement 1/SAT-LB004/5483436?searchresult=1) ENDO 2019.
Baker. et al.; Poster "Paradigm Shifting Beneficial effects of TLANDO (Oral Testosterone) on Liver" $20^{th}$ Annual Fall Scientific Meeting of SMSNA; Oct. 24-27, 2019.
Baluom et al.; "The Importance of Intestinal Residence Time of Absorption Enhancer on Drug Implication on Formulative Considerations;" International Journal of Pharmaceutics; (1998); pp. 21-30; vol. 176.
Barbonetti et al.; "Low Testosterone and Non-Alcoholic Fatty Liver Disease: Evidence for their Independent Association in Men with Chronic Spinal Cord Injury;" The Journal of Spinal Cord Medicine; (2016); pp. 443-449; vol. 39, No. 4; <doi: 10.1179/2045772314Y.0000000288 >.
Bates et al.; "Bioavailability of Micronized Griseofulvin from Corn Oil-in-Water Emulsion, Aqueous Suspension, and Commercial Tablet Dosage Forms in Humans;" Journal of Pharmaceutical Sciences; (1975); pp. 793-797; vol. 64(5).
Bazick et al.; "Clinical Model for NASH and Advanced Fibrosis in Adult Patients With Diabetes and NAFLD: Guidelines for Referral in NAFLD;" Diabetes Care; (2015); pp. 1347-1355; vol. 38; <doi: 10.2337/dc14-1239 >.
Beatch et al.; "Ventricular Fibrillation, an Uncontrolled Arrhythmia Seeking New Targets;" Drug Development Research Journal; (2002); pp. 45-52; vol. 55.
Bernkop-Schnurch; "The Use of Inhibitory Agents to Overcome the Enzymatic Barrier to Orally Administered Therapeutic Peptides and Proteins;" Journal of Controlled Release; (Apr. 1998); pp. 1-16; vol. 52(1-2).
Bhargava et al.; "Using Microemulsions for Drug Delivery;" Pharmaceutical Technology; (Mar. 1987); pp. 46-53.

Bizzaro et al.; "Sex-Dependent Differences in Inflammatory Responses During Liver Regeneration in a Murine Model of Acute liver Injury;" Clinical Science; (2018); pp. 255-272; vol. 132; <doi: 10.1042/CS20171260 >.
Blackman et al.; "Growth Hormone and Sex Steroid Administration in Healthy Aged Women and Men: A Randomized Controlled Trial;" Journal of American Medical Association; (2002); pp. 2282-2292; vol. 288, No. 18.
Blystone et al.; "Toxicity and Carcinogenicity of Androstenedione in F344/N Rats and B6C3F2 Mice;" Food and Chemical Toxicology; (Sep. 2011); pp. 2116-2124; <doi: 10.1016/j.fct.2011.05.026. Epub2011May30 >.
Bond et al.; "Anabolic Androgenic Steroid-Induced Hepatotoxicity;" Medical Hypotheses; (Aug. 2016); pp. 150-153; vol. 93; <doi: 10.1016/j.mehy.2016.06.004 >.
Brooke et al.; "Testosterone Replacement Therapy has Beneficial Effects on Cardiovascular Risk Factors and Liver Function in Hypogonadal Men;" In: Society for Endocrinology; (BES 2012); Harrogate, UK; Endocrine Abstracts 28 P163.
Bugay; "Characterization of the Solid-State: Spectroscopic Techniques;" Advanced Drug Delivery Review; (May 16, 2001); pp. 43-65; vol. 48(1).
Burbello et al.; Sovremennye Lekarstvennyesredstava S-Pb Neva; (2004); p. 567.
Burke et al.; "Sex-Hormone-Binding Globulin is an Oestrogen Amplifier;" Nature; (Nov. 3, 1972); pp. 38-40; vol. 240.
Cai et al.; "The Role of Inflammation in the Mechanisms of Bile Acid-Induced Liver Damage;" Digestive Diseases, Author Manuscript; (2017); pp. 232-234; vol. 35, No. 3; <doi: 10.1159/000450916 >.
Cai et al.; "Transcriptomic Analysis of Hepatic Responses to Testosterone Deficiency in Miniature Pigs Fed a High-Cholesterol Diet;" BioMed Central Genomics; (2015); 19 pages; vol. 16, No. 59; <doi: 10.1186/s12864-015-1283-0 >.
Cantrill; "Which Testosterone Replacement Therapy;" Clinical Endocrinology Journal; (1984); pp. 97-107; vol. 21.
Chalasani et al.; "The Diagnosis and Management of Non-Alcoholic Fatty Liver Disease: Practice Guideline by the American Association for the Study of Liver Diseases, American College of Gastroenterology, and the American Gastroenterological Association;" American Journal of Gastroenterology; (May 29, 2012); pp. 811-826; vol. 107; <doi: 10.1038/ajg.2012.128 >.
Chalasani et al.; "The Diagnosis and Management of Nonalcoholic Fatty Liver Disease: Practice Guidance From the American Association for the Study of Liver Disease;" Hepatology; (2018); pp. 328-357; vol. 67, No. 1; <doi: 10.1002/hep.29367 >.
Charlton et al.; "LPCN 1144 (Oral Testosterone Undecanoate) Resolves Non-Alcoholic Fatty Liver;" Sexual Medicine Society; (2019); Poster Presentation.
Charman et al.; "Physicochemical and Physiological Mechanisms for the Effects of Food on Drug Absorption: The Role of Lipids and pH;" Journal of Pharmaceutical Sciences; (1997); pp. 269-282; vol. 86(3).
Chaudhury et al.; "Testosterone in Men with Chronic Hepatitis C Infection and After Hepatitis C Viral Clearance;" Clinical Infectious Diseases; (Feb. 2019); 6 pages; <doi: 10.1093/cid/ci/965 >.
Chazenbalk et al.; "Androgens Inhibit Adipogenesis During Human Adipose Stem Cell Commitment to Preadipocyte Formation;" Steroids; (2013); pp. 920-926; vol. 78; <doi: 10.1016/j.steroids.2013.05.001 >.
Cheng et al.; "Nonalcoholic Fatty Liver Disease: Prevalence, Influence on Age and Sex, and Relationship with Metabolic Syndrome and Insulin Resistance;" International Journal of Gerontolgoy; (2013); pp. 194-198; vol. 7; <doi: 10.1016/j.ijge.2013.03.008 >.
Chiang; "Bile Acid Metabolism and Signaling;" Comprehensive Physiology, Author Manuscript; (Jul. 2013); pp. 1191-1212; vol. 3. No. 3; <doi: 10.1002/cphy.c120023 >.
Chow et al.; "A Selective Estrogen Receptor a Agonist Ameliorates Hepatic Steatosis in the Male Aromatase Knockout Mouse;" Journal of Endocrinology; (2011); pp. 323-334; vol. 210; <doi: 10.1530/JOE-10-0462 >.
Chow et al.; "The Role of Bile Acids in Nonalcoholic Fatty Liver Disease and Nonalcoholic Steatohepatitis;" Molecular Aspects of

(56) References Cited

OTHER PUBLICATIONS

Medicine, Author Manuscript; (Aug. 2017); pp. 34-44; vol. 56; <doi: 10.1016/j.mam.2017.04.004 >.

Clinical trials.gov; "History of Changes for Study: NCT02081300 Safety and Efficacy of Oral LPCN 1021 in Men with Low Testosterone or Hypogonadism;" U.S. National Library of Medicine: Archive History for NCT02081300; (Mar. 5, 2014); 10 pages; [retrieved Apr. 30, 2018]; Retrieved from <URL: https://clinicaltrials.gov/ct/history/NCT02081300?V_1=View >.

Colak et al.; "Association of Serum Lipoprotein-Associated Phospholipase A2 Level with Nonalcoholic Fatty Liver Disease;" Metabolic Syndrome and Related Disorders; (2012); pp. 103-109; vol. 10, No. 2; <doi: 10.1089/met.2011.0111 >.

Collier et al.; "Guidelines on the Management of Osteoporosis Associated with Chronic Liver Discase;" Gut; (2002); pp. il-i9; vol. 50, Suppl 1.

Constantidides; "Lipid Microemulsion for Improving Drug Dissolution and Oral Absorption: Physical and Biopharmaceutical Aspect;" Pharmaceutical Research; (1995); pp. 1561-1572; vol. 12(11).

Dandona et al.; "A Practical Guide to Male Hypogonadism in the Primary Care Setting;" The International Journal of Clinical Practice; (2010); pp. 663-664; vol. 64, No. 6; <doi: 10.1111/j.1742-1241.2010.02355.x>.

Dandona et al.; "A Practical Guide to Male Hypogonadism in the Primary Care Setting;" The International Journal of Clinical Practice; (May 2010); pp. 682-696; vol. 64, No. 6; <doi: 10.1111/j.1742-1241.2010.02355.x>.

DEPO-TESTOSTERONE® Product Label and Medication Guide; (Sep. 2006); Labeler—Pharmacia & Upjohn Company; Revised Aug. 2013; 12 pages.

Dev et al.; "When and When Not to Use Testosterone for Palliation in Cancer Care;" Current Oncology Reports; (Feb. 9, 2014); pp. 378-385; vol. 16; <doi: 10.1007/s11912-014-0378-0 >.

Dhindsa et al.; "Testosterone Concentrations in Diabetic and Nondiabetic Obese Men;" Diabetes Care; (Jun. 2010); pp. 1186-1192; vol. 33, No. 6; <doi: 10.2337/dc09-1649 >.

Dias et al.; "Effects of Transdermal Testosterone Gel or an Aromatase Inhibitor on Serum Concentration and Pulsatility of Growth Hormone in Older Men with Age-Related Low Testosterone;" Metabolism, Author Manuscript; (Apr. 2017); pp. 143-147; vol. 69; <doi: 10.1016/j.metabol.2017.01.025 >.

Do et al.; "Epidemiology of Nonalcoholic Fatty Liver Disease: A Primer;" Clinical Liver Disease; (May 2016); pp. 106-108; vol. 7, No. 5.

EASL the Home of Hepatology; "Metabolism, Alcohol and Toxicity;" Best of The International Liver Congress™ 2018; (Apr. 11-15, 2018); 26 pages; Paris Expo Porte de Versailles.

ECHOSENS™; "Looming Epidemic: Non-Alcoholic Fatty Liver Disease;" FibroScan® Presentation; (Feb. 2019); 18 pages.

Ekstedt et al.; "Natural History of NAFLD/NASH;" Current Hepatology Reports; (2017); pp. 391-397; vol. 16; <doi: 10.1007/s11901-017-0378-2 >.

Emulsion; IUPAC Compendium of Chemical Terminology; 2nd Ed.; (1997).

Estes et al.; "Modeling the Epidemic of Nonalcoholic Fatty Liver Disease Demonstrates an Exponential Increase in Burden of Disease;" Hepatology; (2018); pp. 123-133; vol. 67, No. 1; <doi: 10.1002/hep.29466 >.

Evercore ISI; "Weekend Musings: A Multi-Trillion dollar Therapeutic Category (that's not a typo);" Healthcare, Biotechnology, Drug Discovery; (Nov. 16, 2018); 14 pages.

Fallatah et al.; "Fibroscan Compared to FIB-4, APRI, and AST/ALT Ratio for Assessment of Liver Fibrosis in Saudi Patients with Nonalcoholic Fatty liver Disease;" Hepatitis Monthly; (Jul. 2016); 6 pages, e38346; vol. 16, No. 7; <doi: 10.5812/hepatmon.38346 >.

Floreani et al.; "Sex Hormone Profile and Endometrial Cancer Risk in Primary Biliary Cirrhosis: A Case-Control Study;" European Journal of Obstetrics & Gynecology and Reproductive Biology; (2002); pp. 154-157; vol. 103.

Foresta et al.; "Male Hypogonadism in Cirrhosis and After Liver Transplantation;" Journal of Endocrinology Investigations; (2008); pp. 470-478; vol. 31.

Francavilla et al.; "Circadian Rhythm of Hepatic Cytosolic and Nuclear Estrogen and Androgen Receptors;" Gastroenterology, Author Manuscript; (Jul. 1986); pp. 182-188; vol. 91, No. 1.

Frey et al.; "Bioavailability of Oral Testosterone in Males;" European Journal of Pharmacology; (1979); pp. 345-349; vol. 16.

Fujihara et al.; "High Sex Hormone-Binding Globulin Concentration is a Risk Factor for High Fibrosis-4 Index in Middle-Aged Japanese Men;" Endocrine Journal Advance Publication; (2019); 9 pages; <doi: 10.1507/endocrj.EJ18-0505 >.

Gagliano-Jucá et al.; "Effects of Testosterone Administration (and its 5-Alpha-Reduction) on Parenchymal Organ Volumes in Healthy Young Men: Findings from a Dose-Response Trial;" Andrology, Author Manuscript; (Sep. 2017); pp. 889-897; vol. 5, No. 5; <doi: 10.1111/andr.12392 >.

Gennaro: "Surfactant Properties in Solution and Micelle Formation, Colloidal Dispersions;" Remington's Pharmaceutical Sciences; (1985); pp. 293-300; Chapter 20.

Gluud et al.; "No Effect of Long-Term Oral Testosterone Treatment on Liver Morphology in Men with Alcoholic Cirrhosis;" The American Journal of Gastroenterology; (Jul. 1987); pp. 660-664; vol. 82, No. 7.

Goldstein et al.; "LPCN 1144 Reduces Liver Fat in Men with Fatty Liver;" Journal of Sexual Medicine; $20^{th}$ Annual Fall Scientific Meeting of SMSNA; (2020); pp. 17S1-S120.

Gómez-Gómez et al.; "Clinical Association of Metabolic Syndrome, C-Reactive Protein and Testosterone Levels with Clinically Significant Prostate Cancer;" Journal of Cellular and Molecular Medicine; (2018); pp. 1-9; <doi: 10.1111/jcmm.13994 >.

Goncharova et al.; "Preparation of Testosterone Esters;" Pharmaceutical Chemistry Journal; (Jul. 1973); pp. 427-428; vol. 7(7).

Gonzalo-Lumbreras et al.; "HPLC Method Development for Testosterone Propionate and Cipionate in Oil-Based Injectables;" Journal of Pharmaceutical and Biomedical Analysis; (2005); pp. 757-762; vol. 38; <doi: 10.1016/j.jpba.2005.02.003 >.

Gooren; "A Ten-year Safety Study of the Oral Androgen Testosterone Undecanoate;" Journal of Andrology; (1994); pp. 212-215; vol. 15(3).

Grahame-Smith et al; The Oxford Textbook of Clinical Pharmacology and Drug Therapy; (1992); pp. 25, 136-137; $2_{nd}$ Edition; M. Meditsina Publishers; (English version included pp. 9-12, 122-124).

Grossmann et al.; "Low Testosterone Levels as an Independent Predictor of Mortality in Men with Chronic Liver Disease;" Clinical Endocrinology; (2012); pp. 323-328; vol. 77; <doi: 10.1111/j.1365-2265.2012.04347.x >.

Guay et al.; "Hypogonadism in Men with Erectile Dysfunction may be Related to a Host of Chronic Illnesses;" International Journal of Impotence Research; (2010); pp. 9-19; vol. 22; <doi: 10.1038/ijir.2009.46 >.

Haider et al.; "Improvement of the Metabolic Syndrome and of Non-Alcoholic Liver Steatosis upon Treatment of Hypogonadal Elderly Men with Parenteral Testosterone Undecanoate;" Experimental and Clinical Endocrinology & Diabetes; (2010); pp. 167-171; vol. 118; <doi: 10.1055/s-0029-1202774 >.

Harrison et al.; "NAFLD-NASH Treatment Outlook;" [PowerPoint]; (May 2019); 65 pages.

Harrison et al.; "The Economic Tsunami of Liver Disease: An Epidemic that is Impacting the Financial Solvency of the U.S. Healthcare System;" Echosens; (2019); 14 pages.

HealthLine; "What are the symptoms of Hypogonadism?;" 1 page; [Internet]; [Retrieved on Apr. 1, 2014] [Retrieved from <URL: http://www.healthline.com/health/hypogonadism#Overview1 >].

Himoto et al.; "Clinical Efficacy of Free Androgen Index, a Surrogate Hallmark of Circulating Free Testosterone Level, in Male Patients with HCV-Related Chronic Liver Disease;" Journal Clinical Biochemistry and Nutrition Impact Factor; (Nov. 2018); pp. 238-245; vol. 63, No. 3; <doi: 10.3164/jcbn.18-30 >.

Home; "Safety of PPAR Agonists;" Diabetes Care; (May 2011); pp. S215-S219; vol. 34, Supplement 2; <doi: 10.2337/dc11-s233 >.

(56) References Cited

OTHER PUBLICATIONS

Hong, B.S., et al.; "Recent trends in the treatment of testosterone deficiency syndrome;" International Journal of Urology; (2007); pp. 981-985; vol. 14; the Japanese Urological Association; <doi: 10.1111/j.1442-2042.2007.01882.x>.

Hoofnagle et al.; "Vitamin E and Changes in Serum Alanine Aminotransferase Levels in Patients with Non-Alcoholic Steatohepatitis;" Alimentary Pharmacology & Therapeutics, Author Manuscript; (Jul. 2013); 15 pages; vol. 38, No. 2; <doi: 10.1111/apt.12352>.

Horter et al.; "Influence of Physiochemical Properties on Dissolution of Drugs in the Gastrointestinal Tract;" Advanced Drug Delivery Reviews; (1997); pp. 3-14; vol. 25.

Houwing et al.; "Pharmacokinetic Study in Women of Three Different Doses of a New Formulation of Oral Testosterone Undecanoate, Andriol® Testocaps™;" Pharmacotherapy; (2003); pp. 1257-1265; vol. 23(10); <doi: 10.1592/phco.23.12.1257.32707>.

Huang et al.; "Effect of Testosterone Administration on Liver Fat in Older Men with Mobility Limitation: Results from a Randomized Controlled Trial;" The Journals of Gerontology. Series A, Biological Sciences and Medical Sciences; (Jan. 3, 2013); pp. 954-959; vol. 68, No. 8; <doi: 10.1093/gerona/gls259>.

Humberstone et al.; "Lipid-based Vehicles for the Oral Delivery of Poorly Water Soluble Drugs;" Advanced Drug Delivery Reviews; (1997) pp. 103-128.

Hutchison; "Digestible Emulsions and Microemulsions for Optimum Oral Delivery of Hydrophobic Drugs;" Bulletin Technique Gattefosse; (1994); pp. 67-74; vol. 87.

Immuron; "Company Presentation;" Global On-Line Conference; (Oct. 2015); 23 pages.

Iruarrizaga-Lejarreta et al.; "Role of Aramchol in Steatohepatitis and Fibrosis in Mice;" Hepatology Communications; (2017); pp. 911-927; vol. 1, No. 9.

Isidori et al.; "Effects of Testosterone on Body Composition, Bone Metabolism and Serum Lipid Profile in Middle-Aged Men: A Meta-Analysis;" Clinical Endocrinology; (2005); pp. 280-293; vol. 63; <doi: 10.1111/j.1365-2265.2005.02339x>.

Iwasa et al.; "Effects of Chronic Testosterone Administration on the Degree of Preference for a High-Fat Diet and Body Weight in Gonadal-Intact and Ovariectomized Female;" Behavioural Brain Research; (2018) pp. 102-108; vol. 349; <doi: 10.1016/j.bbr.2018.02.021>.

Jayakumar et al.; "Longitudinal Correlations Between MRE, MRI-PDFF, and Liver Histology in Patients with Non-Alcoholic Steatohepatitis: Analysis of Data from a Phase II Trial of Selonsertib;" Journal of Hepatology; (2019); pp. 133-141; vol. 70; <doi: 10.1016/j.jhep2018.09.024>.

Jefferies; "Biotechnology NASH Deep Dive + Planner + 3 Events into AASLD Conference Coming up . . . ;" [Industry Note]; Equity Research Americas; (Oct. 7, 2018); 54 pages.

Jia et al.; "Testosterone Protects High-Fat/Low-Carbohydrate Diet-Induced Nonalcoholic Fatty Liver Disease in Castrated Male Rats Mainly via Modulating Endoplasmic Reticulum Stress;" American Journal of Physiology-Endocrinology & Metabolism; (Sep. 19, 2017); pp. E366-E376; vol. 314; <doi: 10.1152/ajpendo.00124.2017>.

Johnson; "Gastrointestinal Physiology;" Department of Physiology; University of Texas Medical School; (1997); pp. 25-26, 93-106, 133-134, 136-137; Houston, Texas.

Julien; "A Concise Nontechnical Guide to the Actions, Uses, and Side3 Effects of Psychoactive Drugs;" A Primer of Drug Action; (2001); pp. 5-6; $9_{th}$ Edition.

Kalinchenko; "Testosterone—King Hormones, hormones kings;" The Journal; Sex and Life; (2004); pp. 12-22: [Retrieved on Mar. 26, 2010]; [Retrieved from <URL: http://www.laz.med.ru/interesting/publications/testosterone.html>].

Kaminetsky et al.; "PD37-08 Efficacy and Pharmacokinetics of LPCN 1021, A Novel Oral Testosterone Replacement Therapy (TRT), in Hypogonadal Men: Study of Androgen Replacement (SOAR);" The Journal of Urology; (May 18, 2015); p. e773; vol. 193, No. 4S, Supplement.

Katznelson et al.; "Increase in Bone Density and Lean Body Mass during Testosterone Administration in Men with Acquired Hypogonadism;" Journal of Clinical Endocrinology and Metabolism; (1996); pp. 4358-4365; vol. 81, No. 12.

Kelly et al.; "Testosterone Differentially Regulates Targets of Lipid and Glucose Metabolism in Liver, Muscle and Adipose Tissues of the Testicular Feminised Mouse;" Endocrine; (2016); pp. 504-515; vol. 54; <doi: 10.1007/s12020-016-1019-1>.

Kelly et al.; "Testosterone Suppresses the Expression of Regulatory Enzymes of Fatty Acid Synthesis and Protects Against Hepatic Steatosis in Cholesterol-fed Androgen Deficient Mice;" Life Sciences; (2014); pp. 95-103; vol. 109.

Kelly et al.; "Testosterone: A Metabolic Hormone in Health and Disease;" Journal of Endocrinology; (2013); pp. R25-R45; vol. 217, No. 3.

Kemp et al.; "Efficacy and Safety of Antenatal Steroids;" The American Journal of Physiology—Regulatory, Integrative and Comparative Physiology; (Apr. 11, 2018); pp. R825-R839; vol. 315; <doi: 10.1152/ajpregu.00193.2017>.

Kenny et al.; "Effects of Transdermal Testosterone on Bone and Muscle in Older Men with Low Bioavailable Testosterone Levels, Low Bone Mass, and Physical Frailty;" Journal of American Geriatrics Society; (2010); pp. 1134-1143; vol. 58; <doi: 10.1111/j.1532-5415.2010.02865.x>.

Khera et al.; "PD50-06: Long-Term Safety and Tolerability of Oral Testosterone (LPCN 1021) in Hypogonadal Men: Results from the 52-Week Phase 3 Study;" The Journal of Urology; (May 10, 2016); pp. e1187-1188; vol. 195, No. 4 S, Supplement.

Kim et al.; "A Low Level of Serum Total Testosterone is Independently Associated with Nonalcoholic Fatty Liver Disease;" BioMed Central Gastroenterology; (2012); 8 pages; vol. 12, No. 69.

Kim et al.; "Bone-Forming Peptide-2 Derived from BMP-7 Enhances Osteoblast Differentiation from Multipotent Bone Marrow Stromal Cells and Bone Formation;" Experimental & Molecular Medicine; (2017); 7 pages; vol. 49, No. e328; <doi: 10.1038/emm.2017.40>.

Kim et al.; "Hepatic STAMP2 Alleviates High Fat Diet-Induced Hepatic Steatosis and Insulin Resistance;" Journal of Hepatology; (2015); pp. 477-485; vol. 63.

Kim et al.; "Improved Patient Reported Sexual and Mental Domain Outcomes with Oral Testosterone (TLANDO) Relative to Topical Testosterone in Treated Hypogonadal Men" Sexual Medicine Society 2019 Poster Presentation.

Kim et al.; "Male Hypogonadism and Liver Disease;" Contemporary Endocrinology; (Apr. 26, 2017); 42 pages; Chapter 11.

Köhn et al.; "A New Oral Testosterone Undecanoate Formulation;" World Journal of Urology; (Nov. 2003); pp. 311-315; vol. 21(5); <doi: 10.1007/s00345-003-0372-x>.

Konerman et al.; "Pharmacotherapy for NASH: Current and Emerging;" Journal of Hepatology; (2017); 7 pages; <doi: 10.1016/j.jhep.2017.10.015>.

La Colla et al.; "17β-Estradiol and Testosterone in Sarcopenia: Role of Satellite Cells;" Ageing Research Reviews; (2015); pp. 166-177; vol. 24; <doi: 10.1016/4.arr.2015.07.011>.

Laaksonen et al.; "Testosterone and Sex Hormone-Binding Globulin Predict the Metabolic Syndrome and Diabetes in Middle-Aged Men;" Diabetes Care; (May 2004); pp. 1036-1041; vol. 27, No. 5.

Langer; "New Methods of Drug Delivery;" Science; (Sep. 1990); pp. 1527-1533; vol. 249(4976).

Le et al.; "Prevalence of Non-Alcoholic Fatty Liver Disease and Risk Factors for Advanced Fibrosis and Mortality in the United States;" PLoS One; (Mar. 27, 2017); 13 pages; vol. 12, No. 3, e0173499; <doi: 10.1371/journal.pone.0173499>.

Lecluyse et al.; "In Vitro Models for Selection of Development Candidates. Permeability Studies to Define Mechanisms of Absorption Enhancement;" Advanced Drug Delivery Reviews; (1997); pp. 163-183; vol. 23.

Lee et al.; "Male-Specific Association Between Subclinical Hypothyroidism and the Risk of Non-Alcoholic Fatty Liver Disease Estimated by Hepatic Steatosis Index: Korea National Health and

(56) References Cited

OTHER PUBLICATIONS

Nutrition Examination Survey 2013 to 2015;" Nature Scientific Reports; (2018); 7 pages; vol. 8, No. 15145; <doi: 10.1038/s41598-018-32245-0 >.
Leichtnam et al.; "Testosterone Hormone Replacement Therapy: State-of-the-Art and Emerging Technology;" Pharmaceutical Research; (2006); pp. 1117-1132; vol. 23(6).
LGC; Reference Standard Testosterone Undecanoate; Certificate of Analysis; (Jul. 5, 2015); 6 pages; LGC GmBH; Germany.
Li et al.; "Evaluation of APRI and FIB-4 for Noninvasive Assessment of Significant Fibrosis and Cirrhosis in HBeAg-Negative CHB Patients with ALT ≤ 2 ULN: A Retrospective Cohort Study;" Medicine; (2017); 7 pages; vol. 96, No. 12; <doi: 10.1097/MD.0000000000006336 >.
Lin et al.; "Increased Hepatic Steatosis and Insulin Resistance in Mice Lacking Hepatic Androgen Receptor;" Hepatology; (2008); pp. 1924-1935; vol. 47, No. 6; <doi: 10.1002/hep.22252 >.
Lipocine; LPCN 1144: Comparison with Injectable TU for ALT and AST Mean Change from BL in Diabetic Patients; Injectable TU Data; [Poster]; (2012); 1 page.
Liu et al.; "Anti-Androgenic Activity of Fatty Acids;" Chemistry & Biodiversity; (2009); pp. 503-512; vol. 6.
Liu et al.; "The Short-Term Effects of High-Dose Testosterone on Sleep, Breathing, and Function in Older Men;" The Journal of Clinical Endocrinology & Metabolism; (2003); pp. 3605-3613; vol. 88, No. 8; <doi: 10.1210/jc.2003-030236 >.
Livingstone et al.; "5α-Reductase Type 1 Deficiency or Inhibition Predisposes to Insulin Resistance, Hepatic Steatosis, and Liver Fibrosis in Rodents;" Diabetes; (Feb. 2015); pp. 447-458; vol. 64; <doi: 10.2337/db14-0249 >.
Lonardo et al.; "Hypertension, Diabetes, Atherosclerosis and NASH: Cause of Consequence?;" Journal of Hepatology; (2018); pp. 335-352; vol. 68.
Loomba et al.; "The ASK1 Inhibitor Selonsertib in Patients with Nonalcoholic Steatohepatitis: A Randomized, Phase 2 Trial;" Hepatology; (2018); pp. 549-559; vol. 67, No. 2; <doi: 10.1002/hep.29514 >.
Loomba; "Serum Alanine Aminotransferase as a Biomarker of Treatment Response in Nonalcoholic Steatohepatitis;" Clinical Gastroenterology and Hepatology, Author Manuscript; (Oct. 2014); pp. 1731-1732; vol. 12, No. 10; <doi: 10.1016/j.cgh.2014.03.026 >.
Lopez-Berestein et al. (Eds.); Liposomes in the Therapy of Infectious Disease and Cancer; (1989); pp. 353-365; Liss; New York.
Ly et al.; "A Double-Blind, Placebo-Controlled, Randomized Clinical Trial of Transdermal Dihydrotestosterone Gel on Muscular Strength, Mobility, and Quality of Life in Older men with Partial Androgen Deficiency;" The Journal of Clinical Endocrinology & Metabolism; (Sep. 2001); pp. 4078-4088; vol. 86, No. 9.
Ma et al.; "Androgen Receptor Roles in Hepatocellular Carcinoma, Fatty liver, Cirrhosis and Hepatitis;" Endocrine Related Cancer; (2014); pp. R165-R182; vol. 21, No. 3; <doi: 10.1530/ERC-13-0283 >.
MacGregor et al.; "Influence of Lipolysis on Drug Absorption From the Gastro-Intestinal Tract;" Advanced Drug Delivery Reviews; (1997); pp. 33-46; vol. 25.
Machado et al.; "Hepatic Histology in Obese Patients Undergoing Bariatric Surgery;" Journal of Hepatology; (2006); pp. 600-606; vol. 45; <doi: 10.1016/j.jhep.2006.06.013 >.
Machado et al.; "Non-Alcoholic Fatty Liver Disease: What the Clinician Needs to Know;" World Journal of Gastroenterology; (Sep. 28, 2014); pp. 12956-12980; vol. 20, No. 36; <doi: 10.3748/wjg.v20.136.12956>.
Magnussen et al.; "MR Spectroscopy of Hepatic Fat and Adiponectin and Leptin Levels During Testosterone Therapy in Type 2 Diabetes: A Randomized, Double-Blinded, Placebo-Controlled Trial;" European Journal of Endocrinology; (2017); pp. 157-168; vol. 177; <doi: 10.1530/EJE-17-0071 >.
Maher et al.; "Cytokeratin 18 as a Non Invasive Marker in Diagnosis of NASH and its Usefulness in Correlation with Disease Severity in Egyptian Patients;" The Egyptian Journal of Medical Human Genetics; (2015); pp. 41-46; vol. 16; <doi: 10.1016/j.ejmhg.2014.11.003 >.
Maisey et al; "Clinical Efficacy of Testosterone Undecanoate in Male Hypogonadism;" Clinical Endocrinology; (1981); pp. 625-629; vol. 14.
Mancini et al.; "Relationships Between Thyroid Hormones, Insulin-Like Growth Factor-1 and Antioxidant Levels in Hypothalamic Amenorrhea and Impact on Bone Metabolism;" Hormone and Metabolic Research; (2019); pp. 302-308; vol. 51; <doi: 10.1055/a-0859-4285 >.
Márin et al.; "Androgen Treatment of Abdominally Obese Men;" Obesity Research; (Jul. 1993); pp. 245-251; vol. 1, No. 4.
Márin et al.; "The Effects of Testosterone Treatment on Body Composition and Metabolism in Middle-Aged Obese Men;" International Journal of Obesity and Related Metabolic Disorders; (Dec. 1992); pp. 991-997; vol. 16, No. 16; [Abstract].
McAuley et al.; "Oral Administration of Micronized Progesterone: A Review and More Experience;" Pharmacotherapy; (May 1996); pp. 453-457; vol. 16(3).
Meinert et al.; Clinical Trials: Design, Conduct and Analysis (Monographs in Epidemiology and Biostatistics; (1986); vol. 8.
Mendenhall; "Anabolic Steroid Therapy as an Adjunct to Diet in Alcoholic Hepatic Steatosis;" New Series; (1968); pp. 783-791; vol. 13, No. 9.
Merck Index, "Alpha Tocopherol;" Monograph 09571; (2001-2004); Merck & Co. Inc.
Merck Index; "Amiodarone;" Monograph 504; (1996); p. 84; $12_{th}$ Edition; Merck & Co., Inc.
Merck Index; "Carvedilol"; Monograph 01888; (2001-2004); Merck & Co., Inc.
Merck Index; "Fenofibrate;" Monograph 3978; (2006); pp. 679-680; $14_{th}$ Edition; Merck & Co., Inc.
Merck Index; "Risperidone;" Monograph 08316; (2001-2004); Merck & Co., Inc.
Merck Index; "Shellac;" Monograph 8623; (1996); p. 8526; $12_{th}$ Edition.
Merck Index; "Testosterone;" Monograph 9322; (1996); p. 9326; $12_{th}$ Edition; Merck & Co., Inc.
Merck Index; "Vitamin E;" Monograph 10021; (2006); p. 1726; $14_{th}$ Edition; Merck & Co., Inc.
Merck Index; "Vitamin E" and "Vitamin E Acetate;" Monographs 9931 and 9932; (1989); pp. 1579-1580; $11_{th}$ Edition; Merck & Co., Inc.
Merck Index; "Ziprasidone;" Monograph 10224;(2001-2004); Merck & Co., Inc.
Merriam-Webster Dictionary; "Granule;" [Retrieved Dec. 17, 2009] [Retrieved from <URL: http://www.mw.com/dictionary/granule >].
Meryn; "The Epidemiology and Burden of Male Hypogonadism;" Mens Health School; [PowerPoint]; (2012); 29 pages.
Middleton et al.; "Agreement Between Magnetic Resonance Imaging Proton Density Fat Fraction Measurements and Pathologist-Assigned Steatosis Grades of Liver Biopsies from Adults with Nonalcoholic Steatohepatitis;" Gastroenterology, Author Manuscript; (Sep. 2017); pp. 753-761; vol. 153, No. 3; <doi: 10.1053/j.gastro.2017.06.005 >.
Mintziori et al.; "Review: Endocrine and Metabolic Disorders Interplaying with Non-Alcoholic Fatty Liver Disease: Hypogonadism and Non-Alcoholic Fatty Liver Disease;" Minerva Endocrinologica; (Jun. 2017); pp. 145-150; vol. 42, No. 2; <doi: 10.23736/S0391-1977.16.02570-0 >.
Mittal et al; "The Wide World of Micelles;" In: International Symposium on Micellization, Solubilization, and Microemulsions, $7_{th}$ Northeastern Regional Meeting of the American Society; Albany, New York; (1976); pp. 1-21; vol. 1 <ISBN: 0-306-31023-6(v.1) >.
Miyauchi et al.; "Free Testosterone Concentration is Inversely Associated with Markers of Liver Fibrosis in Men with Type 2 Diabetes Mellitus;" Endocrine Journal; (2017); pp. 1137-1142; vol. 64, No. 12.
Mody et al.; "Relevance of Low Testosterone to Non-Alcoholic Fatty Liver Disease;" Cardiovascular Endocrinology, Author Manuscript; (Sep. 1, 2015); pp. 83-89; vol. 4, No. 3; <doi: 10.1097/XCE.0000000000000057 >.

(56) References Cited

OTHER PUBLICATIONS

Moellering; "Vancomycin: A 50-Year Reassessment;" Clinical Infectious Diseases; (2006); pp. S3-S4; vol. 42.
Morooka et al.; "Androgen-Androgen Receptor System Improves Chronic Inflammatory Conditions by Suppressing Monocyte Chemoattractant Protein-1 Gene Expression in Adipocytes via Transcriptional Regulation;" Biochemical and Biophysical Research Communications; (2016); pp. 895-901; vol. 477; <doi: 10.1016/j.bbrc.2016.06.155 >.
Mulligan et al.; "Prevalence of Hypogonadism in Males Aged at Least 45 Years: the HIM Study;" International Journal of Clinical Practice; (Jul. 2006); pp. 762-769; vol. 60, No. 7; <doi: 10.1111/j.1742-1241.2006.00992.x>.
Muranishi; "Absorption Enhancers;" Critical Reviews in Therapeutic Drug Carrier Systems; (1990); pp. 1-33; vol. 7(1).
Muranishi; "Potential Absorption of Heparin from the Small Intestine and the Large Intestine in the Presence of Monoolein Mixed Micelles;" Chemical and Pharmaceutical Bulletin Journal; (1977); pp. 1159-1161; vol. 24(5).
Myers; "Nonalcoholic Fatty Liver Disease;" [PowerPoint]; (May 2018); 24 pages.
Neri et al.; "Anabolic Androgenic Steroids Abuse and Liver Toxicity;" Mini-Reviews in Medicinal Chemistry; (2011); pp. 430-437; vol. 11, Issue 5; <doi: 10.2174/138955711795445916 >, Abstract only.
Newell-Fugate; "The Role of Sex Steroids in White Adipose Tissue Adipocyte Function;" Reproduction; (2017); pp. R133-R149; vol. 153; <doi: 10.1530/REP-16-0417 >.
Nieschlag et al.; "Plasma Androgen Levels in Men after Oral Administration of Testosterone or Testosterone Undecanoate;" Acta Endocrinologica; (1975); pp. 366-374; vol. 79(2); (Abstract).
Nikolaenko et al.; "Testosterone Replacement Ameliorates Nonalcoholic Fatty Liver Disease in Castrated Male Rats;" Endocrinology; (2014); pp. 417-428; vol. 155, No. 2; <doi: 10.1210/en.2013-1648 >.
No Authors Listed; "Testosterone Treatment of Men with Alcoholic Cirrhosis: A Double-Blind Study. The Copenhagen Study Group for Liver Diseases;" Hepatology; (Sep.-Oct. 1986); pp. 807-813; vol. 6, No. 5; [Abstract].
Noguchi et al.; "The Effect of Drug Lipophilicity and Lipid Vehicles on the Lymphatic Absorption of Various Testosterone Esters;" International Journal of Pharmaceutics; (May 1985); pp. 173-184; vol. 24(2-3).
Noureddin; "Looking Into the Crystal Ball: Predicting the Future Challenges of Fibrotic NASH;" Cedars Sinai Medical Center; [PowerPoint]; (May 2019); 59 pages; #3 Gastroenterology.
Omokaro; "FDA Regulatory Considerations for NASH Clinical Trial Endpoints;" Global NASH Congress; (Feb. 26, 2018); 54 pages.
Osol (Ed.); "Emulsions;" Remington's Pharmaceutical Sciences; (1975); pp. 327-339, 1452-1456; $15_{th}$ Edition.
Paternostro et al.; "Dysbalanced Sex Hormone Status is an Independent Predictor of Decompensation and Mortality in Patients with Liver Cirrhosis;" Hepatology Research; (2018); 11 pages; <doi: 10.1111/hepr.13253 >.
Paternostro et al.; "Dysbalanced Sex Hormone Status is an Independent Predictor of Decompensation and Mortality in Patients with Liver Cirrhosis;" Hepatology Research; (2019); pp. 201-211; vol. 49; <doi: 10.1111/hepr.13253 >.
Perchersky et al. "Androgen Administration in Middle-Aged and Aging Men: Effects of Oral Testosterone Undecanoate on Dihydrotestosterone, Oestradiol and Prostate Volume;" International Journal of Andrology; (2002); pp. 119-125; vol. 25.
Pollo-Flores et al.; "Liver, Pancreas and Biliary Tract: Three Months of Simvastatin Therapy vs. Placebo for Severe Portal Hypertension in Cirrhosis: A Randomized Controlled Trial;" Digestive and Liver Disease; (2015); pp. 957-963; vol. 47; <doi: 10.1016/j.did.2015.07.156 >.

Pouton; "Formulation of Self-Emulsifying Drug Delivery Systems;" Advanced Drug Delivery Reviews; (1997); pp. 47-58; vol. 25.
Pozo et al.; "Quantification of Testosterone Undecanoate in Human Hair by Liquid Chromatography Tandem Mass Spectrometry;" Biomedical Chromatography; (Aug. 2009); pp. 873-880; vol. 23(8).
Ramachandran et al.; "The Association of Sex Hormone-Binding Globulin with Mortality is Mediated by Age and Testosterone in Men with Type 2 Diabetes;" Andrology; (2018); 8 pages; <doi: 10.1111/andr.12520 >.
Rector et al.; "Non-Alcoholic Fatty Liver Disease and the Metabolic Syndrome: An Update;" World Journal of Gastroenterology; (Jan. 14, 2008); pp. 185-192; vol. 14, No. 2; <doi: 10.3748/wjg.14.185 >.
Reymond et al.; "In Vivo Model for Ciclosporin Intestinal Absorption in Lipid Vehicles;" Pharmaceutical Research; (1988); pp. 677-679; vol. 5(10).
Rossetti et al.; "Disruptions to the Limb Muscle Core Molecular Clock Coincide with Changes in Mitochondrial Quality Control following Androgen Depletion;" American Journal of Physiology—Endocrinology and Metabolism; (Jul. 2019); 63 pages.
Russo; "The Care of the Postliver Transplant Patient;" Journal of Clinical Gastroenterology; (2017); pp. 683-692; vol. 51; <doi: 10.1097/MCG.000000000000886 >.
SI SEC Filing (Securities and Exchange Commission) for Clarus Therapeutics, Inc.; Filed May 23, 2014, with the Securities and Exchange Commission; 207 pages.
Saad et al.; "Effects of Long-Term Treatment with Testosterone on Weight and Waist Size in 411 Hypogonadal Men with Obesity Classes I-III: Observational Data from Two Registry Studies;" International Journal of Obesity; (2016); pp. 162-170; vol. 40; <doi: 10.1038/ijo.2015.139 >.
Sakr et al.; "Possible Mechanisms Underlying Fatty Liver in a Rat Model of Male Hypogonadism: A Protective Role for Testosterone;" Steroids; (2019; pp. 21-30; vol. 135; <doi: 10.1016/j.steroids.2018.04.004 >.
Sanyal et al.; "Challenges and Opportunities in Drug and Biomarker Development for Nonalcoholic Steatohepatitis: Findings and Recommendations from and American Association for the Study of Liver Diseases—U.S. Food and Drug Administration Joint Workshop;" Hepatology; (2015); pp. 1392-1405; vol. 61, No. 4; <doi: 10.1002/hep.27678 >.
Sanyal et al.; "Oral Testosterone (LPCN 1144) Undecanoate Normalizes Liver Function Measures and Serum Triglycerides in Subjects at Risk for Non-Alcoholic Fatty Liver Disease (NAFLD);" In: AASLD The Liver Meeting; [PowerPoint]; (Nov. 2018); 1 page.
Sanyal et al.; "Profile of Liver Enzymes in Non-Alcoholic Fatty Liver Disease in Patients with Impaired Glucose Tolerance and Newly Detected Untreated Type 2 Diabetes;" Indian Journal of Endocrinology and Metabolism; (Sep.-Oct. 2015); pp. 597-601; vol. 19, Issue 5; <doi: 10.4103/2230-8210.163172 >.
Saraç et al.; "Causes of High Bone Alkaline Phosphatase;" Biotechnology & Biotechnological Equipment; (2007); pp. 194-197; vol. 21, No. 2; <doi: 10.1080/13102818.2007.10817444 >.
Sarkar et al.; Low Testosterone is Associated with NASH and Fibrosis Severity in Men with Non-Alcoholic Fatty Liver Disease (NAFLD); National Institute of Diabetes and Digestive and Kidney Diseases; [Poster]; (Jul. 2019); 1 page.
Sarkar et al.; "Low Testosterone is Associated with NASH and Fibrosis Severity in Men with NAFLD;" Gastroenterology; (2019); S-1258; vol. 156; <doi: 10.1016/S0016-5085(19)40146-7 >.
Sarkar et al.; "Testosterone Levels in Pre-Menopausal Women are Associated with Nonalcoholic Fatty Liver Disease in Midlife;" American Journal of Gastroenterology; (2017); pp. 755-762; vol. 112; <doi: 10.1038/ajg.2017.44 >.
Sattler et al; "Testosterone Supplementation Improves Carbohydrate and Lipid Metabolism in Some older Men with Abdominal Obesity;" Journal of Gerontology and Geriatric Research; [Author Manuscript]; (Nov. 10, 2014); 18 pages; vol. 3, Issue 3; 1000159; <doi: 10.4172/2167-7182.1000159 >.
Saudek et al.; "A Preliminary Trial of the Programmable Implantable Medication System for Insulin Delivery;" The New England Journal of Medicine; (Aug. 31, 1989); pp. 574-579; vol. 321.

(56) References Cited

OTHER PUBLICATIONS

Schnabel et al.; "The Effect of Food Composition on Serum Testosterone Levels after Oral Administration of Adriol® Testocaps™;" Clinical Endocrinology; (2007); pp. 579-585; vol. 66(4).

Schott; "Comments on Hydrophile-Lipophile Balance Systems;" Journal of Pharmaceutical Sciences; (Jan. 1990); pp. 87-88; vol. 79(1); American Pharmaceutical Association.

Schubert et al.; "Intramuscular Testosterone Undecanoate: Pharmacokinetic Aspects of a Novel Testosterone Formulation during Long-Term Treatment of Men with Hypogonadism;" The Journal of Clinical Endocrinology & Metabolism; (2004); pp. 5429-5434; vol. 89, No. 11; <doi: 10.1210/jc.2004-0897 >.

Schwinge et al.; "Testosterone Suppresses Hepatic Inflammation by the Downregulation of IL-17, CXCL-9, and CXCL-10 in a Mouse Model of Experimental Acute Cholangitis;" Journal of Immunology; (2015); pp. 2522-2530; vol. 194.

sciencelab.com; "MSDS: Glyceryl Monooleate;" Material Safety Data Sheet; (Oct. 2005); 5 pages; <URL: www.sciencelab.com >.

Sefton; "Implantable Pumps;" Critical Reviews in Biomedical Engineering; (1987); pp. 201-240; vol. 14, No. 3; (Abstract); [Sourcelink] <URL: http://www.ncbi.nlm.nih.gov/pubmed/3297487 >.

Seidman et al.; "Testosterone Replacement Therapy for Hypogonadal Men with SSRI-Refractory Depression;" Journal of Affective Disorders; (1998); pp. 157-161; vol. 48.

Shackleford et al., "Contribution of Lymphatically Transported Testosterone Undecanoate to the Systemic Exposure of Testosterone after Oral Administration of two Andriol Formulations in Conscious Lymph Duct-Cannulated Dogs;" The Journal of Pharmacology and Experimental Therapeutics: (2003); pp. 925-933; vol. 306(3).

Shanghai PI Chemicals Ltd.; "MSDS: Testosterone Undecanoate;" Material Safety Data Sheet; (2007); [Retrieved on Jun. 3, 2009] [retrieved from <URL: http://www.pipharm.com/product/msds-13457.pdf>].

Shen et al.; "Sex Hormones and their Receptors Regulate Liver Energy Homeostasis;" International Journal of Endocrinology; (2015); 12 pages; vol. 2015, Article ID 294278; <doi: 10.1155/2015/294278 >.

Sherif et al.; "Global Epidemiology of Non-Alcoholic Fatty Liver Disease and Perspectives on US Minority Populations;" Digestive Disease & Sciences, Author Manuscript; (May 2016); pp. 1214-1215; vol. 61, No. 5; <doi: 10.1007/s10620-016-4143-0 >.

Shetty et al.; "Role of the Circadian Clock in the Metabolic Syndrome and Nonalcoholic Fatty Liver Disease;" Digestive Diseases and Sciences; (Aug. 18, 2018); 20 pages; <doi: 10.1007/s10620-018-5242-x >.

Sinclair et al.; "Liver Failure, Cirrhosis and their Complications: High Circulating Oestrone and Low Testosterone Correlate with Adverse Clinical Outcomes in Men with Advanced Liver Discase;" Liver International; (2016); pp. 1619-1627; vol. 36; <doi: 10.1111/liv.13122 >.

Sinclair et al.; "Low Serum Testosterone Is Associated with Adverse Outcome in Men with Cirrhosis Independent of the Model for End-Stage Liver Disease Score;" Liver Transplantation; (2016); pp. 1482-1490; vol. 22, No. 11 >.

Sinclair et al.; "Low Testosterone as a Better Predictor of Mortality than Sarcopenia in Men with Advanced Liver Disease;" Journal of Gastroenterology and Hepatology; (2016); pp. 661-667; vol. 31; <doi: 10.1111/jgh.13182 >.

Sinclair et al.; "Muscle Mass and Mortality in Chronic Liver Disease: The Impact of Testosterone;" Liver Transplantation: (2014); pp. 504-505; vol. 20; <doi: 10.1002/lt.23808 >.

Sinclair et al.; Testosterone in Men with Advanced Liver Disease: Abnormalities and Implications; Journal of Gastroenterology and Hepatology; (2015); pp. 244-251; vol. 30; <doi: 10.1111/jgh.12695 >.

Snyder et al.; "Effect of Testosterone Treatment on Body Composition and Muscle Strength in Men Over 65 Years of Age;" The Journal of Clinical Endocrinology & Metabolism; (1999); pp. 2647-2653; vol. 84, No. 8 >.

Stedman's Medical Dictionary; "Dehydro-E-Epiandrosterone;" "Dehydroisoandroteron;" and "Steriod;" (1972); pp. 329, 1195-1197; $22_{nd}$ Edition; Williams & Wilkins Co.

Stedman's Medical Dictionary; "Hydroxy-Acid and Vitamin E;" (1973); pp. 595, 14000; $22_{nd}$ Edition: Williams & Wilkins Co.

Stedman's Medical Dictionary; "Surfactants;" (1972); p. 1225; $22_{nd}$ Edition; Williams & Wilkins Co.

Stedman's Medical Dictionary; "Surfactants;" (2006); $28_{th}$ Edition; Williams & Wilkins Co.

Stefan et al.; "The Metabolically Benign and Malignant Fatty Liver;" Diabetes; (Aug. 2011); pp. 2011-2017; vol. 60; <doi: 10.2337/db11.0231 >.

Stellato et al.; "Testosterone, Sex Hormone-Binding Globulin, and the Development of Type 2 Diabetes in Middle-Aged Men;" Diabetes Care; (Apr. 2000); pp. 490-494; vol. 23, No. 4.

Stephens; "The Fat Controller: Adipocyte Development;" Public Library of Science Biology; (Nov. 2012); 3 pages; vol. 10, Issue 11, e1001436; <doi: 10.1371/journal.pbio.1001436 >.

Sumida et al.; "The Association of Low Free Testosterone with Histological Severity of Nonalcoholic Fatty Liver Disease in Japanese Men;" Gastroenterology & Hepatology; (2015); 11 pages; vol. 2, Issue 4.

Swerdloff, et al.; "Long Term Pharmaceokinetics of Transdermal Testosterone Gel in Hypogonadal Men;" Journal of Clinical Endocrinology & Metabolism; (2000); pp. 4500-4510; vol. 85.

Szulc et al.; "Assessment of the Role of 17β-Oestradiol in Bone Metabolism in Men: Does the Assay Technique Matter? The MINOS Study;" Clinical Endocrinology; (2004); pp. 447-457; vol. 61; <doi: 10.1111/j.1365-2265.2004.02117.x>.

Tarr et al.; "Enhanced Intestinal Absorption of Cyclosporine in Rats Through the Reduction of Emulsion Droplet Size;" Pharmaceutical Research; (1989); pp. 40-43; vol. 6(1).

Tarumi et al.; "Androstenedione Induces Abnormalities in Morphology and Function of Developing Oocytes, Which Impairs Oocyte Meiotic Competence;" Journal of Fertility and Sterility; (Feb. 2012); pp. 469-476; vol. 97(2); <doi: 10.1016/j.fertnstert.2011.11.040 >.

Tauber et al.; "Absolute Bioavailability of Testosterone after Oral Administration of Testosterone-Undecanoate and Testosterone;" European Journal of Drug Metabolism and Pharmacokinetics; (1986); pp. 145-149; vol. 11(2); [Sourcelink] <URL: http://www.ncbi.nlm.nih.gov/pubmed/3770015>; [Abstract].

Temina et al.; "Diversity of the Fatty Acids of the *Nostoc* Species and their Statistical Analysis;" Microbiological Research; (2007); pp. 308-321; vol. 162; <doi: 10.1016/j.micres.2006.01.010 >.

Tenover; "The Androgen-Deficient Aging Male: Current Treatment Options;" Reviews in Urology; (2003); pp. S22-S28; vol. 5, Suppl. 1.

TESTIM® Product Label and Medication Guide; (Sep. 2009); Labeler—A-S Medications Solutions LLC; Revised Jun. 2013; 17 pages.

Tomizawa et al.; "Triglyceride is Strongly Associated with Nonalcoholic Fatty Liver Disease among Markers of Hyperlipidemia and Diabetes;" Biomedical Reports; (2014); pp. 633-636; vol. 2; <doi: 10.3892/br.2014.309 >.

Toone et al.; "Sex Hormones, Sexual Activity and Plasma Anticonvulsant Levels in Male Epileptics;" Journal of Neurology, Neurosurgery, and Psychiatry; (1983); pp. 824-826; vol. 46.

TORPAC® Inc.; "Capsule Size Chart, Metric Table and English Table;" (2000); 3 pages; Torpac Inc., Fairfield, New Jersey; [Internet] [retrieved on Sep. 2014] [retrieved from <URL: www.torpac.com >].

Torres et al.; "Predictive Value of ALT Levels for NASH and Advanced Fibrosis;" Nature Reviews Gastroenterology Hepatology; (2013); pp. 510-511; vol. 10; <doi: 10.1038/nrgastro.2013.138 >.

Traish et al.; "Do Androgens Modulate the Pathophysiological Pathways of Inflammation? Appraising the Contemporary Evidence;" Journal of Clinical Medicine; (Dec. 14, 2018); 33 pages; vol. 7, No. 549; <doi: 10.3390/jcm7120549 >.

Treat et al.; "Liposome Encapsulated Doxorubicin Preliminary Result of Phase I and Phase II Trials;" Liposomes in the Therapy of

(56) References Cited

OTHER PUBLICATIONS

Infectious Diseases and Cancer; Lopez-Berestein and Fidler (Eds.); (1989); pp. 353-365; Liss, New York.
Tso, et al.; "Intestinal Absorption and Lymphatic Transport of a High γ-Linolenic Acid Canola Oil in Lymph Fistula Sprague-Dawley Rats;" The Journal of Nutrition; (2002); pp. 218-221; American Society for Nutritional Sciences.
U.S. Department of Health and Human Services et al.; "Noncirrhotic Nonalcoholic Steatohepatitis with Liver Fibrosis: Developing Drugs for Treatment;" [Guidance for Industry]; (Dec. 2018); 12 pages; Clinical/Medical.
Velázquez et al.; "Association Between Low Testosterone Levels and Sarcopenia in Cirrhosis: A Cross-Sectional Study;" Annals of Hepatology; (Jul./Aug. 2018); pp. 615-623; vol. 17, No. 4; <doi: 10.5604/01.3001.0012.0930 >.
Veldhuis et al.; "Testosterone and Estradiol Regulate Free Insulin-Like Growth Factor I (IGF-I), IGF Binding Protein 1 (IGFBP-1), and Dimeric IGF-I/IGFBP-1 Concentrations;" The Journal of Clinical Endocrinology & Metabolism; (Feb. 15, 2005); pp. 2941-2947; vol. 90, No. 5; <doi: 10.1210/jc.2004-1314 >.
Vermeulen et al.; "A Critical Evaluation of Simple Methods for the Estimation of Free Testosterone in Serum;" The Journal of Clinical Endocrinology & Metabolism; (1999); pp. 3666-3672; vol. 84, No. 10.
Vic et al.; "Complete Liver Regeneration in One-Stage 90% Hepatectomized Rats Treated with Testosterone;" Hepatology; (1982); pp. 247-248; vol. 2, No. 2.
Vignozzi et al.; "Nonalcoholic Steatohepatitis as a Novel Player in Metabolic Syndrome-Induced Erectile Dysfunction: An Experimental Study in the Rabbit;" Molecular and Cellular Endocrinology; (2014); pp. 143-154; vol. 384; <doi: 10.1016/j.mce.2014.01.014 >.
Völzke et al.; "Hepatic Steatosis is Associated with Low Serum Testosterone and High Serum DHEAS Levels in Men;" International Journal of Andrology; (2010); pp. 45-53; vol. 33; <doi: 10.1111/j1365-2605.2009.00953.x >.
Wang et al.; "Long-Term Testosterone Gel (AndroGel®) Treatment Maintains Beneficial Effects on Sexual Function and Mood, Lean and Fat Mass and Bone Mineral Density in Hypogonadal Men;" Journal of Clinical Endocrinology & Metabolism; (2004); pp. 2085-2098; vol. 89.
Webster et al.; "Validation of Pharmaceutical Potency Determinations by Quantitative Nuclear Magnetic Resonance Spectrometry;" Journal of Applied Spectroscopy; (May 2010); pp. 537-542; vol. 64(5).
Wildman-Tobriner et al.; "Association Between Magnetic Resonance Imaging-Proton Density Fat Fraction and Liver Histology Features in Patient with Nonalcoholic Fatty Liver Disease or Nonalcoholic Steatohepatitis;" Gastroenterology; (Nov. 2018); pp. 1428-1435; vol. 155, No. 1.
Williams et al.; "Clinical Advances in Liver, Pancreas, and Biliary Tract: Prevalence of Nonalcoholic Steatohepatitis Among a Largely Middle-Aged Population Utilizing Ultrasound and Liver Biopsy: A Prospective Study;" Gastroenterology; (2011); pp. 124-131; vol. 140; <doi: 10.1053/j.gastro.2010.09.038 >.
Wilson et al.; "The Behaviour of Fats and Oils in the Upper G.I. Tract;" Bulletin Technique Gattefosse; (1997); pp. 13-18; vol. 90.
Winne; "Dependence of Intestinal Absorption in Vivo on the Unstirred Layer;" Archives of Pharmacology; (1978); pp. 175-181; vol. 304.
Wittert et al.; "Oral Testosterone Supplementation Increases Muscle and Decreases Fat Mass in Healthy Elderly Males with Low-Normal Gonadal Status;" Journal of Gerontology: Medical Sciences; (2003); pp. 618-625; vol. 58A, No. 7.
Xiao et al.; "Comparison of Laboratory Tests, Ultrasound, or Magnetic Resonance Elastography to Detect Fibrosis in Patients with Nonalcoholic Fatty Liver Disease: A Meta-Analysis;" Hepatology; (2017); pp. 1486-1501; vol. 66, No. 5; <doi: 10.1002/hep.29302 >.
Xu et al.; "Emerging Role of Testosterone in Pancreatic β Cell Function and Insulin Secretion;" Journal of Endocrinology; (2019); pp. R97-R105; vol. 240; <doi: 10.1530/JOE-18-0573 >.
Yanguas et al.; "Experimental Models of Liver Fibrosis;" Archives of Toxicology, Author Manuscript; (May 2016); pp. 1025-1048; vol. 90, No. 5; <doi: 10.1007/s00204-015-1543-4 >.
Yassin et al.; "Long-Acting Testosterone Undecanoate for Parenteral Testosterone Therapy;" Therapy, Future Drugs; (2006); pp. 709-721; vol. 3(6).
Yim et al.; "Serum Testosterone and Non-Alcoholic Fatty Liver Disease in Men and Women in the US;" Liver International; (2018); pp. 2051-2059; vol. 38; <doi: 10.1111/liv.13735 >.
Yin et al.; "Dietary Fat Modulates the Testosterone Pharmacokinetics of a New Self-Emulsifying Formulation of Oral Testosterone Undecanoate in Hypogonadal Men;" Journal of Andrology; (Nov./Dec. 2012); pp. 1282-1290; vol. 33(6).
Yin et al.; "Reexamination of Pharmacokinetics of Oral Testosterone Undecanoate in Hypogonadal Men with a New Self-Emulsifying Formulation;" Journal of Andrology; (2012); pp. 190-201; vol. 33(2).
Younossi et al.; "Global Burden of NAFLD and NASH: Trends, Predictions, Risk Factors and Prevention;" Nature Reviews: Gastroenterology & Hepatology; (Jan. 2018); pp. 11-20; vol. 15; <doi: 10.1038/nrgastro.2017.109 >.
Younossi et al.; "Global Epidemiology of Nonalcoholic Fatty Liver Disease—Meta-Analytic Assessment of Prevalence, Incidence, and Outcomes;" Hepatology; (Jul. 2016); pp. 73-84; vol. 64, No. 1; <doi: 10.1002/hep.28431 >.
Younossi et al.; "Nonalcoholic Steatofibrosis Independently Predicts Mortality in Nonalcoholic Fatty Liver Disease;" Hepatology Communications; (2017); pp. 421-428; vol. 1, No. 5; <doi: 10.1002/hep4.1054 >.
Younossi et al.; "Supplementary Material;" Hepatology; (Jul. 2016); 33 pages.
Yurci et al.; "Effects of Testosterone Gel Treatment in Hypogonadal Men with Liver Cirrhosis;" Clinics and Research in Hepatology and Gastroenterology; (2011); pp. 845-854; vol. 35; <doi: 10.1016/j.clinre.2011.09.005 >.
Zhang et al.; "Differential Effects of Estrogen/Androgen on the Prevention of Nonalcoholic Fatty liver Disease in the Male Rat;" Journal of Lipid Research; (2013); pp. 345-357; vol. 54; <doi: 10.1194/jlr.M028969 >.
Zhao et al.; "Shift from Androgen to Estrogen Action Causes Abdominal Muscle Fibrosis, Atrophy, and Inguinal Hernia in a Transgenic Male Mouse Model;" Proceedings of the National Academy of Sciences of the United States of America; (Oct. 16, 2018); pp. E10427-E10436; vol. 115, No. 44; <doi: 10.1073/pnas.18017765115 >.
Zhi et al.; "Effects of Dietary Fat on Drug Absorption;" Clinical Pharmacology & Therapeutics; (Nov. 1995); pp. 487-491; vol. 58(5).
Zietz et al.; "Dysfunction of the Hypothalamic-Pituitary-Glandular Axes and Relation to Child-Pugh Classification in Male Patients with Alcoholic and Virus-Related Cirrhosis;" European Journal of Gastroenterology & Hepatology; (2003); pp. 495-501; vol. 15; <doi: 10.1097/01.meg.0000059115.41030.e0 >.
Zifroni et al.; "Sexual Function and Testosterone Levels in Men with Nonalcoholic Liver Disease;" Hepatology; (1991); pp. 479-482; vol. 14.
Zitzmann et al.; "Androgen Receptor Gene CAG Repeat Length and Body Mass Index Modulate the Safety of Long-Term Intramuscular Testosterone Undecanoate Therapy in Hypogonadal Men;" The Journal of Clinical Endocrinology & Metabolism; (2007); pp. 3844-3853; vol. 92, No. 10; <doi: 10.1210/jc.2007-0620 >.
Zohar; "NAFLD Histology and Score;" [PowerPoint]; (Nov. 2016); 20 pages.
Thomsen et al.; "The Macrophage Low-Grade Inflammation Marker sCD163 is Modulated by Exogenous Sex Steroids;" Endocrine Connections; (Nov. 2013); pp. 216-224; vol. 2, No. 4; <doi: 10.1530/EC-13-0067 >.
International Search Report issued Nov. 5, 2019, in International Application No. PCT/US19/42709, filed Jul. 19, 2019; 3 pages.

(56) References Cited

OTHER PUBLICATIONS

Haider et al.; "Beneficial Effects of 2 Years of Administration of Parenteral Testosterone Undecanoate on the Metabolic Syndrome and on Non-Alcoholic Liver Steatosis and C-reactive Protein;" Hormone Molecular Biology and Clinical Investigation; (2010); pp. 27-33; vol. 1, No. 1; <doi: 10.1515/HMBCI.2010.002 >.

A. Haider, et al., Improvement of the Metabolic Syndrome and of Non-alcoholic Liver Steatosis upon Treatment of Hypogonadal Elderly Men with Parenteral Testosterone Undecanoate, 167-171, May 26, 2009, Exp Clin Endocrinol Diabetes.

\* cited by examiner

* Non-HDL cholesterol is obtained from subtraction of HDL cholesterol from total cholesterol.

FIGURE 16
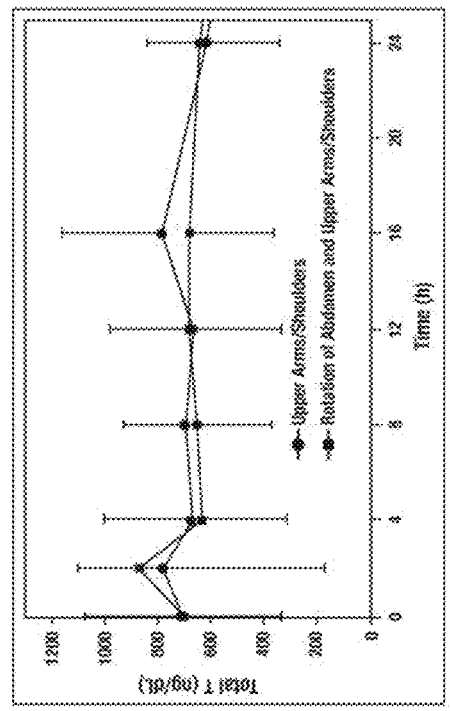
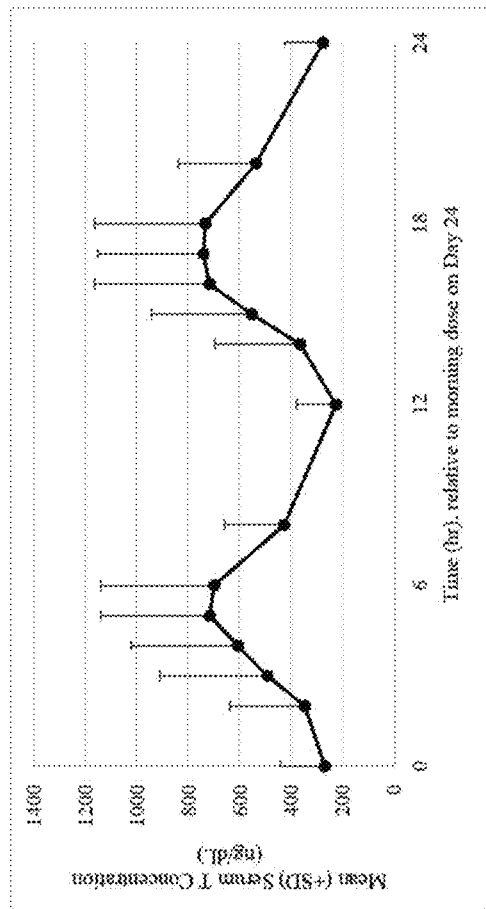

LIVER DISEASE

CROSS-REFERENCE TO RELATED APPLICATIONS

This application claims the benefit of United States Provisional Patent Application Serial Nos. 62/701,309, filed on Jul. 20, 2018; 62/714,968 filed on Aug. 6, 2018; 62/728,580 filed on Sep. 7, 2018; 62/783,190, filed Dec. 20, 2018; and 62/793,724, filed on Jan. 17, 2019, each of which is incorporated herein by reference.

FIELD OF THE INVENTION

This disclosure relates to compositions and methods for treating liver disease and reducing mortality in specific patient populations.

BACKGROUND

Historically, some androgens like anabolic-androgenic compounds were considered to have toxic effects on the liver. See e.g., Bond et al. PMID: 27372877; Neri et al. PMID: 21443508; and Kemp C J et al. PMID: 2798421.

Despite evidence of hepatotoxicity of androgens in the literature, studies have examined the effect of testosterone on liver fat reduction in fatty liver disease and have general reported inconclusive or negative results in humans. For example, Huang et al. (PMID: 23292288) concluded "Testosterone administration in older men with mobility limitation and low testosterone levels was not associated with a reduction in hepatic fat." Moreover, elevated testosterone levels in females can associated with fatty liver, liver disease and related comorbidities. Magnussen et al PMID: 28522646 reported "hepatic fat content and VAT were unchanged" in males with type 2 diabetes and low testosterone levels that were treated for 24-weeks with a testosterone gel. Sattler et al PMID: 25392748 also reported that testosterone replacement did not have an effect of liver fat in 20 men with lower baseline levels of testosterone when treated for 20 weeks with a testosterone gel.

There is a need for testosterone/androgen based therapies for specific populations of individuals. More specifically, there is a need for new therapies for liver disease.

SUMMARY

Described herein are methods and composition for use in treating, preventing, slowing the progression, or reducing the risk of liver disease (or comorbidities thereof) or symptoms thereof. In particular, it was discovered that androgen receptor modulators e.g., agonists are useful for improving liver function, liver diseases or conditions and related comorbidities. While a number of modalities for treating liver disease are described herein in the context of oral androgen therapy e.g., oral administration of testosterone esters like testosterone undecanoate, the skilled artisan recognizes in view of this disclosure, other androgen receptor agonist can be adapted and employed in these methods such as transdermal, nasal, buccal, and injectable testosterone products. In addition to testosterone, testosterone esters and the such, other androgen receptor agonists may be employed herein as well as methods and compounds, pharmaceuticals, nutritional or vitamin supplements that increase serum testosterone levels, serum free testosterone levels, or androgen receptor signaling in target tissues or compartments.

It was surprisingly discovered that oral testosterone (or androgen) therapy e.g., oral administration of a pharmaceutical composition containing a testosterone ester (e.g., or an androgen receptor agonist or anabolic agent), is particularly useful for treating liver disease. For example, it was found that the instant methods and compositions reduce relevant biomarker levels in patients having elevated biomarkers related to liver disease (e.g., fatty liver disease, liver fibrosis, alcoholic liver disease, hepatitis, steatosis, NAFLD, NASH, NASH with cirrhosis, and comorbidities of testosterone deficiency). Unexpectedly, the methods and compositions disclosed herein, demonstrated a reduction in serum alkaline phosphatase levels that was significantly better than that observed with a once a day topical testosterone product (e.g, ANDROGEL™ (testosterone gel for topical use)), a marketed testosterone replacement therapy administered via the transdermal route. Other unexpected findings include substantial reductions (or improvements) in triglyceride levels, biomarkers of liver injury, and biomarkers for other diseases and conditions (e.g., lipoprotein-associated phospholipase A2), a biomarker of cardiovascular disease. Thus, in one implementation, the methods described herein increase the ratio of serum testosterone levels to alkaline phosphatase (e.g., by 5%, 10%, 15%, 20%, or 25% or more). In another implementation the methods described herein increase the ratio of serum testosterone levels to serum triglyceride levels (e.g., by 5%, 10%, 15%, 20%, or 25% or more). In other implementations, the methods and compositions disclosed herein, improve diseases and conditions (or symptoms or related biomarkers) in conditions that are co-morbid with low testosterone levels (e.g., either total testosterone or free testosterone).

Without wishing to be bound by theory, it is believed that in some contexts, as illustrated herein, testosterone deficient subjects with specific biomarkers in the high normal range or above normal are particularly sensitive to the methods and compositions described herein and see surprising reductions or improvements in the levels of these biomarkers. Again, in many cases these biomarker improvements are both over baseline values and in comparison to an active control (transdermal testosterone preparation). Moreover, populations of individuals that are at higher risk for developing specific diseases and conditions are particularly amenable to the treatments described herein (including those that do not have testosterone deficiency). Thus, the methods and compositions described herein improve or ameliorate biomarkers associated with diseases by 5%, 10%, 15%, 20%, 25%, 30%, 40%, 50%, 60%, or 70% or more compared to baseline values. It is also believed that the method and compositions described herein have utility and can be used in subjects that do not have testosterone deficiency.

It was unexpectedly found that normalization or improvement of biomarkers (e.g., one or more biomarkers) can occur relatively quickly after commencement of the methods using the compositions described herein. For example, treatment for 1, 2, 3, 4, 5, 6, or 7 or more weeks can provide substantial improvements in one or more biomarkers associated with liver disease or mortality. Moreover, the methods and compositions provide sustained responses e.g., 1, 2, 3, 4, 5, 6, 7, 8, 9, 10, 11 or 12 months or more. As illustrated in the Examples, treatment with the methods and compositions described herein for 3 weeks can result in substantial improvements of biomarker levels. Typically, the treatments described herein are once-a-day or twice-a-day dosing regimens, although other dosing regimens are contemplated and have been shown to be effective e.g., three times a day. It is also notable that both testosterone undecanoate based oral dosing regimens and testosterone tridecanoate dosing regimens are effective in these treatments. Thus, without wishing to be bound by theory, it is believed that the methods and compositions described herein can be used with numerous testosterone esters and other steroid (and steroid ester containing compositions). For example, the methods and compositions described herein can be used with testosterone esters wherein the ester moiety can have from 2-20 carbons (e.g., the ester moiety is derived from a 2 carbon to 20 carbon fatty acid or fatty acid derivative including straight chain, branched chain, cyclic (e.g., cypionate or cypionic acid), saturated, and unsaturated (oleate or oleic acid) versions of 2 carbon to 20 carbon alkanoic acids). Thus, the compositions including two or more testosterone esters (e.g., testosterone undecanoate and testosterone tridecanoate) can be useful in the methods disclosed herein and have unexpected effects.

Provided herein are methods and compositions useful for treating conditions associated with increased mortality such as liver disease and particularly fatty liver disease, non-alcoholic fatty liver disease, non-alcoholic steatohepatitis, steatosis, cirrhosis, alcoholic liver disease and other liver diseases. Moreover, provided herein are methods for treating liver disease or a symptom thereof. Furthermore, provided herein are compositions and methods for modulating biomarkers associated with liver disease or symptoms thereof.

Accordingly, in one embodiment, a method of treating a liver disease or condition is provided, said method comprising identifying a subject in need of treatment e.g., has a liver disease or condition. In one aspect, said method comprises oral administration of 200 mg to 750 mg of testosterone undecanoate per day to a male subject (e.g., in need of treatment). In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect, the subject is from 1 to 18 years old, 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH ("Non-Alcoholic Steato-Hepatitis"), NAFLD ("Non-Alcoholic Fatty Liver Disease"), primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specifically incorporated into each specific method or method embodiment described in the Detailed Description.

Accordingly, in one embodiment, a method of treating a liver disease or condition is provided, said method comprising identifying a subject with a biomarker associated with said liver disease or condition where the biomarker is in the upper normal range and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $1/10^{th}$ of these values for a female subject. In one aspect, said method comprise oral administration of 200 mg to 750 mg of testosterone undecanoate per day to a male subject. In one aspect, said method comprises oral administration of 300 mg to 600 mg of testosterone undecanoate per day to a male subject. In one aspect, said method comprise oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specifically incorporated into each specific method or method embodiment described in the Detailed Description.

Accordingly, in one embodiment, a method of treating a liver disease or condition is provided, said method comprising identifying a subject with a biomarker associated with said disease or condition where the biomarker is outside of the normal range (e.g., above or below) and orally administering to said subject a pharmaceutical composition comprising a testosterone ester (e.g., testosterone undecanoate or testosterone tridecanoate) in an amount sufficient to ameliorate or improve the level of the biomarker (e.g., move the level in the direction of the normal range), reduce the rate of increase or decrease of the biomarker, or treat the disease or condition. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or 1110$^{th}$ of these values for a female subject. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specifically incorporated into each specific method or method embodiment described in the Detailed Description.

Accordingly, in yet another embodiment, a method of treating a liver disease or condition is provided, said method comprising identifying a subject with a biomarker associated with said disease or condition where the biomarker is above the upper normal limit and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $1/10^{th}$ of these values for a female subject. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect, the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specific incorporated into each specific method or method embodiment described in the Detailed Description.

Accordingly, in one embodiment, a method of treating a disease or condition is provided, said method comprising identifying a subject with a biomarker associated with said disease or condition where the biomarker is above twice the upper normal range limit and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $1/10$th of these values for a female subject. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect, the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specifically incorporated into each specific method or method embodiment described in the Detailed Description.

Accordingly, in one embodiment, a method of treating a liver disease or condition is provided said method comprising identifying a subject with a biomarker associated with said disease or condition where the biomarker is above 3 times the upper normal limit and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $1/10^{th}$ of these values for a female subject. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprise oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specifically incorporated into each specific method or method embodiment described in the Detailed Description.

Accordingly, in one embodiment, a method of treating a liver disease or condition is provided, said method comprising identifying a subject with a biomarker associated with said disease or condition where the biomarker is between the upper normal limit and twice or thrice the upper normal limit, and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $1/10^{th}$ of these values for a female subject. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specific incorporated into each specific method or method embodiment described in the Detailed Description.

Accordingly, in one embodiment, a method of treating a liver disease or condition is provided said method comprising identifying a subject with a biomarker that is greater than the upper normal limit, greater than 2 times the upper normal limit, greater than 3 times the upper normal limit, greater than 4 times the upper limit, or defined by any two of these bounds (e.g., 3-4 times upper normal limit) associated with said disease or condition and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $\frac{1}{10}^{th}$ of these values for a female subject. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $\frac{1}{10}^{th}$-$\frac{1}{15}$th of these values. In one aspect the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specific incorporated into each specific method or method embodiment described in the Detailed Description.

Accordingly, in one embodiment, a method of treating a liver disease or condition is provided, said method comprising identifying a subject with a biomarker associated with said liver disease or condition where the biomarker is an imaging biomarker (e.g., liver) or a liver histology biomarker and orally administering to said subject a pharmaceutical composition comprising a testosterone ester (e.g., testosterone undecanoate or testosterone tridecanoate) in an amount sufficient to reduce the level of the biomarker or reduce the rate of increase of the biomarker. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL for a male subject or $\frac{1}{10}$th of these values for a female subject. In one aspect, said method comprise oral administration of 200 mg to 750 mg of testosterone undecanoate per day to a male subject. In one aspect, said method comprise oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $\frac{1}{10}$th-$\frac{1}{15}$th of these values. In one aspect the subject is from 18-25 years old, 26-35 years old, 36-45 years old, 45-55 years old, 56-65 years old or older than 65 years old. In one aspect, said subject (e.g., in need of treatment) has a disease or condition chosen from metabolic syndrome, diabetes (e.g., Type 2 Diabetes), hypertension, obesity, hypogonadism, hypertriglyceridemia, fatty liver disease, liver fibrosis, steatosis, cirrhosis, hepatitis, cardiovascular disease, NASH, NAFLD, primary sclerosing cholangitis, is waiting for a liver transplant, has received a liver transplant, primary biliary cholangitis, a liver disease or condition associated with chronic inflammation, hepatocellular carcinoma, graft versus host disease e.g., related to liver transplant, an autoimmune disease related to the liver (or has a biomarker level related to or indicative of one or more of these diseases). In one aspect, said method comprises identifying a subject in need of treatment. In one aspect, the disease or condition is a comorbidity of testosterone deficiency. In a specific aspect, the subject in need of treatment is treated with one or more additional therapeutic agents (e.g., combination therapy). Additionally, this paragraph is to be read as being specifically incorporated into each specific method or method embodiment described in the Detailed Description.

In some aspects of the methods described above and elsewhere in this disclosure, male subjects having serum testosterone levels in the range of less than 400 ng/dL, less than 450 ng/dL, less than 500 ng/dL, less than 550 ng/dL, less than 600 ng/dL, or less than 700 ng/dL can be treated with the compositions described herein in accordance with methodology described herein.

In some aspects of the methods described above and elsewhere in this disclosure, male subjects having serum testosterone levels in the range of 50-100 ng/dL, 100-150 ng/dL, 150-200 ng/dL, 200-250 ng/dL, 250-300 ng/dL, 300-350 ng/dL, 350-400 ng/dL, 400-450 ng/dL, 450-500 ng/dL, 550-600 ng/dL, 600-700 ng/dL, or any combination of these ranges can be treated with the compositions described herein in accordance with methodology described herein.

In some aspects of the methods described above and elsewhere in this disclosure, male subjects having serum SHBG levels in the range of less than 20 nmol/L, less than 30 nmol/L, less than 40 nmol/L, less than 50 nmol/L, less than 60 nmol/L, less than 70 nmol/L, less than 80 nmol/L, less than 90 nmol/L, less than 100 nmol/L, less than 150 nmol/L, less than 200 nmol/L, less than 300 nmol/L, less than 400 nmol/L, or e.g., less than 1000 ng/dL can be treated with the compositions described herein in accordance with methodology described herein. These serum SHBG ranges can be used in conjunction with the serum testosterone levels described herein for specific populations particularly suited to treatment as described herein.

In some aspects of the methods described above and elsewhere in this disclosure, male subjects having serum testosterone levels in the range of 1-20 nmol/L, 20-25 nmol/L, 25-30 nmol/L, 30-35 nmol/L, 35-40 nmol/L, 40-45 nmol/L, 45-50 nmol/L, 50-55 nmol/L, 55-60 nmol/L, 60-65 nmol/L, 65-80 nmol/L, 80-100 nmol/L, 100-125 nmol/L, 125-150 nmol/L, 150-200 nmol/L, 200-300 nmol/L, 300-450 nmol/L, or e.g., 450-750 nmol/L, or any combination of these ranges can be treated with the compositions described herein in accordance with methodology described herein. These serum SHBG ranges can be used in conjunction with the serum testosterone levels described herein for specific populations particularly suited to treatment as described herein.

In one aspect of each of the methods described herein (e.g., each paragraph above in the Summary and each method embodiment of the Detailed Description), the method increases the serum testosterone level of the subject. In one aspect, the method increases the serum testosterone level (e.g., $C_{ave0-24}$) of the subject by at least 10, 20, 30, 40, or 50 ng/dL over the subject's baseline (pre-treatment) value (e.g., for a male subject or adjusted accordingly for female or pediatric subjects). In one aspect, the method increases the serum testosterone level (e.g., $C_{ave0-24}$) of the subject by at least 30, 50, 75, 100, 150, 200, 300, 400 or 500 ng/dL over the subject's baseline (pre-treatment) value (e.g., for a male subject or adjusted accordingly for female or pediatric subjects). The baseline serum testosterone level for the subject can be determined by a single morning blood draw. Alternatively, the baseline serum testosterone level can be determined by the average of two morning blood draws from different days. The increase over the baseline value can be estimated as a $C_{ave}$ serum testosterone level in a manner deemed appropriate by a relevant medical professional. For example, the $C_{ave}$ serum testosterone level can be estimated as $C_{ave0-24}$, $C_{ave0-12}$, $C_{ave0-8}$, $C_{ave0-6}$, $C_{ave0-4}$, $C_{ave0-3}$ and $C_{ave0-2}$. Alternatively, a clinician can ascertain that a sufficient increase in serum testosterone level has occurred via the observation of clinical outcomes or characteristics (e.g., improvement in symptoms), or modulation of one or more biomarkers.

In another aspect of each of the methods described herein (e.g., each paragraph above in the Summary and each method embodiment of the Detailed Description), the method produces a serum testosterone profile over a 24-hour period that approximates the pattern of a healthy young subject (not necessarily the absolute levels). That is to say there is an increase in serum testosterone levels in the morning which tapers off during the remainder of the day. Thus, in one aspect the 24-hour serum testosterone profile is characterized as substantially different than that provided by other means of testosterone therapy. For example, commonly used and prescribed testosterone therapies include transdermal testosterone therapy which over the course of a 24-hour period produces a relative flat pharmacokinetic profile or injectable testosterone therapies (e.g., intramuscular or subcutaneously) which provide relatively flat pharmacokinetic profiles over a 24-hour period and longer, depending on the specific therapy. Another way of characterizing this difference is the difference or delta between serum testosterone $C_{max}$ and serum testosterone $C_{ave0-24}$. With both transdermal and injectable therapy the difference between serum testosterone $C_{max}$ and serum testosterone $C_{ave0-24}$ is relatively small compared to that of orally administered testosterone therapies. Thus, in some aspects, the methods and compositions described herein provide $C_{max}$ to $C_{ave}$ ratios (e.g., $C_{max}/C_{ave0-24}$) of greater than 1.1, 1.2, 1.3, 1.4, 1.5, 1.6, 1.7, 1.8, 1.9 or 2.0. Thus, in some aspects, the methods and compositions described herein provide $C_{max}$ to $C_{ave}$ ratios (e.g., $C_{max}/C_{ave0-24}$) of less than 100, 90, 80, 70, 60, 50, 40, 35, 30 or 25. In some aspects, the ratio of $C_{max}/C_{ave}$0-24 is defined as a range defined by any two values in the previous two sentences.

In one embodiment, the methods described above can include the use of an injectable or transdermal testosterone therapy in conjunction with an oral therapy. For example, the injectable or transdermal therapy can increase the subject's basal serum testosterone level and the oral therapy can be used to provide a 24-hour serum testosterone profile that mimics a normal physiological profile. Alternatively, the methods described herein can be adapted for use with non-oral testosterone therapies including but not limited to (1) injectable testosterone products e.g., testosterone enanthate, testosterone propionate, testosterone undecanoate, or another testosterone ester (2) transdermal or topical testosterone products like ANDROGEL™ (testosterone gel for topical use), Testim™ (testosterone gel), or Axiron™ (testosterone topical solution), buccal testosterone products, (3) nasal testosterone products or any other androgen based therapy (e.g., androgen receptor agonist). In a specific aspect, these non-oral products can be used to target the specific disease states, populations, biomarkers and the such as described for the oral compositions.

In one embodiment, the methods described herein involve oral administration of a testosterone ester (e.g., testosterone undecanoate, testosterone tridecanoate, or a combination thereof) formulated with vitamin E, a vitamin E prodrug, or a vitamin E derivative. In a preferred aspect, the Vitamin E compound is d-alpha-tocopherol or d-alpha tocopherol acetate. In another preferred aspect, the amount of d-alpha-tocopherol (or it's acetate) administered per day is from about 100 IU to about 2000 IU, 200 IU to about 1600 IU per day, about 400 IU to about 1000 IU per day or about 600 IU to 900 IU per day. These amounts can be co-formulated with the testosterone esters or administered separately. The exemplary formulations described herein can be adapted accordingly to use d-alpha-tocopherol (or e.g., a prodrug thereof (d-alpha-tocopheryl acetate)), tocotrienol and other related Vitamin E related compounds.

Without wishing to be bound by theory, it is believed the compositions and method described herein are useful and can be used to treat steatosis (or fibrosis or symptoms thereof) in any tissue or cell, including, but not limited to, one or more one or more of the following: pancreatic steatosis, renal steatosis, cardiac steatosis, pulmonary steatosis, intestinal steatosis, cerebral steatosis, and muscular steatosis, or a symptom thereof. In some aspects, the cell or tissues expresses androgen receptor.

Without wishing to be bound by theory, it is believed the compositions and method described herein are useful and can be used to treat macrovesicular steatosis or microvesicular steatosis.

Male hypogonadism (testosterone, T, level<300 ng/dL) is an underappreciated comorbidity in non-alcoholic fatty liver disease (NAFLD)/steatohepatitis (NASH). In addition to the well-established link between low T levels and facets of the metabolic syndrome (obesity, hypertension, hypertriglyceridemia, and type 2 diabetes), hypogonadism is also associated with NAFLD/NASH in males.

This disclosure relates to the prevalence of fatty liver in hypogonadal patients, as identified by Magnetic Resonance Imaging-Proton Density Fat Fraction (MRI-PDFF), a non-invasive quantitative biomarker of liver fat content.

In an a prospective design open-label, multi-center, single arm 'Liver Fat Study' evaluating LPCN 1144 (oral testosterone undecanoate) treatment in hypogonadal patients, baseline % liver fat was assessed via MRI-PDFF in a subset of study patients (N=36).

The prevalence of features of the metabolic syndrome in the study population was: 81% obese, 58% hypertriglyceridemia, 28% hypertensive, and 17% type 2 diabetes. Body Mass Index (BMI), T level, and liver fat fraction were 34±6 kg/m2, 199±61 ng/dL, and 8.8±7.9% (mean±SD), respectively. Based on liver fat ≥5%, about 70% of hypogonadal patients were identified as having NAFLD. Among hypogonadal patients with NAFLD, obesity was the most prevalent comorbidity (88%). Moreover, the prevalence of NAFLD increased in hypogonadal patients with increasing BMI, with the prevalence rising to 100% with Class III obesity (BMI≥40 kg/m2).

In conclusion, a high prevalence of NAFLD was observed in this Liver Fat Study. Among the evaluated comorbidities, obesity has the strongest association with NAFLD in the hypogonadal male patients. Thus provided herein is a method of treating a subject in need of treatment, said method comprising determining (1) the subject's serum or plasma testosterone level; (2) the subject's BMI, wherein a subject having (A) low testosterone or is hypogonadal and (B) is obese or has a BMI of 30 kg/m$^2$ or greater, is treated for fatty liver disease. In another implementation, a method of diagnosing a subject is provided, said method comprising determining (1) the subject's serum or plasma testosterone level; (2) the subject's BMI, wherein a subject having (A) low testosterone or is hypogonadal and (B) is obese or has a BMI of 30 kg/m$^2$ or greater, is likely to have fatty liver disease and is assessed by a liver imaging technique or has one or more biomarkers assessed to determine the stage of fatty liver disease. The method can further comprise administering to said subject a pharmaceutical agent for treating NAFLD or NASH.

Thus, also provided herein are methods for diagnosing, staging, prognosing and treating subjects having fatty liver disease.

It is to be understood that the methods described in this section are applicable to the methods described for the specific conditions/diseases in the Detailed Description.

BRIEF DESCRIPTION OF THE DRAWINGS

FIG. 16 illustrates the difference in serum testosterone levels for oral testosterone therapy (results from Example 2) and transdermal therapy (which is also similar to injectable therapies in the sense of a relatively flat profile).

Figure 1:
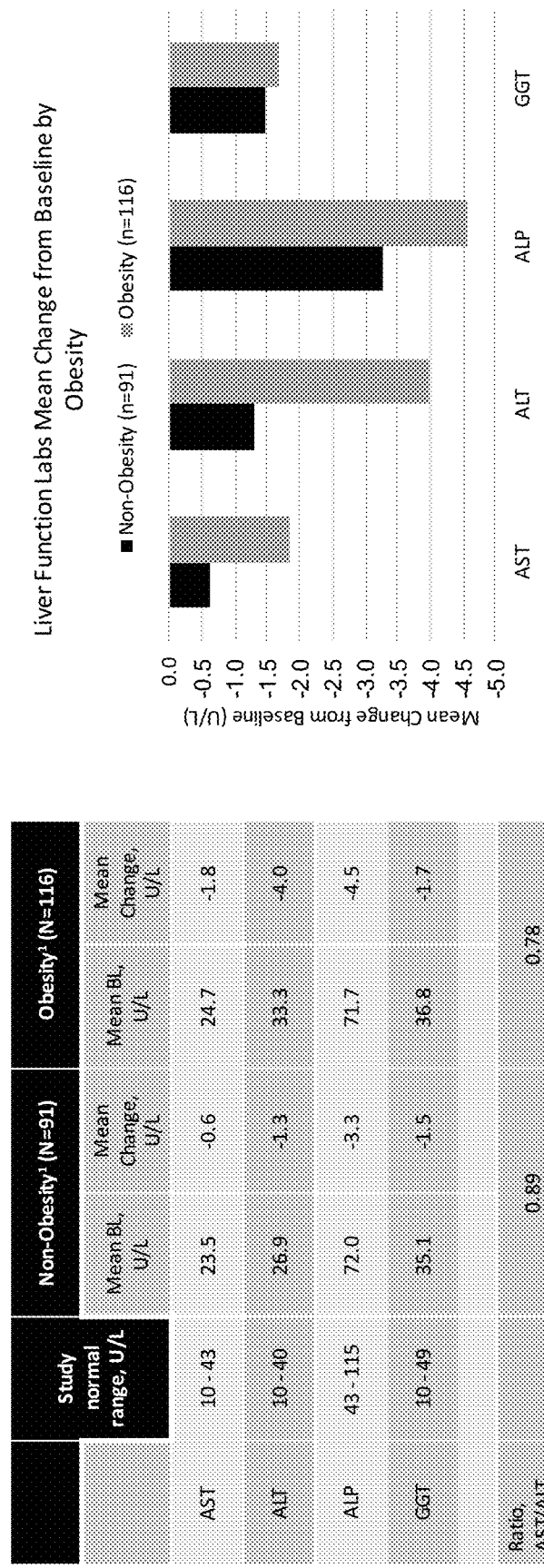
FIG. 1 shows a summary of an analysis of liver function enzyme changes from baseline to end of study values comparing obese (e.g., BMI>30 kg/m$^2$) to non-obese subjects in the study of Example 1.
Figure 2:
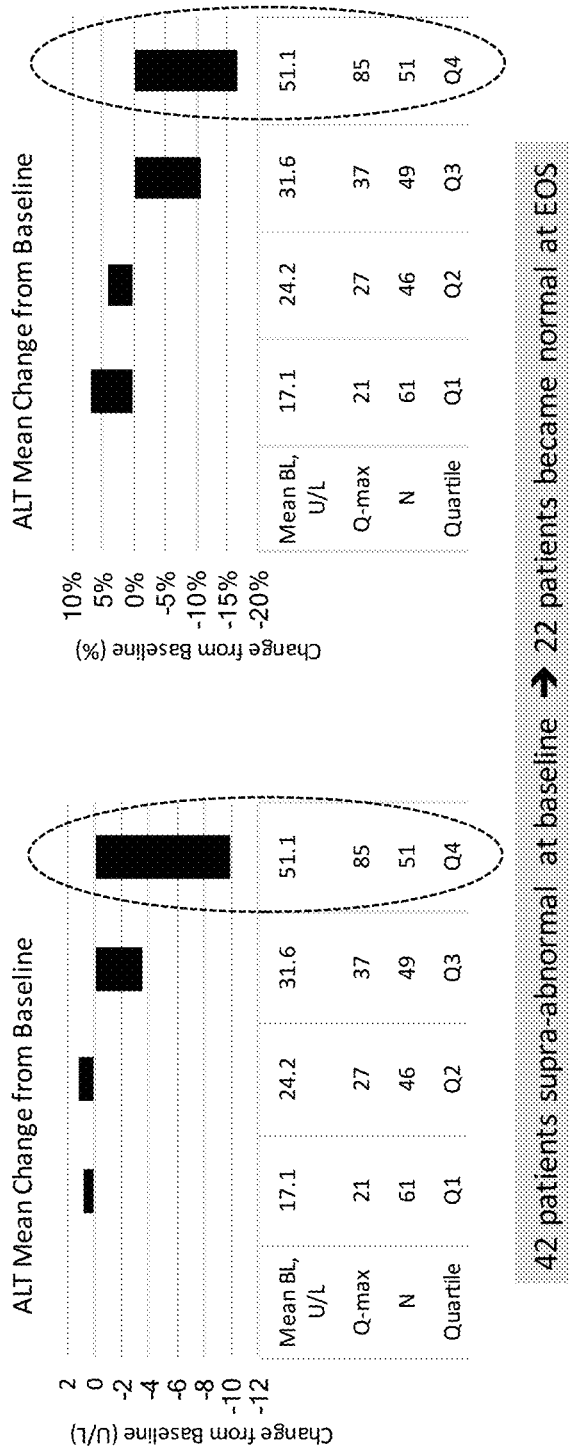
FIG. 2 shows a summary of an analysis of serum alanine transaminase levels of subjects in the study of Example 1, comparing baseline values to end of study values. In this figure and the remaining figures, Q-max refers to the maximum value of the biomarker for the specified quartile. For example, in this figure the first quartile are those subjects having serum alanine transaminase levels of less than or equal to 21 U/L, the second quartile are those subjects having serum alanine transaminase levels between 21 U/L and less than or equal to 27 U/L.
Figure 3:
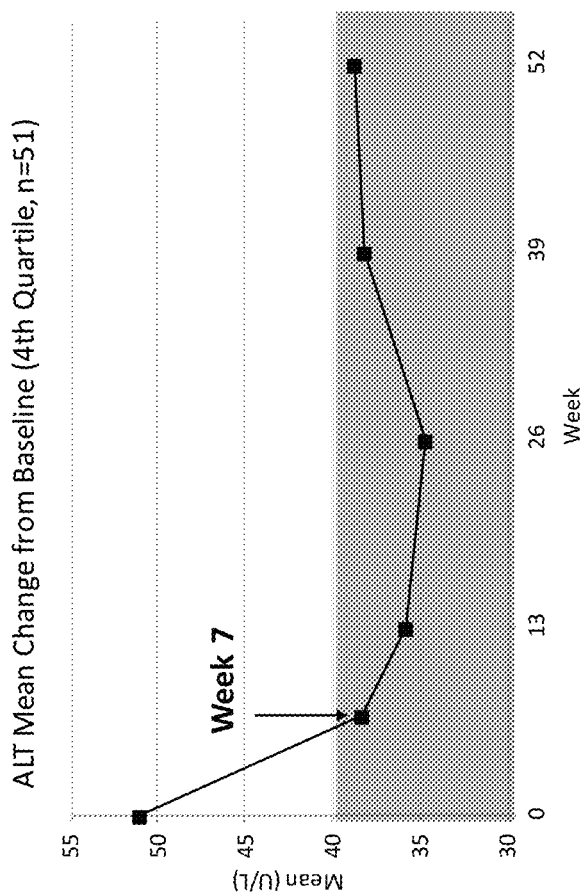
FIG. 3 shows a summary of an analysis of serum alanine transaminase levels of subjects in the highest quartile of alanine transaminase levels at baseline during the course of the study of Example 1.
Figure 4:
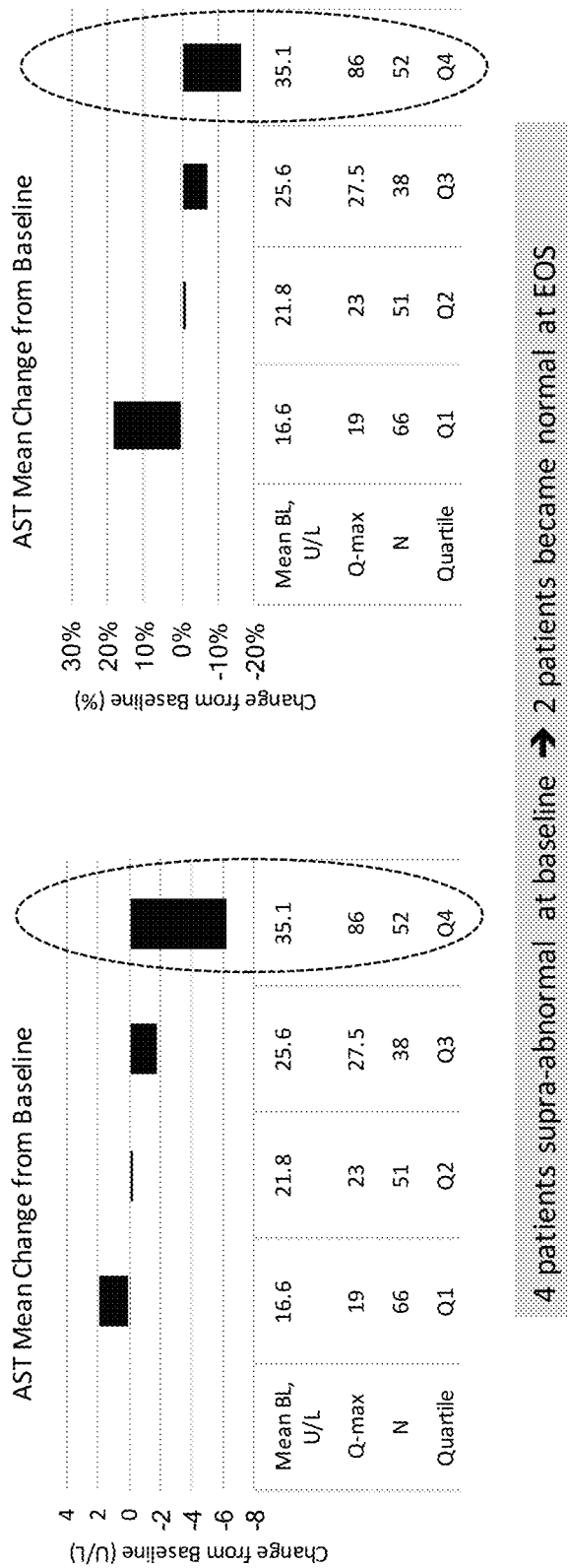
FIG. 4 shows a summary of an analysis of serum aspartate transaminase levels of subjects comparing baseline to end of study values in the study of Example 1.
Figure 5:
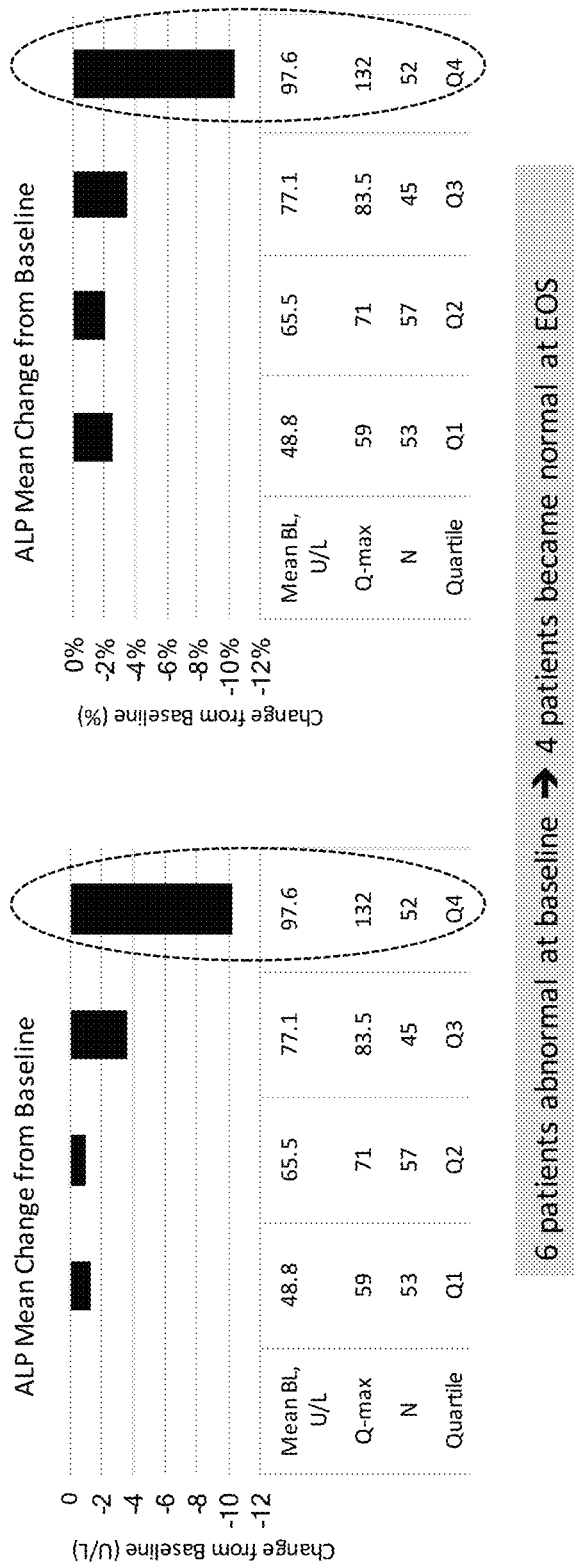
FIG. 5 shows a summary of an analysis of serum alkaline phosphatase levels of subjects comparing baseline to end of study values in the study of Example 1.
Figure 6:
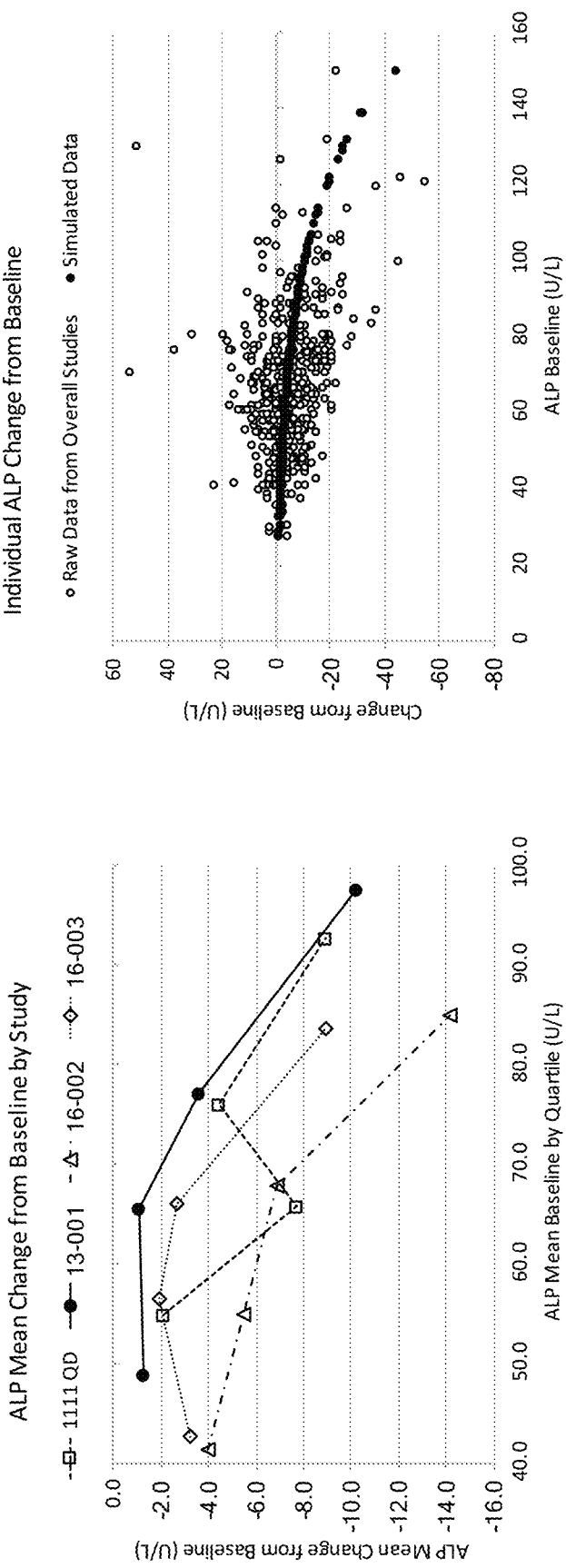
FIG. 6 shows a summary of analyses of serum alkaline phosphatase levels of subjects comparing baseline to end of study values in the studies of Examples 1, 2, 3, and 4.
Figure 7:
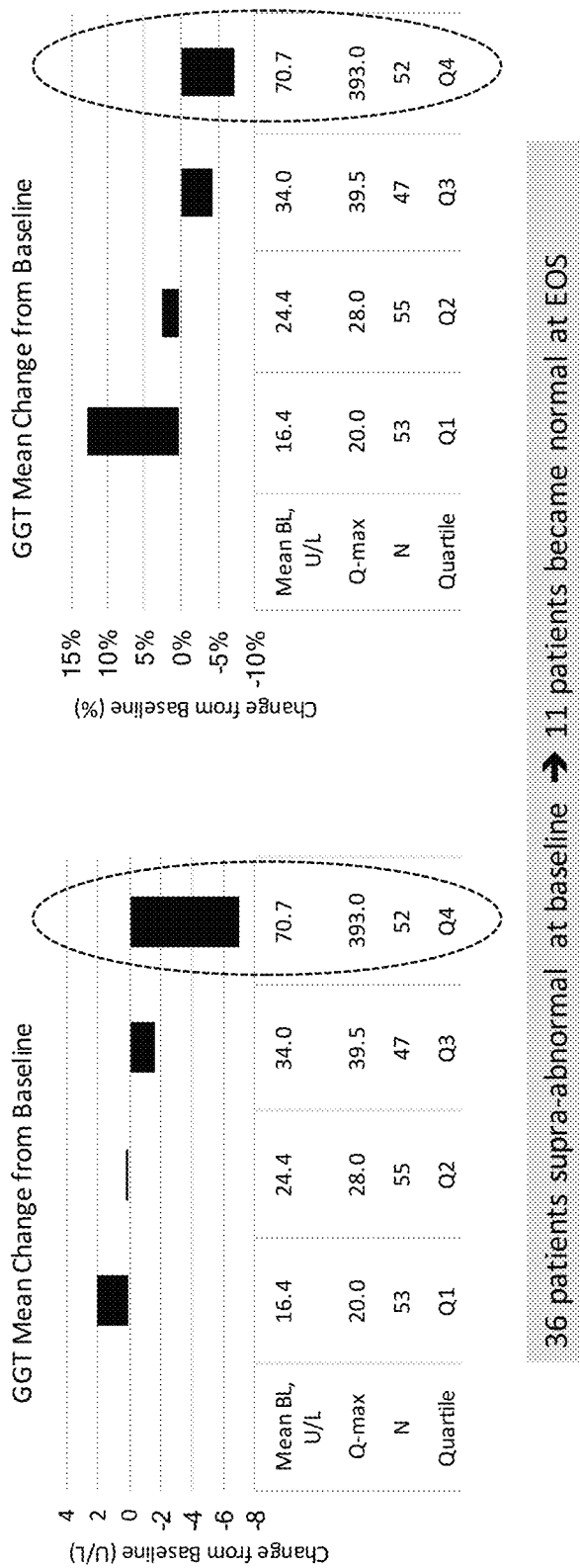
FIG. 7 shows a summary of an analysis of serum gamma-glutamyl transferase levels of subjects comparing baseline to end of study values in the study of Example 1.
Figure 8:
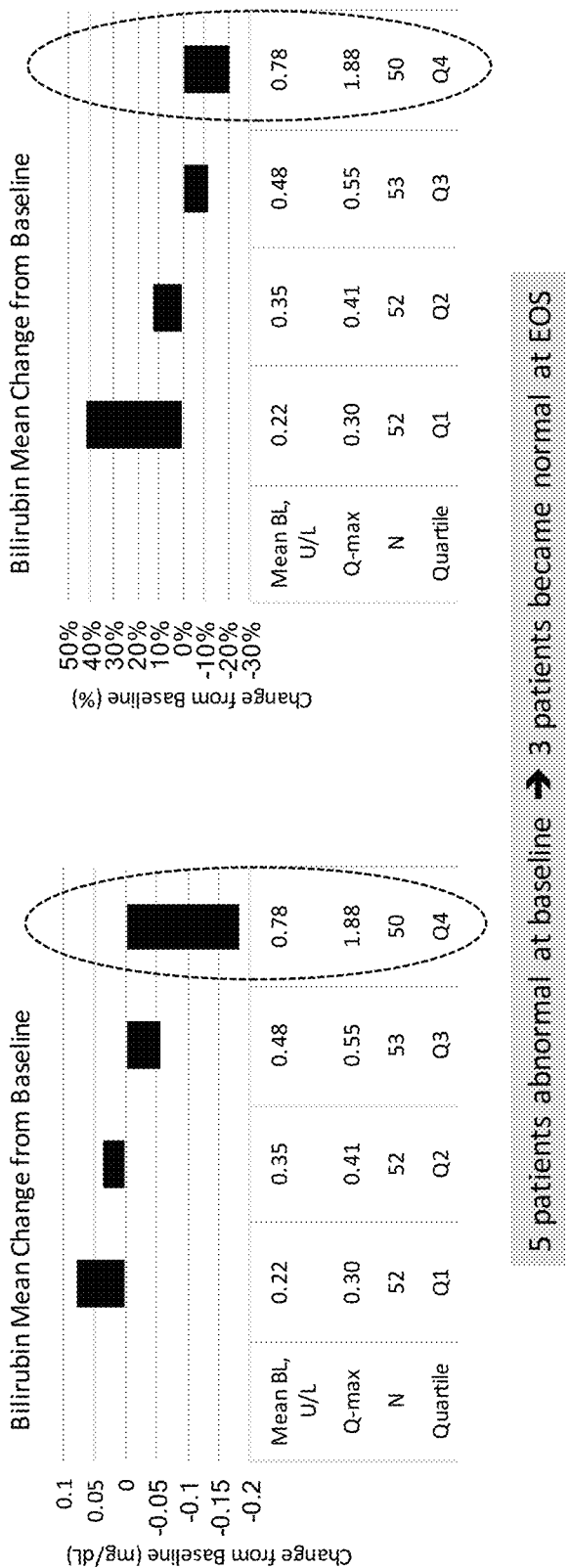
FIG. 8 shows a summary of an analysis of serum bilirubin levels of subjects comparing baseline to end of study values in the study of Example 1.
Figure 9:
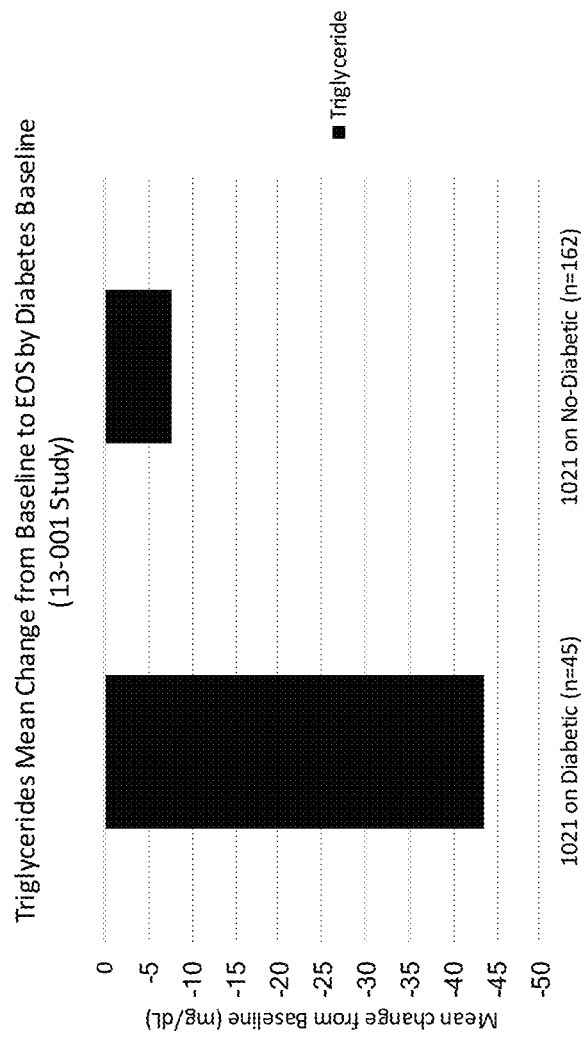
FIG. 9 shows a summary of an analysis of serum triglyceride levels of diabetic and non-diabetic subjects at baseline compared to end of study values in the study of Example 1.
Figure 10:
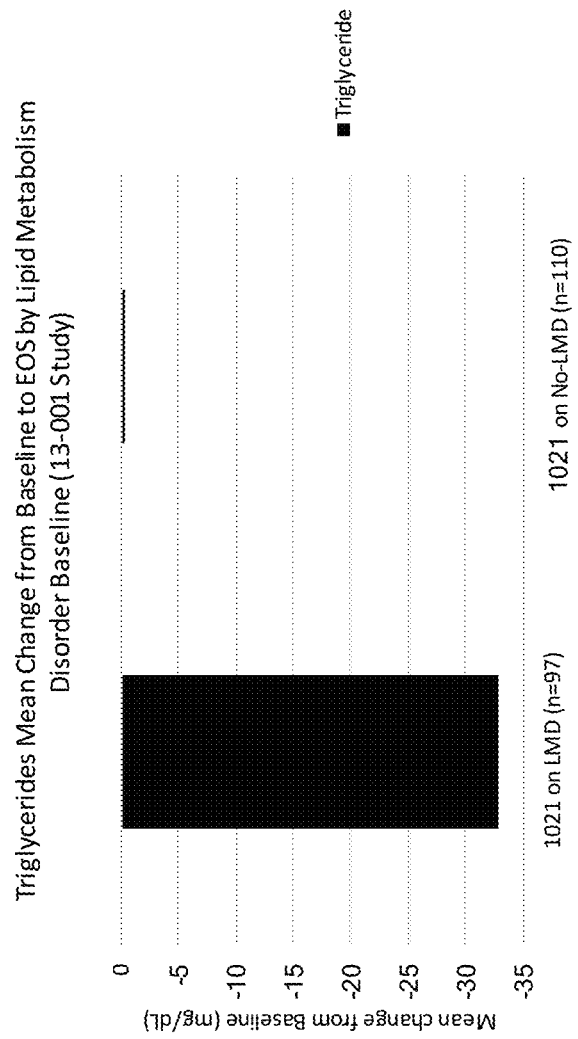
FIG. 10 shows a summary of an analysis of serum triglyceride levels of subjects having lipid metabolism disorder and non-lipid metabolism disorder subjects at baseline compared to end of study values in the study of Example 1.
Figure 11:
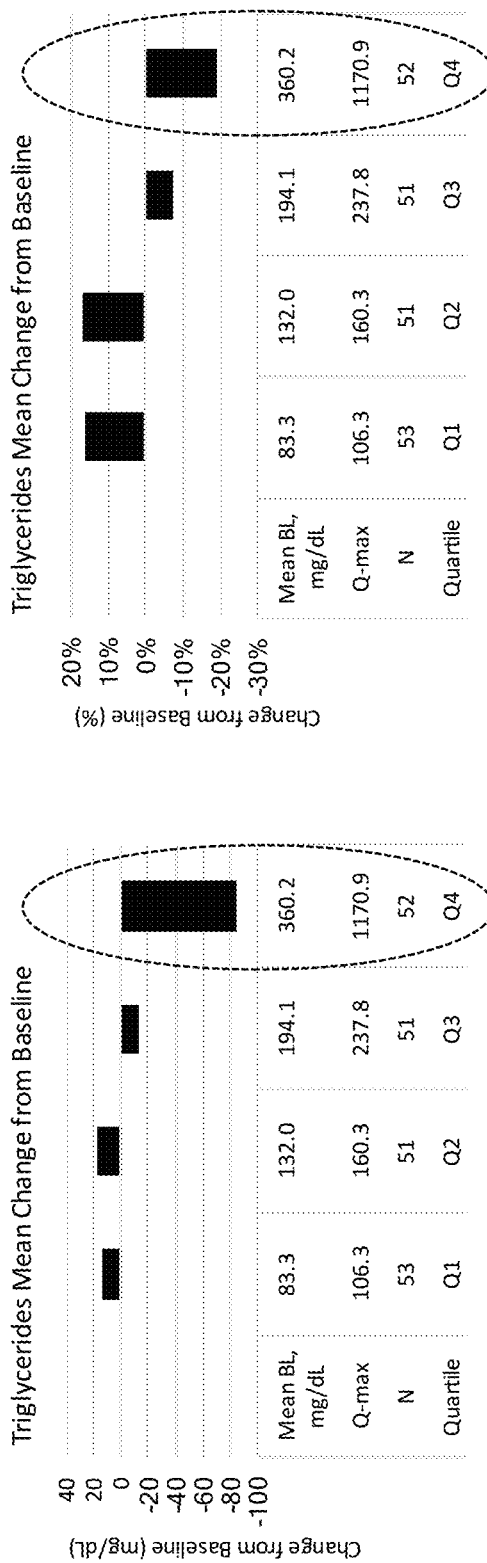
FIG. 11 shows a summary of an analysis of serum triglyceride levels of subjects at baseline compared to end of study in the study of Example 1.
Figure 12:
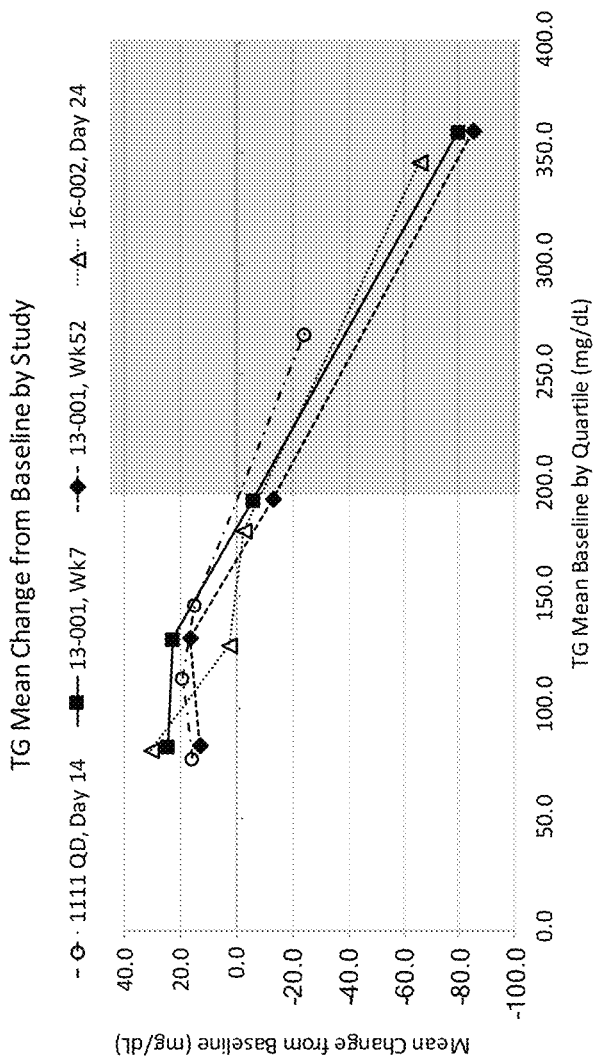
FIG. 12 shows a summary of an analysis of serum triglyceride levels of subjects at baseline compared to end of study in the study of Examples 1, 2, and 4.
Figure 13:
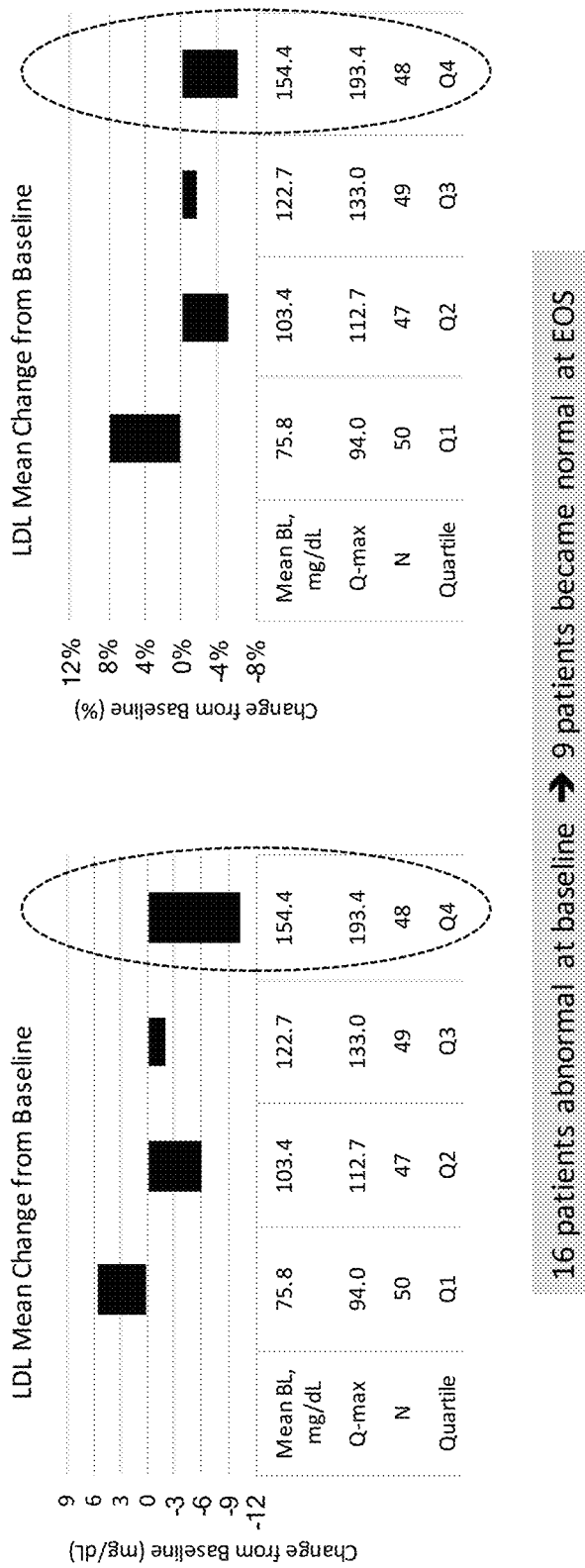
FIG. 13 shows a summary of an analysis of serum LDL levels of subjects at baseline compared to end of study in the study of Example 1.
Figure 14:
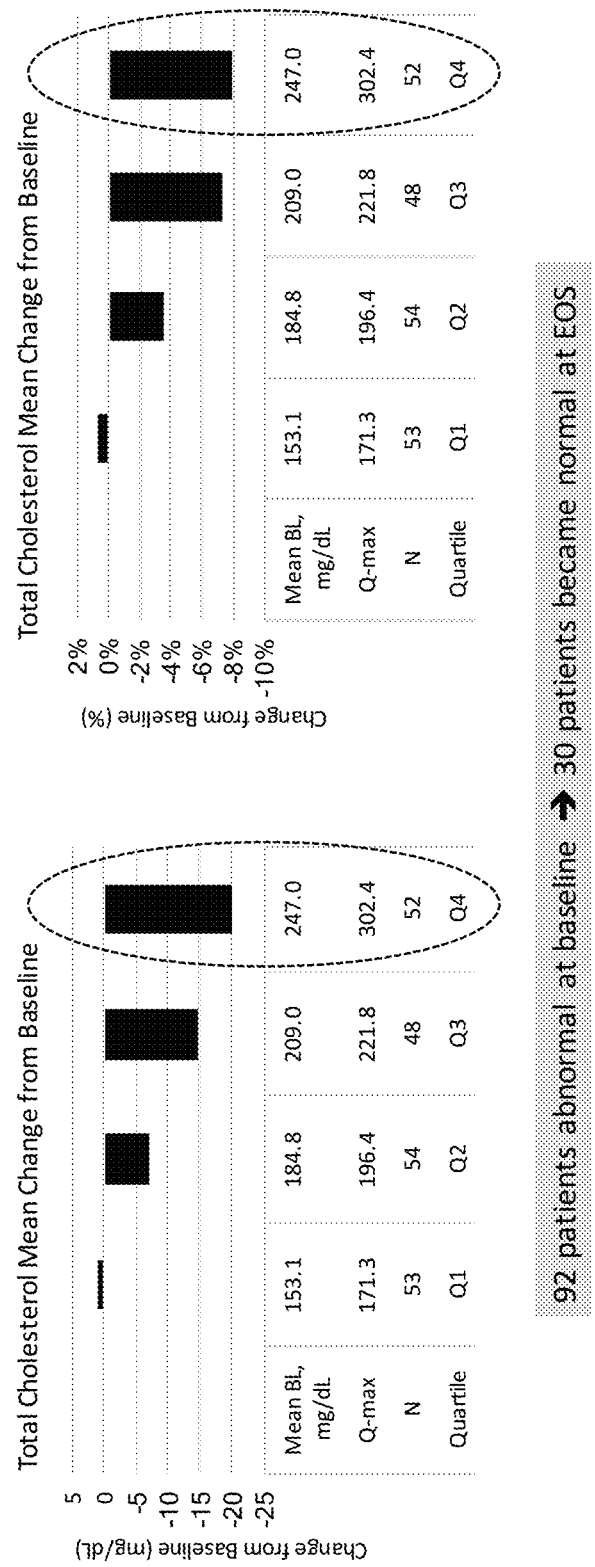
FIG. 14 shows a summary of an analysis of serum total cholesterol levels of subjects at baseline compared to end of study in the study of Example 1.
Figure 15:
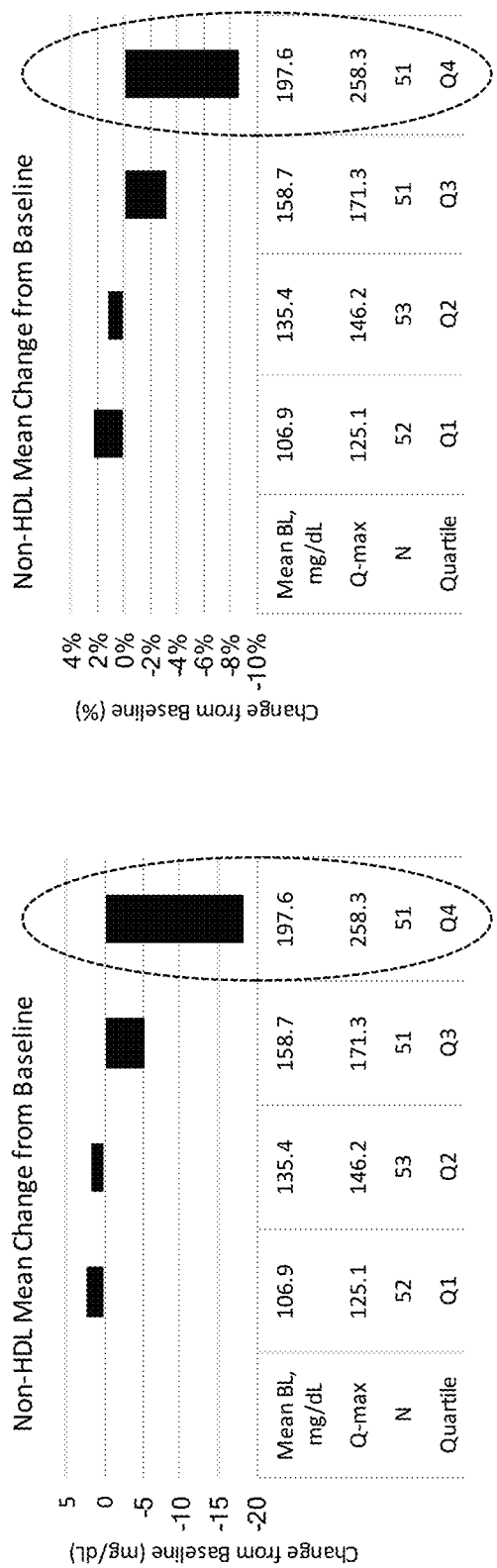
FIG. 15 shows a summary of an analysis of serum non-HDL cholesterol levels of subjects at baseline compared to end of study in the study of Example 1.
Figure 17:
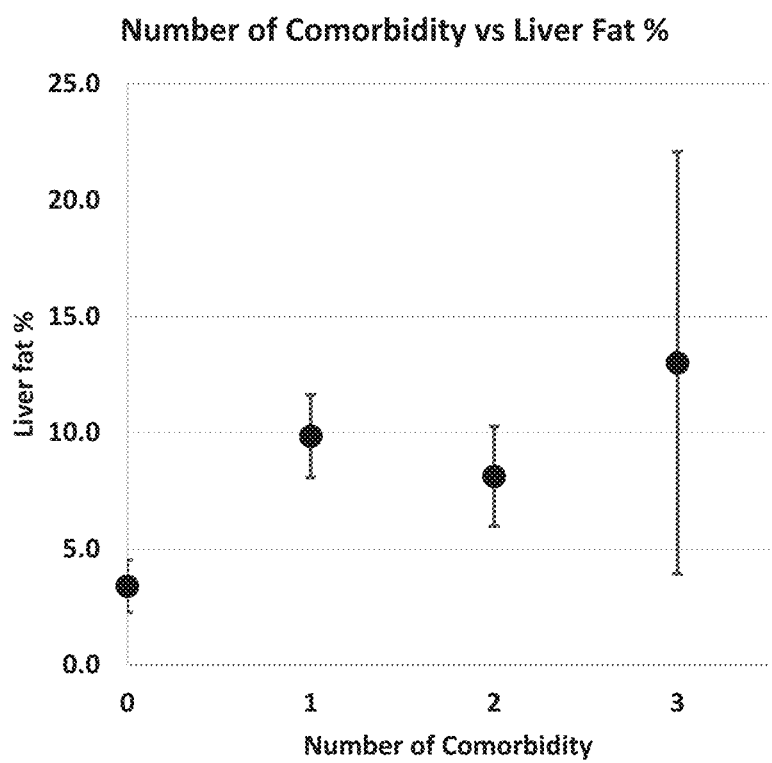
FIG. 17 shows the prevalence of comorbidities in the male hypogonadal population studied herein.
Figure 18:
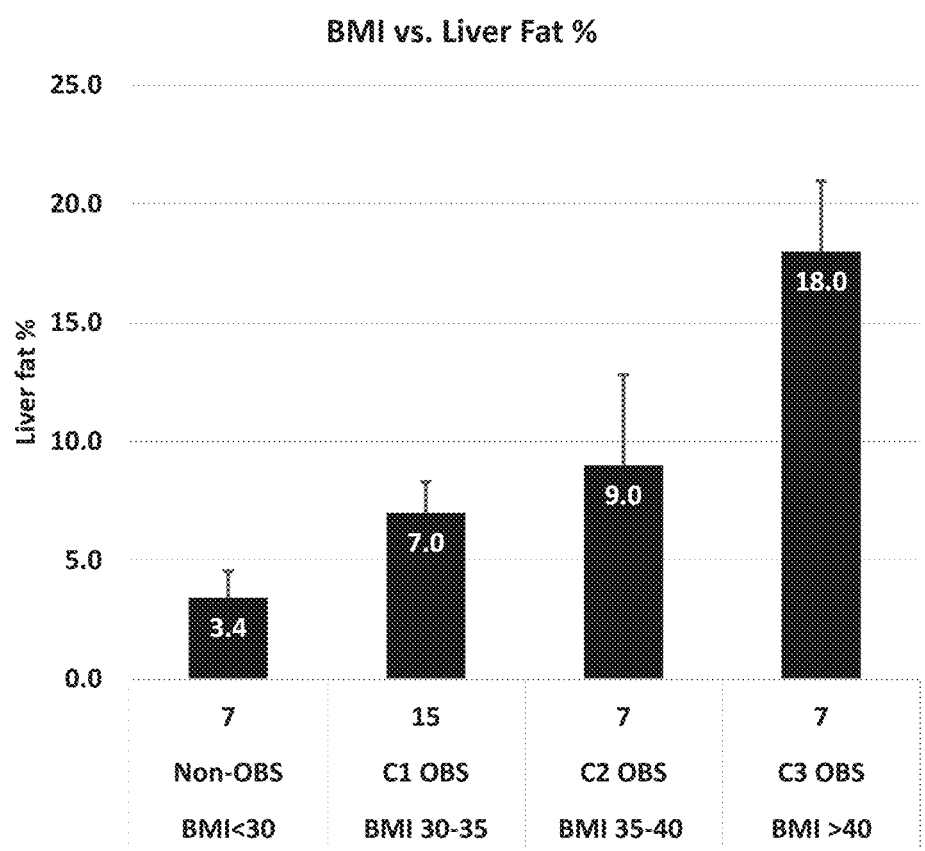
FIG. 18 shows the mean liver fat % as a function of BMI classes in the male hypogonadal population studied herein.
Figure 19:
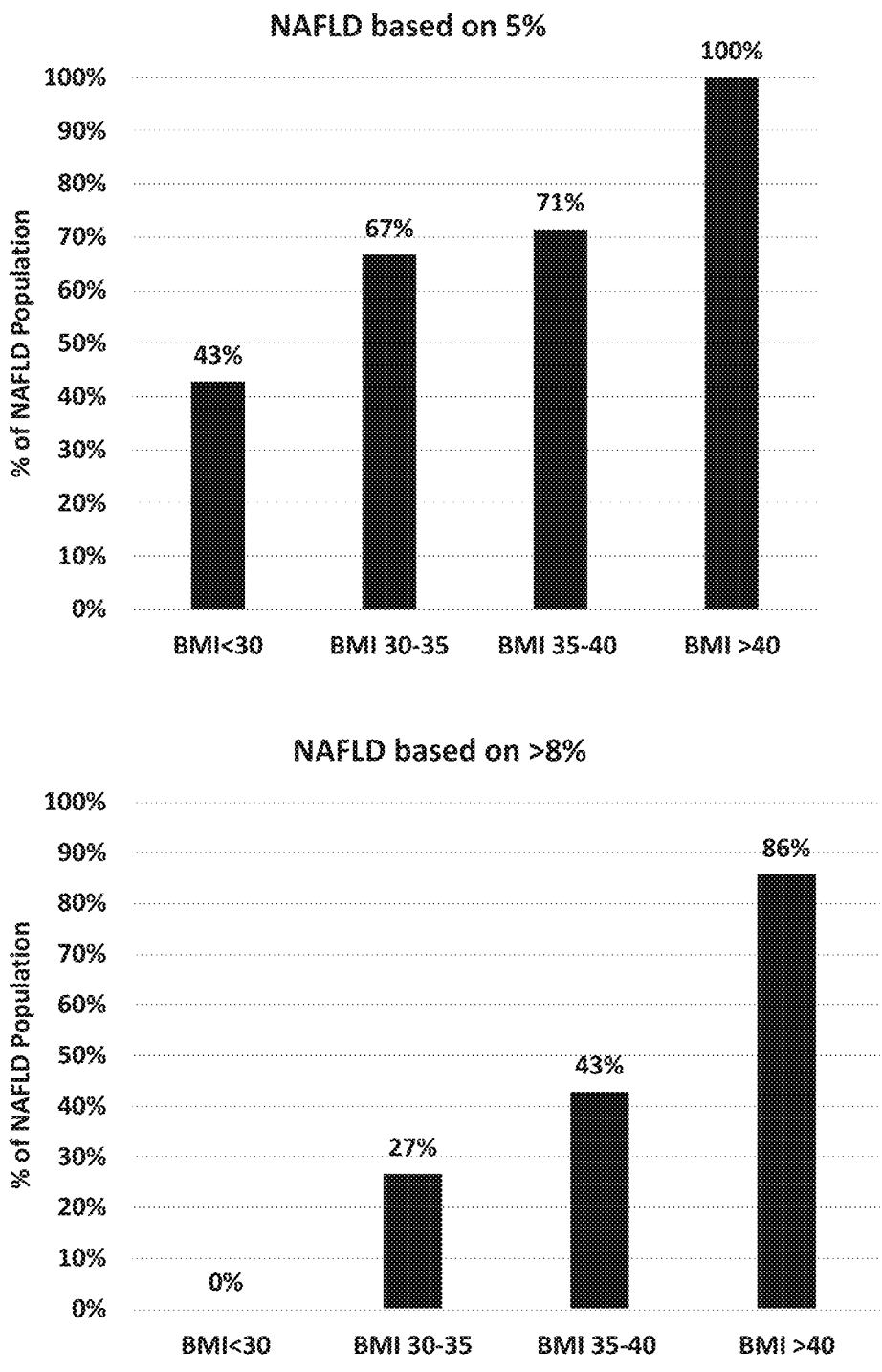
FIG. 19 shows percent of subjects having NAFLD as defined by liver fat cut-off values of 5% and 8%, as a function of BMI class, for male hypogonadal population studied herein.
Figure 20:
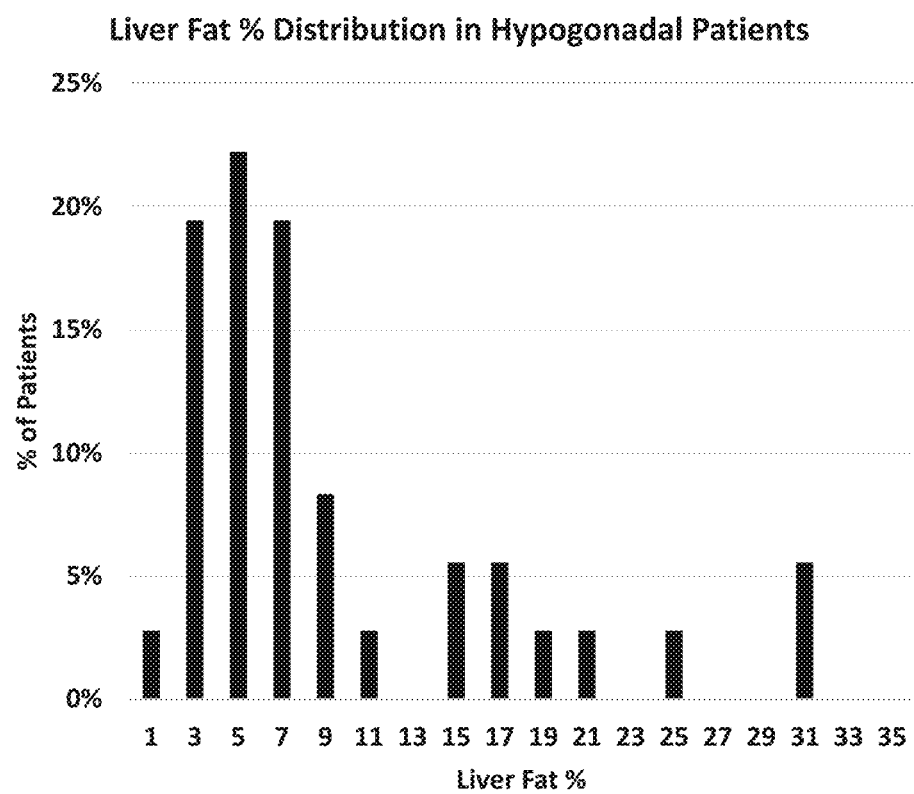
FIG. 20 the distribution of liver fat % values across the male hypogonadal population studied herein.
Figure 21:
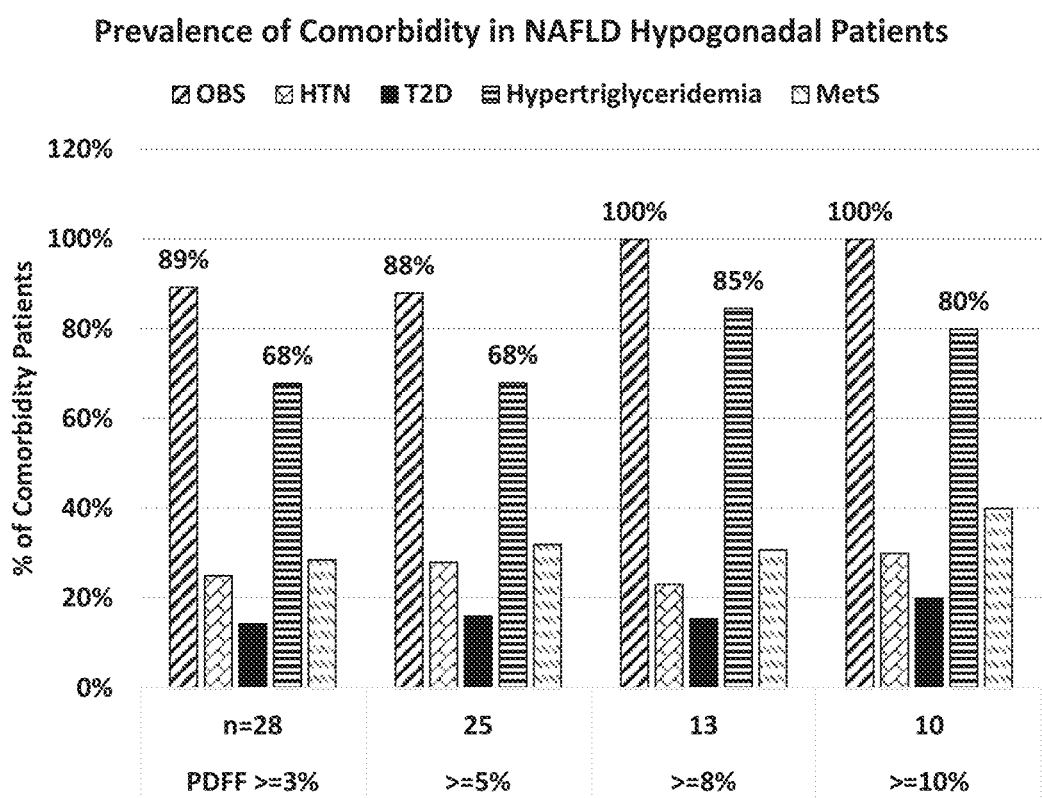
FIG. 21 shows the prevalence of comorbidities in the male hypogonadal population studied herein according to liver fat % cut-offs.

The Figures illustrate specific aspects of the compositions and methods for using such compositions. Together with the following description, the Figures demonstrate and explain the principles of the methods and compositions produced through these methods. In the drawings, the thickness of layers and regions are exaggerated for clarity. Also, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements.

DETAILED DESCRIPTION

It was unexpectedly found that androgen receptor modulators e.g., agonists are useful for improving liver function, liver diseases or conditions and related comorbidities. While a number of modalities for treating liver disease are described herein in the context of oral androgen therapy e.g., oral administration of testosterone esters like testosterone undecanoate, the skilled artisan recognizes in view of this disclosure, other androgen receptor agonist can be adapted and employed in these methods such as transdermal, nasal, buccal, and injectable testosterone products. In addition to testosterone, testosterone esters and the such, other androgen receptor agonists (including selective androgen receptor modulators, anabolic steroids wtc.) may be employed herein as well as methods and compounds, pharmaceuticals, nutritional or vitamin supplements that increase serum testosterone levels, serum free testosterone levels, or androgen receptor signaling in target tissues or compartments.

The following description supplies specific details in order to provide a thorough understanding of the methods and compositions of the invention. Nevertheless, the skilled artisan would understand that the compositions and associated methods of making and using such compositions can be implemented and used without employing these specific details. Indeed, the compositions and associated methods can be placed into practice by modifying the illustrated devices and methods and can be used in conjunction with any other agents and techniques conventionally used in the industry. For example, while the description refers to specific indications, it could be modified to be used in other indications.

It was surprisingly discovered that oral androgen therapy e.g., oral administration of a pharmaceutical compositions containing a testosterone ester (e.g., or an androgen receptor agonist or anabolic agent), is particularly useful for treating liver disease, comorbidities of testosterone deficiency, and can reduce mortality, and ameliorate or improve biomarkers related to these conditions or diseases. For example, it was found that the instant methods and compositions reduce relevant biomarker levels in patients having elevated biomarkers related to liver disease (e.g., fatty liver disease, liver fibrosis, alcoholic liver disease, hepatitis, steatosis, NAFLD, NASH, NASH with cirrhosis, and comorbidities of testosterone deficiency). Unexpectedly, as described herein, the reduction in serum alkaline phosphatase levels was significantly better with oral therapy than that observed with once a day topical testosterone product (e.g, ANDROGEL)™ (testosterone gel for topical use), a marketed testosterone replacement therapy administered via the transdermal route. Other unexpected findings include substantial reductions (or improvements) in triglyceride levels, biomarkers of liver injury, and biomarkers for other diseases and conditions associated with lipoprotein-associated phospholipase A2, a biomarker of cardiovascular disease. Thus, in one implementation, the methods described herein increase the ratio of serum testosterone levels to alkaline phosphatase. Thus, in one implementation, the methods described herein increase the ratio of serum testosterone levels to serum triglycerides.

While not wishing to be bound by theory, it is believed in some aspects described herein, that the methods and compositions present a therapy approximating a normal physiological pattern of serum levels with peaks and troughs of serum testosterone levels as opposed to the relative flat profile of other testosterone therapies like transdermal products and injectable products. It is believed that, in some aspects, the more normal physiological pattern of serum testosterone levels provides less suppression of endogenous serum testosterone levels and relative hormones/biomarkers leading to the unexpected results described herein.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The terms "serum testosterone" or "serum (17-β)-Hydroxy-4-Androsten-3-one levels," "serum T levels," "serum testosterone concentration," "plasma testosterone concentration," "testosterone concentration in the blood," and "serum testosterone concentration," are used interchangeably and refer to the "total" testosterone concentration which is the sum of the bioavailable testosterone including free and bound testosterone concentrations. Unless otherwise specified, these values are "observed" testosterone concentrations without adjusting or correcting for the base-line serum testosterone levels in the subject(s). As with any bio-analytical measure, for increased consistency, the method employed to measure initial serum testosterone levels should be consistent with the method used to monitor and re-measure serum testosterone levels during clinical testing and testosterone therapy for a subject. Unless otherwise stated, "testosterone concentration" refers to serum total testosterone concentration.

Average serum testosterone concentrations can be determined using methods and practices known in the art. For example, the average baseline plasma testosterone concentration of a human male is the arithmetic mean of the total plasma testosterone concentration determined on at least two consecutive time points that are reasonably spaced from each other, for example from about 1 hour to about 168 hours apart. In a particular case, the plasma testosterone concentration can be determined on at least two consecutive times that are about 12 hours to about 48 hours apart. In another particular method, the plasma testosterone concentration of the human male can be determined at a time between about 5 o'clock and about 11 o'clock in the morning. Further, the plasma testosterone concentration can be the determined by standard analytical procedures and methods available in the art, such as for example, automated or manual immunoassay methods, liquid chromatography or liquid chromatography-tandem mass spectrometry (LC-MSMS) etc.

As used herein, "free testosterone serum concentration", refers to the testosterone concentration not bound to protein e.g., SHBG or albumin. In some aspects of the methods described herein, free testosterone serum concentrations are used instead of serum total testosterone concentrations. For example, a subject can appear to have total serum testosterone levels in the normal range but can be still considered hypogonadal or testosterone deficient based on free testosterone levels.

As used herein, "in need of treatment" refers to a subject that has a disease or is suspected of having the disease according to various diagnostic criteria typically used in practice, or desires treatment or is indicated for treatment. Thus, "in need of treatment" can include the step of identifying a subject in need of treatment.

As used herein, "identifying a subject in need of treatment" can include the step of obtaining a biological sample from the subject and determining the level of one or more biomarkers as described herein, assessing the histology of a biological sample obtained from said subject, performing an imaging analysis on the subject, assessing one or more clinical characteristics of said subject (e.g., assessing symptoms or overt symptoms), or a combination thereof.

As used herein, the term $AUC_{t1-t2}$ is the area under the curve of a plasma-versus-time graph determined for the analyte from the time "t1 to time t2". Wherein t1 and t2 are times (in hours) post dosing. For Example, t1 could be 1 hour and t2 could be 2 hours.

As used herein, the term "$C_{avg}$," "$C_{ave}$," or "C-average" are used interchangeably, and is determined as the $AUC_{t1-t2}$ mean AUC divided by the time period (|t1-t2|). For example, $C_{avg\ t0-t8}$ is the average plasma concentration over a period of 8 hours from t1=0 to t2=8 hours) post-dosing determined by dividing the $AUC_{t0-t8}$ value by 8. Similarly, $C_{avg\ t0-t12}$ is the average plasma concentration over a period of 12 hours post-dosing determined by dividing the $AUC_{t0-t12}$ value by 12 (t1=0-t2=12). Similarly, $C_{avg\ t12-t24}$ is the average plasma concentration over a period of 12 hours post-dosing determined by dividing the $AUC_{t1-t24}$ value by 12 (t1=12-t2=24); $C_{avg-t24}$ is the average plasma concentration over a period of 24 hours post-dosing determined by dividing the $AUC_{t0-t24}$ value by 24 (t1=0-t2=24), and so on. Unless otherwise stated, all $C_{avg}$ values are considered to be $C_{avg-t24}$ and unless otherwise stated, all the time values are expressed in hours (h). For example, the term $C_{avgt0-t24}$ denotes $C_{avg}$ from time zero (0) to 24 hours post dosing.

"Androgen receptor agonists" as used herein refers to compounds or molecules such as testosterone that bind and activate the androgen receptor. Androgen receptor agonists include, but are not limited to, dihydrotestosterone, mibolerone, testosterone, methyltrienolone, oxandrolone, nandrolone and fluoxymesterone. Where appropriate, fatty acid esters of these androgen receptor agonists can be used herein accordingly.

"Testosterone ester" as used herein refers to testosterone esterified with a fatty acid and includes but is not limited to, testosterone undecanoate, testosterone tridecanoate, testosterone enanthate, testosterone decanoate, testosterone palmitate, testosterone cypionate, and testosterone propionate. In one aspect, a preferred testosterone ester for oral administration according to the methods and compositions described herein is testosterone undecanoate. In one aspect, a preferred testosterone ester for oral administration according to the methods and compositions described herein is testosterone decanoate. In one aspect, a preferred testosterone ester for oral administration according to the methods and compositions described herein is testosterone dodecanoate. In one aspect, a preferred testosterone ester for oral administration according to the methods and compositions described herein is testosterone tridecanoate. In one aspect, a preferred testosterone ester for oral administration according to the methods and compositions described herein is testosterone tetradecanoate.

"Fibrosis," or "Liver Fibrosis" as used herein, refers to the accumulation of extracellular matrix constituents that occurs following trauma, inflammation, tissue repair, immunological reactions, cellular hyperplasia, and neoplasia.

"Normal Range" as used herein refers to a range of values generally considered to be representative of a healthy individual or population. It is understood that "normal range" is general specific to a type of assay or lab. For example, for a particular analyte, a normal range for one assay or lab can differ as compared to a normal range for another assay or lab for the same analyte. Thus, the normal ranges described herein may vary from lab to lab or assay to assay. The skilled artisan understands that the normal ranges disclosed herein can vary from individual to individual. The skilled artisan understands that the normal ranges described herein are typically appropriate for the indicated sample e.g., serum and that other samples e.g., saliva can have different normal ranges.

"Upper Normal Range" as used herein refers to above the 50% level for that range. For example, a biomarker may have a normal range of 10-40 U/L, according to this definition, the upper normal range is above 25 U/L and below 40 U/L. In another example, consider a biomarker having a range of 43-115 U/L, the high normal range is above 79 U/L and below 115 U/L.

As used herein, "ALT normal range" refers to the range of serum alanine transaminase values considered normal for healthy individuals and is from about 10-40 U/L according to the assay/lab used in Example 1.

As used herein, "AST normal range" refers to the range of serum aspartate transaminase values considered normal for healthy individuals and is from about 10-43 U/L according to the assay/lab used in Example 1.

As used herein, "ALP normal range" refers to the range of serum alkaline phosphatase values considered normal for healthy individuals and is from about 43-115 U/L according to the assay/lab used in Example 1.

As used herein, "GGT normal range" refers to the range of serum gamma-glutamyl transferase values considered normal for healthy individuals and is from about 10-49 U/L according to the assay/lab used in Example 1.

As used herein, "triglyceride normal range" refers to the range of serum triglyceride values considered normal for healthy individuals and is from about 45-200 mg/dL according to the assay/lab used in Example 1.

As used herein, "LDL normal range" and is from about 50-160 mg/dL according to the assay/lab used in Example 1.

As used herein, "desirable total cholesterol" or "total cholesterol normal range" and for adults is from about 125-200 mg/dL according to the assay/lab used in Example 1.

As used herein, "non-HDL cholesterol normal range" for adults is 130-159 mg/dL (3.4 4.0 mmol/L) is considered near ideal. The skilled artisan realizes that an ideal level depends on a number of factors and the normal range is variable depending on these factors.

As used herein, "VLDL" refers to very low density lipoprotein and has a normal range of 2 to 30 mg/dL.

As used herein, "SHBG" refers to sex hormone binding globulin and has a normal range of about 20 to 60 nmol/L for healthy adult males. As with any other of the biomarkers disclosed herein the normal ranges depend on a number of factors including sex and age e.g., Adult female, premenopausal 40-120 nmol/L; Adult female, postmenopausal 28-112 nmol/L; Adult male; 20-60 nmol/L; Infant (1-23 months) 60-252 nmol/L; Prepubertal (2 years-8 years) 72-220 nmol/L; Pubertal female 36-125 nmol/L; and Pubertal male 16-100 nmol/L.

As used herein, terms such as fatty liver disease, liver fibrosis, alcoholic liver disease, hepatitis, steatosis, NAFLD, NASH, and NASH with cirrhosis are given their customary meaning to one of ordinary skill in the art and such condition are identifiable and diagnosable by medical professionals such as physicians, hepatologists, gastroenterologists and the like based on assessment of the relevant disease characteristics in patients.

Methods

As described below, it was discovered that compositions containing steroids e.g., steroid esters can be used to treat subjects e.g., male or female human subjects with a variety of diseases and conditions including, but not limited to, those described in the summary section herein or as described below. The ordinary skilled artisan understand that these composition and methods can be used for other diseases and conditions based on this disclosure.

Although some of the description focuses on the oral administration of testosterone esters, the methods and compositions described herein can be adapted to other pharmaceuticals such as androgen agonists, androgens, androgenic-anabolic compounds, selective androgen receptor modulators and other compounds that target androgen receptor signaling pathways in view of the studies described herein.

In one embodiment, a method of reducing the risk of steatosis progressing to cirrhosis in a subject is provided said method comprising oral administration of a pharmaceutical composition having a testosterone ester (e.g., testosterone undecanoate or testosterone tridecanoate) to said subject. In one aspect, the subject is in need of treatment e.g., having steatosis or at risk for having steatosis progressing to cirrhosis. In one aspect, the subject in need of treatment has one or more biomarkers (or clinical characteristics) indicating an increased risk of steatosis progressing to cirrhosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect of this method, oral administration of the testosterone ester reduces the risk of steatosis progressing to cirrhosis while not substantially increasing serum levels of or decreases serum levels of lipoprotein-associated phospholipase A2. In one aspect of this method, the subject has alcoholic or non-alcoholic steatosis. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia. In one aspect, said method increases said subject's serum testosterone levels over their baseline. In another aspect, said method increases said subject's serum testosterone levels into the normal range. In one aspect, said method comprises oral administration of 200 mg to 750 mg of testosterone undecanoate per day to a male subject. In one aspect, said method comprise oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In another embodiment, a method of increasing the amount of time a subject having cirrhosis can survive while waiting for a liver transplant is provided said method comprising oral administration of a pharmaceutical composition having a testosterone ester (e.g., testosterone undecanoate or testosterone tridecanoate) to said subject. In one aspect, the subject is in need of treatment e.g., having cirrhosis or at risk of dying from cirrhosis or is waiting for a liver transplant. In one aspect, the subject in need of treatment has one or more biomarkers (or clinical characteristics) indicating compromised survival time while waiting for a liver transplant. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect of this method, oral administration of the testosterone ester increases the amount of time a subject having cirrhosis can survive while waiting for a liver transplant while not substantially increasing serum levels of or decreases serum levels of lipoprotein-associated phospholipase A2. In one aspect, the treatment reduces the subject's MELD score or reduces the rate of increase. In one aspect, said method increases said subject's serum testosterone levels over their baseline. In another aspect, said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In yet another embodiment, a method of reducing fatty liver in a subject is provided said method comprising oral administration of a pharmaceutical composition having a testosterone ester (e.g., testosterone undecanoate or testosterone tridecanoate) to said subject. In one aspect, the subject is in need of treatment e.g., has fatty liver or fatty liver disease or has increased risk of having fatty liver disease. In one aspect, the subject in need of treatment has one or more biomarkers (or clinical characteristics) indicating fatty liver or increasing fatty liver. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect of this method, the subject has testosterone deficiency. In one aspect of this method, oral administration of the testosterone ester reduces fatty liver while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In yet another embodiment, a method of reducing the rate of fatty liver increase in a subject is provided said method comprising oral administration of a pharmaceutical composition having a testosterone ester (e.g., testosterone undecanoate or testosterone tridecanoate) to said subject. In one aspect, the subject is in need of treatment e.g., has fatty liver or increasing fatty liver. In one aspect, the subject in need of treatment has one or more biomarkers (or clinical characteristics) indicating increasing fatty liver. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester reduces the rate of fatty liver increase while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $^{1}/_{10}{}^{th}$-$^{1}/_{15}{}^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one embodiment, a method of reducing progression or the risk of progression of fatty liver to NAFLD in a subject having or suspected of having fatty liver is provided said method comprising oral administration of a pharmaceutical composition having a testosterone ester (e.g., testosterone undecanoate or testosterone tridecanoate) to said subject. In one aspect, the subject is in need of treatment e.g., has fatty liver or is at risk of having fatty liver progressing to NAFLD. In one aspect, the subject in need of treatment has one or more biomarkers (or clinical characteristics) indicating an increased risk of fatty liver progressing to NAFLD. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect of this method, oral administration of the testosterone ester reduces progression of fatty liver disease to NAFLD while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprise oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $^{1}/_{10}{}^{th}$-$^{1}/_{15}{}^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In yet another embodiment, a method of reducing progression or the risk of progression of NAFLD to NASH in a subject having or suspected of having NAFLD is provided said method comprising oral administration of a pharmaceutical composition having a testosterone ester (e.g., testosterone undecanoate or testosterone tridecanoate) to said subject. In one aspect, the subject is in need of treatment e.g., has NAFLD or is at risk of having NAFLD progressing to NASH. In one aspect, the subject in need of treatment has one or more biomarkers (or clinical characteristics) indicating an increased risk of NAFLD progressing to NASH. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect of this method, oral administration of the testosterone ester reduces the risk of steatosis progressing to cirrhosis while not substantially increasing serum levels of or decreases serum levels of lipoprotein-associated phospholipase A2. In one aspect of this method, oral administration of the testosterone ester reduces the risk of NAFLD progressing to NASH while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one embodiment, a method of reducing progression or the risk of progression of NASH to cirrhosis in a subject having or suspected of having NASH is provided said method comprising oral administration of a pharmaceutical composition having a testosterone ester (e.g., testosterone undecanoate or testosterone tridecanoate) to said subject. In one aspect, the subject is in need of treatment e.g., has NASH or is at risk of having NASH progressing to cirrhosis. In one aspect, the subject in need of treatment has one or more biomarkers (or clinical characteristics) indicating an increased risk of NASH progressing to cirrhosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester reduces the progression of NASH to cirrhosis while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprise oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In an embodiment, a method for treating a subject at risk of having steatosis progressing to cirrhosis is provided said method comprising oral administration of a pharmaceutical composition having a testosterone ester (e.g., testosterone undecanoate or testosterone tridecanoate) to said subject. In one aspect, the subject is in need of treatment. In one aspect, the subject in need of treatment has one or more biomarkers (or clinical characteristics) indicating an increased risk of steatosis progressing to cirrhosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester reduces the risk of steatosis progressing to cirrhosis while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one embodiment, a method for improving survival of a subject waiting for a liver transplant or decreasing mortality is provided said method comprising oral administration of a pharmaceutical composition having a testosterone ester (e.g., testosterone undecanoate or testosterone tridecanoate) to a subject in need of treatment. In one aspect, the subject is in need of treatment e.g., is on a liver transplant waiting list or is in need of a liver transplant. In one aspect, the subject in need of treatment has one or more biomarkers (or clinical characteristics) indicating compromised survival. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester improves the survival (e.g., reduces mortality) of subjects while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprise oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In an embodiment, a method of improving serum alkaline phosphatase levels in a subject is provided said method comprising oral administration of a pharmaceutical composition having a testosterone ester (e.g., testosterone undecanoate or testosterone tridecanoate) to said subject in need of treatment (e.g., having liver disease or at risk of having liver disease). In one aspect, the subject in need of treatment has one or more biomarkers (or clinical characteristics) indicating a need for reduction in alkaline phosphatase levels. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester improves serum alkaline phosphatase levels while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In another embodiment, a method for improving serum alanine aminotransferase levels in a subject is provided said method comprising oral administration of a pharmaceutical composition having a testosterone ester (e.g., testosterone undecanoate or testosterone tridecanoate) to said subject. In one aspect, the subject is in need of treatment (e.g., has liver disease or is at risk of having liver disease). In one aspect, the subject in need of treatment has one or more biomarkers (or clinical characteristics) indicating a need for improving serum aminotransferase levels. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect of this method, oral administration of the testosterone ester improves serum alanine transaminase levels while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect, the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, cardiovascular disease, thyroid dysfunction, chronic kidney disease, liver disease, osteoporosis, hypogonadism, hypertension, sarcopenia, or cachexia.

In yet another embodiment, a method for improving serum aspartate aminotransaminase levels in a subject is provided said method comprising oral administration of a pharmaceutical composition having a testosterone ester (e.g., testosterone undecanoate or testosterone tridecanoate) to said subject. In one aspect, the subject is in need of treatment (has liver disease or is at risk of having liver disease). In one aspect, the subject in need of treatment has one or more biomarkers (or clinical characteristics) indicating a need for improving serum aspartate aminotransaminase levels. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester reduces the risk of steatosis progressing to cirrhosis while not substantially increasing serum levels of or decreases serum levels of lipoprotein-associated phospholipase A2. In one aspect, said method increases said subject's serum testosterone levels over their baseline. In another aspect, said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 46-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In another embodiment, a method for treating or preventing hepatic steatosis in a subject is provided said method comprising oral administration of a pharmaceutical composition having a testosterone ester (e.g., testosterone undecanoate or testosterone tridecanoate) to said subject. In one aspect, the subject is in need of treatment (e.g., has liver disease or is at risk of having liver disease). In one aspect, the subject in need of treatment has one or more biomarkers (or clinical characteristics) indicating an increased risk of hepatic steatosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect, said method increases said subject's serum testosterone levels over their baseline. In another aspect, said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one embodiment, a method of improving the ratio of serum alkaline phosphatase levels to (a) aspartate aminotransaminase levels, (b) alanine aminotransferase or (c) both (b) and (c) in a subject is provided said method comprising oral administration of a pharmaceutical composition having a testosterone ester (e.g., testosterone undecanoate or testosterone tridecanoate) to said subject. In one aspect, the subject is in need of treatment (has liver disease or is at risk of having liver disease). In one aspect, the subject in need of treatment has one or more biomarkers (or clinical characteristics) indicating a need for improving the ratio of serum alkaline phosphatase levels to (a) aspartate aminotransaminase levels, (b) alanine aminotransferase or (c) both (b) and (c). In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect of this method, oral administration of the testosterone ester improves serum aspartate transaminase levels while not substantially increasing serum levels of or decreases serum levels of lipoprotein-associated phospholipase A2. In one aspect, said method increases said subject's serum testosterone levels over their baseline. In another aspect, said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 46-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In yet another embodiment, a method of treating anemia in a subject is provided said method comprising oral administration of a pharmaceutical composition having a testosterone ester (e.g., testosterone undecanoate or testosterone tridecanoate) to said subject in need of treatment (e.g., has liver disease or is at risk of having liver disease). In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect of this method, oral administration of the testosterone ester treats anemia in a subject having liver disease while not substantially increasing serum levels of or decreases serum levels of Lipoprotein-associated phospholipase A2. In one aspect, said method increases said subject's serum testosterone levels over their baseline. In another aspect, said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15$th of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In again another embodiment, a method of treating graft rejection in a subject is provided said method comprising oral administration of a pharmaceutical composition having a testosterone ester (e.g., testosterone undecanoate or testosterone tridecanoate) to said subject (e.g., has received a liver transplant). In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the subject in need of treatment has one or more biomarkers (or clinical characteristics) indicating an increased risk of graft rejection. In one aspect, the one or more biomarkers are outside the normal range. In one aspect, the one or more biomarkers are above the normal range but below 2 times the upper limit of the normal range. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester treats graft rejection while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprise oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In another embodiment, a method of treating alcoholic steatosis in a subject is provided said method comprising oral administration of a pharmaceutical composition having a testosterone ester (e.g., testosterone undecanoate or testosterone tridecanoate) to said subject. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the subject in need of treatment has one or more biomarkers (or clinical characteristics) related to alcoholic steatosis. In one aspect, said subject is in need of treatment e.g., has an increased risk of alcoholic steatosis or progression of alcoholic steatosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester treats alcoholic steatosis while not substantially increasing serum levels of or decreases serum levels of Lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In another embodiment, a method of treating alcoholic cirrhosis in a subject is provided said method comprising oral administration of a pharmaceutical composition having a testosterone ester (e.g., testosterone undecanoate or testosterone tridecanoate) to said subject (e.g., having alcoholic cirrhosis). In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the subject in need of treatment has one or more biomarkers (or clinical characteristics) related to alcoholic cirrhosis. In one aspect, said subject is in need of treatment e.g., has an increased risk of alcoholic cirrhosis or progression of alcoholic cirrhosis or increased risk of death from alcoholic cirrhosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester treats alcoholic cirrhosis while not substantially increasing serum levels of or decreases serum levels of Lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In another embodiment, a method of treating alcoholic liver disease in a subject is provided said method comprising oral administration of a pharmaceutical composition having a testosterone ester (e.g., testosterone undecanoate or testosterone tridecanoate) to said subject. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the subject in need of treatment has one or more biomarkers (or clinical characteristics) of alcoholic liver disease. In one aspect, said subject is in need of treatment e.g., has an increased risk of alcoholic liver disease or progression of alcoholic liver disease or increased risk of death from alcoholic liver disease. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester treats alcoholic liver disease while not substantially increasing serum levels of or decreases serum levels of Lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $1/10^{th}$-$1/15^{th}$ of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one aspect, the methods described herein are useful for treating a fibrotic condition of the liver. In certain embodiments, the fibrotic condition of the liver is chosen from one or more of: fatty liver disease, steatosis (e.g., nonalcoholic steatohepatitis (NASH), cholestatic liver disease (e.g., primary biliary cirrhosis (PBC), cirrhosis, alcohol-induced liver fibrosis, biliary duct injury, biliary fibrosis, cholestasis or cholangiopathies. In some embodiments, hepatic or liver fibrosis includes, but is not limited to, hepatic fibrosis associated with alcoholism, viral infection, e.g., hepatitis (e.g., hepatitis C, B or D), autoimmune hepatitis, non-alcoholic fatty liver disease (NAFLD), progressive massive fibrosis, exposure to toxins or irritants (e.g., alcohol, pharmaceutical drugs and environmental toxins).

The methods and compositions described herein are also directed to methods of inhibiting or reducing the likelihood of liver injury in a patient at risk for same occurring from or secondary to a variety of etiologies especially including hepatitis (all forms, especially including hepatitis viral), non-alcoholic fatty liver diseases (NAFLD), including non-alcoholic steatohepatitis (NASH), NAFLD or NASH including primary NASH, NASH secondary to liver transplantation (NASH post-liver transplantation), preservation injury of donated organs, acute and chronic liver transplant rejection and metabolic conditions including, for example, Wilson's disease, hemochromatosis, and alpha one antitrypsin deficiency represent alternative aspects of the present invention. In this method, an effective amount of a composition described herein is administered to a patient at risk for liver injury as described above in order to inhibit or reduce the likelihood of liver injury as described above. As a consequence of the actions of compounds according to the present invention in reducing and/or inhibiting liver injury, certain complications of liver injury may be reduced including, for example, liver failure, liver shock, obstructive jaundice, cirrhosis, including primary biliary cirrhosis, primary sclerosing cholangitis, portal hypertension, ascites, variceal bleeding, encephalopathy, depression, malaise, renal disease, arthritis, portal vein thrombosis, and budd chiari. The present disclosure is also directed to treating liver injury and/or reducing the likelihood of further liver injury associated with or occurring directly from or secondary to a variety of etiologies especially including hepatitis (all forms), cirrhosis (all types), non-alcoholic fatty liver diseases (NAFLD), including non-alcoholic steatohepatitis (NASH), NAFLD or NASH including primary NASH, NASH secondary to liver transplantation (NASH post-liver transplantation), preservation injury of donated organs, acute and chronic liver transplant rejection and metabolic conditions including, for example, Wilson's disease, hemochromatosis, and alpha one antitrypsin deficiency. In this method, an effective amount of an androgen receptor agonist according to the present invention is administered to a patient with liver injury and/or at risk for further liver injury as described above in order to treat, inhibit or reduce the likelihood of liver injury which occurs directly as a consequence of or secondary to one or more of the disease states and/or conditions as described above. As a consequence of the treatment methods described above, the occurrence and/or severity of one or more of the following conditions will be substantially reduced: liver failure, liver shock, obstructive jaundice, primary biliary cirrhosis, primary sclerosing cholangitis, portal hypertension, ascites, variceal bleeding, encephalopathy, depression, malaise, renal disease, arthritis, portal vein thrombosis and budd chiari.

As the skilled artisan readily recognizes the embodiments disclosed herein can be adapted to pediatric subjects e.g., subjects less than 18 years old. The doses of active ingredients used can be adjusted accordingly depending on the age and sex of the subject.

In any of the methods disclosed herein, the step of identifying a subject in need of treatment can include the step of determining the number of CAG or GGN repeats in the subject's androgen receptor gene. The skilled artisan is capable of using this information for identifying subjects in need of treatment, providing specific doses of the androgen receptor agonists (e.g., testosterone undecanoate or testosterone tridecanoate), or both, as described herein.

Without wishing to be bound by theory, it is believed that is some aspects of the embodiments described herein, the method and compositions can normalize ratios of serum testosterone to estradiol. Thus, in some aspects, subjects are believed to have a testosterone to estradiol ratio imbalance which can be treated, and therefore become more normal.

Without wishing to be bound by theory, it is believed that is some aspects of the embodiments described herein, the methods and compositions described herein exerted surprising or expected effects in liver and related disease because they are delivered orally e.g., perorally, and absorbed via the intestinal lymphatic system. It is contemplated that delivery via the intestinal lymphatic system provides surprising or unexpected results due to one or more of the following: effects in the lymphatic or interstitial compartment, improved delivery to target tissues or cells (e.g., one or more of fat, adipocytes, preadipocytes, liver, liver cells, hepatocytes, adipose, white blood cells, red blood cells, stem cells, bone, bone cells, stem cells, androgen receptor cells, non-androgen receptor containing cells, cells involved in glucose metabolism, and cells involved in fatty acid metabolism). Thus, in some specific aspects, delivery of the compositions via the methods disclosed herein results in transport of the active agent (e.g., testosterone ester) via intestinal lymphatics, chylomicrons, chylomicron remnants to specific target tissues and cells to exert or provide the unexpected or surprising results described herein.

In some aspects of the method embodiments described herein, the treatments with oral testosterone esters in testosterone deficient subjects, raise the subject's serum testosterone levels over baseline or e.g., into the normal or eugonadal range for from 0-2 hours, 2-4 hours, 4-6 hours, 6-8 hours, 8-10 hours, 10-12-hour, 12-14 hours, 14-18 hours, 18-20 hours, 20-22 hours, or 22-24 hours per day.

Combination Therapy

In some embodiments of the methods disclosed herein, the oral testosterone ester therapy is in conjunction with another therapeutic treatment. In one aspect, the oral testosterone therapy is administered with one or more additional therapeutic agents (not necessarily at the same time or frequency as the oral testosterone ester therapy or androgen receptor agonist therapy). In some embodiments the one or more additional therapeutic agent is a statin. In some embodiments the statin is atorvastatin, rosuvastatin, simvastatin, pravastatin, lovastatin, fluvastatin, or pitavastatin. In one aspect, the amount of atorvastatin administered per day is from about 10 mg to about 60 mg. In one aspect, the amount of rosuvastatin administered per day is from about 5 mg to about 20 mg. In one aspect, the amount of simvastatin administered per day is from about 10 mg to about 40 mg. In one aspect, the amount of pravastatin administered per day is from about 10 mg to about 80 mg.

In one aspect, the amount of lovastatin administered per day is from about 20 mg to about 40 mg. In one aspect, the amount of fluvastatin administered per day is from about 20 mg to about 80 mg. In one aspect, the amount of pitavastatin administered per day is from about 1 mg to about 4 mg. In one aspect, the amount of atorvastatin is from about 10 mg to about 40 mg.

In one aspect, amount of rosuvastatin is from about 10 to about 20 mg. In one aspect, the amount of simvastatin is from about 10 mg to about 20 mg. In one aspect, the amount of pravastatin is from about 10 mg to about 20 mg. In one aspect, the amount of lovastatin is about 40 mg. In one aspect, the amount of fluvastatin is from about 20 mg to about 40 mg. In one aspect, the amount of pitavastatin is from about 1 mg to about 3 mg.

Combination therapies can include administration of more or more of the following: a FXR agonist, a PPAR alpha ordelta agent, a lipid modulator, an anti-inflammatory (e.g., steroidal or non-steroidal anti-inflammatory agents or other), an antioxidant, an immunomodulator, an insulin senitizer, an incretin mimetic, a hemorrheologic agent, an inhibitor of apoptosis, an agonist of the peroxisome proliferator, a thyroid hormone receptor modulator, an ASK1 inhibitor, an Acetyl-CoA Carboxylase (ACC) inhibitor, a fatty-acid/bile-acid Conjugate, galectin inhibitor, caspase protease inhibitor or a combination thereof in conjunction with the androgen receptor agonist (e.g., testosterone ester like testosterone undecanoate or testosterone tridecanoate).

The present disclosure is also directed to methods of treating hepatitis (all types, including non-alcoholic steatohepatitis (NASH)), cirrhosis (all types), fatty liver disease, including non-alcoholic fatty liver disease (NAFLD), including cirrhosis in a patient at risk, primary NASH or NASH secondary to liver transplantation, by administering an effective amount of an androgen receptor agonist compound as otherwise described hereinabove to said patient. In this aspect, a method for treating NAFLD, NASH including primary NASH, cirrhosis and/or NASH secondary to liver transplantation (NASH post-liver transplantation) comprises orally administering to a patient in need thereof an effective amount of a testosterone ester (e.g., testosterone undecanoate, testosterone tridecanoate, or a combination thereof) and vitamin E, a vitamin E prodrug or a vitamin E derivative, as otherwise disclosed herein, optionally in combination with a carrier, additive or excipient. In treating the above disease states and/or conditions there is an inhibition or a reduction in the likelihood of liver injury or that one or more of the following conditions will occur in the treated patient: liver failure, portal hypertension, ascites, variceal bleeding, encephalopathy, depression, malaise, renal disease, arthritis, portal vein thrombosis and/or budd-chiari. Thus, in one aspect, the methods described herein involve oral administration of a testosterone ester (e.g., testosterone undecanoate, testosterone tridecanoate, or a combination thereof) formulated with vitamin E, a vitamin E prodrug, or a vitamin E derivative. In a preferred aspect, the Vitamin E compound is d-alpha-tocopherol or d-alpha tocopherol acetate. In another preferred aspect, the amount of d-alpha-tocopherol (or it's acetate) administered per day is from about 100 IU to about 2000 IU, 200 IU to about 1600 IU per day, about 400 IU to about 1000 IU per day or about 600 IU to 900 IU per day. These amounts can be co-formulated with the testosterone esters or administered separately. The exemplary formulations described herein can be adapted accordingly to use d-alpha-tocopherol (or e.g., a prodrug thereof (d-alpha-tocopheryl acetate)), tocotrienol and other related Vitamin E related compounds. Thus, in certain aspects of this embodiment a method of treating a subject in need of treatment is provided, said method comprising identifying a subject in need of treatment (e.g., has a liver disease or condition) and orally administering a pharmaceutical composition having a testosterone ester (e.g., testosterone undecanoate or testosterone tridecanoate) to said subject in combination with one or more immunosuppressive agents. In one aspect, the subject in need of treatment has one or more biomarkers (or clinical characteristics) indicating a need for combination treatment. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester improves liver disease or reduces the risk of liver disease while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about $\frac{1}{10}$th-$\frac{1}{15}$th of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In certain embodiments related to the treatment of liver disease, liver injury, NAFLD, NASH or cirrhosis which occurs secondary to a liver transplant, including acute and chronic transplant rejection, the compositions described hereincan be co-administered (e.g., according to the methods described herein) to the transplant patient with an effective amount at least one immunosuppressive agent chosen from Sandimmune (cyclosporine), Neoral (cyclosporine), Prograf (tacrolimus), prednisone, Imuran (azathioprine), Cellcept (mycophenolate mofetil), Zenapax (daclizumab), or Simulect (basiliximab). Thus, in certain aspects of this embodiment a method of treating a subject in need of treatment is provided, said method comprising identifying a subject in need of treatment (e.g., a subject that has had a liver transplant) and orally administering a pharmaceutical composition having a testosterone ester (e.g., testosterone undecanoate or testosterone tridecanoate) to said subject in combination with one or more immunosuppressive agents. In one aspect, the subject in need of treatment has one or more biomarkers (or clinical characteristics) indicating a need for combination treatment. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, oral administration of the testosterone ester improves liver disease or reduces the risk of liver disease while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about 1/10th-1/15th of these values. In one aspect the subject is from 18-25 years old, 26-35 years old, 36-45 years old, 45-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In other alternative embodiments, the compositions described herein can be administered to a patient where applicable (in those conditions such as NAFLD, NASH, etc. which occur as a consequence of metabolic syndrome and/or type II diabetes) in combination with an effective amount of one or more agents which are used to treat type II diabetes or metabolic syndrome including metformin, glibenclamide, gliclazide, rosiglitazone, pioglitazone, troglitazone, acarbose, miglitol, nateglinide, repaglinide, exenatide, sitagliptin, pramlintide and mixtures thereof. Thus, in certain aspects of this embodiment a method of treating a subject in need of treatment is provided, said method comprising identifying a subject in need of treatment (e.g., a subject that has liver disease or is at risk of having liver disease) and orally administering a pharmaceutical composition having a testosterone ester (e.g., testosterone undecanoate or testosterone tridecanoate) to said subject in combination with an agent useful for treating type II diabetes or metabolic syndrome. In one aspect, the subject in need of treatment has one or more biomarkers (or clinical characteristics) indicating a need for combination treatment. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect of this method, oral administration of the testosterone ester improves liver disease or reduces the risk of liver disease while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprise oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about 1/10th-1/15th of these values. In one aspect the subject is from 18-25 years old, 26-35 years old, 36-45 years old, 46-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, dyslipidemia, cardiovascular disease, thyroid dysfunction, chronic kidney disease, liver disease, osteoporosis, hypogonadism, hypertension, sarcopenia, or cachexia.

Certain embodiments relate to the treatment of hepatitis (alcoholic and non-alcoholic), which occurs as a consequence of infections (viral and non-viral), drugs, ischemia, toxins, pregnancy, alcohol, toxins, autoimmune conditions (systemic lupus erythematosus) and metabolic conditions, including Wilson's disease, hemochromatosis and alpha one antitrypsin deficieincy. Hepatitis which may be treated according to the present invention includes hepatitis which occurs as a consequence of infectious disease, especially including a viral infection such as a hepatitis A, B, C, D or E viral infection, or hepatitis which occurs as a consequence of a cytomegalovirus, Epstein-Barr, yellow fever, mumps virus, rubella virus, herpes simplex virus, or adenovirus infection or a non-viral selection including an infection from *toxoplasma*, leptospira, Q fever or Rocky Mountain Spotted Fever. In this embodiment, an androgen receptor agonist (e.g., testosterone undecanoate, testosterone tridecanoate, or a combination thereof) is administered in effective amounts to a patient with a viral hepatitis infection in order to inhibit, treat or reduce the likelihood of liver injury which occurs as a consequence of that viral or non-viral infection. Compositions described herein can be administered alone or in combination with an effective amount of an anti-hepatitis infectious agent, such as an anti-viral agent, including Hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof for hepatitis B infections and NM 283, VX-950 (telaprevir), SCH 50304, TMC435, VX-500, BX-813, SCH503034, R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NSSA, NS4B, ANA598, A-689, GNI-104, IDX102, ADX184, GL59728, GL60667, PSI-7851, TLR9 Agonist, PHX1766, SP-30 and mixtures thereof for hepatitis C infections. In some embodiments, additional pharmaceutical compositions especially useful for treating hepatitis from viral infections, in particular, hepatitis b or hepatitis C infections comprise an effective amount of one or more androgen receptor agonists (e.g., testosterone undecanoate or testosterone tridecanoate) as disclosed herein in combination with at least one agent selected from the group consisting of hepsera (adefovir dipivoxil), lamivudine, entecavir, telbivudine, tenofovir, emtricitabine, clevudine, valtoricitabine, amdoxovir, pradefovir, racivir, BAM 205, nitazoxanide, UT 231-B, Bay 41-4109, EHT899, zadaxin (thymosin alpha-1) and mixtures thereof for hepatitis B infections and NM 283, VX-950 (telaprevir), SCH 50304, TMC435, VX-500, BX-813, SCH503034 (boceprevir), R1626, ITMN-191 (R7227), R7128, PF-868554, TT033, CGH-759, GI 5005, MK-7009, SIRNA-034, MK-0608, A-837093, GS 9190, ACH-1095, GSK625433, TG4040 (MVA-HCV), A-831, F351, NS5A, NS4B, ANA598, A-689, GNI-104, IDX102, ADX184, GL59728, GL60667, PSI-7851, TLR9 Agonist, PHX1766, SP-30 and mixtures thereof, in combination with a pharmaceutically acceptable carrier, additive or excipient.

Biomarkers

Any appropriate biomarker can be used in the methods and compositions described herein (including imaging analysis, histology, genetic, microRNA and the such). Specific biomarkers are described herein in the method embodiments and Examples. Additional biomarkers, including some that are described herein elsewhere, are illustrated below.

In one embodiment, the methods and compositions described herein, are useful for treating a subject in need of treatment e.g., having NASH or suspected of having NASH or having fatty liver disease or having liver disease. Thus, the methods and compositions described herein can be used to treat NASH (or suspected of having NASH or having fatty liver disease or having liver disease) of any grade or type. In one aspect, the methods and compositions as disclosed herein, reduce liver fat (or e.g., steatosis) or reduce the rate of increase in liver fat (or steatosis). In one aspect, the methods and compositions can reduce liver fat by greater than 5%, 10%, 15%, 20%, 25% or 30% in at least 1, 5, 10, 20, 30, 40, or 50% of subjects treated. In one aspect, the biomarker (liver fat) is determined as a % mean relative reduction in liver fat reduction with MRI-PDFF (Magnetic Resonance Imaging-Derived Proton Density Fat Fraction). In one aspect, the methods and compositions reduce liver triglyceride concentration or decrease the rate of increase liver triglyceride concentration. In one aspect, the biomarker (liver triglyceride concentration) is measured by NMRS (magnetic resonance spectroscopy). In one aspect, the method and composition can improve or ameliorate diffuse liver disease due to liver fat or iron deposition by 5%, 10%, 15%, 20% or 25% or more. In one aspect, non-invasive magnetic resonance imaging (MRI-PDFF) is sued for the evaluation of liver fat or iron deposition. In one aspect, the methods and compositions disclosed herein, ameliorates fatty infiltration (e.g., reduces fatty infiltration or reduces the rate of increase of fatty infiltration). In one aspect, abdominal ultrasound is used to determine fatty infiltration. In one aspect, CT (computed tomography) is used to assess the liver biomarker. In one aspect, the methods and compositions described herein improve liver stiffness (LS)/fibrosis. In one aspect, improved liver stiffness/fibrosis is at least a 5, 10, 15, 20 or 25% reduction in MRE (Magnetic Resonance Elastography)-stiffness. In one aspect, ultrasound based elastography is used for the assessment of liver tissue stiffness in fibrosis. In one aspect, transient elastography (TE) (e.g., Fibroscan®, Echosens, Paris) is used (ultrasound-based elastography) to determine liver stiffness. In one aspect, pSWE (Elastography point quantification, ElastPQ™, Phillips) or ARFI imaging (Virtual touch tissue Quantification™, Siemens) is (ultrasound-based elastography techniques) used to assess liver stiffness. In one aspect, liver stiffness is monitored via Real Time TE (RTE) which is a qualitative assessment of liver stiffness. Magnetic resonance elastography (MRE) can determine liver stiffness by analysis of mechanical waves propagating through the liver. In one aspect, the methods and compositions disclosed herein reduce liver stiffness by 5, 10, 20, 30, 40, 50, 60 or 75% or more. In one aspect, the methods and compositions disclosed herein reduce the rate of increase of liver stiffness by 5, 10, 20, 30, 40, 50, 60 or 75% or more. In one aspect, the method and compositions disclosed herein improve on liver fibrosis as measured by non-invasive LiverMultiscan. In one aspect, the method and compositions reduce hepatic steatosis as monitored by imaging studies along with decreasing in ALT, CK18, or both. In one aspect, the methods and compositions described herein improve or ameliorate liver fibrosis as assed by histology and reduces risk of progression to cirrhosis. In one aspect, the methods and compositions described herein improve by at least 1 or 2 points (e.g., decrease) the NAFLD activity score (NAS). In one aspect, the methods and compositions described herein improve at least a point reduction in either lobular inflammation or hepatocellular ballooning. In one aspect, the methods and compositions improve or resolve NASH on overall histopathological interpretation by an experienced pathologist (e.g., target score of 0 on ballooning and 0 or 1 for inflammation, but no greater than 1) and no worsening of fibrosis (e.g., no one stage increase in on fibrosis score). In one aspect, the methods and compositions described herein reverse NASH (e.g., change from NAS score from 5 to 3) with no evidence of progression to advanced fibrosis (e.g., stage 3 or 4). In one aspect, the methods and compositions described herein improve fibrosis (e.g., lessen) without worsening of NAS or no progression of steatohepatitis (or reduce progression of steatohepatitis). In one aspect, the methods and compositions described herein do not increase NAFLD activity as assessed by NAS and lessen or reverse fibrosis. In one aspect, the methods and compositions described herein when used in a population of patients, at least 10%, 20%, 30% 40% or 50% or more achieve a ≥1-Stage Improvement in Fibrosis According to the NASH Clinical Research Network (CRN) Classification Without Worsening of NASH. In one aspect, the methods and compositions described herein prevent the development of cirrhosis or lessen the likelihood of progression to cirrhosis. In one aspect, the methods and compositions described herein slowing histological progression to cirrhosis. In one aspect, the methods and compositions described herein improve event free survival (e.g., as assessed by all-cause mortality, new decompensation events, MELD score progression). In one aspect, the methods and compositions described herein decrease in all-cause mortality. In one aspect, the methods and compositions described herein decrease in liver specific mortality. In one aspect, the methods and compositions described herein decrease liver transplantation rates. In one aspect, the methods and compositions described herein increase 12 month survival rates. In one aspect, the methods and compositions described herein increase event free survival (EFS) at week 52 as Assessed by Time to the First Clinical Event. In one aspect, the methods and compositions described herein decrease events/rate of events of decompensation in compensated patients. In one aspect, the methods and compositions described herein decrease rate of ascites events or ascites grade. In one aspect, the methods and compositions described herein decrease rate of HE or progress in HE (e.g., as assessed by MM). In one aspect, the methods and compositions described herein decrease in hospital admissions or hospital admission rates. In one aspect, the methods and compositions described herein decrease unscheduled clinic or ER visit. In one aspect, the methods and compositions described herein decrease the number of tests performed. In one aspect, the methods and compositions described herein decrease lost work days. In one aspect, the methods and compositions described herein decrease infection rates or number of events. In one aspect, the methods and compositions described herein improve the Child-Pugh-Turcotte Score. In one aspect, the methods and compositions described herein lower Progression from A to B In one aspect, the methods and compositions described herein do not worsen CPT. In one aspect, the methods and compositions described herein improve CPT score by at least 1 or 2 points. In one aspect, the methods and compositions described herein improve MELD score. In one aspect, the methods and compositions described herein lessen responder progression to higher MELD score. In one aspect, the methods and compositions described herein do not worsen MELD score. In one aspect, the methods and compositions described herein improve MELD score by at least one or two points. In one aspect, the methods and compositions described herein lower % of subjects achieving transplantation qualifying MELD score of 14. In one aspect, the methods and compositions described herein increase in MELD score from <12 to 15 or higher. In one aspect, the methods and compositions described herein improve the hepatic venous pressure gradient (HVPG). In one aspect, the methods and compositions described herein reduce of proportion of subjects that progress to HVPG>10 mm. In one aspect, the methods and compositions described herein lower HVPG<10 mm. In one aspect, the methods and compositions described herein reduce HVPG by 5, 10, 15, 20, 25 or 30% or more. In one aspect, the methods and compositions described herein improve body composition. In one aspect, the methods and compositions described herein improve bone density (e.g., one or more of femoral, lumbar, neck, and total bone mass. In one aspect, the methods and compositions described herein improve anemia. In one aspect, the methods and compositions described herein improve gynecomastia (e.g., lessen). In one embodiment, a method of reducing progression or the risk of progression of NASH to cirrhosis a subject having or suspected of having NASH is provided said method comprising oral administration of a pharmaceutical composition having a testosterone ester (e.g., testosterone undecanoate or testosterone tridecanoate) to said subject. In one aspect, the subject is in need of treatment e.g., has NASH or is at risk of having NASH progressing to cirrhosis. In one aspect, the subject in need of treatment has one or more biomarkers (or clinical characteristics) indicating an increased risk of NASH progressing to cirrhosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect of this method, oral administration of the testosterone ester reduces the progression of NASH to cirrhosis while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about ¹/₁₀th-¹/₁₅th of these values. In one aspect the subject is from 18-25 years old, 26-35 years old, 36-45 years old, 46-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one aspect, the methods and compositions disclosed herein improve or ameliorate, changes in body composition, muscle mass, appendicular lean mass, total lean mass, fat mass, high VAT (visceral adipose fat), waist circumference, weight gain, change in BMI, mobility/frailty: (e.g., timed up and go-TUG (mobility) score, hand grip strength, liver frailty index as measured by score in functional assessments of grip strength (kg), balance (seconds), and chair stands (seconds)), PROs: functional status of patient-COA-symptoms only known to patients, QOL (quality of life) assessed by the CLDQ, perceived HRQoL score, depression, mobility, sexual dysfunction, and FIS fatigue questionnaire, in a subject in need of treatment (e.g., as described in the method embodiments described herein and specifically subjects having cirrhosis, NASH, NAFLD, steatohepatitis, liver disease). In one embodiment, a method of reducing progression or the risk of progression of NASH to cirrhosis a subject having or suspected of having NASH is provided said method comprising oral administration of a pharmaceutical composition having a testosterone ester (e.g., testosterone undecanoate or testosterone tridecanoate) to said subject. In one aspect, the subject is in need of treatment e.g., has NASH or is at risk of having NASH progressing to cirrhosis. In one aspect, the subject in need of treatment has one or more biomarkers (or clinical characteristics) indicating an increased risk of NASH progressing to cirrhosis. In one aspect, the one or more biomarkers are outside the normal range. In one aspect, the one or more biomarkers are above the normal range but below 2 times the upper limit of the normal range. In one aspect of this method, the subject has testosterone deficiency. In one aspect, said subject in need of treatment has testosterone deficiency with serum testosterone levels of less than 350 ng/dL, 300 ng/dL, 250 ng/dL, 200 ng/dL, 150 ng/dL or 100 ng/dL. In one aspect, the one or more biomarkers are above the normal range but between 2-3 times the upper limit of the normal range or more. In one aspect, the one or more biomarkers are above the normal range but below 2 times the upper limit of the normal range. In one aspect of this method, the subject has testosterone deficiency. In one aspect of this method, oral administration of the testosterone ester reduces the progression of NASH to cirrhosis while not substantially increasing serum levels of or decreases serum levels of lipoprotein-associated phospholipase A2. In one aspect, said method increases said subject's serum testosterone levels over their baseline. In another aspect said method increases said subject's serum testosterone levels into the normal range. In one aspect, said method comprises oral administration of 200 mg to 750 mg of testosterone undecanoate per day to a male subject. In one aspect, said method comprises oral administration of 300 mg to 600 mg of testosterone undecanoate per day to a male subject. In one aspect, said method comprises oral administration of 450 mg of testosterone undecanoate per day to a male subject. In one aspect, said method comprises oral administration of about 400 mg to 2000 mg of testosterone tridecanoate per day to a male subject. In one aspect, said method comprises oral administration of about 600 mg to 1800 mg of testosterone tridecanoate per day to a male subject. In one aspect, said method comprises oral administration of about 500 mg, 750 mg, 1000 mg, or 1250 mg of testosterone tridecanoate per day to a male subject. These dose ranges are typically those for male subjects whereas the female dose range corresponds to about ¹/₁₀th-¹/₁₅th of these values. In one aspect the subject is from 18-25 years old, 26-35 years old, 36-45 years old, 46-55 years old, 56-65 years old or older than 65 years old. In one aspect, the biomarker is one or more chosen from ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, any specific biomarkers disclosed in the Tables of Example 1, imaging biomarkers, liver histology biomarkers, biomarkers in the literature related to the disease and condition described herein, and liver damage biomarkers. In one aspect of this embodiment, the subject has one or more of the following comorbidities: obesity, type 2 diabetes, dyslipidemia, cardiovascular disease, thyroid dysfunction, chronic kidney disease, liver disease, osteoporosis, hypogonadism, hypertension, sarcopenia, or cachexia.

In one aspect, the methods and compositions described herein are utilized in conjunction with one, two or three or more serum biomarkers.

In one aspect, the methods and compositions described herein are utilized in conjunction with one, two or three or more lipogenesis/lipid transporters biomarkers.

In one aspect, the methods and compositions described herein are utilized in conjunction with one, two or three or more lipogenesis/lipid transporters biomarkers chosen from acetyl-coA carboxylase (ACC), fatty acid transport protein-5 (FATP-5) or the fatty acid transporter CD36, liver-fatty acid binding protein (FABP), Ceramides, 3-nitrotyrosine (oxidative stress marker), HNE (4-hydroxy-2-noneal, a marker of lipid peroxidation), 8-hydroxydeoxyguanosine (a marker of oxidative DNA damage), Glutamate dehydrogenase (mitochondrial marker enzyme), Glucose 6-phosphatase (microsomal enzyme marker), LD or LDH (Lactate dehydrogenase), and resitsin.

In one aspect, the methods and compositions described herein are utilized in conjunction with one, two or three or more lipo-Apoptosis biomarkers e.g., CK-18 (cytokeratin 18) Cathepsin B, caspase cleaved CK18, flCK, caspase 3/7, platelet count, full blood cell count (e.g., thrombocytopenia, al-antitrypsin, ferritin, and adipokines (e.g., adiponectin and leptin).

In one aspect, the methods and compositions described herein are utilized in conjunction with one, two or three or more metalloproteinase biomarkers e.g., (MMPs)-MMPs 2, MMP-3, and MMP-9.

In one aspect, the methods and compositions described herein are utilized in conjunction with transforming growth factor (TGF)-β1 as a biomarker.

In one aspect, the methods and compositions described herein are utilized in conjunction with one or more tissue inhibitors of metalloproteinases (TIMPs) as biomarkers e.g., TIMP-1, TIMP-2, Microfibril-associated protein 4 (MFAP4).

In one aspect, the methods and compositions described herein are utilized in conjunction with hyaluronic acid (HA) N Glycans profiles as biomarkers.

In one aspect, the methods and compositions described herein are utilized in conjunction with one or more of the following biomarkers: Laminin, Procollagen type III amino-terminal peptide (PIIINP), Chitinase-3-like protein 1 (CHI3L1 or YKL-40), CTGF (connective tissue growth factor), and Collagen type IV-S or VI.

In one aspect, the methods and compositions described herein are utilized in conjunction with pro-inflammation and pro-fibrotic mediators as biomarkers.

In one aspect, the methods and compositions described herein are utilized in conjunction with one, two or three or more of hs-CRP or cytokine biomarkers. In one aspect, the methods and compositions described herein are utilized in conjunction with one, two or three or more biomarkers chosen from IL-1, IL-1 beta, NF-KappaB, MCP-1(CCL2-Chemokine) IL-6, IL-8, RBP-4, soluble CD14, TNF-alpha, MCP-1, leptin, visfatin, adiponectin, fibrinogen, fibrinonectin, collagens (I-III), undulin, elastin, proteoglycans, PICP (procollagen type 1 carboxy terminal peptide), ICAM, VCAM (adhesion molecules), and JNK (protein kinase).

In one aspect, the methods and compositions described herein are utilized in conjunction with one, two or three or more biomarkers that are liver enzymes. In one aspect, the methods and compositions described herein are utilized in conjunction with one, two or three or more of alanine amino transferase (ALT), aspartate amino transferase (AST), alkaline phosphatase (ALP), and gamma glutamyl transferase (GGT).

In one aspect, the methods and compositions described herein are utilized in conjunction with one, two or three or more biomarkers of synthetic function. In one aspect, the methods and compositions described herein are utilized in conjunction with one, two or three or more biomarkers of synthetic function chosen from prothrombin time (PT/INR), bilirubin, haptoglobin, hemoglobin, albumin, Apolipoprotein A1, α2-macroglobulin, ceruloplasmin, transferrin and hepcidin, sodium serum alpha protein, circulating ammonia, and creatinine.

In one aspect, the methods and compositions described herein are utilized in conjunction with one, two or three or more hormone or endocrine biomarkers. In one aspect, the methods and compositions described herein are utilized in conjunction with one, two or three or more hormone or endocrine biomarkers chosen from Prolactin, LH, FSH, E, TT, freeT, DHT, SHBG, oestrone, thyroid panel, and cortisol.

In one aspect, the methods and compositions described herein are utilized in conjunction with one, two or three or more hypertension related biomarkers.

In one aspect, the methods and compositions described herein are utilized in conjunction with one, two or three or more diabetes related biomarkers. In one aspect, the methods and compositions described herein are utilized in conjunction with one, two or three or more diabetes related biomarkers chosen from HB1AC, Impaired Fasting glucose, fasting insulin, and HOMA-IR (Homeostasis Model Assessment-insulin resistance).

In one aspect, the methods and compositions described herein are utilized in conjunction with one, two or three or more anemia related biomarkers. In one aspect, the methods and compositions described herein are utilized in conjunction with one, two or three or more anemia related biomarkers chosen from hemoglobin levels, hematocrit levels, complete blood count (CBC), and MCV (e.g., a measure of the average size of red blood cells).

In one aspect, the methods and compositions described herein are utilized in conjunction with one, two or three or more dyslipidemia related biomarkers. In one aspect, the methods and compositions described herein are utilized in conjunction with one, two or three or more dyslipidemia related biomarkers chosen from HDL, LDL, total cholesterol, triglycerides, non HDL cholesterol, VLDL, saturated free fatty acid, unsaturated free fatty acid, total free fatty acid, ApoB, and apolipoprotein A1.

In one aspect, the methods and compositions described herein are utilized in conjunction with one, two or three or more sarcopenia related biomarkers. In one aspect, the methods and compositions described herein are utilized in conjunction with one, two or three or more sarcopenia related biomarkers chosen from decrease in fat mass relative to fat free mass (includes muscle mass), DEXA scan for bone mineral, fat, bone-mineral-fat-free mass, fat-free skeletal muscle mass e.g., obtained with an imaging technique (such as computerized tomography (CT) and magnetic resonance imaging (MRI)), bioimpedance analysis (BIA) for muscle mass.

In one aspect, the methods and compositions described herein are utilized in conjunction with one, two or three of creatinine, 3-methylhistidine, and urinary creatinine excretion.

In one aspect, the methods and compositions described herein are utilized in conjunction with one, two or three or more metabolic syndrome related biomarkers e.g., sBP>130, hyper glycemia-fasting glucose >100, waist circumference >40 in men, TG>150, HDL<40

In one aspect, the methods and compositions described herein are utilized in conjunction with one, two or three or more combination biomarkers of liver fibrosis. In one aspect, the methods and compositions described herein are utilized in conjunction with one, two or three or more combination biomarkers of liver fibrosis chosen from AST/ALT ratio, BARD related (e.g., BMI, AST, ALT, and Diabetes Mellitus), and e.g., combinations of FIB-4, Platelet count, AST, ALT, and age.

Other biomarkers for use in the methods include, but are not limited to:

| | |
|---|---|
| Fibrometer test- | Platelet count, prothrombin index, AST, α2-macro-globulin, hyaluronic acid, urea, age |
| Fibrometer A- | Prothrombin index, 'α2 macroglobulin, hyaluronic acid, age |
| Fibrotest (FT)- | Haptoglobin, α2-macro-globulin, apolipoprotein A1. GGT, bilirubin, age, gender |
| NAFLD Fibrosis Score (NFS)- | Age, BMI, platelets, albumin, AST/ALT, IFG/diabetes |
| Fibrospect-II- | Hyaluronic acid, TIMP-1, α2-macroglobulin |

| | |
|---|---|
| PGA-index- | Prothrombin time, GGT, apolipoprotein A1 |
| PGAA-index- | Prothrombin time, GGT, apolipoprotein A1, α2-macroglobulin |
| Pohl score- | AST/ALT-ratio, platelet count |
| ELF score- | Hyaluronic acid, TIMP-1, age, MMP-3 |
| SHASTA- | HA, AST, albumin |
| Fibrosis probability-index, FPI- | Age, AST, cholesterol, insulin resistance (HOMA), past alcohol intake |
| APRI score- | AST, platelet count |
| | alpha2-macroglobulin, age, gamma glutamyl transpeptidase, and hyaluronic acid. |

Other Methods

A method of diagnosing NAFLD in a subject is provided herein said method comprising: determining the subjects serum testosterone level, determining the subjects BMI, or both, wherein a subject having low testosterones levels and a BMI greater than or equal to 30, or the subject is obese, is diagnosed with NAFLD. According to this method, a subject diagnosed with NAFLD is furthered assessed by analyzing one or more biomarkers or performing imaging studies to confirm diagnosis and stage as well as determine treatment. For example, a subject diagnosed with liver is further assessed by MRI-PDFF or MRE, or one or more serum or NAS biomarkers are assessed. In one aspect, the biomarker is one or more chosen from ALP, ALT, AST, GGT, TRI-GLYCERIDES, LDL, Cholesterol, Liver Biopsy, inflammation biomarkers, non-HDL cholesterol, hematocrit, hemoglobin, lipoprotein phospholipase A2, bilirubin, albumin, SHBG, imaging biomarkers, liver histology biomarkers, biomarkers in the literature related to the disease and condition described herein, and liver damage biomarkers.

In one embodiment, the subject diagnosed with the method described herein (in those conditions such as NAFLD, NASH, etc. or which occur as a consequence of metabolic syndrome and/or type II diabetes) can be treated for NAFLD or NASH with of one or more agents which are used to treat type II diabetes or metabolic syndrome including metformin, glibenclamide, gliclazide, rosiglitazone, pioglitazone, troglitazone, acarbose, miglitol, nateglinide, repaglinide, exenatide, sitagliptin, pramlintide and mixtures thereof.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents that inhibits c-Jun N-terminal kinase, p38 mitogen-activated protein kinase, or both.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents that inhibits ASK1 kinase. One example of such an agent is selonsertib.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents is an agonist of farnesoid X receptor. One example of such an agent is obeticholic acid.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents is an inhibitor of the peroxisome proliferator-activated receptor alpha, delta, or both. One example of such an agent is elafibrinor.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents is an antagonist of C—C chemokine receptor types 2, 5, or both. One example of such an agent is cenicriviroc.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents that is chosen from butanoic acid, CER209, evogliptin, DUR928, MK-4074, OPRX-106, PF06865571, PF06882961, PXS-5382A, RG-125, RYI-018, seladelpar, SGM-1019, TVB-2640, or a combination thereof.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents that is chosen from aramchol, ARX618, BI 1467335, DS102, EDP-305, Emricasan, gemcabene, GR-MD-02, GRI-0621, GS-0976, GS-9674, IMM-124E, IONIS-DGAT2Rx, IVA-337, Lipaglyn, LJN452, LMB763, MGL-3196, MN-001, MSDC-0602K, NC101, NGM282, NS-0200, Ozempic, PF-05221304, PF-06835919, remogliflozin etabonate, SHP626, TVB-2640, VK2809, or a combination thereof.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents that is chosen from cenicriviroc, elafibranor, ocaliva (obeticholic acid), selonsertib, or a combination thereof.

In one embodiment, the subject diagnosed (e.g., hypogonadal, obese, having fatty liver, having live fat greater than 8%, MRE, NAFLD, NASH, one or more serum biomarkers described herein, etc.) with the method described herein can be treated for NAFLD or NASH with of one or more pharmaceutical agents is an androgen receptor agonist. One example of such an agent is testosterone or a testosterone ester (and in a preferred aspect testosterone or testosterone ester formulated for and delivered orally).

In some embodiments of the methods disclosed herein, the subject diagnosed according to the instant disclosure is administered oral testosterone ester therapy. In one aspect, the oral testosterone therapy is administered with one or more additional therapeutic agents (not necessarily at the same time or frequency as the oral testosterone ester therapy or androgen receptor agonist therapy).

In some embodiments the one or more additional therapeutic agent is a statin. In some embodiments the statin is atorvastatin, rosuvastatin, simvastatin, pravastatin, lovastatin, fluvastatin, or pitavastatin. In one aspect, the amount of atorvastatin administered per day is from about 10 mg to about 60 mg. In one aspect, the amount of rosuvastatin administered per day is from about 5 mg to about 20 mg. In one aspect, the amount of simvastatin administered per day is from about 10 mg to about 40 mg. In one aspect, the amount of pravastatin administered per day is from about 10 mg to about 80 mg. Combination of the other pharmaceutical agents described herein with a statin and another agent instead of the testosterone or testosterone ester are also contemplated.

In one aspect, the amount of lovastatin administered per day is from about 20 mg to about 40 mg. In one aspect, the amount of fluvastatin administered per day is from about 20 mg to about 80 mg. In one aspect, the amount of pitavastatin administered per day is from about 1 mg to about 4 mg. In one aspect, the amount of atorvastatin is from about 10 mg to about 40 mg.

In one aspect, amount of rosuvastatin is from about 10 to about 20 mg. In one aspect, the amount of simvastatin is from about 10 mg to about 20 mg. In one aspect, the amount of pravastatin is from about 10 mg to about 20 mg. In one aspect, the amount of lovastatin is about 40 mg. In one aspect, the amount of fluvastatin is from about 20 mg to about 40 mg. In one aspect, the amount of pitavastatin is from about 1 mg to about 3 mg.

Combination therapies (or monotherapies) can include administration of more or more of the following with an androgen receptor agonist or modulator as described herein: a FXR agonist, a PPAR alpha or delta agent, a lipid modulator, an anti-inflammatory (e.g., steroidal or non-steroidal anti-inflammatory agents or other), an antioxidant, an immunomodulator, an insulin senitizer, an incretin mimetic, a hemorrheologic agent, an inhibitor of apoptosis, an agonist of the peroxisome proliferator, a thyroid hormone receptor modulator, an ASK1 inhibitor, an Acetyl-CoA Carboxylase (ACC) inhibitor, a fatty-acid/bile-acid Conjugate, galectin inhibitor, caspase protease inhibitor or a combination thereof in conjunction with the androgen receptor agonist (e.g., testosterone ester like testosterone undecanoate or testosterone tridecanoate). Combination therapies also include e.g., an androgen, testosterone, testosterone ester, testosterone undecanoate, testosterone tridecanoate with a glp-1 agonist or modulator (e.g., liraglutide or semaglutide) or slgt-2 inhibitors (e.g., gliflozins, canagliflozin, ertugliflozin, dapagliflozin, empagliflozin, and sotagliflozin).

Subjects for Further Diagnostic/Prognostic Testing and Treatment

As described herein methods are provided for diagnosis/prognosis and treatment of liver disease, particularly fatty liver disease, NAFLD, NASH, Cirrhosis, and symptoms thereof. The treatments and diagnosis/prognosis can be performed for subject or samples obtained from subjects as described in the below paragraph or as deemed appropriate by a medical professional. For example, the subject, as identified below, is assessed for liver fat imaging (e.g., by MRI-PDFF) or liver stiffness (MRE) or a serum sample is assessed or for one or more biomarkers described herein. This information is then used to further diagnose the subject and also can be used determine the most effective treatment.

In one aspect, the subject is a male hypogonadal subject. In one aspect, the subject is a male hypogonadal subject with class I, II, or III obesity. In one aspect, the subject is a male hypogonadal subject with class I, II, or III obesity. In one aspect, the subject is a male hypogonadal subject having elevated or above-normal serum triglycerides. In one aspect, the subject is a male hypogonadal subject having elevated or above normal serum AST or ALT levels. In one aspect, the subject is a male hypogonadal subject having class I, II, or III obesity and elevated or above normal serum triglycerides. In one aspect, the subject is a male hypogonadal subject having class I, II, or III obesity and elevated or above normal serum ALT or AST. In one aspect, the subject is a male hypogonadal subject having class I, II, or III obesity and elevated or above normal serum triglycerides, and elevated or above normal serum ALT or AST.

Pharmaceutical Compositions

In certain embodiments, provided herein is a pharmaceutical composition comprising at least one steroidal compound (e.g., testosterone, dihydrotestosterone, estradiol, or analogs or prodrugs thereof) and at least one pharmaceutically acceptable carrier. In specific embodiments, the steroidal compound is a steroidal androgen (e.g., testosterone, dihydrotestosterone, or prodrugs thereof). In some embodiments, the steroidal compound is an alkylated, hydroxyalkylated and/or hydroxy-alkoylated natural steroid (e.g., testosterone alkyl ester, dihydrotestosterone alkyl ester, estradiol alkyl ester, or the like). In certain embodiments, analogs or prodrugs of testosterone include, e.g., esters of testosterone. In specific embodiments, the esters of testosterone include, e.g., alkyl (e.g., straight chain, branched, cyclic, unsaturated, partially saturated, fully saturated and the like) esters of testosterone. Specifically, alkyl esters of testosterone include, by way of non-limiting example, lower alkyl esters (e.g., testosterone C2-C13 alkyl esters such as testosterone propionate, testosterone enthanate, or testosterone undecanoate), or higher alkyl esters (e.g., testosterone C14+ alkyl esters such as testosterone palmitate). In further embodiments, the alkyl esters of testosterone include, by way of non-limiting example, cycloalkylalkyl esters (e.g., testosterone cypionate), cycloalkyl esters, and alkylcycloalkyl esters. In more specific embodiments, the testosterone alkyl ester is testosterone undecanoate. In some embodiments, the at least one steroidal compound comprises (1) a testosterone lower alkyl ester (e.g., testosterone propionate, testosterone enanthate, or testosterone undecanoate); and (2) a testosterone higher alkyl ester (e.g., testosterone palmitate). Generally, as used herein, a pharmaceutical composition comprising a steroidal compound includes the disclosure of a pharmaceutical composition comprising one or more steroidal compounds.

In some embodiments, dihydrotestosterone or a dihydrotestosterone ester can be used in place or in conjunction with a testosterone ester as described herein. Exemplary dihydrotestosterone esters include, but are not limited to, dihydrotestosterone propionate, dihydrotestosterone enanthate, dihydrotestosterone cypionate, dihydrotestosterone undecanoate, dihydrotestosterone decanoate, dihydrotestosterone dodecanoate, dihydrotestosterone tridecanoate, dihydrotestosterone tetradecanoate, and dihydrotestosterone palmitate.

In certain embodiments, any pharmaceutical composition described herein comprises a therapeutically effective amount of at least one steroidal compound (e.g., a testosterone alkyl ester, such as testosterone undecanoate). In some embodiments, a therapeutically effective amount of a steroidal compound (e.g., a testosterone alkyl ester, such as testosterone undecanoate) is divided into one or more oral dosage form. In some embodiments, the one or more of the oral dosage forms described herein collectively comprise a therapeutically effective amount of a testosterone alkyl ester (e.g., testosterone undecanoate). Thus, in some embodiments, the therapeutically effective amount of a steroidal compound (e.g., a testosterone alkyl ester, such as testosterone undecanoate) within a pharmaceutical composition described herein may vary when the pharmaceutical composition is administered in combination with another therapy. Furthermore, therapeutically effective amounts of a formulation may depend on the specific formulation within which the at least one steroidal compound is found. For example, in some embodiments, more than one steroidal compound is present in a pharmaceutical composition described herein. Thus, when there is a combination of steroidal compounds, in certain instances one or both of the steroidal compounds present has a therapeutically effective amount that is lower than is required when the steroidal compounds are administered separately or alone. In some embodiments, a pharmaceutical composition described herein further comprises an adjuvant, which, in certain instances, allows for a lower amount of a steroidal compound to be utilized as a therapeutically effective amount.

As described in typical total daily dose ranges for adult male and female subjects are given for testosterone undecanoate and testosterone tridecanoate. Based on the doses, doses for other testosterone esters can be estimated on the T-equivalent dose which is determined e.g., by the amount of testosterone per testosterone undecanoate molecule. For example, for calculation purposes, 1 mg of T is equivalent to: 1.39 mg T-enanthate; 1.58 mg T-undecanoate; 1.43 mg T-cypionate ab so on. Although the conversion is not exact due to various properties, a skilled artisan understand how to estimate a dose of one testosterone ester for another testosterone ester based on this calculation.

In certain embodiments, a pharmaceutical composition described herein comprises about 1 mg to about 1.5 g, about 10 mg to about 1000 mg, or about 10 mg to about 200 mg of a steroidal compound (e.g., a testosterone alkyl ester, such as testosterone undecanoate). In specific embodiments, a pharmaceutical composition described herein comprises about 10 mg to about 50 mg, about 15 mg to about 40 mg, about 20 mg, to about 30 mg, or about 25 mg of steroidal compound (e.g., a testosterone alkyl ester, such as testosterone undecanoate). In other embodiments, a pharmaceutical composition described herein comprises about 70 mg to about 150 mg, about 80 mg to about 140 mg, about 90 mg to about 140 mg, about 100 mg to about 130 mg, about 110 mg to about 130 mg, about 110 mg to about 120 mg, about 130 mg to about 180 mg, about 180 mg to about 230 mg, about 230 mg to about 280 mg, about 280 mg to about 330 mg, about 330 mg to about 380 mg, about 380 mg to about 430 mg, about 430 mg to about 480 mg, about 480 mg to about 530 mg, or about 530 mg to about 580 mg of a steroidal compound (e.g., a testosterone alkyl ester, such as testosterone undecanoate). In some embodiments, a pharmaceutical composition described herein comprises about 0.1 mg to about 10 mg of a steroidal compound (e.g., a testosterone alkyl ester such as testosterone undecanoate) per kg of an individual to whom the oral dosage form is to be administered. In certain embodiments, a pharmaceutical composition described herein comprises an amount of a steroidal compound (e.g., a testosterone alkyl ester, such as testosterone undecanoate) sufficient to provide about 1 mg to about 1 g, about 5 mg to about 500 mg, about 10 mg to about 300 mg, or about 20 to about 250 mg of a steroidal compound (e.g., a testosterone alkyl ester, such as testosterone undecanoate) to an individual upon once a day, twice a day, three times a day, or four times a day oral administration.

In some embodiments, the at least one pharmaceutically acceptable carrier is any carrier suitable for delivering an efficacious amount of a steroidal compound, e.g., a testosterone alkyl ester, to an individual. In some embodiments, the at least one pharmaceutically acceptable carrier is or comprises a hydrophilic carrier (e.g., a hydrophilic surfactant or hydrophilic additive). In certain embodiments, the at least one pharmaceutically acceptable carrier is a lipophilic carrier (e.g., a lipophilic surfactant or lipophilic additive). In some embodiments, the at least one pharmaceutically acceptable carrier is a hydrophilic carrier (e.g., a hydrophilic surfactant or hydrophilic additive) and a lipophilic carrier (e.g., a lipophilic surfactant or lipophilic additive). In certain embodiments, the hydrophilic carrier is a hydrophilic triglyceride. In specific embodiments, the hydrophilic triglyceride is a polyoxylated castor oil, or a polyoxylated hydrogenated castor oil. In some embodiments, any pharmaceutical composition provided herein consists essentially of a lipophilic carrier or combination of lipophilic carriers. In certain embodiments, any pharmaceutical composition provided herein comprises a lipophilic carrier and less than 10% w/w, less than 5% w/w or is substantially free of a hydrophilic carrier. In certain embodiments, any pharmaceutical composition provided herein comprises a lipophilic carrier and less than 10% w/w, less than 5% w/w or is substantially free of a hydrophilic carrier. In some embodiments, the pharmaceutical composition comprising a carrier (e.g., a hydrophilic carrier and/or a lipophilic carrier), the pharmaceutical composition is a solid, a semi-solid, a gel, a jelly, a paste, or the like. In certain embodiments, e.g., wherein a pharmaceutical composition comprising a hydrophilic carrier and/or a lipophilic carrier, a viscosity enhancing agent or a solidifying agent is utilized to afford a pharmaceutical composition that is a solid, a semi-solid, a gel, a jelly, a paste, or the like. Thus, in certain embodiments, the at least one pharmaceutically acceptable carrier is a hydrophilic carrier (e.g., a hydrophilic surfactant or hydrophilic additive) and a viscosity enhancing or solidifying agent. In certain embodiments, the at least one pharmaceutically acceptable carrier is a lipophilic carrier (e.g., a lipophilic surfactant or lipophilic additive) and a viscosity enhancing or solidifying agent. In some embodiments, the at least one pharmaceutically acceptable carrier is or comprises a hydrophilic carrier (e.g., a hydrophilic surfactant or hydrophilic additive), a lipophilic carrier (e.g., a lipophilic surfactant or lipophilic additive), and a viscosity enhancing or solidifying agent. In some embodiments, the at least one pharmaceutically acceptable carrier is or comprises an amphiphilic or zwitterionic carrier (e.g., a ampiphilic surfactant or ampiphilic additive). In certain embodiments, the pharmaceutically acceptable carrier is any carrier suitable for achieving one or more of the pharmacokinetic and/or pharmacodynamic profiles set forth herein.

Additives useful herein include chemical substances that are generally pharmacologically inactive. Further, the additive may be solid, liquid or semi-solid in nature at about ambient room temperature. Furthermore, the additive may be hydrophilic or lipophilic. In certain instances, a "hydrophilic additive" is a substance that has at least one polar side group in its chemical structure which will attract water; whereas a "lipophilic additive" exhibits a tendency to repel water.

In some embodiments, the hydrophilic or lipophilic additive is contained within the components forming a composition and/or pharmaceutical dosage form thereof. In certain embodiments, the hydrophilic or lipophilic additive is in an encapsulation coat in compositions. Alternatively, the additives can be comprised in the pharmaceutical composition but not as part of the composition itself. Specific, non-limiting examples of additives are described below.

Suitable additives include any additive that can facilitate the processes involving the preparation of a pharmaceutical composition and/or dosage form described herein. In some instances, such additives include those commonly utilized to facilitate the processes involving the preparation of a composition and/or a pharmaceutical dosage form described herein. These processes include agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or other processes known in the art. In certain instances, the additive is optionally pre-coated or encapsulated. Suitable additives are optionally utilized to influence the drug release from the composition and/or pharmaceutical dosage form.

Suitable additives utilized in various embodiments described herein include, by way of non-limiting example, adsorbing agents, anti-adherents, anticoagulants, antifoaming agents, antioxidants, anti-caking agents, anti-static agents, binders, bile acids, bufferants, bulking agents, chelating agents, coagulants, colorants, co-solvent, opaquants, congealing agents, coolants, cryoprotectants, diluents, dehumidifying agents, desiccants, desensitizers, disintegrants, dispersing agents, enzyme inhibitors, glidants, fillers, hydrating agent, super disintegrants, gums, mucilages, hydrogen bonding agents, enzymes, flavorants, humectants, humidifying agents, lubricant oils, ion-exchange resins, lubricants, plasticizers, pH modifying agents, preservatives, solidifying agent, solvents, solubilizers, spreading agent sweeteners, stabilizers, surface area enhancing agents, suspending agent, thickeners, viscosity increasing agents, waxes and mixtures thereof.

Some non-limiting examples of the hydrophilic or lipophilic additives suitable for the current invention are as follows:

Alcohols and/or Polyols (e.g. ethanol, isopropanol, butanol, benzyl alcohol, ethylene glycol, propylene glycol, glycerol, sorbitol, mannitol, dimethyl isosorbide, polyethylene glycol, fatty acid alcohol, vinyl alcohol polypropylene glycol, polyvinylalcohol, tocopherols, cellulose cyclodextrins, other derivatives, forms, mixtures thereof, or the like); ethers of polyethylene glycols having an average molecular weight of about 200 to about 20,000 (e.g. tetrahydrofurfuryl alcohol PEG ether, methoxy PEG, or the like); Amides (e.g. 2-pyrrolidone, 2-piperidone, 8-caprolactam, N-alkylpyrrolidone, N-hydroxyalkylpyrrolidone, N-alkylpiperidone, N-alkylcaprolactam, dimethylacetamide, polyvinylpyrrolidone and the like.); Esters (e.g. ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, 8-caprolactone and isomers thereof, 6-valerolactone and isomers thereof, (3-butyrolactone and isomers thereof; and other additives known in the art, such as dimethyl acetamide, dimethyl isosorbide, N-methylpyrrolidones, monooctanoin, diethylene glycol monoethyl ether, or the like); Amino acids (e.g. P-aminobenzamidine, sodium glycocholate) mesylate; Amino acids and modified amino acids (e.g. aminoboronic acid derivatives and n-acetylcysteine; Peptides and modified peptides (e.g. bacitracin, phosphinic acid dipeptide derivatives, pepstatin, antipain, leupeptin, chymostatin, elastin, bestatin, phoshporamindon, puromycin, cytochalasin potatocarboxy peptidase inhibitor, amastatin, or the like); Polypeptide protease inhibitors; Mucoadhesive polymers (e.g. polyacrylate derivatives, chitosan, cellulosics, chitosan-EDTA, chitosan-EDTA-antipain, polyacrylic acid, carboxymethyl cellulose etc.); or the like; or combinations thereof.

Some more examples of suitable additives for compositions and/or dosage forms described herein include, by way of non-limiting example, talc, magnesium stearate, silica (e.g. fumed silica, micronized silica, magnesium aluminum silicate etc.) and/or derivatives, polyethylene glycols, surfactants, waxes, oils, cetyl acohol, polyvinyl alcohol, stearic acid, stearic acid salts, stearic acid derivatives, starch, hydrogenated vegetable oils, hydrogenatied castor oils, sodium benzoate, sodium acetate, leucine, PEG, alkyl sulfate salts; acetylated monoglycerides; long-chain alcohols; silicone derivatives; butylated hydroxy toluene (BHT), butylated hydroxyl anisole (BHA), gallic acid, propyl gallate, ascorbic acid, ascorbyl palmitate, 4-hydroxymethyl-2,6-di-tert-butyl phenol, dry starch, dry sugars, polyvinyl pyrrolidones, starch paste, methacrylic copolymers, bentonite, sucrose, polymericcellulose derivatives, shellac, sugar syrup; corn syrup; polysaccharides, acacia, tragacanth, guar gum, xanthan gums; alginates; gelatin; gelatin hydrolysate; agar; sucrose; dextrose; PEG, vinyl pyrrolidone copolymers, poloxamers; pregelatinized starch, sorbitol, glucose); acetic acid, hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, vinegar, pharmaceutically acceptable bases, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamin; salt of a pharmaceutically acceptable cation and an anion; EDTA and EDTA salts; titanium dioxide, food dyes, lakes, natural vegetable colorants, iron oxides, silicates, sulfates, magnesium hydroxide and aluminum hydroxide; halogenated hydrocarbons, trichloroethane, trichloroethylene, dichloromethane, fluorotrichloromethane, diethylether, trehelose, phosphates, citric acid, tartaric acid, gelatin, dextran and mannitol, lactose, mannitol, sodium chloride, potassium chloride, spray-dried lactose, hydrolyzed starches, directly compressible starch, microcrystalline cellulose, cellulosic derivatives, sorbitol, sucrose, sucrose-based materials, calcium sulfate, dibasic calcium phosphate, dextrose, croscarmellose sodium, starch, starch derivatives, clays, gums, cellulose, cellulose derivates, alginates, crosslinked polyvinylpyrrolidone, sodium starch glycolate and microcrystalline cellulose, magnesium oxide, magnesium carbonates; desensitizers, spray-dried flavors, essential oils, ethyl vanillin, styrene/divinyl benzene copolymers, quaternary ammonium compounds, polyethylene glycol, citrate esters (such as triethyl citrate, acetyl triethyl citrate, acetyltributyl citrate), acetylated monoglycerides, glycerin, triacetin, propylene glycol, phthalate esters (e.g., diethyl phthalate, dibutyl phthalate), castor oil, sorbitol and dibutyl sebacate, ascorbic acid, boric acid, sorbic acid, benzoic acid, and salts thereof, parabens, phenols, benzyl alcohol, and quaternary ammonium compounds; alcohols, ketones, esters, chlorinated hydrocarbons water; sweeteners, (e.g. maltose, sucrose, glucose, sorbitol, glycerin and dextrins, aspartame, saccharine, saccharine salts, glycyrrhizin), viscosity modifiers, sugars, polyvinylpyrrolidone, cellulosics, polymers, gums and/or alginates.

Additives can also be materials such as proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum arabic); spermaceti; natural or synthetic waxes; carnuaba wax; fatty acids (e.g., stearic acid, hydroxystearic acid); fatty alcohols; sugars; shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based polymers (e.g., ethyl cellulose, methyl cellulose, microcrystalline cellulose, sodium carboxymethyl cellulose, hydroxypropylmethyl cellulose, ethyl cellulose, hydroxypropyl cellulose, HPMC acid succinates, cellulose acetate, cellulose nitrate, cellulose acetate butyrate, cellulose acetate trimellitate, carboxymethylethyl cellulose, hydroxypropylmethyl cellulose phthalate), shellacs; inorganics, such as dicalcium phosphate, hydroxyapitite, tricalcium phosphate, talc and titania; polyols, such as mannitol, xylitol and sorbitol; polyethylene glycol esters; and polymers, such as alginates, poly(lactide coglycolide), gelalin, crosslinked gelatin, and agar-agar.

It should be appreciated that there is considerable overlap between the above-listed additives in common usage, since a given hydrophilic or lipophilic additive is often classified differently by different practitioners in the field, or is commonly used for any of several different or overlapping functions. Thus, the above-listed hydrophilic or lipophilic additives should be taken as merely exemplary, and not limiting, of the types of additives that can be included in compositions of the present invention. In certain embodiments, the amounts of such additives are optionally adjusted and/or determined by one skilled in the art, according to the particular properties desired.

In certain embodiments, the at least one pharmaceutically acceptable carrier comprises at least one hydrophilic carrier (e.g., hydrophilic surfactant). In some embodiments, the hydrophilic carrier is a polyoxylated glyceride (e.g., mono-, di-, or tri-glyceride), a polyoxylated vegetable oil, a polyoxylated hydrogenated vegetable oil, a polyoxylated fatty acid (mono-, or di-substituted), combinations thereof, or the like. In certain embodiments, the at least one pharmaceutically acceptable carrier comprises or further comprises a lipophilic carrier. Lipophilic carriers are selected from, by way of non-limiting example, a lipophilic surfactant, a vegetable oil (e.g., castor oil), a fatty acid, a fatty alcohol, a glyceride (e.g., mono-, di-, or tri-glyceride), a hydrogenated vegetable oil, a Vitamin E compound (e.g., d,1-α-tocopherol), a triglyceride, a fatty acid, polyoxylated fatty acid, polyoxylated triglyceride, polyoxylated vegetable oil, or combinations thereof. In some embodiments, polyoxylated compounds include polyethoxylated compounds.

In certain embodiments, the at least one hydrophilic carriers make up about 1% to about 99% w/w, about 2% to about 80% w/w, about 2% to about 50% w/w, or about 10% to about 40% w/w of any pharmaceutical composition described herein. In some embodiments, lipophilic carriers make up about 1% w/w to about 99% w/w, about 2% to about 80% w/w, about 10% w/w to about 80% w/w, about 30% w/w, to about 80% w/w, or about 40% to about 80% w/w of any pharmaceutical composition described herein.

In specific embodiments, provided herein is a pharmaceutical composition (e.g., a delayed release dosage form) comprising a hydrophilic carrier. In more specific embodiments, the hydrophilic carrier is or comprises a polyoxylated vegetable oil (e.g., a polyoxylated, hydrogenated vegetable oil). In still more specific embodiments, a polyoxylated vegetable oil is a polyoxylated castor oil (e.g., a polyoxylated, hydrogenated castor oil). In certain embodiments, the lipidic and/or lipophilic carrier is not a C6-C18 fatty acid. In some embodiments, the lipophilic carrier is a C20+ fatty acid. In some embodiments, the lipidic and/or lipophilic carrier is not a fatty acid or an un-modified (e.g., non-polyoxylated) vegetable oil. In more specific embodiments, the lipidic and/or lipophilic carrier is not oleic acid or castor oil. In certain specific embodiments provided herein is a pharmaceutical composition (e.g., a delayed release dosage form) comprising an amphiphilic carrier. In more specific embodiments, the amphiphilic carrier is or comprises a zwitterionic choline (e.g., phosphatidylcholine). In some specific embodiments, provided herein is a pharmaceutical composition (e.g., a delayed release dosage form) comprising a lipophilic carrier. In more specific embodiments, the lipophilic carrier is or comprises, by way of non-limiting example, a mono-, di- or triglyceride (e.g., glycerol monolinoleate).

In some embodiments, the at least one pharmaceutically acceptable carrier comprises at least one hydrophilic carrier, and at least one lipidic and/or lipophilic carrier. In further embodiments, the at least one pharmaceutically acceptable carrier comprises at least one hydrophilic carrier, at least one lipidic and/or lipophilic carrier, and at least one viscosity enhancer or solidifying agent. In some embodiments, the solidifying agent is a polyethylene glycol (e.g., a high molecular weight polyethylene glycol, such as PEG 8000). In specific embodiments, a pharmaceutical composition described herein comprises, along with a steroidal agent (e.g., a testosterone alkyl ester), a hydrogenated and polyoxylated castor oil and a polyethylene glycol. In more specific embodiments, the pharmaceutical composition comprising a hydrogenated and polyoxylated castor oil and a polyethylene glycol further comprises an additional lipidic and/or lipophilic carrier. In some embodiments, the additional lipidic and/or lipophilic carrier is a monoglyceride, a diglyceride, a Vitamin E compound, or a combination thereof.

In certain embodiments, pharmaceutical compositions described herein include oral dosage forms or delayed release oral dosage forms of any of Tables A to Q. In Tables A to Q, approximate weight percentages of the compositions formulated into the capsules are provided. In specific embodiments, the steroidal compound of any of Capsules A1 to Q2 comprises an alkyl ester testosterone (e.g., testosterone undecanoate). In certain instances, provided in the tables are non-limiting grades and/or sources of components utilized. Disclosure provided in Tables A to Q is not limited to the grades and/or sources described. It is noted that any testosterone ester can be used in place of any specific testosterone ester disclosed in these tables (e.g., testosterone tridecanoate can be used in place of testosterone undecanoate or two testosterone esters can be used e.g., testosterone undecanoate and testosterone tridecanoate).

TABLE A

| Component | Capsule A1 % w/w | Capsule A2 % w/w |
| --- | --- | --- |
| Steroidal Compound (~10-1000 mg) | 1-50 | 10-30 |
| Hydrophilic Carrier | 1-90 | 10-30 |
| Lipophilic Carrier | 1-90 | 40-70 |
| Solidifying Agent (additive) | 1-20 | 5-10 |

TABLE B

| Component | Capsule B1 % w/w | Capsule B2 % w/w |
| --- | --- | --- |
| Testosterone undecanoate (~10-1000 mg) | 1-50 | 15 |
| Polyoxyl 40 Hydrogenated Castor Oil, NF | 1-50 | 16 |
| Glycerol Monolinoleate, NF (Maisine 35-1) | 30-90 | 63 |
| Polyethylene Glycol 8000, USP | 1-20 | 6 |

TABLE C

| Component | Capsule C1 % w/w | Capsule C2 % w/w |
| --- | --- | --- |
| Testosterone undecanoate (~10-1000 mg) | 1-50 | 25 |
| Polyoxyl 35 Castor Oil, NF | 1-50 | 21 |
| Vitamin E, USP (d,l-α-tocopherol) | 30-90 | 48 |
| Polyethylene Glycol 8000, USP | 1-20 | 6 |

TABLE D

| Component | Capsule D1 % w/w | Capsule D2 % w/w |
| --- | --- | --- |
| Steroidal Compound (~10-1000 mg) | 15 | 10-30 |
| Lauryl macrogol glyceride (Gelucire 44/14) | 51 | 20-90 |
| Stearoyl macrogol glyceride (Gelucire 50/13) | 34 | 10-90 |

TABLE E

| Component | Capsule E1 % w/w | Capsule E2 % w/w |
| --- | --- | --- |
| Steroidal Compound (~10-1000 mg) | 20 | 10-30 |
| C8-C18 macrogol glyceride (Gelucire 43/01) | 35 | 10-70 |
| Polyglyceryl-3-oleate (CAPROL 3 GO) | 45 | 5-60 |

TABLE F

| Component | Capsule F1 % w/w | Capsule F2 % w/w |
| --- | --- | --- |
| Steroidal Compound (~10-1000 mg) | 15 | 10-25 |
| Lauryl macrogol glyceride (Gelucire 44/14) | 40 | 5-80 |
| Vitamin E | 30 | 2-60 |
| Hypromellose (Methocel K100 MLV, CR) | 15 | 5-25 |

TABLE G

| Component | Capsule G1 % w/w | Capsule G2 % w/w |
| --- | --- | --- |
| Steroidal Compound (~10-1000 mg) | 15 | 10-30 |
| PEG-40 hydrogenated Castor Oil (CREMOPHOR ® RH40) | 60 | 5-80 |
| Polyethylene glycol 8000 | 15 | 5-40 |
| Hypromellose (Methocel K100 MLV, CR) | 10 | 5-25 |

TABLE H

| Component | Capsule H1 % w/w | Capsule H2 % w/w |
| --- | --- | --- |
| Steroidal Compound (~10-1000 mg) | 15 | 10-30 |
| Corn Glycerides (Maisine 35-1) | 60 | 5-90 |
| Polyethylene glycol 8000 | 20 | 5-70 |

TABLE I

| Component | Capsule I1 % w/w | Capsule I2 % w/w |
| --- | --- | --- |
| Steroidal Compound (~10-1000 mg) | 25 | 10-30 |
| PEG-40 hydrogenated Castor Oil (CREMOPHOR ® RH40) | 15 | 5-80 |
| Vitamin E | 20 | 2-60 |
| Corn Glycerides (Maisine 35-1) | 30 | 5-50 |
| Polyethylene Glycol 8000 | 10 | 5-20 |

TABLE J

| Component | Capsule J1 % w/w | Capsule J2 % w/w |
| --- | --- | --- |
| Steroidal Compound (~10-1000 mg) | 15 | 10-30 |
| Hydrogenated vegetable oil | 50 | 2-80 |
| Polyethylene glycol 8000 | 35 | 2-80 |

TABLE K

| Component | Capsule K1 % w/w | Capsule K2 % w/w |
| --- | --- | --- |
| Steroidal Compound (~10-1000 mg) | 50 | 30-60 |
| Corn Glycerides (Maisine 35-1) | 50 | 30-60 |

TABLE L

| Component | Capsule L1 % w/w | Capsule L2 % w/w |
| --- | --- | --- |
| Steroidal Compound (~10-1000 mg) | 40 | 30-60 |
| Fish Oil | 50 | 30-60 |
| Vitamin E | 10 | 3-15 |

TABLE M

| Component | Capsule M1 % w/w | Capsule M2 % w/w |
| --- | --- | --- |
| Steroidal Compound (~10-1000 mg) | 40 | 30-60 |
| Omega-3-acid esters | 50 | 30-60 |
| Polyethylene glycol 8000 | 5 | 3-15 |

TABLE N

| Component | Capsule N1 % w/w | Capsule N2 % w/w |
| --- | --- | --- |
| Testosterone undecanoate | 5-30 | 10-20 |
| Polyoxyl 40 Hydrogenated Castor Oil, NF | 5-30 | 10-20 |
| Glyceryl Monolinoleate, NF (Maisine 35-1) | 50-90 | 55-70 |
| Polyethylene Glycol 8000, USP | 1-15 | 3-8 |

TABLE O

| Component | Capsule O1 % w/w | Capsule O2 % w/w |
| --- | --- | --- |
| Testosterone undecanoate | 10-40 | 20-30 |
| Polyoxyl 35 Castor Oil, NF | 10-30 | 15-25 |
| Vitamin E, USP (d,l-α-tocopherol) | 30-70 | 40-55 |
| Polyethylene Glycol 8000, USP | 1-15 | 3-8 |

TABLE P

| Component | Capsule P1 % w/w | Capsule P2 % w/w |
| --- | --- | --- |
| Testosterone undecanoate | 10-40 | 20-25 |
| Vitamin E Polyethylene Glycol Succinate, NF | 10-40 | 20-25 |
| Vitamin E, USP (d,l-tocopherol) | 15-60 | 30-40 |
| Polyethylene Glycol 8000, USP | 1-10 | 2-6 |
| Hypromellose (100 cP, K100 Premium LV) | 5-40 | 15-25 |

TABLE Q

| Component | Capsule Q1 % w/w | Capsule Q2 % w/w |
| --- | --- | --- |
| Testosterone undecanoate | 10-40 | 20-25 |
| Vitamin E Polyethylene Glycol Succinate, NF | 10-40 | 20-25 |
| Vitamin E, USP (d,l-tocopherol) | 15-60 | 30-40 |
| Polyethylene Glycol 8000, USP | 1-10 | 2-6 |
| Hypromellose (4,000 cP, K4M) | 5-40 | 15-25 |

It is noted that the above compositions (or elsewhere) can also be prepared without any of the specific solidifying agents and used in the methods described herein.

In certain embodiments, any pharmaceutical composition described herein, e.g., a pharmaceutical composition of any of Tables A to Q can be prepared by (i) combining and heating all ingredients until a molten mixture is obtained (e.g., 50-70° C.); and (ii) encapsulating an amount of molten mixture comprising a select dose (e.g., a therapeutically effective amount or a partial dose of a therapeutically effective amount) of steroidal compound to obtain an oral dosage form. In certain instances, the molten mixture is spray-congealed to obtain beads. In some instances, the molten mixture is sprayed onto inert cores (e.g., sugar spheres) to obtain coated cores. In certain embodiments, such beads, cores, or similar forms are encapsulated or otherwise formulated to provide an oral dosage form. In some instances, the molten mixture is admixed, uniformly dispersed, or granulated over a carrier and compressed into a tablet dosage form. In certain embodiments, prior to compression, the molten mixture/carrier composition is further mixed with one or more pharmaceutical aid including, by way of non-limiting example, glidants, lubricants, binders, or the like. In some embodiments, the carrier is a therapeutically inert carrier such as, by way of non-limiting example, microcrystalline cellulose, starch, lactose, or the like.

In some embodiments, compositions described herein (e.g., compositions set forth in Tables K to M), are optionally filled into a delayed release capsule or shell, or are otherwise coated or encapsulated with a delayed release coat.

Carriers

Provided herein are pharmaceutical compositions comprising a steroidal compound (e.g., one or more testosterone alkyl ester (e.g., testosterone ester), such as testosterone undecanoate) and at least one pharmaceutically acceptable carrier. In certain embodiments, the at least one pharmaceutically acceptable carrier comprises at least one hydrophilic carrier (e.g., hydrophilic surfactant or additive), at least one lipophilic carrier (e.g., lipophilic surfactant or additive), and/or at least one viscosity enhancer or solidifying agent. In specific embodiments, the at least one pharmaceutically acceptable carrier is a hydrophilic carrier. In more specific embodiments, the at least one pharmaceutically acceptable carrier comprises or further comprises a lipophilic carrier. In further embodiments, the at least one pharmaceutically acceptable carrier comprises at least one hydrophilic carrier, at least one lipidic and/or lipophilic carrier, and at least one viscosity enhancer or solidifying agent.

In certain embodiments, hydrophilic carriers include, by way of non-limiting example, a hydrophilic surfactant. In various instances, hydrophilic surfactants are used to provide any one or more of several advantageous characteristics to the compositions, including, by way of non-limiting example: increased solubility of the active ingredient in at least one of the fractions of the carrier that is a solid carrier, improved dissolution of the active ingredient; improved dispersion and/or dissolution of the lipidic carrier; improved solubilization of the active ingredient upon dissolution; enhanced absorption and/or bioavailability of the active ingredient, particularly a hydrophilic, hydrophobic, or lipophilic active ingredient, and improved stability, both physical and chemical, of the active ingredient. In various embodiments, the hydrophilic surfactant includes either a single hydrophilic surfactant or a mixture of hydrophilic surfactants. Hydrophilic surfactants also include both ionic or non-ionic surfactants.

In some embodiments, lipophilic carriers include or further include, by way of non-limiting example, one or more lipophilic surfactant, including one or more lipophilic surfactant, one or more mono-, di-, or triglyceride, or mixtures thereof. In various instances, lipophilic surfactants provide any one or more of the advantageous characteristics listed above for hydrophilic surfactants, and/or enhance the function of other (e.g., hydrophilic) surfactants present in the pharmaceutical composition.

The terms "hydrophilic" and "lipophilic" are relative terms. Hydrophilicity and/or lipophilicity are determined in any manner suitable. In one instances, an empirical parameter is used to characterize the relative hydrophilicity and lipophilicity of the carriers described herein. For example, in one manner, the hydrophilicity and/or lipophilicity non-ionic amphiphilic compounds is the hydrophilic-lipophilic balance (the "HLB" value). Carriers or surfactants with lower HLB values are more lipophilic, and have greater solubility in oils, whereas surfactants with higher HLB values are more hydrophilic, and have greater solubility in aqueous mediums. This measure is suitable for the surfactants described herein because, generally, surfactants are amphiphilic as they comprise both a polar moiety (e.g., a polar non-charged or charged moiety) and a lipophilic moiety (e.g., an aliphatic group).

Using HLB values as a rough guide, hydrophilic surfactants are generally considered to be those compounds having an HLB value greater than about 10, as well as non-ionic, anionic, cationic, or zwitterionic compounds for which the HLB scale is not generally applicable. Similarly, lipophilic surfactants are compounds having an HLB value less than about 10.

It should be appreciated that the HLB value of a surfactant is merely a rough guide generally used to enable formulation of industrial, pharmaceutical and cosmetic emulsions. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)) Likewise, for certain polypropylene oxide containing block copolymers (poloxamers, available commercially as PLURONIC® surfactants, BASF Corp.), the HLB values are not always authoritative indicators of the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Thus, keeping these considerations involved, a person of ordinary skill in the art is able to utilize HLB values and the identity of a given product to determine surfactants for suitable lipophilicity and/or hydrophilicity for use in the pharmaceutical compositions described herein.

As used herein, useful surfactants include any surfactant that is pharmaceutically acceptable and is suitable for use in a pharmaceutical composition. Suitable surfactants include anionic, cationic, zwitterionic and non-ionic surfactants. Provided herein (e.g., in the Tables) are several general classes of surfactants. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

Surfactants described in the Tables are illustrative and are provided as non-limiting examples. For example, refined, distilled or fractionated surfactants, purified fractions thereof, or re-esterified fractions, are also within the scope of surfactants described herein, although they are not specifically listed in the Tables.

In some embodiments, surfactants described herein include polyoxylated fatty acids, such as polyethoxylated fatty acids (i.e., PEG-fatty acid esters). Provided in Table 1 is a list of illustrative and non-limiting examples of polyethoxylated fatty acid monoester surfactants.

TABLE 1

PEG-Fatty Acid Monoester Surfactants

| COMPOUND | COMMERCIAL PRODUCT (Supplier) | HLB |
| --- | --- | --- |
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400-1000 monostearate | Cithrol MS series (Croda) | >10 |
| PEG-1 stearate | Nikkol MYS-IEX (Nikko), Coster KI (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | MAPEG ® 200 ML (PPG), KESSCO ® PEG 200ML (Stepan), LIPOPEG 2L (LIPO Chem.) | 9.3 |
| PEG-4 oleate | MAPEG ® 200 MO (PPG), KESSCO ® PEG200 MO (Stepan) | 8.3 |
| PEG-4 stearate | KESSCO ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), KESSCO ® PEG 300 MO (Stepan), Nikkol MYO-6 (Nikko), Emulgante A6 (Condea) | 8.5 |
| PEG-7 oleate | Algon GL 70 (Auschem SpA) | 10.4 |
| PEG-6 laurate | KESSCO ® PEG300 ML (Stepan) | 11.4 |
| PEG-7 laurate | Lauridac 7 (Condea) | 13 |
| PEG-6 stearate | KESSCO ® PEG300 MS (Stepan) | 9.7 |
| PEG-8 laurate | MAPEG ® 400 ML (PPG), LIPOPEG 4DL (Lipo Chem.) | 13 |

TABLE 1-continued

PEG-Fatty Acid Monoester Surfactants

| COMPOUND | COMMERCIAL PRODUCT (Supplier) | HLB |
|---|---|---|
| PEG-8 oleate | MAPEG ® 400 MO (PPG), Emulgante A8 (Condea); Kessco PEG 400 MO (Stepan) | 12 |
| PEG-8 stearate | MAPEG ® 400 MS (PPG), Myrj 45 | 12 |
| PEG-9 oleate | Emulgante A9 (Condea) | >10 |
| PEG-9 stearate | CREMOPHOR 59 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | KESSCO ® PEG 600ML (Stepan) | 15 |
| PEG-12 oleate | KESSCO ® PEG 600MO (Stepan) | 14 |
| PEG-12 ricinoleate | (CAS #9004-97-1) | >10 |
| PEG-12 stearate | MAPEG ® 600 MS (PPG), KESSCO ® PEG 600MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | KESSCO ® PEG 1000 ML (Stepan) | 17 |
| PEG-20 oleate | KESSCO ® PEG 1000 MO (Stepan) | 15 |
| PEG-20 stearate | MAPEG ® 1000 MS (PPG), KESSCO ® PEG 1000 MS (Stepan), Myrj 49 | 16 |
| PEG-25 stearate | Nikkol MYS-25 (Nikko) | 15 |
| PEG-32 laurate | KESSCO ® PEG 1540 ML (Stepan) | 16 |
| PEG-32 oleate | KESSCO ® PEG 1540 MO (Stepan) | 17 |
| PEG-32 stearate | KESSCO ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet 0-100 (Croda) | 18.8 |
| PEG-100 stearate | Myrj 59, Arlacel 165 (ICI) | 13 |
| PEG-200 oleate | Albunol 200 MG (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf) | >10 |

Furthermore, in some embodiments, surfactants described herein include, by way of non-limiting example, polyethylene glycol (PEG) fatty acid diesters. Illustrative and non-limiting examples of PEG-fatty acid diesters are shown in Table 2

TABLE 2

PEG-Fatty Acid Diester Surfactants

| COMPOUND | COMMERCIAL PRODUCT (Supplier) | HLB |
|---|---|---|
| PEG-4 dilaurate | MAPEG ® 206 DL (PPG), KESSCO ® PEG 200 DL (Stepan), LIPOPEG 2-DL (Lipo Chem.) | 7 / 6 |
| PEG-4 dioleate | MAPEG ® 200 DO (PPG), | 6 |
| PEG-4 distearate | KESSCO ® 200 DS (Stepan) | 5 |
| PEG-6 dilaurate | KESSCO ® PEG 300 DL (Stepan) | 9.8 |
| PEG-6 dioleate | KESSCO ® PEG 300 DO (Stepan) | 7.2 |
| PEG-6 distearate | KESSCO ® PEG 300 DS (Stepan) | 6.5 |
| PEG-8 dilaurate | MAPEG ® 400 DL (PPG), KESSCO ® PEG 400 DL (Stepan), LIPOPEG 4 DL (Lipo Chem.) | 11 |
| PEG-8 dioleate | MAPEG ® 400 DO (PPG), KESSCO ® PEG 400 DO (Stepan), LIPOPEG 4 DO (Lipo Chem.) | 8.8 |

TABLE 2-continued

PEG-Fatty Acid Diester Surfactants

| COMPOUND | COMMERCIAL PRODUCT (Supplier) | HLB |
|---|---|---|
| PEG-8 distearate | MAPEG ® 400 DS (PPG), CDS 400 (Nikkol) | 11 |
| PEG-10 dipalmitate | Polyaldo 2PKFG | >10 |
| PEG-12 dilaurate | KESSCO ® PEG 600 DL (Stepan) | 11.7 |
| PEG-12 distearate | KESSCO ® PEG 600 DS (Stepan) | 10.7 |
| PEG-12 dioleate | MAPEG ® 600 DO (PPG), KESSCO ® 600 DO (Stepan) | 10 |
| PEG-20 dilaurate | KESSCO ® PEG 1000 DL (Stepan) | 15 |
| PEG-20 dioleate | KESSCO ® PEG 1000 DO (Stepan) | 13 |
| PEG-20 distearate | KESSCO ® PEG 1000 DS (Stepan) | 12 |
| PEG-32 dilaurate | KESSCO ® PEG 1540 DL (Stepan) | 16 |
| PEG-32 dioleate | KESSCO ® PEG 1540 DO (Stepan) | 15 |
| PEG-32 distearate | KESSCO ® PEG 1540 DS (Stepan) | 15 |
| PEG-400 dioleate | Cithrol 4DO series (Croda) | >10 |
| PEG-400 distearate | Cithrol 4DS series (Croda) | >10 |

As discussed above, in some embodiments, pharmaceutical compositions described herein comprise mixtures of surfactants, including, e.g, mixtures of two or more commercial surfactant products. Several PEG-fatty acid esters are marketed commercially as mixtures or mono- and diesters. Illustrative and non-limiting examples of surfactant mixtures are shown in Table 3.

TABLE 3

PEG-Fatty Acid Mono-and Diester Mixtures

| COMPOUND | COMMERCIAL PRODUCT (Supplier) | HLB |
|---|---|---|
| PEG 4-150 mono, dilaurate | KESSCO ® PEG 200-6000 mono, dilaurate (Stepan) | |
| PEG 4-150 mono, dioleate | KESSCO ® PEG 200-6000 mono, dioleate (Stepan) | |
| PEG 4-150 mono, distearate | KESSCO ® 200-6000 mono, distearate (Stepan) | |

In some embodiments, surfactants described herein include, by way of non-limiting example, polyethylene glycol glycerol fatty acid esters (PEG glycerol fatty acid esters) Illustrative and non-limiting examples of PEG glycerol fatty acid esters are shown in Table 4.

TABLE 4

PEG Glycerol Fatty Acid Esters

| COMPOUND | COMMERCIAL PRODUCT (Supplier) | HLB |
|---|---|---|
| PEG-20 glyceryl laurate | TAGAT ® L (Goldschmidt) | 16 |
| PEG-30 glyceryl laurate | TAGAT ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | CAPMUL ® EMG (ABITEC), ALDO ® MS-20 KFG (Lonza) | 13 |
| PEG-20 glyceryl oleate | TAGAT ® O (Goldschmidt) | >10 |
| PEG-30 glyceryl oleate | TAGAT ® O2 (Goldschmidt) | >10 |

In certain embodiments, surfactants of different degrees of lipophilicity or hydrophilicity are prepared by reaction of alcohols or polyalcohols with a variety of natural and/or hydrogenated oils. In some embodiments, the oils used are castor oil or hydrogenated castor oil or an edible vegetable oil such as corn oil, olive oil, peanut oil, palm kernel oil, apricot kernel oil, or almond oil. In specific embodiments, alcohols include glycerol, propylene glycol, ethylene glycol, polyethylene glycol, sorbitol, and pentaerythritol. In certain embodiments, such surfactants are utilized in the pharmaceutical compositions described herein. Illustrative and non-limiting examples of surfactants of this class suitable for use in the pharmaceutical compositions described herein are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6-7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), ALKAMULS ® EL 620 (Rhone-Poulenc), Incrocas 30 (Croda) | 11 |
| PEG-35 castor oil | CREMOPHOR EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), ALKAMULS ® EL 719 (Rhone-Poulenc) | 13 |
| PEG-50 castor oil | Emalex C-50 (Nihon Emulsion) | 14 |
| PEG-56 castor oil | EUMULGIN ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | EUMULGIN ® PRT 200 (Pulcra SA) | >10 |
| PEG-5 hydrogenated castor oil | Nikkol HCO-5 (Nikko) | 6 |
| PEG-7 hydrogenated castor oil | SIMUSOL ® 989 (Seppic), CREMOPHOR WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | SIMUSOL ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | CREMOPHOR RH 40 (BASE), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCG-60 (Nikko); CREMOPHOR RH 60 (BASE) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | LABRAFIL ® M 2125 CS (Gattefosse) | 4 |
| PEG-6 almond oil | LABRAFIL ® M 1968 CS (Gattefosse) | 4 |
| PEG-6 apricot kernel oil | LABRAFIL ® M 1944 CS (Gattefosse) | 4 |
| PEG-6 olive oil | LABRAFIL ® M 1980 CS (Gatfefosse) | 4 |
| PEG-6 peanut oil | LABRAFIL ® M 1969 CS (Gattefosse) | 4 |
| PEG-6 hydrogenated palm kernel oil | LABRAFIL ® M 2130 BS (Gattefosse) | 4 |
| PEG-6 palm kernel oil | LABRAFIL ® M 2130 CS (Gattefosse) | 4 |
| PEG-6 triolein | LABRAFIL ® M 2735 CS (Gattefosse) | 4 |
| PEG-8 corn oil | LABRAFIL ® WL 2609 BS (Gattefosse) | 6-7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70(Croda) | 15 |
| PEG-60 almond glycerides | Crovol A70 (Croda) | 15 |
| PEG-4 caprylic/capric triglyceride | LABRAFAC ® Hydro (Gattefosse) | 4-5 |
| PEG-8 caprylic/capric glycerides | Labrasol (Gattefosse), Labrafac CM 10 (Gattefosse) | >10 |
| PEG-6 caprylic/capric glycerides | SOFTIGEN ®767 (Huls), Glycerox 767 (Croda) | 19 |
| Lauroyl macrogol-32 glyceride | GELUCIRE 44/14 (Gattefosse) | 14 |
| Stearoyl maorogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |

TABLE 5-continued

Transesterification Products of Oils and Alcohols

| COMPOUND | COMMERCIAL PRODUCT (Supplier) | HLB |
|---|---|---|
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

In some embodiments, surfactants utilized in the pharmaceutical compositions described herein include, by way of non-limiting example, polyglycerized fatty acids. Illustrative and non-limiting examples of suitable polyglyceryl esters are shown in Table 6.

TABLE 6

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5-7 |
| Polyglyceryl-2 oleate | Nikkol DGMO (Nikko) | 5-7 |
| Polyglyceryl-2 isostearate | Nikkol DGMIS (Nikko) | 5-7 |
| Polyglyceryl-3 oleate | CAPROL ® 3GO (ABITEC), Drewpol 3-1-O (Stepan) | 6.5 |
| Polyglyceryl-4 oleate | Nikkol Tetraglyn 1-O (Nikko) | 5-7 |
| Polyglyceryl-4 stearate | Nikkol Tetraglyn 1-S (Nikko) | 5-6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | |
| Polyglyceryl-10 linoleate | Nikkol Decaglyn I-LN (Nikko) | 12 |
| Polyglyceryl-6 pentaoleate | Nikkol Hexaglyn S—O (Nikko) | <10 |
| Polyglyceryl-3 dioleate | CREMOPHOR GO32 (BASF) | <10 |
| Polyglyceryl-3 distearate | CREMOPHOR GS32 (BASF) | <10 |
| Polyglyceryl-4 pentaoleate | Nikkol Tetraglyn 5-O (Nikko) | <10 |
| Polyglyceryl-6 dioleate | CAPROL ® 6G2O | 8.5 |
| Polyglyceryl-2 dioleate | (ABITEC); Hodag PGO-62 (Calgene), PLUROL OLEIQUE CC 497 (Gattefosse) Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | CAPROL ® 10G40 (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-10 decaoleate | Drewpol 10-10-O (Stepan), CAPROL 10G10O (ABITEC), Nikkol Decaglyn 10-O | 3.5 |
| Polyglyceryl-10 mono, dioleate | CAPROL ® PGE 860 (ABITEC) | 11 |
| Polyglyceryl polyricinoleate | Polymuls (Henkel) | 3-20 |

In some embodiments, surfactants utilized in the pharmaceutical compositions described herein include, by way of non-limiting example esters of propylene glycol and fatty acids. Illustrative and non-limiting examples of surfactants of this class are given in Table 7

TABLE 7

Propylene Glycol Fatty Acid Esters

| COMPOUND | COMMERCIAL PRODUCT (Supplier) | HLB |
|---|---|---|
| Propylene glycol monocaprylate | CAPRYOL 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lrstrol OP2000 (BASF) | <10 |
| Propylene glycol myristate | Mirpyl | <10 |
| Propylene glycol monostearate | ADM PGME-03 (ADM), | 3-4 |
| Propylene glycol hydroxystearate | LIPO PGMS (Lipo Chem.), ALDO ® PGHMS (Lanza) | <10 |
| Propylene glycol ricinoleate | PROPYMULS (Henkel) | <10 |
| Propylene glycol isostearate | | <10 |
| Propylene glycol monooleate | Myverol P-06 (Eastman) | <10 |
| Propylene dicaprylate/dicaprate | glycol Captex ® 200 (ABITEC), MIGLYOL ® 840 (Huls), NEOBEE ® M-20 (Stepan) | >6 |
| Propylene glycol dioctanoate | CAPTEX ® 800 (ABITEC) | |
| Propylene caprylate/caprate | glycol LABRAFAC PG (Gattefosse) | >6 |
| Propylene glycol dilaurate | | >6 |
| Propylene glycol distearate | KESSCO ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

As discussed above, mixtures of surfactants are also used, in some embodiments, in the pharmaceutical compositions described herein. Mixtures of surfactants include, by way of non-limiting example, mixtures of propylene glycol fatty acid esters and glycerol fatty acid esters are suitable and are commercially available. Illustrative and non-limiting examples of such mixtures of surfactants include, by way of non-limiting example, those shown in Table 8.

TABLE 8

Glycerol/Propylene Glycol Fatty Acid Esters

| COMPOUND | COMMERCIAL PRODUCT (Supplier) | HLB |
|---|---|---|
| Oleic | ATMOS 300, ARLACEL 186 (ICI) | 3-4 |
| Stearic | ATMOS 150 | 3-4 |

In certain embodiments, an important class of surfactants includes the class of mono- and diglycerides. These surfactants are generally lipophilic. Illustrative and non-limiting examples of these surfactants are given in Table 9.

TABLE 9

Mono- and Diglyceride Surfactants

| COMPOUND | COMMERCIAL PRODUCT (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3-4 |
| Glyceryl monooleate (C18:1) | PECEOL (Gattefosse), Hodag GMO-D, Nikkol MGO (Nikko) | 3-4 |
| Glyceryl monooleate | RYLO series (Danisco), DIMODAN series (Danisco), EMULDAN (Danisco), | 3-4 |

TABLE 9-continued

Mono- and Diglyceride Surfactants

| COMPOUND | COMMERCIAL PRODUCT (Supplier) | HLB |
|---|---|---|
| Glycerol monooleate/ linoleate | ALDO ® MO FG (Lonza), KESSCO GMO (Stepan), MONOMULS ® series (Henkel), TEGIN O, DREWMULSE GMO (Stepan), Atlas G-695 (ICI), GMOrphic 80 (Eastman), ADM DMG-40, 79, and 100 (ADM), Myverol (Eastman) OLICINE (Gattefosse) | 3-4 |
| Glycerol monolinoleate | Maisine (Gattefosse), MYVEROL 18-92, Myverol 18-06 (Eastman) | 3-4 |
| Glyceryl ricinoleate | SOFTIGEN ® 701 (Huls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | CAPMUL ® GMS. (ABITEC), Myvaplex (Eastman), IMWITOR ® 191 (Hüls), CUTINA GMS, ALDO ® MS (Lonza), Nikkol MGS series (Nikko) | 5-9 |
| Glyceryl mono-, dioleate | CAPMUL ® GMO-K (ABITEC) | <10 |
| Glyceryl palmitic/stearic | CUTINA MD-A, ESTAGEL-G18 | <10 |
| Glyceryl acetate | LAMEGIN ® EE (Grünau GmbH) | <10 |
| Glyceryl laurate | INWITOR ® 312 (Hüls), MONOMULS ® 90-45 (Grünau GmbH), ALDO ® MLD (Lonza) | 4 |
| Glyceryl citrate/ lactate/oleate/linoleate | IMWITOR ® 375 (Hüls) | <10 |
| Glyceryl caprylate | IMWITOR ® 308 (Hüls), CAPMUL ® MCMC8 (ABITEC) | 5-6 |
| Glyceryl caprylate/caprate | CAPMUL ® MCM (ABITEC) | 5-6 |
| Caprylic acid mono, diglycerides | IMWITOR ® 988 (Hüls) | 5-6 |
| Caprylic/capric glycerides | IMWITOR ® 742 (Hüls) | <10 |
| Mono-and diacetylated monoglycerides | MYVACET ® 9-45, MYVACET ® 9-49, MYVACET ® 9-08 (Eastman), LAMEGIN ® (Grünau) | 3.8-4 |
| Glyceryl monostearate | ALDO ® MS, Arlacel 129 (ICI), LIPO GMS (Lipo Chem.), IMWITOR ® 191 (Hüls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | CAPMUL ® GDL (ABITEC) | 3-4 |
| Glyceryl dioieate | CAPMUL ® GDO (ABITEC) | 3-4 |
| Glycerol esters of fatty acids | GELUCIRE 39/01 (Gattefosse), GELUCIRE 43/01 (Gattefosse), GELUCIRE 37/08 (Gattefosse) | 1 6 |
| Dipalmitolein (C16:1) | (Larodan) | |
| 1,2 and 1,3-diolein (C18:1) | (Larodan) | <10 |
| Dielaidin (C18:1) | (Larodan) | <10 |
| Dilinolein (C18:2) | (Larodan) | <10 |

In some embodiments, surfactants utilized in the pharmaceutical compositions described herein include sterols and derivatives of sterols. In various embodiments, these surfactants are hydrophilic or lipophilic Illustrative and non-limiting examples of surfactants of this class are shown in Table 10.

TABLE 10

Sterol and Sterol Derivative Surfactants

| COMPOUND | COMMERCIAL PRODUCT (Supplier) | HLB |
|---|---|---|
| Cholesterol, sitosterol, lanosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-S (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

In some embodiments, surfactants useful in the pharmaceutical compositions described herein include a variety of PEG-sorbitan fatty acid esters. In general, these surfactants are hydrophilic, although several lipophilic surfactants of this class can be used. Illustrative and non-limiting examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet. 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PBG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoieate | Nikkol GO-430 (Nikko) | 12 |
| PEG-40 sorbitan tetraoieate | Nikkol GO-440 (Nikko) | 13 |
| PEG-20 monoisostearate | sorbitan Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

In some embodiments, surfactants utilized herein include ethers of polyethylene glycol and alkyl alcohols. Illustrative and non-limiting examples of these surfactants are shown in Table 12.

TABLE 12

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

In certain embodiments, surfactants utilized in the pharmaceutical compositions described herein include esters of sugars Illustrative and non-limiting examples of such surfactants are shown in Table 13.

TABLE 13

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/ monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

In some embodiments, surfactants utilized in the pharmaceutical compositions described herein include polyethylene glycol alkyl phenols, e.g., hydrophilic PEG-alkyl phenol surfactants. Illustrative and non-limiting examples of these surfactants are shown in Table 14

TABLE 14

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

In certain embodiments, surfactants utilized in pharmaceutical compositions described herein include polyoxyethylene-polyoxypropylene block copolymers. POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including Synperonic PE series (ICI), PLURONIC® series (BASF). Emkalyx, Lutrol (BASF), Supronic. Monolan, Pluracare, and Plurodac. The generic term for these polymers is "poloxamer" (CAS 9003-11-6). These polymers have the formula. $HO(C_2H_4O)_a(C_3H_6O)_b(C_2H_4O)_aH$; wherein the terms "a" and "b" denote the number of polyoxyethylene and polyoxypropylene units, respectively.

Illustrative and non-limiting examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in $HO(C_2H_4O)_a(C_3H_8O)_b(C_2H_4O)_aH$ | HLB |
|---|---|---|
| Poloxamer 105 | a = 11; b = 16 | 8 |
| Poloxamer 108 | a = 46; b = 16 | >10 |
| Poloxamer 122 | a = 5; b = 21 | 3 |
| Poloxamer 123 | a = 7; b = 21 | 7 |
| Poloxamer 124 | a = 11; b = 21 | >7 |
| Poloxamer 181 | a = 3; b = 30 | |
| Poloxamer 182 | a = 8; b = 30 | 2 |
| Poloxamer 183 | a = 10; b = 30 | |
| Poloxamer 184 | a = 13; b = 30 | |
| Poloxamer 185 | a = 19; b = 30 | |
| Poloxamer 188 | a = 75; b = 30 | 29 |
| Poloxamer 212 | a = 8; b = 35 | |
| Poloxamer 215 | a = 24; b = 35 | |
| Poloxamer 217 | a = 52; b = 35 | |
| Poloxamer 231 | a = 16; b = 39 | |
| Poloxamer 234 | a = 22; b = 39 | |
| Poloxamer 235 | a = 27; b = 39 | |
| Poloxamer 237 | a = 62; b = 39 | 24 |
| Poloxamer 238 | a = 97; b = 39 | |
| Poloxamer 282 | a = 10; b = 47 | |
| Poloxamer 284 | a = 21; b = 47 | |
| Poloxamer 288 | a = 122; b = 47 | >10 |
| Poloxamer 331 | a = 7; b = 54 | 0.5 |
| Poloxamer 333 | a = 20; b = 54 | |
| Poloxamer 334 | a = 31; b = 54 | |
| Poloxamer 335 | a = 38; b = 54 | |
| Poloxamer 338 | a = 128; b = 54 | |
| Poloxamer 401 | a = 6; b = 67 | |
| Poloxamer 402 | a = 13; b = 67 | |
| Poloxamer 403 | a = 21; b = 67 | |
| Poioxamer 407 | a = 98; b = 67 | |

In some embodiments, surfactants utilized in pharmaceutical compositions described herein include sorbitan esters of fatty acids. Illustrative and non-limiting examples of such surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monapalmitate | Span-40 (Atlas/ICI), Crill 2 (Croda), Nikkol SP-10 (Nikko) | 6.7 |
| Sorbitan monooleate | Span-86 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-36 (Nikko) | 4.3 |

TABLE 16-continued

Sorbitan Fatty Acid Ester Surfactants

| COMPOUND | COMMERCIAL PRODUCT (Supplier) | HLB |
| --- | --- | --- |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

In certain embodiments, surfactants utilized in pharmaceutical compositions described herein include esters of lower alcohols ($C_2$ to $C_4$) and fatty acids ($C_8$ to $C_{18}$). Illustrative and non-limiting examples of these surfactants are shown in Table 17.

TABLE 17

Lower Alcohol Fatty Acid Ester Surfactants

| COMPOUND | COMMERCIAL PRODUCT (Supplier) | HLB |
| --- | --- | --- |
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

In some embodiments, hydrophilic surfactants utilized in pharmaceutical compositions described herein include ionic surfactants (e.g., cationic, anionic and zwitterionic surfactants). In specific embodiments, anionic surfactants include fatty acid salts and bile acid salts. In certain specific embodiments, cationic surfactants include carnitines. In some specific embodiments, ionic surfactants include, by way of non-limiting example, sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Illustrative and non-limiting examples of such surfactants are shown in Table 18. For simplicity, exemplary counterions are shown in the entries in the Table. In various embodiments, such counterions are optionally substituted with any suitable counterion. For example, although the fatty acids are shown as sodium salts, other cation counterions are optionally used, such as alkali metal cations or ammonium. Unlike certain non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
| --- | --- |
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco cheno deoxycholate | |
| Sodium cholylsarcosinate | |
| Sodium N-methyl taurocholate | |
| Sodium lithocholate | |
| PHOSPHOLIPIDS | |
| Egg/Soy lecithin [EPIKURON ™ (Lucas Meyer), OVOTHIN ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |

TABLE 18-continued

Ionic Surfactants

| COMPOUND | HLB |
|---|---|
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

In some embodiments, surfactants utilized in pharmaceutical compositions described herein include ionizable surfactants. In certain embodiments, ionizable surfactants, when present in their unionized (neutral, non-salt) form, are lipophilic surfactants suitable for use in the compositions of the present invention Particular examples of such surfactants include free fatty acids, particularly $C_6$-$C_{22}$ fatty acids, and bile acids. More specifically, suitable unionized ionizable surfactants include the free fatty acid and bile acid forms of any of the fatty acid salts and bile salts shown in Table 18.

In some instances, derivatives of oil-soluble vitamins, such as vitamins A, D, E, K, etc., are also useful surfactants for use in the pharmaceutical compositions described herein. An example of such a derivative is tocopheryl PEG-1000 succinate (TPGS, available from Eastman).

In specific embodiments, surfactants or mixtures of surfactants that solidify (e.g, form a solid, a semi-solid, a gel, a jelly, a paste, or the like) at ambient room temperature are utilized in the pharmaceutical compositions described herein. In certain specific embodiments, surfactants or mixtures of surfactants utilized in the pharmaceutical compositions described herein solidify (e.g., form a solid, a semi-solid, a gel, a jelly, a paste, or the like) at ambient room temperature when combined with additional agents (e.g., particular lipophilic components, such as triglycerides, vitamins (e.g., Vitamin E), or the like, viscosity modifiers, stabilizers, solidifying agents, binders, thickeners, or the like). Such additional agents are optionally utilized in the pharmaceutical compositions described herein. In certain embodiments, pharmaceutical compositions described herein comprise a hydrophilic carrier (e.g., a hydrophilic surfactant), a lipophilic carrier, and/or a viscosity modifier or solidifying agent.

In some specific embodiments, non-ionic hydrophilic surfactants include alkylglucosides; alkylmaltosides; alkylthioglucosides, lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters, polyoxyethylene-polyoxypropylene block copolymers; polyglycerol fatty acid esters; polyoxyethylene glycerides; polyoxyethylene sterols, derivatives, and analogues thereof; polyoxyethylene vegetable oils, polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; polyethoxylated fat-soluble vitamins or derivatives; and mixtures thereof.

In certain specific embodiments, the non-ionic hydrophilic surfactant is selected from, by way of non-limiting example, polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers: polyglyceryl fatty acid esters; polyoxyethylene glycerides; polyoxyethylene vegetable oils, and polyoxyethylene hydrogenated vegetable oils in various embodiments, the glyceride is a monoglyceride, diglyceride, triglyceride, or a mixture thereof.

In some specific embodiments, non-ionic hydrophilic surfactants are the products of reaction mixtures of polyols and fatty acids, glycerides, vegetable oils, hydrogenated vegetable oils or sterols. These reaction mixtures are largely composed of the transesterification products of the reaction, along with often complex mixtures of other reaction products. In more specific embodiments, the polyol is glycerol, ethylene glycol, polyethylene glycol, sorbitol, propylene glycol, pentaerythritol, or a saccharide.

In certain specific embodiments, the hydrophilic surfactant is or includes an ionic surfactant Specific ionic surfactants include alkyl ammonium salts; bile acids and salts, analogues, and derivatives thereof; fusidic acid and derivatives thereof, fatty acid derivatives of amino acids, oligopeptides, and polypeptides; glyceride derivatives of amino acids, oligopeptides, and polypeptides; acyl lactylates; mono-, diacetylated tartaric acid esters of mono-, diglycerides; succinylated monoglycerides; citric acid esters of mono-, diglycerides; alginate salts; propylene glycol alginate; lecithins and hydrogenated lecithins: lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

In some specific embodiments, ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono-, diacetylated tartaric acid esters of mono-, diglycerides; succinylated monoglycerides; citric acid esters of mono-diglycerides; carnitines, and mixtures thereof. In more specific embodiments, ionic surfactants include, by way of non-limiting example, lecithin, lysolecithin, phosphatidylcholine, phosphatidylethanol amine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine. PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine. N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof. In more specific embodiments, ionic surfactants are selected from lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof, with the most preferred ionic surfactants being lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

In various embodiments, lipophilic surfactants are selected from, by way of non-limiting example, alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; and polyoxyethylene hydrogenated vegetable oils. As with the hydrophilic surfactants, lipophilic surfactants are optionally the products of reaction mixtures of polyols and fatty acids, glycerides, vegetable oils, hydrogenated vegetable oils, and sterols. In specific embodiments, lipophilic surfactants are selected from fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols. In certain specific embodiments, lipophilic surfactants are selected from lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof, with glycerol fatty acid esters and acetylated glycerol fatty acid esters being most preferred Among the glycerol fatty acid esters, the esters are, e.g., mono- or diglycerides, or mixtures of mono- and diglycerides, where the fatty acid moiety is a $C_6$ to $C_{22}$ fatty acid. In some specific embodiments, lipophilic surfactants are selected from the products of reaction mixture of polyols and fatty acids, glycerides, vegetable oils, hydrogenated vegetable oils, and sterols. In more specific embodiments, polyols are polyethylene glycol, sorbitol, propylene glycol, and pentaerythritol.

In certain embodiments, pharmaceutical compositions described herein include a lipophilic component or carrier. In some embodiments, the lipophilic carrier is selected from lipophilic surfactants, triglycerides, and Vitamin E compounds (e.g, d,1-α-tocopherol). In specific embodiments, triglycerides utilized in the pharmaceutical compositions described herein are those that solidify (e.g, form a solid, a semi-solid, a gel, a jelly, a paste, or the like) at ambient room temperature, with or without addition of appropriate additives, or those which in combination with particular surfactants and/or active ingredients solidify at room temperature. Illustrative and non-limiting examples examples of triglycerides suitable for use in the pharmaceutical compositions described herein are shown in Table 19. In general, these triglycerides are readily available from commercial sources. For several triglycerides, representative commercial products and/or commercial suppliers are listed.

TABLE 19

| Triglycerides | |
|---|---|
| Triglyceride | Commercial Source |
| Aceituno oil | |
| Almond oil | Super Refined Almond Oil (Croda) |
| *Araehis* oil | |
| Babassu oil | |
| Beeswax | |
| Blackcurrant seed oil | |
| Borage oil | |
| Buffalo ground oil | |
| Candlenut oil | |
| Canola oil | Lipex 108 (Abitec) |
| Castor oil | |
| Chinese vegetable tallow oil | |
| Cocoa butter | |
| Coconut oil | Pureco 76 (Abitec) |
| Coffee seed oil | |
| Corn oil | Super Refined Corn Oil (Croda) |
| Cottonseed oil | Super Refined Cottonseed Oil (Croda) |
| *Crambe* oil | |
| *Cuphea* species oil | |
| Evening primrose oil | |
| Grapeseed oil | |
| Groundnut oil | |
| Hemp seed oil | |
| Illipe butter | |
| Kapok seed oil | |
| Linseed oil | |
| Menhaden oil | Super Refined Menhaden Oil (Croda) |
| Mowrah butter | |
| Mustard seed oil | |
| Oiticica oil | |
| Olive oil | Super Refined Olive Oil (Croda) |
| Palm oil | |
| Palm kernel oil | |
| Peanut oil | Super Refined Peanut Oil (Croda) |
| Poppy seed oil | |
| Rapeseed oil | |
| Rice bran oil | |
| Safflower oil | Super Refined Safflower Oil (Croda) |
| Sal fat | |
| Sesame oil | Super Refined Sesame Oil (Croda) |
| Shark liver oil | Super Refined Shark Liver Oil (Croda) |
| Shea nut oil | |
| Soybean oil | Super Refined Soybean Oil (Croda) |
| *Stillingia* oil | |
| Sunflower oil | |
| Tall oil | |
| Tea seed oil | |
| Tobacco seed oil | |
| Tung oil (China wood oil) | |
| Ucuhuba | |
| *Vernonia* oil | |
| Wheat germ oil | Super Refined Wheat Germ Oil (Croda) |
| Hydrogenated castor oil | Castorwax |
| Hydrogenated coconut oil | Pureco 100 (Abitec) |
| Hydrogenated cottonseed oil | Dritex C (Abitec) |
| Hydrogenated palm oil | Dritex PST (Abitec); Softisan 154 (Hüls) |
| Hydrogenated soybean oil | Sterotex HM NF (Abitec); Dritex S (Abitec) |
| Hydrogenated vegetable oil | Sterotex NF (Abitec); Hydrokote M (Abitec) |
| Hydrogenated cottonseed and castor oil | Sterotex K (Abitec) |

TABLE 19-continued

Triglycerides

| Triglyceride | Commercial Source |
| --- | --- |
| Partially hydrogenated soybean oil | Hydrokote AP5 (Abitec) |
| Partially hydrogenated soy and cottonseed oil | Apex B (Abitec) |
| Glyceryl mono-, di-, tri-behenate | Compritol 888 |
| Glycerol tributyrate | (Sigma) |
| Glyceryl tricaproate | (Sigma) |
| Glyceryl tricaprylate | (Sigma) |
| Glyceryl tricaprate | CAPTEX 1000 (Abitec) |
| Glyceryl triundecanoate | CAPTEX 8227 (Abitec) |
| Glyceryl trilaurate | (Sigma) |
| Glyceryl trimyristate | Dynasan 114 (Hüls) |
| Glyceryl tripalmitate | Dynasan 116 (Hüls) |
| Glyceryl tristearate | Dynasan 118 (Hüls) |
| Glyceryl triarohidate | (Sigma) |
| Glyceryl trimyristoleate | (Sigma) |
| Glyceryl tripalmitoleate | (Sigma) |
| Glyceryl trioleate | (Sigma) |
| Glyceryl trilinoleate | (Sigma) |
| Glyceryl trilinolenate | (Sigma) |
| Glyceryl tricaprylate/caprate | CAPTEX 300 (Abitec); CAPTEX 355 (Abitec); MIGLYOL 810 (Hüls); MIGLYOL 812 (Hüls) |
| Glyceryl tricaprylate/caprate/laurate | CAPTEX 350 (Abitec) |
| Glyceryl tricaprylate/caprate/linoleate | CAPTEX 810 (Abitec); MIGLYOL 818 (Hüls) |
| Glyceryl tricaprylate/caprate/stearate | Softisan 378 (Hüls); (Larodan) |
| Glyceryl tricaprylate/laurate/stearate | (Larodan) |
| Glyceryl 1,2-caprylate-3-linoleate | (Larodan) |
| Glyceryl 1,2-caprate-3-stearate | (Larodan) |
| Glyceryl 1,2-laurate-3-myristate | (Larodan) |
| Glyceryl 1,2-myristate-3-laurate | (Larodan) |
| Glyceryl 1,3-palmitate-2-butyrate | (Larodan) |
| Glyceryl 1,3-stearate-2-caprate | (Larodan) |
| Glyceryl 1,2-linoleate-3-caprylate | (Larodan) |

In certain embodiments, the triglycerides utilized in the pharmaceutical compositions described herein include fractionated triglycerides, modified triglycerides, synthetic triglycerides, and mixtures of triglycerides are also within the scope of the invention. In specific embodiments, triglycerides include, by way of non-limiting example, vegetable oils, fish oils, animal fats, hydrogenated vegetable oils, partially hydrogenated vegetable oils, medium and long-chain triglycerides, and structured triglycerides. It should be appreciated that several commercial surfactant compositions contain small to moderate amounts of triglycerides, typically as a result of incomplete reaction of a triglyceride starting material in, for example, a transesterification reaction Such commercial surfactant compositions, while nominally referred to as "surfactants", may be suitable to provide all or part of the triglyceride component for the compositions of the present invention. Examples of commercial surfactant compositions containing triglycerides include some members of the surfactant families Gelucires (Gattefosse), Maisines (Gattefosse), and IMWITOR (Huls). Specific examples of these compositions are: Gelucire 44/14 (saturated polyglycolized glycerides); Gelucire 50/13 (saturated polyglycolized glycerides); Gelucire 53/10 (saturated polyglycolized glycerides); Gelucire 33/01 (semi-synthetic triglycerides of $C_8$-Clssaturated fatty acids); Gelucire 39/01 (semi-synthetic glycerides); other Gelucires, such as 37/06, 43/01, 35/10, 37/02, 46/07, 48/09, 50/02, 62/05, or the like; Maisine 35-I (linoleic glycerides); and IMWITOR 742 (capiylic/capric glycerides).

Additional Agents

The pharmaceutical compositions described herein optionally include one or more additional agents or additives. In certain instances, suitable additives include those that facilitate formulating a pharmaceutical composition described herein as an oral dosage form and include, e.g., coatings and capsule components. Further additives include, by way of non-limiting example, solubilizers, enzyme inhibitors, anti-foaming agents, antioxidants, binders, buffering agents, chelating agents, diluents, disintegrants, flavoring agents, preservatives, sweeteners, thickeners, or the like.

In some embodiments, pharmaceutical compositions provided herein optionally include one or more solubilizers, i.e., additives to increase the solubility of the pharmaceutical active ingredient or other composition components in the solid carrier. Suitable solubilizers for use in the compositions of the present invention include: alcohols, polyols, ethers of polyethylene glycols, amides, esters or the like. Alcohols and polyols include, by way of non-limiting example, ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives. Ethers of polyethylene glycols include those having an average molecular weight of about 200 to about 6000, such as, by way of non-limiting example, tetrahydrofurfuryl alcohol PEG ether (glycofurol, available commercially from BASF under the trade name Tetraglycol) and methoxy PEG (Union Carbide). Amides include, by way of non-limiting example, 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone. Esters include, by way of non-limiting example, ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof. Other solubilizers include, by way of non-limiting example, dimethyl acetamide, dimethyl isosorbide (Arlasolve DMI (ICI)), N-methylpyrrolidones (Pharmasolve (ISP)), monooctanoin, diethylene glycol monoethyl ether (available from Gattefosse under the trade name Transcutol), and water. Mixtures of solubilizers are also within the scope of the present disclosure. Except as indicated, these compounds are readily available from standard commercial sources. In specific embodiments, solubilizers include, by way of non-limiting example, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-600, glycofurol, transcutol, propylene glycol, and dimethyl isosorbide. In certain specific embodiments, solubilizers include sobitol, glycerol, triacetin, ethyl alcohol, PEG-400, glycofurol and propylene glycol. The amount of solubilizer included in the pharmaceutical compositions described herein is any suitable amount.

Anti-adherents (anti-sticking agents, glidants, flow promoters, lubricants) include, by way of non-limiting example, talc, magnesium stearate, fumed silica (Carbosil, Aerosil), micronized silica (Syloid No. FP 244. Grace U.S.A.), polyethylene glycols, surfactants, waxes, stearic acid, stearic acid salts, stearic acid derivatives, starch, hydrogenated vegetable oils, sodium benzoate, sodium acetate, leucine, PEG-4000 and magnesium lauryl sulfate. Antioxidants include, by way of non-limiting example, BHT, BHA, gallic acid, propyl gallate, ascorbic acid, ascorbyl palmitate, 4-hydroxymethyl-2,6-di-tert-butyl phenol, and tocopherol Binders (adhesives), i.e., agents that impart cohesive properties to powdered materials through particle-particle bonding, include, by way of non-limiting example, matrix binders (dry starch, dry sugars), film binders (PVP, starch paste, celluloses, bentonite, sucrose), and chemical binders (polymeric cellulose derivatives, such as carboxy methyl cellulose, HPC and HPMC; sugar syrups, corn syrup; water soluble polysaccharides such as acacia, tragacanth, guar and alginates; gelatin, gelatin hydrolysate; agar; sucrose; dextrose; and non-cellulosic binders, such as PVP, PEG, vinyl pyrrolidone copolymers, pregelatinized starch, sorbitol, and glucose). Buffering agents, include an acid and a base, wherein the acid is a pharmaceutically acceptable acid, such as hydrochloric acid, hydrobromic acid, hydriodic acid, sulfuric acid, nitric acid, boric acid, phosphoric acid, acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid, and the base is a pharmaceutically acceptable base, such as an amino acid, an amino acid ester, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrotalcite, magnesium aluminum hydroxide, diisopropylethylamine, ethanolamine, ethylenediamine, triethanolamine, triethylamine, triisopropanolamine, or a salt of a pharmaceutically acceptable cation and acetic acid, acrylic acid, adipic acid, alginic acid, alkanesulfonic acid, an amino acid, ascorbic acid, benzoic acid, boric acid, butyric acid, carbonic acid, citric acid, a fatty acid, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, and uric acid. Chelating agents include, by way of non-limiting example, EDTA and EDTA salts. Colorants or opaquants include, by way of non-limiting example, titanium dioxide, food dyes, lakes, natural vegetable colorants, iron oxides, silicates, sulfates, magnesium hydroxide and aluminum hydroxide. Diluents or fillers include, by way of non-limiting example, lactose, mannitol, talc, magnesium stearate, sodium chloride, potassium chloride, citric acid, spray-dried lactose, hydrolyzed starches, directly compressible starch, microcrystalline cellulose, cellulosics, sorbitol, sucrose, sucrose-based materials, calcium sulfate, dibasic calcium phosphate and dextrose. Disintegrants and super disintegrants include, by way of non-limiting example, croscarmellose sodium, starch, starch derivatives, clays, gums, cellulose, cellulose derivatives, alginates, crosslinked polyvinypyrrolidone, sodium starch glycolate and microcrystalline cellulose. Flavorants or desensitizers include, by way of non-limiting example, spray-dried flavors, essential oils and ethyl vanillin. Plasticizers include, by way of non-limiting example, polyethylene glycol, citrate esters (e.g., triethyl citrate, acetyl triethyl citrate, acetyltributyl citrate), acetylated monoglycerides, glycerin, triacetin, propylene glycol, phthalate esters (e.g, diethyl phthalate, dibutyl phthalate), castor oil, sorbitol and dibutyl seccate. Preservatives include, by way of non-limiting example, ascorbic acid, boric acid, sorbic acid, benzoic acid, and salts thereof, parabens, phenols, benzyl alcohol, and quaternary ammonium compounds. Solvents include, by way of non-limiting example, alcohols, ketones, esters, chlorinated hydrocarbons and water. Sweeteners include, by way of non-limiting example, natural sweeteners such as maltose, sucrose, glucose, sorbitol, glycerin and dextrins, and artificial sweeteners, such as aspartame, saccharine and saccharine salts Thickeners (viscosity modifiers, thickening agents) include, by way of non-limiting example, sugars, polyvinylpyrrolidone, cellulosics, polymers, high molecular weight polyethylene glycols (e.g., PEG 8000), and alginates. Additives also include, by way of non-limiting example, proteins (e.g., collagen, gelatin, Zein, gluten, mussel protein, lipoprotein); carbohydrates (e.g., alginates, carrageenan, cellulose derivatives, pectin, starch, chitosan); gums (e.g., xanthan gum, gum arabic); spermaceti; natural or synthetic waxes; carnuaba wax, fatty acids (e.g., stearic acid, hydroxystearic acid); fatty alcohols; sugars, shellacs, such as those based on sugars (e.g., lactose, sucrose, dextrose) or starches; polysaccharide-based shellacs (e.g., maltodextrin and maltodextrin derivatives, dextrates, cyclodextrin and cyclodextrin derivatives); cellulosic-based shellacs (e.g., microcrystalline cellulose, sodium carboxymethyl cellulose, hydroxypropylmethyl cellulose, ethyl cellulose, hydroxypropyl cellulose, cellulose acetate, cellulose nitrate, cellulose acetate butyrate, cellulose acetate trimellitate, carboxymethylethyl cellulose, hydroxypropylmethyl cellulose phthalate); inorganics, such as dicalcium phosphate, hydroxyapitite, tricalcium phosphate, talc and titania; polyols, such as mannitol, xylitol and sorbitol; polyethylene glycol esters; and polymers, such as alginates, poly(lactide coglycolide), gelatin, crosslinked gelatin, and agar-agar.

It should be appreciated that there is considerable overlap between the above-listed additives in common usage, since a given additive is often classified differently by different practitioners in the field, or is commonly used for any of several different functions. Thus, the above-listed additives should be taken as merely exemplary, and not limiting, of the types of additives that can be included in compositions of the present invention. The amounts of such additives can be readily determined by one skilled in the art, according to the particular properties desired.

The compositions and unit dosage forms can be prepared by any suitable method known to the skilled artisan or developed in view of the teachings herein.

In one specific aspect, the carrier(s) and API are brought to or maintained at a temperature at which they are flowable (e.g., above 10° C., 20° C., 25° C., 30° C., 35° C., or 40 OC). In one aspect, the mixture of carrier and API is a clear solution at a specified temperature (e.g., above 10° C., 20° C., 25° C., 30° C., 35° C., or 40 OC). In one aspect, the mixture of carrier and API is a cloudy or hazy solution at a specified temperature (e.g., below 10° C., 20° C., 25° C., 30° C., 35° C., or 40° C.).

In one example, the composition is prepared by weighing all of the components, except the API into a clean stainless steel container and mixed together at ambient temperature or at elevated temperatures e.g., at about 25° C. to about 30° C., at about 30° C. to about 35° C., at about 35° C. to about 40° C., at about 40° C. to about 45° C., at about 45° C. to about 45° C., or 50° C. to about 70° C., using a stirrer. The API is added and stirred into the mixture of other components until the API dissolves. A predetermined quantity of this "liquid fill material" is disposed into a capsule (for example, hard gelatin capsule) to get the required API dose per dosage unit.

The capsules are allowed to cool at room temperature, banded (if required) and packaged in a HDPE bottle and tightly closed with an appropriate lid. It is noted that various capsule sizes (e.g., hard gel or soft gel) are available to the skilled artisan and allow for variations in the amount of loading of API in mg per unit dosage form. Typically, soft gel capsules for oral administration have fill volumes of less than 1.5 mL, 1.3 mL or 1.25 mL with numerous incremental fill volumes in these ranges. Similarly, hard gel capsules typically have fill volumes of less than 1.25 mL, 1.10 mL or 1 mL. Due to the nature of some hard gel capsules, the total fill volume may not be useable. There is a practical limit on the temperature at which capsules can be filled—for example temperature above 40° C. typically melt, deform, or otherwise damage soft gel capsules typically employed in the industry. Hard gel capsules are typically less sensitive to temperature and can be filled at higher temperatures e.g., above 40° C.

In certain embodiments, any pharmaceutical composition described herein, e.g., a can be prepared by (i) combining and heating all ingredients until a molten mixture is obtained (e.g., 50-70° C.); and (ii) encapsulating an amount of molten mixture comprising a select dose (e.g., a therapeutically effective amount or a partial dose of a therapeutically effective amount) API to obtain an oral dosage form. In certain instances, the molten mixture is spray-congealed to obtain beads. In some instances, the molten mixture is sprayed onto inert cores (e.g., sugar spheres) to obtain coated cores. In certain embodiments, such beads, cores, or similar forms are encapsulated or otherwise formulated to provide an oral dosage form. In some instances, the molten mixture is admixed, uniformly dispersed, or granulated over a carrier and compressed into a tablet dosage form. In certain embodiments, prior to compression, the molten mixture/carrier composition is further mixed with one or more pharmaceutical aid including, by way of non-limiting example, glidants, lubricants, binders, or the like. In some embodiments, the carrier is a therapeutically inert carrier such as, by way of non-limiting example, microcrystalline cellulose, starch, lactose, or the like.

In various embodiments, pharmaceutical compositions described herein are formulated as oral dosage forms. Oral dosage forms are prepared by any suitable process including one or more steps of, by way of non-limiting example, agglomeration, air suspension chilling, air suspension drying, balling, coacervation, comminution, compression, pelletization, cryopelletization, encapsulation, extrusion, granulation, homogenization, inclusion complexation, lyophilization, nanoencapsulation, melting, mixing, molding, pan coating, solvent dehydration, sonication, spheronization, spray chilling, spray congealing, spray drying, or the like.

In some embodiments, a pharmaceutical composition described herein is formulated with a substrate to form an oral dosage form. In various embodiments, substrates useful for formulating pharmaceutical compositions described herein as oral dosage forms include or comprise, by way of non-limiting example, a powder or a multiparticulate (e.g., one or more granule, one or more pellet, one or more bead, one or more spherule, one or more beadlet, one or more microcapsule, one or more millisphere, one or more mini capsule, one or more microcapsule, one or more nanocapsule, one or more nanosphere, one or more microsphere, one or more minitablet, one or more tablet, one or more capsule, or one or more combinations thereof). In certain instances, a powder constitutes a finely divided (milled, micronized, nanosized, precipitated) form of an active ingredient or additive molecular aggregates or a compound aggregate of multiple components or a physical mixture of aggregates of an active ingredient and/or additives.

Exemplary Formulation Embodiments

Provided in this section are formulations for use in the methods described herein. It is noted that any testosterone ester can used in place of the specified API (e.g., testosterone undecanoate or a combination of testosterone undecanoate and testosterone tridecanoate).

TABLE 1A

Drug + Carriers

| Composition | Compositions (w/w %) | | Ratio of API: Carrier in a pharmaceutical composition |
|---|---|---|---|
| | Testosterone tridecanoate* | Carrier | |
| A | 5-15 | 85-95 | 1:5.7-1:9.0 |
| B | 15-20 | 80-85 | 1:4.0-1:5.7 |
| C | 20-30 | 70-80 | 1:2.3-1:4.0 |
| D | 30-40 | 60-70 | 1:1.5-1:2.3 |
| E | 40-50 | 50-60 | 1:1.0-1:1.5 |

*As an active ingredient, it can be untreated, sieved (PS < 450 micron), milled (PS < 150 micron), micronized (1 micron < PS < 25 micron), or nanosized (PS < 1 micron).

TABLE 2A

Carrier Components

| Component | | Carrier No. | | | | | | | | | | | |
|---|---|---|---|---|---|---|---|---|---|---|---|---|---|
| | | I | II | III | IV | V | VI | VII | VIII | IX | X | XI | XII | XIII |
| Solubilizer | Propylene glycol mono or di-laurate | Y | — | — | — | — | — | — | — | — | — | — | — | — |
| | Propylene glycol mono or di-caprylate | — | Y | — | — | — | — | — | — | — | — | — | — | — |
| | Corn glycerides (e.g. Glyceryl mono or di-linoleate) | — | — | Y | — | — | — | — | — | — | — | — | — | — |
| | Vegetable glycerides (e.g. Glyceryl mono or di-oleate) | — | — | — | Y | — | — | — | — | — | — | — | — | — |

TABLE 2A-continued

| | | Carrier Components | | | | | | | | | | | | |
|---|---|---|---|---|---|---|---|---|---|---|---|---|---|---|
| | | Carrier No. | | | | | | | | | | | | |
| | Component | I | II | III | IV | V | VI | VII | VIII | IX | X | XI | XII | XIII |
| | Glyceryl mono or di-stearate | — | — | — | — | Y | — | — | — | — | — | — | — | — |
| | Glyceryl palmito-stearate | — | — | — | — | — | Y | — | — | — | — | — | — | — |
| | (9Z)-Octadec-9-enoic acid | — | — | — | — | — | — | Y | — | — | — | — | — | — |
| | Octadecanoic acid | — | — | — | — | — | — | — | Y | — | — | — | — | — |
| | (9Z,12Z)-9,12-Octa-decadienoic acid | — | — | — | — | — | — | — | — | Y | — | — | — | — |
| | Peppermint oil | — | — | — | — | — | — | — | — | — | Y | — | — | — |
| | Omega-3 EPA/DHA | — | — | — | — | — | — | — | — | — | — | Y | — | — |
| | Vitamin E | — | — | — | — | — | — | — | — | — | — | — | Y | — |
| | Combinations * | — | — | — | — | — | — | — | — | — | — | — | — | Y |
| Hydrophilic Add. | CREMOPHOR, Tween, SLS, Poloxamer, Polymer, and/or combinations | Y | Y | Y | Y | Y | Y | Y | Y | Y | Y | Y | Y | Y |
| Other Add. | Anti-oxidant, solidifier, flow agent, solvent, and/or combinations | q.s. | q.s. | q.s. | q.s. | q.s. | q.s. | q.s. | q.s. | q.s. | q.s. | q.s. | q.s. | q.s. |

* Combinations of solubilizers can be a combination of 2 or more solubilizers that are listed in this table as well as include propylene glycol, polyethylene glycol, glycerol, sorbitol, DMA, and so on.
Add. = additive.
Y = Yes.

Carrier I. Compositions composed of solubilizer (Propylene glycol mono or di-laurate), hydrophilic additives, and other additives for Composition A to E

| | Carrier Compositions (w/w %) | | | | | | |
|---|---|---|---|---|---|---|---|
| | Propylene glycol | Hydrophilic additives[1] (e.g. CREMOPHOR[2] RH 40, Tween[3] 80, SLS, Poloxamer[4] 407, Polymer[5], and/or | Other additives[7] | | | | % Release in 8% Triton Aqueous Media ≥50% in 2 hrs |
| Comp I No. | mono or di-laurate | combinations[6]) | Anti-oxidant[8] | Solidify agent[9] | Combinations[10] | Total % in Carrier | and ≥75% in 4 hrs |
| a | 90-100 | — | 0-1 | 0-10 | 0-10 | 100 | Yes |
| b | 45-99 | 1-40 | 0-1 | 0-15 | 0-15 | 100 | Yes |
|  |  | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
|  |  | 10-20 | 0-1 | 10-20 | 10-20 | 100 | No |
| g | 50-80 | 30-40 | 0-1 | 0-10 | 0-10 | 100 | Yes |
|  |  | 20-30 | 0-1 | 0-10 | 0-10 | 100 | Yes |
|  |  | 10-20 | 0-1 | 10-20 | 10-20 | 100 | No |

Descriptions for from [1] to [10] are applied to tables of all carrier compositions (from Carrier I to Carrier XIII tables) shown below.

[1] Hydrophilic additives can be, but are not limited to ones listed in this table, e.g., hydrophilic surfactants having an HLB value of greater than 10, which are PEG-8 caprylic/capric glycerides (Labrasol), lauroyl macrogol-32 glyceride (Gelucire 44/14), stearoyl niacrogol glyceride (Gelucire 50/13), sodium dioctyl sulfosuccinate. polyethylene glycol fatty acids mono- and di-ester mixtures, polyethylene glycol 1000 tocopherol succinate, phytosterols, phytosterol fatty acid esters, lanosterol PEG-24 cholesterol ether. PEG-30 soya sterol. PEG-25 phyto sterol. PEG-30 cholestanol, and so on. [2] CREMOPHOR includes, but is not limited to, CREMOPHOR RH 40, but CREMOPHOR EL, RH 40, and RH 60. [3] Tween includes, but is not not limited to, Tween 80, but Tween 20, 60, and 80 [4] Poloxamer includes, but is not limited to Poloxamer 407, but Poloxamcr 124, 188, 234, 335, and 407. [5] Polymer includes, but is not limited to, Polyethylene glycol, Hydroxv propyl cellulose. Hydroxypropylmcthyl cellulose, Hydroxypropylmethyl cellulose acetate succinate, Polyvinylpyrrolidone, Polyvinyl acetate, Polylactic-co-glycolic acid, Polyvinyl caprolactame, Carbomer, and a combination thereof. [6] Combinations of hydrophilic additiv es can be 2 or more hydrophilic additives. [7] Other additives can be, but are not not limited to ones listed in this table, e.g., adsorbing agents, anti-adherents, anticoagulants, antifoaming agents, anticaking agents, anti-static agents, binders, bile acids, buffcrants, bulking agents, chelating agents, coagulants, colorants, opaquants, coolants, cryoprotcctants, diluents, dehumidifying agents, desiccants, desensitizers, disintegrants, dispersing agents, enzyme inhibitors, fillers, hydrating agent, super disintegrants, gums, mucilages, hydrogen bonding agents, enzymes, flavorants, humcctants, humidifying agents, ion-exchange resins, lubricants, plasticizers, pH modifying agents, preservatives, organic solvents, spreading agent, stabilizers, suspending agent, thickeners, viscosity increasing agents, waxes, and so on. [8] Anti-oxidant can be, but is not limited to, ascorbyl palmitate, ascorbic acid, butylatcd hydroxyanisole (BHA), butylatcd hydroxytoluene (BHT). propyl gallatc, cysteine, sodium metabisulfite (SMB), thiol derivatives, alpha-tocopherol, and so on. [9] Solidifying (solidify) agent can be, but is not limited, to PEG 3350, PEG 4000. PEG 6000, PEG 8000. Poloxamer 188. Poloxamer 407, cetyl esters, wax, beeswax, glyceryl monostearate, glyceryl distearate, glyceryl palmitostearate. stearic acid, and so on. [10] Combinations of other additives can be 2 or more other additives.

Carrier II. Compositions composed of solubilizer (Propylene glycol mono or di-caprylate), hydrophilic additives, and other additives for Composition A to E

| Comp II No. | Propylene glycol mono or di-caprylate | Hydrophilic additives[1] (e.g. CREMOPHOR[2] RH 40, Tween[3] 80, SLS, Poloxamer[4] 407, Polymer[5], and/or combinations[6]) | Anti-oxidant[8] | Solidify agent[9] | Combinations[10] | Total % in Carrier | % Release in 8% Triton Aqueous Media ≥50% in 2 hrs and ≥75% in 4 hrs |
|---|---|---|---|---|---|---|---|
| a | 90-100 | — | 0-1 | 0-10 | 0-10 | 100 | Yes |
| b | 45-99 | 1-40 | 0-1 | 0-15 | 0-15 | 100 | Yes |
|   |       | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
|   |       | 10-20 | 0-1 | 10-20 | 10-20 | 100 | No |
| g | 50-80 | 30-40 | 0-1 | 0-10 | 0-10 | 100 | Yes |
|   |       | 20-30 | 0-1 | 0-10 | 0-10 | 100 | Yes |
|   |       | 10-20 | 0-1 | 10-20 | 10-20 | 100 | No |

[1]Hydrophilic additives can be, but are not limited to ones listed in this table, e.g., hydorphilic surfactants having an HBL value of greater than 10, which are PEG-8 caprylic/capric glycerides (Labrasol), lauroyl macrogol-32 glyceride (Gelucire 44/14), stearoyl macrogol glyceride (Gelucire 50/13), sodium dioctyl sulfosuccinate, polyethylene glycol fatty acids mono- and di- ester mixures, polyethylene glycol 1000 tocopherol succinate, phytosterols, phytosterol fatty acid esters, lanosterol PEG-24 cholesterol ether, PEG-30 soya sterol, PEG-25 phyto sterol, PEG-30 sholesterol and so on.

[2]CREMOPHOR includes, but is not limited to, CREMOPHOR RH 40, but CREMOPHOR EL, RH 40, and RH 60.

[3]Tween includes, but is not limited to, Tween 80, but Tween 20, 60, and 80.

[4]Poloxamer includes, but is not limited to, Poloxamer 407, but Poloxamer 124, 188, 234, 335, and 407.

[5]Polymer includes, but is not limited to, Polyethylene glycol, Hydroxypropyl cellulose, Hydroxypropylmethyl cellulose, Hydroxypropylmethyl cellulose acetate succinate, Polyvinylpyrrolidone, Polyvinyl acetate, Polylactic-co-glycolic acid, Polyvinyl caprolactame, Carbomer, and a combination thereof.

[6]Combinations of hydrophilic additives can be 2 or more hydrophilic additives.

[7]Other additives can be, but are not limited to ones listed in this table, e.g., adsorbing agents, antiadherents, anticoagulants, antifoaming agents, anti-caking agents, anti-static agents, binders, bile acids, bufferants, bulking agents, chelating agents, coagulants, colorants, o[aquants, coolants, cryoprotectants, dilutenst, dehumidifying agents, desiccants, desensitizers, disintegrants, dispersing agents, enzyme inhibitors, fillers, hydrating agent, super disintergrants, gums, mucilages, hydrogen bonding agents, enzymes, flavorants, humectants, humidifying agents, ion-exchange resins, lubricants, plasticizers, pH modifying agents, preservatives, organic solvents, spreading agent, stabilizers, suspending agent, thickeners, viscosity increasing agents, waxes, and so on.

[8]Anti-oxidant can be, but is not limited to, ascorbyl palmitate, ascorbic acid, butylated hydroxyanisole (BHA), butylated hydroxytolune (BHT), propyl gallatc, systeine, sodium metabisulfite (SMB), thiol derivatives, alpha-tocopherol, and so on.

[9]Solidifying (solidify) agent can be, but is not limited to, to PEG 3350, PEG4000, PEG 6000, PEG 8000, Poloxamer 188, Poloxamer 407, cetyl esters, wax, beeswax, glyceryl monostearate, glyceryl distearate, glyceryl palmitostearate, stearic acid, and so on.

[10]Combinations of other additives can be 2 or more other additives.

Carrier III. Compositions composed of solubilizer (Corn glycerides: e.g. Glyceryl mono or di-linoleate), hydrophilic additives, and other additives for Composition A to E

| | Carrier Compositions (w/w %) | | | | | | % Release in 8% Triton Aqueous Media ≥50% in 2 hrs and ≥75% in 4 hrs |
|---|---|---|---|---|---|---|---|
| | Corn glycerides (e.g. Glyceryl mono or di-linoleate) | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | |
| Comp III No. | | | Anti-oxidant[8] | Solidify agent[9] | Combinations[10] | | |
| a | 90-100 | — | 0-1 | 0-10 | 0-10 | 100 | Yes |
| b | 45-99 | 1-40 | 0-1 | 0-15 | 0-15 | 100 | Yes |
| | | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
| | | 10-20 | 0-1 | 10-20 | 10-20 | 100 | No |
| | | 30-40 | 0-1 | 0-10 | 0-10 | 100 | Yes |
| g | 50-80 | 20-30 | 0-1 | 0-10 | 0-10 | 100 | Yes |
| | | 10-20 | 0-1 | 10-20 | 10-20 | 100 | No |

Carrier IV. Compositions composed of solubilizer (Vegetable glycerides: e.g. Glyceryl mono or di-oleate), hydrophilic additives, and other additives for Composition A to E

| | Carrier Compositions (w/w %) | | | | | | % Release in 8% Triton Aqueous Media ≥50% in 2 hrs and ≥75% in 4 hrs |
|---|---|---|---|---|---|---|---|
| | Vegatable glycerides (e.g. Glyceryl mono or di-oleate) | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | |
| Comp IV No. | | | Anti-oxidant[8] | Solidify agent[9] | Combinations[10] | | |
| a | 90-100 | — | 0-1 | 0-10 | 0-10 | 100 | Yes |
| b | 45-99 | 1-40 | 0-1 | 0-15 | 0-15 | 100 | Yes |
| | | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| | | 20-30 | 0-1 | 0-10 | 0-10 | 100 | Yes |
| f | 60-80 | 20-30 | 0-1 | 0-10 | 0-10 | 100 | Yes |
| | | 10-20 | 0-1 | 10-20 | 10-20 | 100 | No |
| g | 50-80 | 30-40 | 0-1 | 0-10 | 0-10 | 100 | Yes |
| | | 20-30 | 0-1 | 0-10 | 0-10 | 100 | Yes |
| | | 10-20 | 0-1 | 10-20 | 10-20 | 100 | No |

Carrier V. Compositions composed of solubilizer (Glyceryl mono or di-stearate), hydrophilic additives, and other additives for Composition A to E

| | Carrier Compositions (w/w %) | | | | | | |
|---|---|---|---|---|---|---|---|
| Comp V No. | Glyceryl mono or di-stearate | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | % Release in 8% Triton Aqueous Media ≥50% in 2 hrs and ≥75% in 4 hrs |
| | | | Anti-oxidant[8] | Solidify agent[9] | Combinations[10] | | |
| a | 90-100 | — | 0-1 | 0-10 | 0-10 | 100 | No |
| | | 1-40 | 0-1 | 0-15 | 0-15 | 100 | No |
| b | 45-99 | 1-40 | 0-1 | 0-15 | 0-15 | 100 | No |
| | | 1-25 | 0-1 | 15-20 | 15-20 | 100 | No |
| c | 85-99 | 1-4.5 | 0-1 | 0-10 | 0-10 | 100 | No |
| d | 80-95 | 5-10 | 0-1 | 0-10 | 0-10 | 100 | No |
| e | 70-90 | 10-20 | 0-1 | 0-10 | 0-10 | 100 | No |
| f | 60-80 | 20-30 | 0-1 | 0-10 | 0-10 | 100 | No |
| | | 10-20 | 0-1 | 10-20 | 10-20 | 100 | No |
| g | 50-80 | 30-40 | 0-1 | 0-10 | 0-10 | 100 | No |
| | | 20-30 | 0-1 | 0-10 | 0-10 | 100 | No |
| | | 10-20 | 0-1 | 10-20 | 10-20 | 100 | No |

Carrier VI. Compositions composed of solubilizer (Glyceryl palmito-stearate), hydrophilic additives, and other additives for Composition A to E

| | Carrier Compositions (w/w %) | | | | | | |
|---|---|---|---|---|---|---|---|
| Comp VI No. | Glyceryl palmito-stearate | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | % Release in 8% Triton Aqueous Media ≥50% in 2 hrs and ≥75% in 4 hrs |
| | | | Anti-oxidant[8] | Solidify agent[9] | Combinations[10] | | |
| a | 90-100 | — | 0-1 | 0-10 | 0-10 | 100 | No |
| b | 45-99 | 1-40 | 0-1 | 0-15 | 0-15 | 100 | No |
| | | 1-25 | 0-1 | 15-20 | 15-20 | 100 | No |
| c | 85-99 | 1-4.5 | 0-1 | 0-10 | 0-10 | 100 | No |
| d | 80-95 | 5-10 | 0-1 | 0-10 | 0-10 | 100 | No |
| e | 70-90 | 10-20 | 0-1 | 0-10 | 0-10 | 100 | No |
| f | 60-80 | 20-30 | 0-1 | 0-10 | 0-10 | 100 | No |
| | | 10-20 | 0-1 | 10-20 | 10-20 | 100 | No |
| g | 50-80 | 30-40 | 0-1 | 0-10 | 0-10 | 100 | No |
| | | 20-30 | 0-1 | 0-10 | 0-10 | 100 | No |
| | | 10-20 | 0-1 | 10-20 | 10-20 | 100 | No |

Carrier VII. Compositions composed of solubilizer ((9Z)-Octadec-9-enoic acid), hydrophilic additives, and other additives for Composition A to E

| Comp VII No. | (9Z)-Octadec-9-enoic acid | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | % Release in 8% Triton Aqueous Media ≥50% in 2 hrs and ≥75% in 4 hrs |
|---|---|---|---|---|---|---|---|
| | | | Anti-oxidant[8] | Solidify agent[9] | Combinations[10] | | |
| a | 90-100 | — | 0-1 | 0-10 | 0-10 | 100 | Yes |
| b | 45-99 | 1-40 | 0-1 | 0-15 | 0-15 | 100 | Yes |
| | | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
| | | 10-20 | 0-1 | 10-20 | 10-20 | 100 | No |
| g | 50-80 | 30-40 | 0-1 | 0-10 | 0-10 | 100 | Yes |
| | | 20-30 | 0-1 | 0-10 | 0-10 | 100 | Yes |
| | | 10-20 | 0-1 | 10-20 | 10-20 | 100 | No |

Carrier VIII. Compositions composed of solubilizer (octadecanoic acid), hydrophilic additives, and other additives for Composition A to E

| Comp. VIII No. | Octa-decanoic acid | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | % Release in 8% Triton Aqueous Media ≥50% in 2 hrs and ≥75% in 4 hrs |
|---|---|---|---|---|---|---|---|
| | | | Anti-oxidant[8] | Solidify agent[9] | Combinations[10] | | |
| a | 90-100 | — | 0-1 | 0-10 | 0-10 | 100 | No |
| b | 45-99 | 1-40 | 0-1 | 0-15 | 0-15 | 100 | No |
| | | 1-25 | 0-1 | 15-20 | 15-20 | 100 | No |
| c | 85-99 | 1-4.5 | 0-1 | 0-10 | 0-10 | 100 | No |
| d | 80-95 | 5-10 | 0-1 | 0-10 | 0-10 | 100 | No |
| e | 70-90 | 10-20 | 0-1 | 0-10 | 0-10 | 100 | No |
| f | 60-80 | 20-30 | 0-1 | 0-10 | 0-10 | 100 | No |
| | | 10-20 | 0-1 | 10-20 | 10-20 | 100 | No |
| g | 50-80 | 30-40 | 0-1 | 0-10 | 0-10 | 100 | No |
| | | 20-30 | 0-1 | 0-10 | 0-10 | 100 | No |
| | | 10-20 | 0-1 | 10-20 | 10-20 | 100 | No |

Carrier IX. Compositions composed of solubilizer ((9Z, 12Z)-9,12-Octadecadienoic acid), hydrophilic additives, and other additives for Composition A to E

| | Carrier Compositions (w/w %) | | | | | | % Release in 8% Triton Aqueous Media ≥50% in 2 hrs |
|---|---|---|---|---|---|---|---|
| Comp. IX No. | Octa- decadienoic acid | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | and ≥75% in 4 hrs |
| | | | Anti- oxidant[8] | Solidify agent[9] | Combi- nations[10] | | |
| a | 90-100 | — | 0-1 | 0-10 | 0-10 | 100 | Yes |
| b | 45-99 | 1-40 | 0-1 | 0-15 | 0-15 | 100 | Yes |
| | | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
| | | 10-20 | 0-1 | 10-20 | 10-20 | 100 | No |
| g | 50-80 | 30-40 | 0-1 | 0-10 | 0-10 | 100 | Yes |
| | | 20-30 | 0-1 | 0-10 | 0-10 | 100 | Yes |
| | | 10-20 | 0-1 | 10-20 | 10-20 | 100 | No |

Carrier X. Compositions composed of solubilizer (Peppermint oil), hydrophilic additives, and other additives for Composition A to E

| | Carrier Compositions (w/w %) | | | | | | % Release in 8% Triton Aqueous Media ≥50% in 2 hrs |
|---|---|---|---|---|---|---|---|
| Comp. X No. | Peppermint oil | Hydrophilic additives[1] (e.g. CREMOPHOR[2] RH 40, Tween[3] 80, SLS, Poloxamer[4] 407, Polymer[5], and/or combinations[6]) | Other additives[7] | | | Total % in Carrier | and ≥75% in 4 hrs |
| | | | Anti- oxidant[8] | Solidify agent[9] | Combi- nations[10] | | |
| a | 90-100 | — | 0-1 | 0-10 | 0-10 | 100 | Yes |
| b | 45-99 | 1-40 | 0-1 | 0-15 | 0-15 | 100 | Yes |
| | | 1-25 | 0-1 | 15-20 | 15-20 | 100 | Yes |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
| | | 10-20 | 0-1 | 10-20 | 10-20 | 100 | Yes |
| g | 50-80 | 30-40 | 0-1 | 0-10 | 0-10 | 100 | Yes |
| | | 20-30 | 0-1 | 0-10 | 0-10 | 100 | Yes |
| | | 10-20 | 0-1 | 10-20 | 10-20 | 100 | Yes |

Carrier XI. Compositions composed of solubilizer (Omega-3 EPA/DHA), hydrophilic additives, and other additives for Composition A to E

| | | Carrier Compositions (w/w %) | | | | | |
|---|---|---|---|---|---|---|---|
| Comp. XI No. | Omega-3 EPA/DHA | Hydrophilic additives[1] (e.g. CREMOPHOR[2] RH 40, Tween[3] 80, SLS, Poloxamer[4] 407, Polymer[5], and/or combinations[6]) | Anti-oxidant[8] | Solidify agent[9] | Combi-nations[10] | Total % in Carrier | % Release in 8% Triton Aqueous Media ≥50% in 2 hrs and ≥75% in 4 hrs |
| a | 90-100 | — | 0-1 | 0-10 | 0-10 | 100 | Yes |
| b | 45-99 | 1-40 | 0-1 | 0-15 | 0-15 | 100 | Yes |
|   |       | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
|   |       | 10-20 | 0-1 | 10-20 | 10-20 | 100 | No |
| g | 50-80 | 30-40 | 0-1 | 0-10 | 0-10 | 100 | Yes |
|   |       | 20-30 | 0-1 | 0-10 | 0-10 | 100 | Yes |
|   |       | 10-20 | 0-1 | 10-20 | 10-20 | 100 | No |

Carrier XII. Compositions composed of solubilizer (Vitamin E), hydrophilic additives, and other additives for Composition A to E

| | | Carrier Compositions (w/w %) | | | | | |
|---|---|---|---|---|---|---|---|
| Comp. XII No. | Vitamin E | Hydrophilic additives[1] (e.g. CREMOPHOR[2] RH 40, Tween[3] 80, SLS, Poloxamer[4] 407, Polymer[5], and/or combinations[6]) | Anti-oxidant[8] | Solidify agent[9] | Combi-nations[10] | Total % in Carrier | % Release in 8% Triton Aqueous Media ≥50% in 2 hrs and ≥75% in 4 hrs |
| a | 90-100 | — | 0-1 | 0-10 | 0-10 | 100 | Yes |
| b | 45 99 | 1-40 | 0-1 | 0-15 | 0-15 | 100 | Yes |
|   |       | 1-25 | 0-1 | 15-20 | 15-20 | 100 | Yes |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
|   |       | 20-30 | 0-1 | 0-10 | 0-10 | 100 | Yes |
| f | 60 80 | 10-20 | 0-1 | 10-20 | 10-20 | 100 | Yes |
|   |       | 30-40 | 0-1 | 0-10 | 0-10 | 100 | Yes |
| g | 50-80 | 20-30 | 0-1 | 0-10 | 0-10 | 100 | Yes |
|   |       | 10-20 | 0-1 | 10-20 | 10-20 | 100 | Yes |

Carrier XIII. Compositions composed of a combination of solubilizers, hydrophilic additives, and other additives for Composition A to E

| | Carrier Compositions (w/w %) | | | | | | |
|---|---|---|---|---|---|---|---|
| Comp. XIII No. | Combination of solubilizers[†] (e.g. oleic acid and GDS, oleic acid and peppermint oil, maisine 35-1 and GMC, etc) | Hydrophilic additives[1] (e.g. CREMOPHOR[2] RH 40, Tween[3] 80, SLS, Poloxamer[4] 407, Polymer[5], and/or combinations[6]) | Other additives[7] | | | % Release in 8% Triton Aqueous Media ≥50% in 2 hrs | |
| | | | Anti-oxidant[8] | Solidify agent[9] | Combi-nations[10] | Total % in Carrier | and ≥75% in 4 hrs |
| a | 90-100 | — | 0-1 | 0-10 | 0-10 | 100 | Yes |
| b | 45-99 | 1-40 | 0-1 | 0-15 | 0-15 | 100 | Yes |
| | | 1-25 | 0-1 | 15-20 | 15-20 | 100 | No |
| c | 85-99 | 1-4.5 | 0-1 | 0-10 | 0-10 | 100 | Yes |
| d | 80-95 | 5-10 | 0-1 | 0-10 | 0-10 | 100 | Yes |
| e | 70-90 | 10-20 | 0-1 | 0-10 | 0-10 | 100 | Yes |
| f | 60-80 | 20-30 | 0-1 | 0-10 | 0-10 | 100 | Yes |
| | | 10-20 | 0-1 | 10-20 | 10-20 | 100 | No |
| g | 50-80 | 30-40 | 0-1 | 0-10 | 0-10 | 100 | Yes |
| | | 20-30 | 0-1 | 0-10 | 0-10 | 100 | Yes |
| | | 10-20 | 0-1 | 10-20 | 10-20 | 100 | No |

Shown below are various compositions suitable for oral administration as described herein. In these Examples the amount of excipient adds up to 100% (does not include the API) and the API weight percent is the final weight percent in the pharmaceutical composition.

| Composition No. Component (w/w %) | 1 | 2 | 3 | 4 | 5 | 6 | 7 |
|---|---|---|---|---|---|---|---|
| API | 22 | 23 | 24 | 26 | 28 | 30 | 32 |
| Excipient 1 (e.g., liquid carrier) | 35-80 | 35-80 | 35-80 | 35-80 | 35-80 | 35-80 | 35-80 |
| Excipient 2 (e.g., additive) | 1-40 | 1-40 | 1-40 | 1-40 | 1-40 | 1-40 | 1-40 |
| Excipient 3 (e.g., hydrophilic additive) | 0-20 | 0-20 | 0-20 | 0-20 | 0-20 | 0-20 | 0-20 |
| Excipient 4 (e.g., anti-oxidant) | 0.01-3 | 0.01-3 | 0.01-3 | 0.01-3 | 0.01-3 | 0.01-3 | 0.01-3 |
| Additional Excipients (e.g., other pharmaceutically acceptable excipients) | Qs | qs | qs | qs | qs | Qs | qs |

The API in these compositions in specific compositions is testosterone tridecanoate, testosterone undecanoate, or a combination thereof. Alternatively, the skilled artisan understands that any other testosterone ester or steroid, or steroid ester can be used in these compositions accordingly. Excipient 1 in specific compositions is (9Z)-octadec-9-enoic acid. Excipient 2 in specific compositions is a combination of mono-, di-, or tri-propane-1,2,3-triol esters of octadecanoic acid and hexadecanoic acid; H—(O—$CH_2$—$CH_2$)$_n$—OH where n is an integer from 3 to 900; octadecanoic acid; (1R,2S,5R)-2-isopropyl-5-methylcyclohexanol or a combination of one or more of (1R,2S,5R)-2-isopropyl-5-methyl-cyclohexanol, (2S,5R)-2-Isopropyl-5-methylcyclo-hexanone, Acetic acid [(1R,2S,5R)-2-isopropyl-5-methylcyclohexyl]ester, 1,3,3-Trimethyl-2-oxabicyclo[2,2,2]octane, and (R)-1-methyl-4-(1-methylethenyl) cyclohexene; or a combination thereof. Excipient 3 in specific compositions is a polyoxylated hydrogenated vegetable oil. Excipient 4 in specific compositions is ascorbyl palmitate. These compositions can be filled into soft gel or hard gel capsules depending on its flowability at the temperatures useful for making these dosage forms.

Examplary Compositions

Shown below are various compositions suitable for oral administration as described herein. In these Examples the amount of excipient adds up to 100% (does not include the API) and the API weight percent is the final weight percent in the pharmaceutical composition.

| Composition No. Component (w/w %) | 10 | 11 | 12 | 13 | 14 | 15 | 16 | 17 | 18 |
|---|---|---|---|---|---|---|---|---|---|
| API | 23 | 24 | 25 | 26 | 27 | 28 | 29 | 30 | 31 |
| Excipient 1 (e.g., C14-C20 fatty acid) | 40-70 | 30-70 | 40-70 | 40-70 | 40-70 | 40-70 | 40-70 | 30-70 | 40-70 |
| Excipient 2 (e.g., glyceryl palmitostearate) | 0.5-20 | | | 1-20 | | | 1-20 | | |
| Excipient 3 | | 0.5-30 | | | 5-35 | | | 10-30 | |
| Excipient 4 (e.g., polyethylene glycol (high molecular weight)) | | | 0.5-15 | | | 1-12 | | | 2-11 |
| Excipient 4 (e.g., anti-oxidant (ascorbyl palmitate)) | 0.01-3 | 0.01-3 | 0.01-3 | 0.01-3 | 0.01-3 | 0.01-3 | 0.01-3 | 0.01-3 | 0.01-3 |
| Additional Excipients | qs | qs | qs | Qs | qs | Qs | qs | qs | qs |

The API in these compositions in specific compositions is testosterone tridecanoate, testosterone undecanoate, or a combination thereof. Alternatively, the skilled artisan understands that any other testosterone ester or steroid, or steroid ester can be used in these compositions accordingly. Excipient 1 in specific compositions is (9Z)-octadec-9-enoic acid. Excipient 2 in specific compositions is a combination of mono-, di-, or tri-propane-1,2,3-triol esters of octadecanoic acid and hexadecanoic acid, octadecanoic acid or a combination thereof. Excipient 3 in specific compositions is (1R, 2S,5R)-2-isopropyl-5-methylcyclohexanol or a combination of one or more of (1R,2S,5R)-2-isopropyl-5-methylcyclohexanol, (2S,5R)-2-Isopropyl-5-methylcyclohexanone, Acetic acid [(1R,2S,5R)-2-isopropyl-5-methylcyclohexyl] ester, 1,3,3-Trimethyl-2-oxabicyclo[2,2,2]octane, and (R)-1-methyl-4-(1-methylethenyl)cyclohexene. Excipient 4 in specific compositions is H—(O—$CH_2$—$CH_2$)$_n$—OH where n is an integer from 3 to 900 (e.g., PEG having an average molecular weight in the range of 2000-12000). These compositions can be filled into soft gel or hard gel capsules depending on its flowability at the temperatures useful for making these dosage forms. These compositions may include a hydrophilic additive.

Shown below are various compositions suitable for oral administration as described herein. In these Examples the amount of excipient adds up to 100% (does not include the API) and the API weight percent is the final weight percent in the pharmaceutical composition.

| Composition No. Component (w/w%) | 19 | 20 | 21 | 22 | 23 | 24 | 25 | 26 | 27 |
|---|---|---|---|---|---|---|---|---|---|
| API | 23 | 24 | 25 | 26 | 27 | 28 | 29 | 30 | 31 |
| Excipient 1 | 40-90 | 40-90 | 40-90 | 40-90 | 40-90 | 40-90 | 40-90 | 40-90 | 40-90 |
| Excipient 2 | 1-20 | | 1-20 | | 1-20 | | 1-20 | | 1-20 |
| Excipient 3 | | 1-10 | | 1-10 | | 1-10 | | 1-10 | |
| Excipient 4 | 0-25 | 0-25 | 0-25 | 0-25 | 0-25 | 0-25 | 0-25 | 0-25 | 0-25 |
| Additional Excipients | qs | qs | qs | qs | qs | qs | Qs | qs | qs |

The API in these compositions in specific compositions is testosterone tridecanoate, testosterone undecanoate, or a combination thereof. Alternatively, the skilled artisan understands that any other testosterone ester or steroid, or steroid ester can be used in these compositions accordingly. Excipient 1 in specific compositions is (9Z)-octadec-9-enoic acid. Excipient 2 in specific compositions is a combination of mono-, di-, or tri-propane-1,2,3-triol esters of octadecanoic acid and hexadecanoic acid, octadecanoic acid or a combination thereof. Excipient 3 in specific compositions is H—(O—CH$_2$—CH$_2$)$_n$—OH where n is an integer from 3 to 900 (e.g., PEG having an average molecular weight in the range of 2000-12000). Excipient 4 in specific compositions is (1R,2S,5R)-2-isopropyl-5-methylcyclohexanol or a combination of one or more of (1R,2S,5R)-2-isopropyl-5-methylcyclohexanol, (2S,5R)-2-Isopropyl-5-methylcyclohexanone, Acetic acid [(1R,2S,5R)-2-isopropyl-5-methylcyclohexyl]ester, 1,3,3-Trimethyl-2-oxabicyclo[2,2,2]octane, and (R)-1-methyl-4-(1-methylethenyl)cyclohexene. These compositions can be filled into soft gel or hard gel capsules depending on its flowability at the temperatures useful for making these dosage forms.

Examplary Compositions

Shown below are various compositions suitable for oral administration as described herein. In these Examples the amount of excipient adds up to 100% (does not include the API) and the API weight percent is the final weight percent in the pharmaceutical composition.

| Composition No.<br>Component (w/w %) | 28 | 29 | 30 | 31 | 32 | 33 | 34 | 35 | 36 |
|---|---|---|---|---|---|---|---|---|---|
| API | 23 | 24 | 25 | 26 | 27 | 28 | 29 | 30 | 31 |
| Excipient 1 | 40-90 | 45-90 | 50-90 | 55-90 | 40-90 | 45-90 | 55-90 | 50-90 | 50-90 |
| Excipient 2 | 5-15 | 1-15 | 5-15 | 1-15 | | | | | 5-15 |
| Excipient 3 | | | | | 1-10 | 1-10 | 1-10 | 1-10 | |
| Excipient 4 | 0-25 | 0-25 | 0-25 | 0-25 | 0-25 | 0-25 | 0-25 | 0-25 | 0-25 |
| Additional Excipients | Qs | qs | qs | qs | qs | qs | Qs | qs | qs |

The API in these compositions in specific compositions is testosterone tridecanoate, testosterone undecanoate, or a combination thereof. Alternatively, the skilled artisan understands that any other testosterone ester or steroid, or steroid ester can be used in these compositions accordingly. Excipient 1 in specific compositions is (9Z)-octadec-9-enoic acid. Excipient 2 in specific compositions is a combination of mono-, di-, or tri-propane-1,2,3-triol esters of octadecanoic acid and hexadecanoic acid, octadecanoic acid, or a combination thereof. Excipient 3 in specific compositions is H—(O—CH$_2$—CH$_2$)$_n$—OH where n is an integer from 3 to 900 (e.g., PEG having an average molecular weight in the range of 2000-12000). Excipient 4 in specific compositions is (1R,2S,5R)-2-isopropyl-5-methylcyclohexanol or a combination of one or more of (1R,2S,5R)-2-isopropyl-5-methylcyclohexanol, (2S,5R)-2-Isopropyl-5-methylcyclohexanone, Acetic acid [(1R,2S,5R)-2-isopropyl-5-methylcyclohexyl]ester, 1,3,3-Trimethyl-2-oxabicyclo[2,2,2]octane, and (R)-1-methyl-4-(1-methylethenyl)cyclohexene. These compositions can be filled into soft gel or hard gel capsules depending on its flowability at the temperatures useful for making these dosage forms.

Examplary Compositions

Shown below are various compositions suitable for oral administration as described herein. In these Examples the amount of excipient adds up to 100% (does not include the API) and the API weight percent is the final weight percent in the pharmaceutical composition

| Composition No.<br>Component(w/w %) | 37 | 38 | 39 | 40 | 41 | 42 | 43 | 44 | 45 |
|---|---|---|---|---|---|---|---|---|---|
| API | 23 | 24 | 25 | 26 | 27 | 28 | 29 | 30 | 31 |
| Excipient 1 (e.g., Fatty acid) | 45-80 | 45-80 | 45-80 | 45-80 | 45-80 | 45-80 | 45-80 | 45-80 | 45-80 |
| Excipient 2 | 1-15 | 1-15 | 1-15 | 1-15 | 1-15 | 1-15 | 1-15 | 1-15 | 1-15 |
| Excipient 3 | 0-10 | 0-10 | 0-10 | 0-10 | 0-10 | 0-10 | 0-10 | 0-10 | 0-10 |
| Excipient 4 | 0.1-0.3 | 0.1-0.3 | 0.1-0.3 | 0.1-0.3 | 0.1-0.3 | 0.1-0.3 | 0.1-0.3 | 0.1-0.3 | 0.1-0.3 |
| Additional Excipients | Qs | qs | qs | qs | qs | qs | qs | Qs | Qs |

The API in these compositions in specific compositions is testosterone tridecanoate, testosterone undecanoate, or a combination thereof. Alternatively, the skilled artisan understands that any other testosterone ester or steroid, or steroid ester can be used in these compositions accordingly. Excipient 1 in specific compositions is (9Z)-octadec-9-enoic acid, hexadecanoic acid or a combination thereof. Excipient 2 in specific compositions is a combination of mono-, di-, or tri-propane-1,2,3-triol esters of octadecanoic acid and hexadecanoic acid. Excipient 3 in specific compositions polyoxylated hydrogenated castor oil (CREMOPHOR R40). Excipient 4 in specific compositions is ascorbyl palmitate. These compositions can be filled into soft gel or hard gel capsules depending on its flowability at the temperatures useful for making these dosage forms.

It is to be understood that various formulations of androgen receptor agonists, testosterone and testosterone esters can be used in the methods described herein. Such exemplary formulations can be found e.g., US Patent Application Publication Nos. 20170354663; 20180028542; 20180125787; 20180147215; 20180021349; 20170065614; 20150328233; 20170136033; 20140011780; 20170056415; 20170020893; 20170246187; 20180110786; and 20170106002; each of which is incorporated by reference in its entirety.

Examples of such formulations are as follows:

Formulation AAA Ingredients mg/capsule (% w/w): Testosterone Undecanoate 158.3 mg (19.8%); Oleic Acid 413.1 mg (51.6%); CREMOPHOR RH 40 128.4 mg (16.1%); Borage Seed Oil 80.0 mg (10%); Peppermint Oil 20.0 mg (2.5%); BHT 0.2 mg (0.03%); Total 800 mg (100%).

Formulation AAB Ingredients mg/capsule (% w/w): Testosterone Undecanoate 158.3 mg (19.8%); Oleic Acid 412.5 mg (51.6%); CREMOPHOR RH 40 128.4 mg (16.0%); Peppermint Oil 20.0 mg (2.5%); Borage Seed Oil 80.0 mg (10%); BHT 0.2 mg (0.03%) Ascorbyl Palmitate 0.8 mg (0.1%); Total 800 mg (100%).

Thus, the formulation can comprise: (a) 15-25 percent by weight of a solubilized testosterone undecanoate; (b) 12-18 percent by weight of at least one hydrophilic surfactant; (c) 50-65 percent by weight of at least one lipophilic surfactant; and (d) 10-15 percent by weight of a mixture of borage oil and peppermint oil.

Thus, the formulation can comprise: (a) 18-22 percent by weight of a solubilized testosterone undecanoate; (b) 15-17 percent by weight of at least one hydrophilic surfactant; (c) 50-55 percent by weight of at least one lipophilic surfactant; and (d) 10-15 percent by weight of a mixture of borage oil and peppermint oil.

Thus, the formulation comprises: a) a phytosterol or phytosterol ester; b) a non-sterol solubilizing agent; and c) at least one lipophilic, poorly water soluble therapeutic agent (e.g., a testosterone ester such as testosterone undecanoate or testosterone tridecanaote), in a composition, wherein the composition is effective to enhance solubility of at least one therapeutic agent, as compared to the solubility of the same therapeutic agent in the absence of a) a phytosterol or phytosterol ester and b) a non-sterol solubilizing agent. Exemplary formulations of type are given in the next two tables.

| Component (% as W/W) | BBA | BBB | BBC |
|---|---|---|---|
| Tesiosterone Undecanoate | 11.54 | 11.54 | 11.54 |
| Castor oil | 25.40 | | |
| Oleic acid | | 25.93 | 25.93 |
| Lipoid E PC S (Egg Lecithin) | 0.85 | 0.85 | 0.85 |
| CREMOPHOR RH40 | 29.63 | 9.88 | 9.87 |
| Polysorbate-80 | | 19.74 | 19.73 |
| LABRAFIL M 1944 CS | 12.70 | 11.69 | 5.17 |
| Lauroglycol 90 | 16.93 | | |
| Glyceryl mono-oleate Type 40 | | 15.37 | 8.85 |
| PRECIROL ® | | | 13.26 |
| Phytosterols as CardioAid XF | 2.12 | 2.11 | 2.12 |
| Hypromellose 2910 (HPMC) | 0.85 | 0.85 | 0.85 |
| dl-α-Tocopherol | | 2.00 | 1.77 |
| Butylated Hydroxyanisole | 0.05 | 0.05 | 0.05 |

| Component | Formulation CCA | Formulation CCB | Formulation CCC |
|---|---|---|---|
| TU | 20.3% | 71.7% | 42.2% |
| Oleic acid | 18.5% | 6.7% | 4.0% |
| GMO | 11.1% | 4.0% | 2.4% |
| LABRAFIL M 1944 CS | 8.4% | 3.1% | 1.8% |
| CREMOPHOR RH40 | 7.1% | 2.6% | 1.5% |
| Tween 80 | 14.1% | 5.1% | 3.0% |
| Phytosterols | 18.2% | 5.8% | 44.6% |
| Lyso Lecithin | 0.6% | 0.2% | 0.1% |
| HPMC | 0.6% | 0.2% | 0.1% |
| Vitamin E | 1.3% | 0.5% | 0.3% |

Some formulation of the formulations described herein include a water soluble (hydrophilic) surfactant, a non-ionic surfactant and a water insoluble (hydrophobic) surfactant. The surfactants can be in any ratio that will give the desired properties of the formulations with the testosterone ester (e.g., testosterone undecanoate or testosterone tridecanoate). In certain embodiments of the formulations described herein the ratio by weight of the water soluble surfactant, a non-ionic surfactant and a water insoluble surfactant is about 1:1:1, 1:2:1, 1:3:1, 1:4:1, 1:5:1, 2:1:1, 2:2:1, 2:3:1, 2:4:1, 2:5:1, 3:1:1, 3:2:1, 3:3:1, 3:4:1, 3:5:1, 4:1:1, 4:2:1, 4:3:1, 4:4:1, 4:5:1, 5:1:1, 5:2:1, 5:3:1, 5:4:1 or 5:5:1. In certain embodiments of the formulations described herein the ratio by weight of the water soluble surfactant, a non-ionic surfactant and a water insoluble surfactant is about 1:1:2, 1:2:2, 1:3:2, 1:4:2, 1:5:2, 2:1:2, 2:2:2, 2:3:2, 2:4:2, 2:5:2, 3:1:2, 3:2:2, 3:3:2, 3:4:2, 3:5:2, 4:1:2, 4:2:2, 4:3:2, 4:4:2, 4:5:2, 5:1:2, 5:2:2, 5:3:2, 5:4:2 or 5:5:2. In certain embodiments of the formulations described herein the ratio by weight of the water soluble surfactant, a non-ionic surfactant and a water insoluble surfactant is about 1:1:3, 1:2:3, 1:3:3, 1:4:3, 1:5:3, 2:1:3, 2:2:3, 2:3:3, 2:4:3, 2:5:3, 3:1:3, 3:2:3, 3:3:3, 3:4:3, 3:5:3, 4:1:3, 4:2:3, 4:3:3, 4:4:3, 4:5:3, 5:1:3, 5:2:3, 5:3:3, 5:4:3 or 5:5:3. In certain embodiments of the formulations described herein the ratio by weight of the water soluble surfactant, a non-ionic surfactant and a water insoluble surfactant is about 1:1:4, 1:2:4, 1:3:4, 1:4:4, 1:5:4, 2:1:4, 2:2:4, 2:3:4, 2:4:4, 2:5:4, 3:1:4, 3:2:4, 3:3:4, 3:4:4, 3:5:4, 4:1:4, 4:2:4, 4:3:4, 4:4:4, 4:5:4, 5:1:4, 5:2:4, 5:3:4, 5:4:4 or 5:5:4. In certain embodiments of the formulations described herein the ratio by weight of the water soluble surfactant, a non-ionic surfactant and a water insoluble surfactant is about 1:1:5, 1:2:5, 1:3:5, 1:4:5, 1:5:5, 2:1:5, 2:2:5, 2:3:5, 2:4:5, 2:5:5, 3:1:5, 3:2:5, 3:3:5, 3:4:5, 3:5:5, 4:1:5, 4:2:5, 4:3:5, 4:4:5, 4:5:5, 5:1:5, 5:2:5, 5:3:5, 5:4:5 or 5:5:5. In certain embodiments the ratio of by weight of the water soluble surfactant, a non-ionic surfactant and a water insoluble surfactant is 1:3:5.

Examples of these types of formulation can have e.g. from 5%-30% and preferably 5%-15% loading (w/w %) of testosterone ester (e.g., testosterone undecanoate or testosterone tridecanoate) and Formulation XA (CAPRYOL 90/TWEEN 80/TRANSCUTOL P (2:5:5)); Formulation XB (Propylene glycol/CREMOPHOR EL/CAPRYOL 90 (1:3:5)); Formulation XC (Sunflower Seed Oil/CREMOPHOR EL/SPAN 80 (3/4/3 w/w/w)); Formulation XD (Corn Oil/CREMOPHOR EL/SPAN 80 (3/4/3 w/w/w)); and Formulation E (Sunflower Seed Oil/CREMOPHOR EL/Maisine (1:1:1)). Related formulation are disclosed below (other testosterone esters can be sued including testosterone tridecanoate). Moreover the formulation that do not include testosterone undecanoate below can be adapted to include testosterone esters such as testosterone undecanoate, testosterone tridecanoate or other testosterone esters.

| Testosterone Undecanoate Formulation (%) | Propylene glycol (mg) | CREMOPHOR EL (mg) | Capryol 90 (mg) | 5% ethyl oleate | Testosterone Undecanoate (mg) | Total |
|---|---|---|---|---|---|---|
| Formulation 0 B0 | 116.5 | 354.1 | 529.5 | — | — | 1000 |
| Formulation 9 B | 106.0 | 322.2 | 481.8 | — | 90.0 | 1000 |
| Formulation 7.5 B1 | 107.7 | 327.5 | 489.7 | — | 75.0 | 1000 |
| Formulation 0 H0 | 110.6 | 336.4 | 503.0 | — | 50.0 | 1000 |
| Formulation 9 H1 | 100.7 | 306.1 | 457.7 | 45.5 | 90.0 | 1000 |
| Formulation 7.5 H2 | 102.3 | 311.2 | 465.3 | 46.3 | 75.0 | 1000 |

Another composition which can be used with the methods described here include Andriol or Andriol Testocaps which are or were commercially available.

(a) testosterone undecanoate, (b) cholesterol, and (c) at least one phospholipid, wherein (a) and (b) are present in a weight ratio (a):(b) ranging from 1.0.0.05 to 10:0.30 and (a), (b) and (c) are present in a weight ratio of (a):((b)+(c)) ranging from 1.0:1.0 and 1.0:2.5.

In one aspect, the phospholipid is selected from distearoyl phos phatidylcholine, dipalmitoyl phosphatidylcholine, dimyris toyl phosphatidylcholine, egg phosphatidylcholine, soy phosphatidylcholine, dimyrsityl phosphatidyl glycerol Sodium, 1,2-dimyristoyl-phosphatidic acid, dipalmitoyl phosphatidylglycerol, dipalmitoyl phosphate, 1,2-dis tearoyl-sn-glycero-3-phospho-rac-glycerol. 1,2-distearoyl sn-glycero-3-phosphatidic acid, phosphatidylserine and sphingomyelin, or a combination thereof. In one aspect, the phospholipid is distearoyl phosphatidylcholine.

An oral pharmaceutical composition comprising a testosterone derivative having a log P of at least 5, wherein the testosterone derivative is selected from testosterone undecanoate, testosterone enanthate, testosterone oleate, or testosterone palmitate, wherein the testosterone derivative is present in an amount from 0.5% to 20% by weight based on 100% total weight of the composition, and a vehicle, wherein the vehicle comprises (a) a fat component in an amount of at least 500 mg sufficient to achieve lymphatic absorption in a mammal, wherein the fat component comprises a mono-glyceride of long chain fatty acids, a triglyceride of long chain fatty acids, or a mono- and triglyceride of long chain fatty acids, wherein the long chain fatty acids in the monoglycerides are selected from fatty acid chains having from 14 to 22 carbon atoms and the long chain fatty acids in the triglycerides are selected from fatty acid chains having from 14 to 22 carbon atoms, and (b) a hydrophilic surfactant, wherein the hydrophilic surfactant is selected from hydrogenated castor oil ethoxylates, polysorbates or any other hydrophilic surfactant with a Hydrophile-Lipophile Balance (HLB) value of 10 or higher, and any combination thereof, wherein the weightratio (a):(b) is from 10:1 to 1:1.

It is also to be understood that although this disclosure is described mainly in the context of oral testosterone/testosterone ester treatments, other routes of administration used in the art can be adapted to the methods described in this disclosure.

The following examples are provided to promote a more clear understanding of certain embodiments of this disclosure and are in no way meant as a limitation thereon.

EXAMPLES

Example 1: Clinical Trial

Oral testosterone therapy was evaluated in a multicenter, phase 3, randomized, open-label, active controlled, parallel-group study that included a 13-week efficacy phase and a 52-week safety phase. An active arm in which subjects received T gel was included for safety evaluation only.

Materials and Methods

Study Centers and Ethics

Forty US sites enrolled subjects from February 2014 to April 2015. Each site received Institutional Review Board approval of the protocol before study commencement.

Study Population

Males 18 through 80 years old with a documented diagnosis of primary hypogonadism (congenital or acquired) or hypogonadotropic hypogonadism (congenital or acquired) and with morning serum T<300 ng/dL based on 2 consecutive blood samples obtained between 0600 and 1000 on 2 separate days at approximately the same time were eligible to participate. Subjects were either naïve to T therapy or completed an adequate washout of T therapy (eg, 12 weeks after intramuscular androgen injections excluding TU injections which required a longer waiting period; 4 weeks after topical or buccal androgens; and 3 weeks after oral androgens). Exclusion criteria included abnormal prostate digital rectal examination with palpable nodule(s) or International Prostate Symptom Score (IPSS)>19 points; body mass index ≥38 kg/m$^2$, clinically significant laboratory values (baseline hemoglobin <11.5 or >16.5 g/dL, hematocrit <35% or >54%, serum transaminases >2.5 times upper limit of normal, serum bilirubin >2.0 mg/dL, creatinine >2.0 mg/dL, prostate specific antigen [PSA]>2 ng/mL, prolactin >17.7 ng/mL); history of seizures or convulsions; any surgical procedure that might interfere with gastrointestinal motility, pH, or absorption; stroke or myocardial infarction within 5 years; current or suspected prostate or breast cancer; severe, untreated, obstructive sleep apnea; long QT syndrome or unexplained sudden death in first-degree relative; concurrent medication use that could impact absorption, distribution, metabolism, or excretion of TU or place subject at risk for treatment with T; and dose changes of antihypertensive, lipid-lowering, or hypoglycemic agents within previous 3 months.

Study Design and Procedures

Subjects were randomized in a 2:1 ratio to oral testosterone undecanoate or T gel. oral testosterone undecanoate subjects started at a dose of 225 mg TU ("testosterone undecanoate") taken twice daily (total daily dose: 450 mg TU) every 12 hours. For optimal lymphatic absorption oral testosterone undecanoate must be administered with a meal [15,16]. Therefore, subjects were instructed to administer oral testosterone undecanoate after a standard meal (defined as a meal consisting of 800 to 1400 calories with approximately 20% to 35% fat content). The oral testosterone undecanoate dose was titrated at Weeks 4 and 8, if necessary, based on results of intensive 24-hour PK blood sampling obtained at Weeks 3 and 7, respectively. Oral testosterone undecanoate subjects stayed at the clinic overnight during each intensive PK blood sampling period. Dose titration was based on serum T average concentration over 24 hours (Cavg0-24 h) and maximum observed serum concentration (Cmax) and was titrated by 75 mg dose adjustments. Oral testosterone undecanoate dose levels permitted during the study were 150 mg BID, 225 mg BID, and 300 mg BID. Data collected during an intensive 24-hour PK sampling overnight stay at Week 13 were used for efficacy analysis; dose was not adjusted at this visit. Additional outpatient visits were conducted at Weeks 26, 39, and 52 during which single blood draws were performed 3 to 6 hours post morning dose. Dose was not adjusted during these visits.

T gel (ANDROGEL®) (testosterone gel for topical use) 1.62%, AbbVie, Chicago, Illinois, US) was supplied in non-aerosol, metered dose pumps that deliver 20.25 mg T per complete pump actuation. T gel was dosed according to product labeling. Subjects receiving T gel completed outpatient visits at Weeks 2 and 4 with single blood draws to determine titration and at Weeks 3 and 5 for dose changes, if necessary. They also completed an outpatient visit at Week 7 for safety assessments and at Weeks 13, 26, 39 and 52 during which single blood samples were obtained 3 to 6 hours after the morning dose. Dose was not adjusted during these visits. Overnight clinic stays were not required for T gel subjects.

Assessments

Safety endpoints included adverse events (AEs), physical examination findings, vital signs, electrocardiograms (ECGs), and clinical laboratory tests. AEs were classified using the Medical Dictionary for Regulatory Activities (Version 16.1). Safety endpoints were summarized using descriptive statistics. Lab parameters were evaluated using two sample t-tests comparing change from baseline to end of study (EOS) across oral testosterone undecanoate and T gel subjects with p-values <0.05 considered statistically significant.

Hormone Assessment and Statistical Analysis

Serum levels of T, TU, dihydrotestosterone (DHT), dihydrotestosterone undecanoate (DHTU), and estradiol (E2) were evaluated in oral testosterone undecanoate treated subjects. Pharmacokinetic parameters were calculated for T Cmax and T Cavg0-24 h. Sex hormone binding globulin (SHBG) was evaluated in data from all subjects. Serum T concentrations at screening were measured using chemiluminescence immunoassay kits. Hormone assays for pharmacokinetic assessment were analyzed at PPD Bioanalytical Laboratory in Richmond, Virginia Serum samples were analyzed for T, DHT, TU, DHTU, and E2 using a validated liquid chromatography-tandem mass spectrometry (LC-MS/MS) assay.

Subjects

Demographic characteristics were similar for oral testosterone undecanoate and T gel subjects (Table 1). The study was completed by 61.9% and 67.6% of oral testosterone undecanoate treated and T gel subjects, respectively. Non-safety related reasons for early discontinuation included lost to follow-up (6.7% and 11.4%), consent withdrawn due to confinement or schedule conflict (6.7% and 2.9%), consent withdrawn due to reason other than confinement or schedule (4.8% and 1.9%), met Cmax or Cavg stopping criteria (4.3% of oral testosterone undecanoate treated subjects and not applicable for T gel subjects), protocol deviation (3.3% and 2.9%), lack of efficacy (2.4% and 3.8%), and subject enrolled at more than one study site (1.9% and 2.9%). Table 2 presents safety-related reasons for early discontinuation.

Pharmacokinetic Assessments

Efficacy and pharmacokinetic results of this study are described elsewhere [14]. In brief, at Week 13, serum T Cavg0-24 h was between 300 and 1140 ng/dL in 87.4% of LPCN 1021 subjects (95% lower bound CI: 81.7%), which met predefined efficacy criteria. Week 13 Cavg0-24 h was 446 ng/dL and Cmax was 1134 ng/dL. Average serum T levels remained within eugonadal levels throughout the study (481±371, 543±438, and 538±545 ng/dL at Weeks 26, 39, and 52, respectively). Calculated free T levels, were consistently within normal values, 9 to 30 ng/dL. Measured DHT concentrations increased as T concentrations increased, indicating that T converts to DHT via 5-alpha reductase activity leading to DHT pharmacokinetics that simulated those of T. Overall ratios of DHT/T for oral testosterone undecanoate treated subject based on Cavg0-24 h at Weeks 3, 7, and 13 were 0.24, 0.26, and 0.26, respectively, and based on Cmax at Weeks 3, 7, and 13 were 0.16, 0.18, and 0.18, respectively, which were within the normal range for DHT/T ratio of 0.05 to 0.33. Serum E2 concentrations for oral testosterone undecanoate treated subjects remained within normal levels throughout Week 52 for oral testosterone undecanoate treated subjects.

Mean SHBG levels decreased at each post-baseline visit following oral testosterone undecanoate administration, but not T gel (FIG. 1). The largest decrease in oral testosterone undecanoate treated subjects occurred at Week 13 (change from baseline of −11.75 nmol/L), after which SHBG levels increased slightly and remained relatively stable.

Lipoprotein-associated phospholipase A2 decreased significantly from baseline to EOS for both oral testosterone undecanoate and T gel, but the difference in the change from baseline between groups was not significant.

TABLE 1

Trial. Demographic and Baseline Characteristics

| Characteristic[a] | Oral testosterone undecanoate (N = 210) | T Gel (N = 105) |
|---|---|---|
| Age, years | 52.6 (10.2) | 54.2 (9.4) |
| ≤65, n (%) | 190 (90.5) | 96 (91.4) |
| >65, n (%) | 20 (9.5) | 9 (8.6) |
| Race, n (%) | | |
| Asian | 3 (1.4) | 3 (2.9) |
| Black or African American | 32 (15.2) | 10 (9.5) |
| White | 172 (81.9) | 92 (87.6) |
| Other | 3 (1.4) | 0 |
| Weight, kg | 97.1 (15.0) | 99.2 (14.8) |
| Height, cm | 177.24 (7.4) | 178.76 (7.1) |
| Body mass index, kg/m$^2$ | 30.8 (3.9) | 31.0 (3.9) |
| ≥30 kg/m$^2$, n (%) | 118 (56.2) | 67 (63.8) |
| <30 kg/m$^2$, n (%) | 92 (43.8) | 38 (36.2) |
| Prior Androgen Therapy | | |
| Reported prior use | 108 (51.4%) | 58 (55.2%) |
| Reported no prior use | 102 (48.6%) | 47 (44.8%) |
| Serum T[b], ng/dL | 205.6 (66.3) | 201.9 (71.9) |

TABLE 1-continued

Trial. Demographic and Baseline Characteristics

| Characteristic[a] | Oral testosterone undecanoate (N = 210) | T Gel (N = 105) |
|---|---|---|
| Luteinizing hormone, IU/L | 5.8 (7.3) | 4.8 (4.4) |
| Follicle stimulating hormone, IU/L | 8.4 (10.3) | 7.2 (7.6) |

[a]Mean (SD) except where noted otherwise.
[b]Serum T levels for last two collected measurements at baseline (n = 420 for oral testosterone undecanoate treated subjects and n = 208 for T gel subjects).

TABLE 2

Trial. Mean (SD) Change from Baseline to End of Study in Androgenic Parameters, Liver Enzymes and Lipid Parameters (Safety Set, N = 314)

| Laboratory Parameter | Oral testosterone undecanoate N = 210 | | | T Gel N = 104 | | | P-Value Oral TU vs T Gel |
|---|---|---|---|---|---|---|---|
| | N | Mean (SD) | P-Value | N | Mean (SD) | P-Value | |
| Androgenic Parameters | | | | | | | |
| Hematocrit (%) | 174 | 2.54(3.41) | <.0001 | 81 | 2.10(3.19) | <.0001 | 0.3333 |
| Hemoglobin (g/L) | 174 | 7.2(10.65) | <.0001 | 81 | 6.1(10.91) | <.0001 | 0.4624 |
| Platelets ($10^9$/L) | 170 | 8.5(31.34) | 0.0005 | 81 | 6.3(25.91) | 0.0310 | 0.5824 |
| APTT | 174 | 0.61(4.07) | 0.0485 | 80 | 0.39(3.41) | 0.3146 | 0.6651 |
| Prothrombin time (sec) | 175 | 0.31(1.14) | 0.0004 | 82 | 0.51(3.69) | 0.2129 | 0.5132 |
| PSA (mcg/L) | 177 | 0.27(0.97) | 0.0002 | 83 | 0.13(0.24) | <.0001 | 0.1857 |
| Liver Function Tests | | | | | | | |
| Alkaline phosphatase (U/L) | 175 | −4.1(13.33) | <.0001 | 82 | 0.4(9.29) | 0.6785 | 0.0062 |
| ALT (U/L) | 175 | −3.07(11.22) | 0.0004 | 82 | −2.76(11.65) | 0.0351 | 0.8358 |
| AST (U/L) | 174 | −1.5(7.52) | 0.0113 | 82 | −2.2(8.39) | 0.0190 | 0.4684 |
| GGT (U/L) | 177 | −2.0(12.50) | 0.0336 | 83 | −0.6(11.94) | 0.6736 | 0.3749 |
| Bilirubin (mcmol/L) | 175 | −0.43(3.66) | 0.1237 | 82 | −0.57(3.45) | 0.1402 | 0.7709 |
| Lipid Parameters | | | | | | | |
| HDL cholesterol (mmol/L) | 176 | −0.14(0.22) | <.0001 | 82 | −0.06(0.22) | 0.0178 | 0.0035 |
| LDL cholesterol (mmol/L) | 163 | −0.05(0.66) | 0.3120 | 75 | −0.21(0.69) | 0.0103 | 0.0942 |
| Triglyceride (mmol/L) | 176 | −0.18(1.14) | 0.0371 | 82 | 0.12(1.43) | 0.4657 | 0.0750 |
| Cholesterol (mmol/L) | 177 | −0.24(0.82) | 0.0001 | 83 | −0.21(0.89) | 0.0325 | 0.8001 |
| Other | | | | | | | |
| C-Reactive Protein (nmol/L)a | 166 | −4.68(30.94) | 0.3098 | 82 | −7.55(55.31) | 0.1893 | 0.6009 |
| Lp-PLA2 (ng/mL) | 179 | −9.6(42.07) | 0.0044 | 78 | −13.0(49.54) | 0.0233 | 0.5774 |

[a]Subjects with CRP values > 95.23 were excluded.

ALT = alanine aminotransferase, APTT = activated partial thromboplastin time, AST = aspartate aminotransferase, GGT = gamma-glutamyl transferase HDL = high density lipoprotein, LDL = low density lipoprotein, Lp-PLA2 = lipoprotein-associated phospholipase A2, PSA = prostate specific antigen Mean hematocrit increase from baseline to EOS was similar for treatments. To minimize excessive hematocrit increases, investigators could prematurely withdraw subjects with hematocrit >54%. Elevated hematocrit (>54%) occurred in 8 oral TU treated subjects and 1 T gel subject: 3 of these 8 oral TU treated subjects (1.4%) and the T gel subject (1.0%) were withdrawn; 3 oral TU treated subjects were not withdrawn because hematocrit levels decreased at a subsequent laboratory evaluation; and 2 subjects were withdrawn due to reasons other than elevated hematocrit.

Small and similar increases in hemoglobin from pretreatment to EOS occurred in oral TU and T gel subjects.

Serum HDL cholesterol showed a significantly larger decrease at EOS for oral testosterone undecanoate than T gel. For HDL cholesterol, 19.0% of oral testosterone undecanoate subjects and 14.5% of T gel subjects had a shift from normal at baseline to low at EOS. No statistically significant differences between oral testosterone undecanoate and T gel were found between treatments for other lipid parameters.

Oral Testosterone Undecanoate Trial Results—Liver Function Enzymes and Lipids Analysis

TABLE 3

Trial. Mean change from baseline of liver function enzymes for 4th quartile patients based on lab parameter level in 1 year oral testosterone undecanoate study

| Lab function Enzymes | Normal range for the study | # of patients | Mean baseline | Baseline range | Mean change from baseline | Mean change from baseline, % |
|---|---|---|---|---|---|---|
| Albumin (g/L) | 35-55 | 31 | 49.4 | 47-53 | −2.5 | −3.1 % |
| AST (U/L) | 10-43 | 52 | 35.1 | 27.5-86 | −6.3 | −16.6 % |
| ALT (U/L) | 10-40 | 51 | 51.1 | 37-85 | −10.0 | −16.7 % |
| ALP (U/L) | 43-115 | 52 | 97.6 | 83.5-132 | −10.2 | −10.4 % |
| GGT (U/L) | 10-49 | 52 | 70.7 | 39.5-393 | −7.0 | −7.4 % |
| Bilirubin (mg/dL) | 0.1-1.0 | 50 | 0.78 | 0.55-1.88 | −0.18 | −20.5 % |
| Creatinine (mg/dL) | 0.7-1.4 | 59 | 1.2 | 1.1-1.7 | 0.01 | 0.8 % |

TABLE 4

Trial. Mean Change from Baseline of lipids for 4th quartile patients based on lab parameter level in 1 Year Oral TU Study

| Lipids | Normal range for the study | # of patients | Mean baseline | Baseline range | Mean change from baseline | Mean change from baseline, % |
|---|---|---|---|---|---|---|
| Triglycerides (mg/dL) | 45-200 | 52 | 360.2 | 238-1171 | −85.1 | −19.0 % |
| Total Cholesterol (mg/dL) | 125-200 | 52 | 247.0 | 222-302 | −20.2 | −7.9 % |
| LDL-C (mg/dL) | 50-160 | 48 | 154.4 | 133-193 | −10.2 | −6.1 % |
| Non-HDL-C (mg/dL) | N/A | 51 | 197.6 | 171-258 | −18.2 | −8.7 % |
| Lp-PLA2 (ng/mL) | <235 | 43 | 256.3 | 220-363 | −47.8 | −17.1 % |

Example 2: Clinical Trial

The following study was designed and performed to evaluate twice-daily dosing of 225 mg TU in a population of male subjects having testosterone deficiency. This trial was conducted in a manner similar to that of Example 1.

All subjects received 225 mg TU BID (two capsules of 112.5 mg) taken twice daily (total daily dose of 450 mg taken as 225 mg in the morning and 225 mg in the evening), approximately 12 hours apart, approximately 30 minutes after morning and evening meals, with water.

Labs were collected at baseline and end of study. Subjects were dosed for 24 days. In the Figure legends, this trial is referred to as "16-002".

Example 3: Clinical Trial

The following study was designed and performed to evaluate thrice-daily dosing of 150 mg TU (450 mg TU per day) in a population of male subjects having testosterone deficiency. This trial was conducted in a manner similar to that of Example 1.

All subjects received 150 mg TU BID (two capsules of 75 mg) taken thrice (total daily dose of 450 mg taken as 150 mg after breakfast, 150 mg after lunch and 150 mg after dinner approximately 30 minutes after meals, with water.

Labs were collected at baseline and end of study. Subjects were dosed for 24 days. In the Figure legends to this trial is referred to as "16-003".

Example 4: Clinical Trial

This was a multi-center, open-label, randomized, parallel, 2-period, multiple-dose study that evaluated the safety, tolerability, and PK of oral testosterone tridecanoate in 5 groups of hypogonadal males. Period 1 and Period 2 each include an up to 28-day Screening Period, a 14-day Treatment Period, and an Exit Evaluation performed following the final PK blood sample collection.

In Period 1, 3 groups of approximately 12 hypogonadal male subjects each (approximately 36 subjects total) were randomized to receive administration of either Treatment A (500 mg oral testosterone tridecanoate), Treatment B (750 mg oral testosterone tridecanoate), or Treatment C (1000 mg oral testosterone tridecanoate) once daily (QD) for 14 days following standardized meals. Following completion of Period 1, the appropriate dose of oral testosterone tridecanoate for Treatment D (either 250 mg or 1250 mg oral testosterone tridecanoate) in Period 2 was determined based on an evaluation of Period 1 data. Subjects who completed Period 1 proceeded to Period 2 following a 2-day washout.

In Period 2, two groups of approximately 12 hypogonadal male subjects each (approximately 24 subjects total) will be randomized to receive administration of either Treatment D (250 mg or 1250 mg oral testosterone tridecanoate) QD for 14 days following standardized meals, or Treatment E (500 mg oral testosterone tridecanoate) twice daily (BID) for 14 days following standardized meals.

Each subject in Period 1 or Period 2 underwent 3 overnight clinic confinements (on Day 1, Day 8, and Day 14). Subjects entered the clinic at least 2 hours prior to the anticipated morning dosing and remained in confinement for 24 hours after the morning dose. During this time, subjects received each assigned dose of oral testosterone tridecanoate, 30 minutes (plus/minus 5 minutes) after starting a standardized meal. Blood samples for PK analysis were collected at regular intervals for 24 hours after the morning dose. Following the Hour 24 blood draw, subjects were discharged from the clinic. At the end of the Day 1 and Day 8 clinic confinements, subjects received a sufficient quantity of oral testosterone tridecanoate to administer their assigned treatment at home until the next confinement. Subjects also received specific instructions on the standardized meals (approximate composition and/or example meals from various restaurants and instructions for preparation of meals) to be consumed approximately 30 minutes prior to oral testosterone tridecanoate administration, at approximately the same-time of day as the administration during confinement.

In addition to the 3 confinements, subjects in Period 1 returned to the clinic on the morning of Day 6, Day 7, Day 12, and Day 13 for a single pre-dose blood sample collection.

The total number of subjects planned for Period 1 of this study is approximately 36; approximately 24 of these subjects are expected to continue participation into Period 2. If this is not the case, additional subjects are enrolled for Period 2 at the discretion of the Sponsor.

The maximum treatment duration for a subject who participates in both treatment periods will be 28 days (i.e., 14 days for each period). The maximum duration of subject participation depended on the number of days between the end of Period 1 and the beginning of Period 2. This is intended to be less than or equal to 30 days; however, subjects will be informed at the time of consent that this duration may extend beyond 30 days. Assuming 30 days between periods, the maximum duration of subject participation is 86 days (i.e., up to 28 days for screening, 14 days for Period 1, 30 days between periods, and 14 days for Period 2). In the Figure legends this trial is referred to as "1111" or "1111 QD".

Example 5: Pharmaceutical Composition, Formulations and Unit Dosage Forms

The API in this example in specific compositions is testosterone tridecanoate, testosterone undecanoate, or a combination thereof. Alternatively, the skilled artisan understands that any other testosterone ester or steroid, or steroid ester can be used in this compositions accordingly.

These compositions can be made by any suitable method and filled into hard gel or soft gel capsules as appropriate. For example, the one or more of the ingredients are warmed or heated to a temperature that allows for dissolving any solid ingredients, the API is added and mixed until a homogenous mixture is obtained, and the capsule can be filled at an appropriate temperature and if needed, allowed to cool to room temperature.

Composition (A)

| Ingredient Name | Quantity Fill Material per Hard Gel Capsule | |
|---|---|---|
| | % w/w | Mg |
| API | 13%-16% | 100-120 |
| Glyceryl Monolinoleate, NF | 58%-68% | 440-490 |
| Polyoxyl 40 Hydrogenated Castor Oil, NF | 0%-19% | 0-125 |
| Ascorbyl Palmitate, NF | 0.1%-0.3% | 0.5-2.5 |
| Polyethylene Glycol 8000, NF | 3%-9% | 35-55 |
| Total | 100.0 | 733.3 |

Composition (B)

| Ingredient Name | Quantity Fill Material per Hard Shell Capsule | |
|---|---|---|
| | % w/w | Mg |
| API | 23%-28% | 160-200 |
| Oleic Acid, NF ((9Z)-Octadec-9-enoic acid) | 60%-70% | 450-530 |
| Polyoxyl 40 Hydrogenated Castor Oil, NF | 0%-7% | 0-37 |
| Ascorbyl Palmitate, NF | 0.1%-0.3% | 0.5-2.5 |
| Polyethylene Glycol 8000, NF | 3%-9% | 35-55 |
| Total | 100.0 | 750.0 |

Composition (C)

| Ingredient Name | Quantity Fill Material per Hard Gel Capsule | | Quantity Fill Material per Softgel Capsule |
|---|---|---|---|
| | % w/w | mg | mg |
| API | 23%-28% | 160-205 | 304-390 |
| Oleic Acid, NF ((9Z)-Octadec-9-enoic acid) | 37%-46% | 280-330 | 532-627 |
| Peppermint Oil, NF | 15-21 | 120-150 | 228-285 |
| Polyoxyl 40 Hydrogenated Castor Oil, NF | 0%-7% | 0-35 | 0-67 |
| Ascorbyl Palmitate, NF | 0.20 | 0.5-2.5 | 1.0-4.8 |
| Glyceryl Palmitostearate (Glyceryl Distearate, NF) | 9%-15% | 80-100 | 152-190 |
| Total | 100.0 | 750.0 | 1250 |

Composition (D)

| Ingredient Name | Quantity Fill Material per Hard Gel Capsule | | Quantity Fill Material Softgel Capsule |
|---|---|---|---|
| | % w/w | mg | mg |
| API | 25%-32% | 160-205 | 304-390 |
| Oleic Acid, NF ((9Z)-Octadec-9-enoic acid) | 50%-60% | 340-400 | 646-760 |
| Polyoxyl 40 Hydrogenated Castor Oil, NF | 0%-7% | 21-32 | 0-61 |
| Stearic Acid, NF | 0%-7% | 0-32 | 0-61 |
| Glyceryl Palmitostearate (Glyceryl Distearate, NF; Precirol ATO 5) | 3%-13% | 47-58 | 89-110 |
| Ascorbyl Palmitate, NF | 0.1%-3% | 0.5-2.5 | 1.0-4.8 |
| Total | 100.00 | 654.60 | 1250 |

Composition (E)

| Ingredient Name | Quantity Fill Material per Hard Gel Capsule | |
|---|---|---|
| | % w/w | Mg |
| API | 27%-33% | 160-205 |
| Oleic Acid, NF ((9Z)-Octadec-9-enoic acid) | 50%-70% | 335-395 |
| Polyoxyl 40 Hydrogenated Castor Oil, NF | 0%-7% | 0-30 |
| Ascorbyl Palmitate, NF | 0.1%-0.3% | 0.5-2.5 |
| Polyethylene Glycol 8000, NF | 3%-9% | 32-42 |
| Total | 100.0 | 611 |

Example 7: Pharmaceutical Composition, Formulations and Unit Dosage Forms

The API in this example in specific compositions is testosterone tridecanoate, testosterone undecanoate, or a combination thereof. Alternatively, the skilled artisan understands that any other testosterone ester or steroid, or steroid ester can be used in this compositions accordingly.

These compositions can be made by any suitable method and filled into hard gel or soft gel capsules as appropriate. For example, the one or more of the ingredients are warmed or heated to a temperature that allows for dissolving any solid ingredients, the API is added and mixed until a homogenous mixture is obtained and the capsule can be filled at an appropriate temperature and if needed, allowed to cool to room temperature.

Composition (F)

| Ingredient Name | Weight Percent of Fill Pharmaceutical Composition (±1%) % w/w | Quantity Fill Material per Hard Gel Capsule (±1%) Mg |
|---|---|---|
| API | 15 | 110 |
| Glyceryl Monolinoleate, NF | 63 | 463 |
| Polyoxyl 40 Hydrogenated Castor Oil, NF | 15 | 114 |
| Ascorbyl Palmitate, NF | 0.2 | 1.5 |
| Polyethylene Glycol 8000, NF | 6 | 44 |
| Total | 100 | 733.3 |

Composition (G)

| Ingredient Name | Weight Percent of Fill Pharmaceutical Composition (±1%) % w/w | Quantity Fill Material per Hard Gel Capsule (±1%) mg |
|---|---|---|
| API | 24 | 183 |
| Oleic Acid, NF ((9Z)-Octadec-9-enoic acid) | 65 | 490 |
| Polyoxyl 40 Hydrogenated Castor Oil, NF | 4 | 30 |
| Ascorbyl Palmitate, NF | 0.2 | 1.5 |
| Polyethylene Glycol 8000, NF | 6 | 45 |
| Total | 100 | 750 |

Composition (H)

| Ingredient Name | Weight Percent of Fill Pharmaceutical Composition (±1%) % w/w | Quantity Fill Material per Hard Gel Capsule (±1%) Mg | Quantity Fill Material per Softgel Capsule (±1%) mg |
|---|---|---|---|
| API | 24 | 183 | 300 |
| Oleic Acid, NF ((9Z)-Octadec-9-enoic acid) | 41 | 308 | 513 |
| Peppermint Oil, NF | 18 | 136 | 225 |
| Polyoxyl 40 Hydrogenated Castor Oil, NF | 4 | 30 | 50 |
| Ascorbyl Palmitate, NF | 0.2 | 1.5 | 2.5 |
| Glyceryl Palmitostearate (Glyceryl Distearate, NF) | 12 | 90 | 150 |
| Total | 100 | 750 | 1241 |

Composition (I)

| Ingredient Name | Weight Percent of Fill Pharmaceutical Composition (±1%) % w/w | Quantity Fill Material per Hard Gel Capsule (±1%) Mg | Quantity Fill Material per Soft Gel Capsule (±1%) mg |
|---|---|---|---|
| API | 28 | 183 | 350 |
| Oleic Acid, NF ((9Z)-Octadec-9-enoic acid) | 55 | 365 | 688 |
| Polyoxyl 40 Hydrogenated Castor Oil, NF | 4 | 26 | 50 |
| Stearic Acid, NF | 4 | 26 | 50 |
| Glyceryl Palmitostearate (Glyceryl Distearate, NF; Precirol ATO 5) | 8 | 52 | 100 |
| Ascorbyl Palmitate, NF | 0.2 | 1.3 | 2.5 |
| Total | 100 | 654 | 1241 |

Composition (J)

| Ingredient Name | Weight Percent of Fill Pharmaceutical Composition (±1%) % w/w | Quantity Fill Material per Hard Gel Capsule (±1%) mg |
|---|---|---|
| API | 30 | 183 |
| Oleic Acid, NF ((9Z)-Octadec-9-enoic acid) | 59 | 365 |
| Polyoxyl 40 Hydrogenated Castor Oil, NF | 4 | 24 |
| Ascorbyl Palmitate, NF | 0.2 | 1.2 |
| Polyethylene Glycol 8000, NF | 6 | 36 |
| Total | 100 | 611 |

Based on the description provided herein and the results of the clinical trial, it is now possible to provide pharmaceutical compositions similar to those described as Compositions (A)-(J) having API The API in this example in specific compositions is testosterone tridecanoate, testosterone undecanoate, or a combination thereof (alternatively, the skilled artisan understands that any other testosterone ester or steroid, or steroid ester can be used in this compositions accordingly) in an amount of e.g., 1 mg to 10 mg, 10 mg to 25 mg, 25 mg to 50 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, 425 mg to 450 mg, 450 mg to 475 mg, 475 mg to 500 mg, 525 mg to 550 mg, 550 mg to 575 mg, or 575 mg to 600 mg.

Other formulation for use in the method include, but are not limited to Formulation XX1 Ingredients mg capsule %, w/w Testosterone Undecanoate 158.3 mg (19.8 w/w %) Oleic Acid 413.1 mg (51.6%) CREMOPHOR RH 40 128.4 mg (16.1 w/w %) Borage Seed Oil 80.0 mg (10 w/w %) Peppermint Oil 20.0 mg (2.5%) BHT 0.2 mg (0.03 w/w %) Total 800 mg (100 w/w %) and XX2 Ingredients mg/capsule w/w %, Testosterone Undecanoate 158.3 mg (19.8%) Oleic Acid 412.5 mg (51.6% w/w) CREMOPHOR RH 40 128.4 mg (16.0 w/w %) Peppermint Oil 20.0 mg (2.5 w/w %) Borage Seed Oil 80.0 mg (10% w/w) 0.03% w/w BHT Ascorbyl Palmitate 0.8 mg (0.1% w/w) Total 800 mg (100% w/w).

Similar composition to any specific compositions describe herein can also have for example:
  (a) a different fatty acid, an additional fatty acid or a both,
  (b) a different hydrophilic surfactant, an additional hydrophilic surfactant or both,
  (c) a mono- or di-glyceride in place of the fatty acid or in combination with the fatty acid,
  (d) a different solidifying agent, an additional solidifying agent, or both,
  (e) a different diglyceride than glyceryl palmitostearate, an additional diglyceride or both,
  (f) a different antioxidant, an additional antioxidant or both,
  (g) have additional additives,
  (h) use menthol or another alcohol in place of or in addition to peppermint oil,
  (i) use a tocopherol in place of fatty acid, in combination with fatty acid, in place of peppermint oil, in addition to peppermint oil or a combination thereof,
  (j) use a different monoglyceride than glyceryl monolinoleate, an additional monoglyceride, a diglyceride in place of glyceryl monolinoleate, a diglyceride in combination with glyceryl monolinoleate or a combination thereof, or
  (k) a combination of any of the above.

Moreover, it is noted that any of the formulations disclosed herein can include Vitamin E (e.g., tocopherol), Vitamin E derivatives, Vitamin E prodrugs, Omega-3 fatty acids and the such by adjusting the relative amounts of the other formulation components to achieve the desired formulation.

| Ingredients Name | Theoretical Qty. per Capsule % w/w |
|---|---|
| Testosterone Undecanoate (or testosterone ester) | 5-40 |
| Oleic Acid, NF | 30-70 |
| Polyoxyl 35 Castor Oil, NF | 0-10 |
| Stearic Acid, NF | 0-10 |
| Glyceryl Palmitostearate (Glyceryl Distearate, NF; Precirol ATO 5) | 0-20 |
| Ascorbyl Palmitate, NF | 0-5 |
| Total | 100.0 |

1144-06 Formula

| Ingredients Name | Theoretical Qty. per Capsule % w/w |
|---|---|
| Testosterone Undecanoate (or testosterone ester) | 5-40 |
| Vitamin E Acetate, USP | 10-60 |
| Oleic Acid, NF | 0-50 |
| Polyoxyl 35 Castor Oil, NF | 0-20 |
| Stearic Acid, NF | 0-10 |
| Glyceryl Palmitostearate (Glyceryl Distearate, NF; Precirol ATO 5) | 0-20 |
| Ascorbyl Palmitate, NF | 0-5 |
| Total | 100.0 |

Other tocopherols, tocotrienols and the such can be sued in this formulations such as d-alpha tocopherol or its acetate as described elsewhere herein.

Example 6: Clinical Study

This example is part of an ongoing Liver Fat Study which is an open-label, multi-center, single arm study evaluating LPCN 1144 treatment (e.g., androgen therapy, testosterone therapy, oral testosterone ester, or 225 mg testosterone undecanoate orally) in a cohort of 36 hypogonadal males (NCT03868059). Subjects with at least 10% baseline liver fat were evaluated which is indicative of subjects with NAFLD with the potential to have NASH. Interim results of seven of the nine subjects in the Liver Fat Study with baseline liver fat of at least 10% are presented as two subjects were unable to schedule an eight-week MRI-PDFF visit. Baseline mean liver fat of these seven subjects was 21.0%.

Baseline Results

An MRI-PDFF study of 36 male hypogonadal subjects (having 2 morning testosterone levels of 300 ng/dL or less) was performed as part of an ongoing trial. Basic baseline labs including liver function tests (e.g., AST & ALT) and serum triglycerides were collected and analyzed. It was found by non-linear regression, that BMI (ALT, AST, serum Triglyceride) was associated with liver fat (P<0.006). It was found by non-linear regression, that serum triglyceride levels (obesity, hypertension, type 2 diabetes) were associated with liver fat (P<0.006). The analysis of this data is summarized in the figures.

Interim Results

Treatment results showed an absolute mean reduction from baseline of 7.6% liver fat and demonstrated a 38% relative mean liver fat reduction from baseline. Moreover, there was an 86% responder rate in which subjects experienced at least a 4.1% absolute reduction in liver fat from baseline and a 71% responder rate in which subjects experienced at least a 29% reduction in liver fat from baseline.

End of Study Results 34 subjects were evaluable at end-of-study. 21 subjects had NAFLD at baseline (liver fat greater than or equal to 5%, mean liver fat=12.1%), 10 subjects had greater than 8% liver fat at baseline (mean=12.1%), and 8 subjects had greater than 10% liver fat at baseline (mean=20.5%). Mean relative liver fat % change after 16 weeks of treatment was −33% for subjects having NAFLD (e.g., baseline liver fat of 5% or greater), −42% for baseline liver fat of 8% or greater, and −40% for baseline liver fat of 10% or greater. The responder rates (% of patients with at least a 30% relative reduction in liver fat from baseline) was 71% for greater than or equal to 5% baseline liver fat, 80% for greater than or equal to 8% baseline liver fat, and 70% for greater than or equal to 10% baseline liver fat. NAFLD was resolved (baseline liver fat greater than or equal to 5% going to less than 5% at end of study) in 48% of subject. 100% of subjects with above normal ALT levels (mean baseline=48.7) ended the study with normal ALT levels. %0% of subjects with above normal GGT levels ended the study with normal GGT levels. 60% of subjects had BUN normalization. The normalization rates for total cholesterol, LDL-C, triglyceride were 29%, 50% and 21% respectively. The mean relative liver fat change is patients with NAFLD resolution was −55%. As the duration of therapy increased from 8 weeks to 16 weeks, liver fat reductions were improved as well as the percent of subject achieving NAFLD resolution.

A recent publication in Therapeutic Advances in Gastroenterology (Patel et al., Therapeutic Advances in Gastroenterol. 2016 September; 9(5): 692-701) quantified the magnitude of MRI-PDFF reduction corresponding to a histologic response in NASH in a clinical setting with paired liver biopsy. The results concluded that histologic responders had a statistically significant reduction in MRI-PDFF of −4.1% with a mean relative percent change of −29.3%.

This is a particularly surprising and unexpected finding since oral testosterone undecanoate lowers serum SHBG levels—the skilled artisan would expect that lower SHBG would be expected to result in greater liver fat according to the art.

Thus, the skilled artisan can apply these teaching and examples to employ androgen therapy for treating or preventing liver disease as described herein.

It is understood that the above-described various types of compositions, dosage forms and/or modes of applications are only illustrative of preferred embodiments of the present invention. Numerous modifications and alternative arrangements may be devised by those skilled in the art without departing from the spirit and scope of the present invention and the appended claims are intended to cover such modifications and arrangements. Thus, while the present invention has been described above with particularity and detail in connection with what is presently deemed to be the most practical and preferred embodiments of the invention, it will be apparent to those of ordinary skill in the art that variations including, but not limited to, variations in size, materials, shape, form, function and manner of operation, assembly and use may be made without departing from the principles and concepts set forth herein.

What is claimed is:

1. A method of treating a fatty liver condition comprising orally administering a pharmaceutical composition to a subject having hepatocellular ballooning, wherein said pharmaceutical composition includes a testosterone ester component (TEC) consisting essentially of testosterone dodecanoate (TD), said TEC being in an amount of about 200 mg to about 750 mg when said subject is male and said TEC being in an amount of about ⅒th-1/15th of about 200 mg to about 750 mg when said subject is female, and wherein in response to said administration, said hepatocellular ballooning is resolved, and wherein said hepatocellular ballooning resolution comprises a reduction of hepatocellular ballooning in said subject by at least one NAS point.

2. The method of claim 1 wherein said method ameliorates the level of one or more biomarkers in said subject compared to the baseline value, wherein the one or more biomarkers are selected from the group consisting of ALP, ALT, AST, GGT, triglycerides, LDL, cholesterol, liver biopsy, inflammation biomarkers, non-HDL cholesterol, hematocrit, hemoglobin, lipoprotein phospholipase A2, bilirubin, albumin, SHBG, and combinations thereof.

3. The method of claim 1 wherein the subject is a male.

4. The method of claim 1 wherein the subject has low testosterone or testosterone deficiency prior to commencing therapy.

5. The method of claim 2 wherein said subject has a number of biomarkers of a liver disease or condition in the upper normal range or above, and wherein said number of biomarkers comprises at least one of at least one, at least two, at least three, and at least four.

6. The method of claim 2 wherein said subject has a number of biomarkers of a liver disease or condition elevated above the upper normal limit, and wherein said number of biomarkers comprises at least one of at least one, at least two, and at least three.

7. The method of claim 2 wherein said method reduces the level of said subject's serum alkaline phosphatase levels compared to said subject's baseline alkaline phosphatase value.

8. The method of claim 1 wherein said administration prolongs the amount of time the subject can wait for a liver transplant or survive.

9. The method of claim 1 wherein said TEC amount is about 300 mg to about 600 mg per day.

10. The method of claim 1 wherein said TEC amount is about 450 mg per day.

11. The method of claim 1, wherein the pharmaceutical composition comprises vitamin E or an omega-3 fatty acid.

12. The method of claim 1 wherein said subject has one, two, or three, or more co-morbid diseases or conditions chosen from obesity, type 2 diabetes, dyslipidemia, cardiovascular disease, thyroid dysfunction, chronic kidney disease, liver disease, osteoporosis, hypogonadism, hypertension, sarcopenia, and cachexia.

13. The method of claim 1 wherein when said subject is male, said method comprises a daily oral administration of said pharmaceutical composition to said subject wherein said TEC is in at least one of the following amounts comprising about 200 mg to about 400 mg, about 300 mg to about 600 mg, and about 450 mg.

14. The method of claim 1 wherein when said subject is female, said method comprises a daily oral administration of said pharmaceutical composition to said subject wherein said TEC is in about ⅒th-1/15th of at least one of the following amounts comprising about 200 mg to about 400 mg, about 300 mg to about 600 mg, and about 450 mg.

15. The method of claim 1 wherein said subject has an age chosen from 1 to 18 years old, 18-25 years old, 26-35 years old, 36-45 years old, 45-55 years old, 56-65 years old, or older than 65 years old.

16. The method of claim 1 wherein said subject has NASH with fibrosis.

17. The method of claim 1 wherein said subject has NASH with F2 or F3 fibrosis (NASH CRN scale).

18. The method of claim 1 further comprising treating said subject with one or more additional pharmaceuticals agents suitable for treating liver disease or a comorbidity of liver disease.

19. The method of claim 1 wherein said TEC amount is in an amount of about 300 mg to about 600, and wherein said method further results in a reduction in liver fat, a reduction in inflammation, and no worsening of fibrosis.

20. The method of claim 1 wherein said subject has NASH, and wherein said administration results in resolution of said NASH.

21. The method of claim 20 wherein said resolution of said NASH is confirmed by a histopathological interpretation of said subject by an experienced pathologist, wherein said histopathological interpretation indicates a hepatocellular ballooning score of zero and an inflammation score of no more than one.

22. A method of treating a fatty liver condition comprising orally administering a pharmaceutical composition to a subject having at least one of NASH, NASH with cirrhosis, and NAFLD, wherein said pharmaceutical composition includes a TEC consisting essentially of TD, said TEC being in an amount of about 200 mg to about 750 mg when said subject is male and said TEC being in an amount of about 1/10th-1/15th of about 200 mg to about 750 mg when said subject is female, and wherein in response to said administration, at least one of said NASH, NASH with cirrhosis, and NAFLD is resolved, and wherein said resolution is confirmed by a histopathological interpretation of said subject, and wherein said histopathological interpretation indicates a hepatocellular ballooning score of zero and an inflammation score of no more than one.

23. The method of claim 22 wherein said subject is a male having low testosterone or testosterone deficiency prior to said administration, and wherein said pharmaceutical composition comprises at least one of vitamin E and an omega-3 fatty acid, and wherein said method ameliorates the level of at least one biomarker in said subject compared to a baseline value of said at least one biomarker, wherein said at least one biomarker comprises ALP, ALT, AST, GGT, a triglyceride, LDL, cholesterol, a liver biopsy, an inflammation biomarker, non-HDL cholesterol, hematocrit, hemoglobin, lipoprotein phospholipase A2, bilirubin, albumin, and SHBG.

24. The method of claim 22 wherein when said subject is male, said method comprises a daily oral administration of said pharmaceutical composition to said subject wherein said TEC is in at least one of the following amounts comprising about 200 mg to about 400 mg, about 300 mg to about 600 mg, and about 450 mg, and wherein when said subject is female, said method comprises a daily oral administration of said pharmaceutical composition to said subject wherein said TEC is in about 1/10th-1/15th of at least one of the following amounts comprising about 200 mg to about 400 mg, about 300 mg to about 600 mg, and about 450 mg, and wherein said subject has at least one co-morbid disease or condition comprising obesity, type 2 diabetes, dyslipidemia, cardiovascular disease, thyroid dysfunction, chronic kidney disease, liver disease, osteoporosis, hypogonadism, hypertension, sarcopenia, and cachexia.

25. A method of treating a fatty liver condition comprising orally administering a pharmaceutical composition to a subject having at least one of NASH, NASH with cirrhosis, and NAFLD, wherein said pharmaceutical composition includes a TEC consisting essentially of TD, said TEC being in an amount of about 200 mg to about 750 mg when said subject is male and said TEC being in an amount of about 1/10th-1/15th of about 200 mg to about 750 mg when said subject is female, and wherein in response to said administration, at least one of said NASH, NASH with cirrhosis, and NAFLD is resolved, and wherein said resolution comprises at least one of a reduction in liver fat, a reduction in hepatocellular ballooning, a reduction in inflammation, and no worsening of fibrosis.

26. The method of claim 25 wherein said reduction in liver fat comprises a % reduction of greater than at least one of 5%, 10%, 15%, 20%, 25% and 30%, and wherein said reduction in hepatocellular ballooning comprises a reduction of at least one point, and wherein said reduction in inflammation comprises a reduction of at least one point, and wherein said no worsening of fibrosis comprises a lessening of fibrosis.

27. The method of claim 26 wherein said % reduction comprises a relative % reduction.

28. The method of claim 25 wherein said subject is a male having low testosterone or testosterone deficiency prior to said administration, and wherein said pharmaceutical composition comprises at least one of vitamin E and an omega-3 fatty acid, and wherein said method ameliorates the level of at least one biomarker in said subject compared to a baseline value of said at least one biomarker, wherein said at least one biomarker comprises ALP, ALT, AST, GGT, a triglyceride, LDL, cholesterol, a liver biopsy, an inflammation biomarker, non-HDL cholesterol, hematocrit, hemoglobin, lipoprotein phospholipase A2, bilirubin, albumin, and SHBG.

29. The method of claim 25 wherein when said subject is male, said method comprises a daily oral administration of said pharmaceutical composition to said subject wherein said TEC is in at least one of the following amounts comprising about 200 mg to about 400 mg, about 300 mg to about 600 mg, and about 450 mg, and wherein when said subject is female, said method comprises a daily oral administration of said pharmaceutical composition to said subject wherein said TEC is in about 1/10th-1/15th of at least one of the following amounts comprising about 200 mg to about 400 mg, about 300 mg to about 600 mg, and about 450 mg, and wherein said subject has at least one co-morbid disease or condition comprising obesity, type 2 diabetes, dyslipidemia, cardiovascular disease, thyroid dysfunction, chronic kidney disease, liver disease, osteoporosis, hypogonadism, hypertension, sarcopenia, and cachexia.

30. A method of treating a fatty liver condition comprising orally administering a pharmaceutical composition to a subject having at least one of NASH, NASH with cirrhosis, and NAFLD, wherein said pharmaceutical composition includes a TEC consisting essentially of TD, said TEC being in an amount of about 200 mg to about 750 mg when said subject is male and said TEC being in an amount of about 1/10th-1/15th of about 200 mg to about 750 mg when said subject is female, and wherein in response to said administration, at least one of said NASH, NASH with cirrhosis, and NAFLD is resolved, and wherein said resolution comprises a reduction in hepatocellular ballooning and at least one of a reduction in liver fat, a reduction in inflammation, and no worsening of fibrosis.

* * * * *